United States Patent
Ginsburg et al.

(10) Patent No.: US 10,685,743 B2
(45) Date of Patent: Jun. 16, 2020

(54) DATA COMMAND CENTER VISUAL DISPLAY SYSTEM

(71) Applicant: EHR Command Center, LLC, Merion Station, PA (US)

(72) Inventors: Leonard Ginsburg, Merion, PA (US); Richard J. Kedziora, Maple Glen, PA (US)

(73) Assignee: EHR COMMAND CENTER, LLC, Merion Station, PA (US)

( * ) Notice: Subject to any disclaimer, the term of this patent is extended or adjusted under 35 U.S.C. 154(b) by 937 days.

(21) Appl. No.: 15/275,223

(22) Filed: Sep. 23, 2016

(65) Prior Publication Data

US 2017/0116373 A1    Apr. 27, 2017

Related U.S. Application Data

(63) Continuation-in-part of application No. 15/204,900, filed on Jul. 7, 2016, which is a continuation-in-part
(Continued)

(51) Int. Cl.
*G16H 10/60* (2018.01)
*G06F 3/0481* (2013.01)
(Continued)

(52) U.S. Cl.
CPC .......... *G16H 10/60* (2018.01); *G06F 3/0482* (2013.01); *G06F 3/04817* (2013.01);
(Continued)

(58) Field of Classification Search
None
See application file for complete search history.

(56) References Cited

U.S. PATENT DOCUMENTS

| 2006/0064020 A1 | 3/2006 | Burnes et al. |
| 2010/0057646 A1 | 3/2010 | Martin et al. |

(Continued)

FOREIGN PATENT DOCUMENTS

| JP | 2017510015 | 4/2017 |
| WO | WO-2015143455 | 9/2015 |
| WO | WO-2018/057918 A1 | 3/2018 |

OTHER PUBLICATIONS

"U.S. Appl. No. 14/666,278, Response filed Jun. 11, 2018 to Non Final Office Action dated Jan. 9, 2018", 33 pgs.
(Continued)

*Primary Examiner* — Jonathan Durant
(74) *Attorney, Agent, or Firm* — Schwegman Lundberg & Woessner, P.A.

(57) ABSTRACT

A data command center visual display system presents dynamic data to a display screen. The command center visual display system includes a plurality of adjustable display panels configured to display predetermined combinations of patient identification information, patient insurance information, patient medical history information, a patient's insurance billing regulations, preferred practice patterns, and patient payment information, and a patient flowsheet that integrates the patient medical history information and patient payment information into a table that presents the patient's medical history by visit to one or more physicians with respective procedures or actions performed during each visit represented as icons identifying the procedure performed and icons indicating whether the procedure has been paid for in part or in full, the icons providing links to associated medical history data and/or financial data. The respective procedures or actions may also be activated directly from the table or display panels without leaving the display screen. In response to selection by a user of the visual display system, the adjustable display panels and
(Continued)

patient flowsheet are moved into a task-based or specialty-specific display configuration such that the patient identification information, patient insurance information, patient medical history information, and patient payment information may be accessed without leaving the display screen.

31 Claims, 97 Drawing Sheets

Related U.S. Application Data of application No. 14/666,278, filed on Mar. 23, 2015, now Pat. No. 10,319,468.

(60) Provisional application No. 61/968,693, filed on Mar. 21, 2014.

(51) Int. Cl.

| | | |
|---|---|---|
| *G06F 3/0482* | (2013.01) | |
| *G06F 3/0484* | (2013.01) | |
| *G16H 50/70* | (2018.01) | |
| *G16H 40/20* | (2018.01) | |
| *G16H 10/40* | (2018.01) | |
| *G16H 15/00* | (2018.01) | |

(52) U.S. Cl.
CPC ......... *G06F 3/04842* (2013.01); *G16H 10/40* (2018.01); *G16H 40/20* (2018.01); *G16H 50/70* (2018.01); *G16H 15/00* (2018.01)

(56) References Cited

U.S. PATENT DOCUMENTS

| | | |
|---|---|---|
| 2011/0004494 A1 | 1/2011 | Denny, Jr. et al. |
| 2011/0202370 A1 | 8/2011 | Green, III et al. |
| 2011/0276348 A1 | 11/2011 | Ahn et al. |
| 2012/0078664 A1 | 3/2012 | Hasan et al. |
| 2012/0130197 A1 | 5/2012 | Kugler et al. |
| 2013/0024206 A1 | 1/2013 | Hughes et al. |
| 2013/0027411 A1 | 1/2013 | Hebler et al. |
| 2013/0083185 A1 | 4/2013 | Coleman, III |
| 2013/0290005 A1 | 10/2013 | Vesto et al. |
| 2014/0012597 A1 | 1/2014 | Nolte et al. |
| 2014/0074509 A1 | 3/2014 | Rubendran et al. |
| 2014/0236631 A1 | 8/2014 | Perrin et al. |
| 2014/0236635 A1 | 8/2014 | Liberty et al. |
| 2015/0269323 A1 | 9/2015 | Ginsburg |
| 2016/0063212 A1 | 3/2016 | Monier et al. |
| 2016/0198996 A1 | 7/2016 | Dullen |
| 2016/0321404 A1 | 11/2016 | Ginsburg |

OTHER PUBLICATIONS

"Placement of Inventor work by MD Office in "EyeNet Extra" distributed as a Supplement to an EyeNet magazine available in Oct. 2014 at the American Academy of Ophthalmology (AAO) 2014 Conference", (Oct. 18-21, 2014), 2 pgs.
"International Application Serial No. PCT/US2015/022091, International Preliminary Report on Patentability dated Sep. 29, 2016", 7 pgs.
"International Application Serial No. PCT/US2015/022091, International Search Report dated Jun. 29, 2015", 3 pgs.
"International Application Serial No. PCT/US2015/022091, Written Opinion dated Jun. 29, 2015", 5 pgs.
U.S. Appl. No. 14/666,278, filed Mar. 23, 2015, Medical Services Tracking System and Method.
U.S. Appl. No. 15/204,900, filed Jul. 7, 2016, Medical Services Tracking Server System and Method.
"Australian Application Serial No. 2015230980, First Examination Report dated Dec. 24, 2019", 3 pages.
"U.S. Appl. No. 14/666,278, Non-Final Office Action dated Jan. 9, 2018", 22 pgs.
"U.S. Appl. No. 14/666,278, Non-Final Office Action dated Dec. 21, 2017", 20 pgs.
"U.S. Appl. No. 15/204,900, Non-Final Office Action dated Jan. 9, 2018", 32 pgs.
"International Application Serial No. PCT/US2017/052993, International Search Report dated Dec. 1, 2017", 2 pgs.
"International Application Serial No. PCT/US2017/052993, Written Opinion dated Dec. 1, 2017", 9 pgs.
"Medication Ordering Screenshots 1A, 1B, 1C", MDoffice EHR, 3 pgs.
"Scheduling Screenshots 2A, 2B, 2C", MDoffice EHR, 3 pgs.
"Test Ordering Screenshots 3A, 3B, 3C, 3D, 3E", MDoffice EHR, 5 pgs.

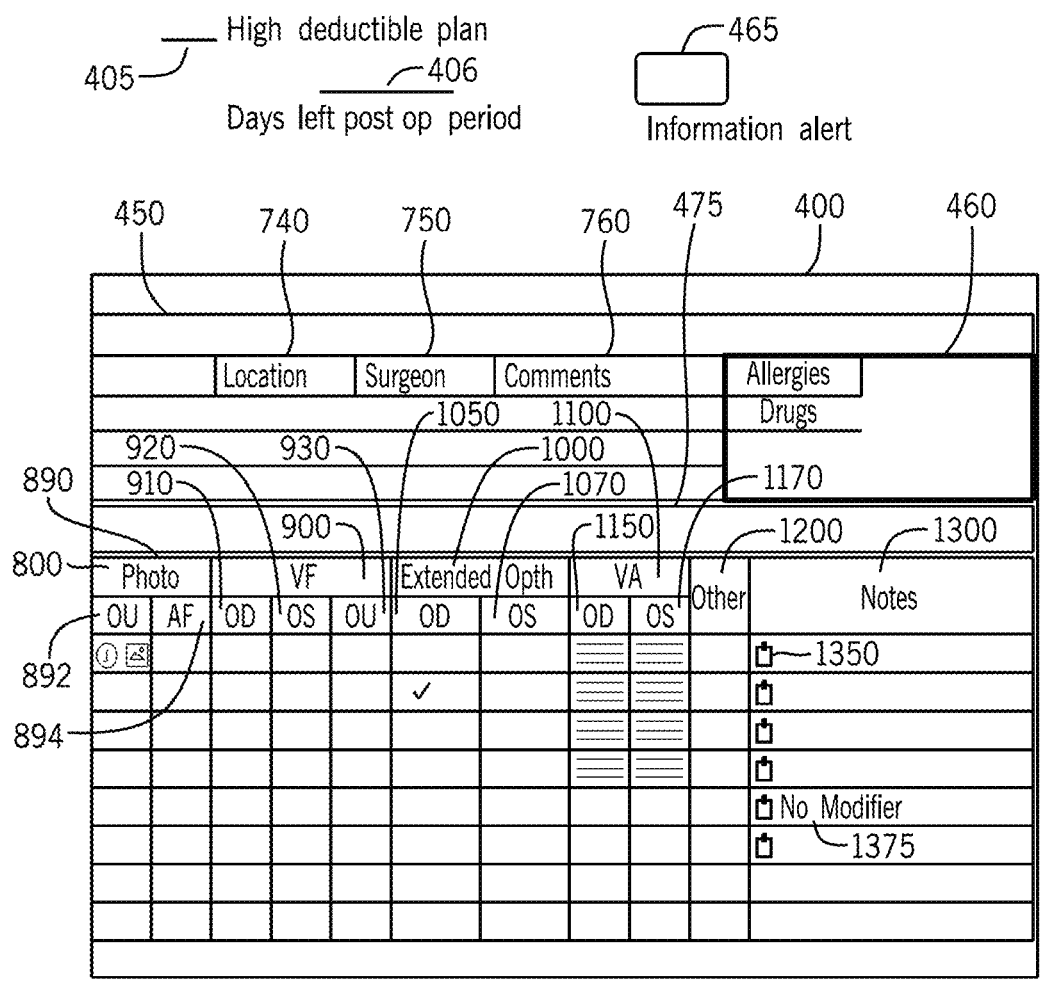
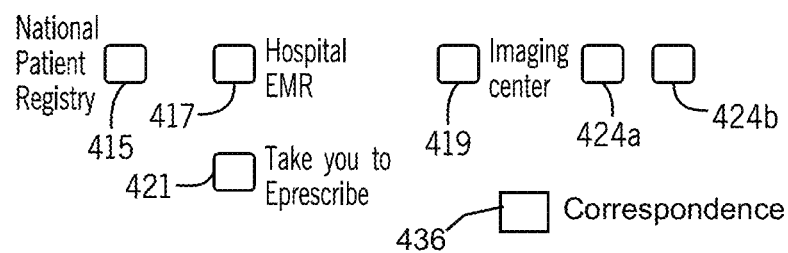
FIG. 4C

| Summary | | | | | | | | | | | | | | |
|---|---|---|---|---|---|---|---|---|---|---|---|---|---|---|
| Retina Flowsheet — 400 | | | | | | | | | | | | | | |
| Problems | | | | | ● All ○ Active | | Surgeries | | | | | | | |
| Entered | Timeline | ICD | Location | Diagnosis | | | Timeline | | Procedure | | | Description | | |
| | | | OU | --- | | | ◄ | | | | | | | |
| | | | OU | --- | | | ▬▬ | | | | | | | |
| | | | | | | | ► | | | | | | | |

Summary: — 500

| Date | Procedure | | Provider | Unit | Office Visit | OCT | | FA | | ICG | |
|---|---|---|---|---|---|---|---|---|---|---|---|
| | OD | OS | | | | OD | OS | OD | OS | OD | OS |
| | --- | --- | LHG | 5 | 887 | ①✎ | ①✎ | | | | |
| | --- | --- | LHG | 5 | 4/20/14 | ①✎ | ①✎ | | | | |
| | --- | --- | LHG | 1 | 885b | | | | | | |
| | --- | --- | LHG | 5 | 4/20/14 | ①✎ | ①✎ | ① | ①✎ | | |
| | --- | --- | LHG | 5 | | ①✎ | ①✎ | | | | |
| | --- | --- | LHG | 5 | 4/20/14 | ①✎ | ①✎ | | | ✓ | ✓ |
| | --- | --- | LHG | 1 | | | | | | | |
| | --- | --- | LHG | 5 | | ①✎ | ①✎ | | | | |

| Summary | | | | | | | | | | | | | | |
|---|---|---|---|---|---|---|---|---|---|---|---|---|---|---|
| Retina Flowsheet | | | | | | | | | | | | | | |

Problems ● All ○ Active

| Entered | Timeline | ICD | Location | Diagnosis |
|---|---|---|---|---|
| | | | OU | |
| | | | OU | |

Surgeries

| Timeline | Procedure | Description |
|---|---|---|

Summary:

| Date | Procedure | | Provider | Unit | Office Visit | OCT | | FA | | ICG | | Photo | |
|---|---|---|---|---|---|---|---|---|---|---|---|---|---|
| | OD | OS | | | | OD | OS | OD | OS | OD | OS | OD | AF |
| | | | LHG | 1 | 5/20/14 | ⊙◪ | ◪ | | | | | | |
| | | | LHG | 5 | | ⊙ | ⊙ | ⊙◪ | ⊙◪ | | | | |
| | | | LHG | 5 | | ⊙ | ⊙ | | | | | | |
| | | | LHG | 5 | | ⊙ | ◪ | | | | | | |
| | | | LHG | 5 | | | | | | ✓ | ✓ | | |
| | | | LHG | 1 | 5/20/14 | | | | | | | | |
| | | | LHG | 5 | 5/20/14 | | | ⊙◪ | ⊙◪ | ✓ | ✓ | | |

FIG. 12A

| Patient Name | Date Exam | F/U Appt | E&M Code | Additional CPT Code | Diagnosis ICD-9 | Colon polyp 45385 | Colon Bx 45380 | Colon Dx 45378 | Upper GI/Bx 43242 | Upper GI/Dx 43235 | Sigmoid oscopy 45330 | Lab Results | BP | Other | Notes | EMR | Mssg | Billing |
|---|---|---|---|---|---|---|---|---|---|---|---|---|---|---|---|---|---|---|
| | | A | | B | | | C | | | | | | D | | E | F | | G |
| Mr. A | 3.14.15 | | | | | | | | | | | | | | | | | |
| Mr. B | 3.14.15 | | | | | | | | | | | | | | | | | |
| Mr. C | 3.14.15 | | | | | | | | | | | | | | | | | |
| Mr. D | 3.14.15 | | | | | | | | | | | | | | | | | |
| Mr. E | 3.14.15 | | | | | | | | | | | | | | | | | |
| Mr. F | 3.14.15 | | | | | | | | | | | | | | | | | |
| Mr. G | 3.14.15 | | | | | | | | | | | | | | | | | |
| Mr. H | 3.14.15 | | | | | | | | | | | | | | | | | |
| Mr. I | 3.14.15 | | | | | | | | | | | | | | | | | |
| Mr. J | 3.14.15 | | | | | | | | | | | | | | | | | |

Color coded: Green if payment paid, yellow if pending, red if denied

FIG. 12D

| Patient Name | Insurance Coverage | Date of Dx of Diabetes | Patient Age | Patient Weight | Patient Height | Body Mass Index | Initial Presenting HbA1C | Most Recent HbA1C | Hypertension | Recent BP | All ICD Diagnosis | Medications | Other | Patient Next Appointment | Patient Contact Information | Notes |
|---|---|---|---|---|---|---|---|---|---|---|---|---|---|---|---|---|
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |
| | | | | | | | | | Y/N | | | | | | | ☐ |

Patient: Susan Calvin (34, Female)   Race: Caucasian   Phone: (610) 444-3433   Outstanding Balance: $200

| Topic | Data |
|---|---|
| Patient since | June 6, 2012 |
| Referred by | Dr. Mark Twain |
| Interesting facts | 3 kids, went to same college, friends with the Kleins |

DOB: 05/12/1982

Revenue Summary

| Year | Billed | Insurance | Patient | Write-Offs | Adjustments |
|---|---|---|---|---|---|
| 2014 | $30,000 | $20,000 | $5,000 | $2,000 | $3,000 |
| 2013 | $42,000 | $40,000 | $2,000 | $0 | $0 |
| 2012 | $10,000 | $4,000 | $1,000 | $0 | $0 |
| Total | $82,000 | $64,000 | $8,000 | $2,000 | $3,000 |

| 2524b | | | 2690 2692 | |
|---|---|---|---|---|
| Problems | | | Sort by ⊙ Date ○ Importance _ ☐ ✕ | |
| Entered | ICD10 | Location | Diagnosis | |
| 11/02/15 | Z96.1 | OU | Lens Replaced | |
| 11/02/15 | H35.32 | OU | Exudative Senile... | |
| 11/26/14 | Z96.1 | OD | Lens Replaced ● 2506 | |
| 2682 | 2684 | 2686 | 2688 | |

Patient: Susan Calvin (34, Female)     Outstanding Balance: $200

DOB: 05/12/1982     Race: Caucasian     Phone: (610) 999-3433

EXAM FINDINGS: 09/30/2016

| | OD | OS |
|---|---|---|
| Test: | WNL | WNL |
| Conj: | Injected (I) | Injected (I) |
| Cornea: | Edematous (E) | Edematous (E) |
| A/C: | Cells (C)<br>Flares (F) | Cells (C)<br>Flares (F) |
| Pupil: | Round (R) | Round (R) |
| IOL: | Well Positioned (WP) | Well Positioned (WP) |
| Cup/Disk: | 0.7 (CD) | 0.7 (CD) |
| Optic Nerve: | Pink with Temporal Pallor (PTP) | Pink with Temporal Pallor (PTP) |
| Macular: | Normal (N) | Normal (N) |

| 2526b | | 2728 |
|---|---|---|
| Allergies | | ☐ Ocular only _ O ✕ |
| Diagnosed ▲ | ICD 10 | Description |
| 7/23/2012 | J30.81 | Allergic rhinitis... |
| 5/13/2010 | T63.444 | Toxic effect bees... |
| 2725 | 2726 | 2727 |

Figure 26

| 2526c | 2744 | | | | 2740 | 2742 | |
|---|---|---|---|---|---|---|---|
| Active Medications | New Prescription | | | | Display only ☑ Active | ☐ Ocular Meds | _ □ ✕ |
| Prescribed ▲ | Medication | Dosage | Freq | Qty | Filled (left) | By | |
| 8/1/2016 | Metformin | 500 mg | 1x/day | 30 | 8/2/2016 (2) | Dr. Gamar | |
| 7/13/2016 | Lucentis | 0.5 mg | office | | | Dr. Smith | |
| 6/10/2016 | Amoxicilin | 250 mg | 3x/day | 15 | 6/10/2016 () | Dr. Listman | |

| Date | Panel | Lab | Result | Abnormal | Notes |
|---|---|---|---|---|---|
| 8/1/2015 | Lipid | HbA1c | 7.8 mg/dL | High | |
| 8/1/2015 | Lipid | LDL | 157 mg/dL | | |
| 3/14/2015 | Lipid | HbA1c | 7.5 mg/dL | High | |
| 3/14/2015 | Lipid | LDL | 181 mg/dL | High | |

| Abnormal Tests | | | | |
|---|---|---|---|---|
| YEAR | Chem 7 | Lipid | Comp. Blood Count | C React. |
| 2016 | | | | |
| 2015 | Potassium High | | | |
| 2014 | | | Normal Test | Normal Test |
| 2013 | | HDL 530 | | |
| 2012 | | | Platelets Low | |
| 2011 | Normal Test | Normal Test | | |

Diabetes Flowsheet Example

| Date | Height | Weight | BMI | Waist Circ | Presenting HbA1c | Current HbA1c | LDL | Trig. | Meds | Vaccines | Hypertension | Last BP | Exams | Assessments | Other | Notes |
|---|---|---|---|---|---|---|---|---|---|---|---|---|---|---|---|---|
| 5/5/2015 | 5'11" | 195 lbs. | 27.2 | 35 in | 8.9 | 7.6 | 95 mg/dL | 135 mg/dL | Oral | | No | 120/80 | | | | |

Coverage — 3210

Medication Alternatives (Suggested)

You selected Eylea at a cost of $1,800.

Please consider the alternate drug, Avastin, at $50 — 3212

Caution:
Using Avastin is not FDA approved for treating Macular Edema.
/ 3214

Contraindications / Warnings

Education Resources

Savings Programs / Coupons

Pharmacy: Walmart, 100 Walton Road, Framingham, MA  Select Alternative

Figure 45

Hospital Use Case

| Category | Costs | Expected Reimbursement |
|---|---|---|
| Labor | $450 | $400 |
| Supplies | $1,234 | $200 |
| Overhead (25%) | $421 | $123 |
| Total | $2,105 | $723 |

Patient Costs: $150.00

Figure 54

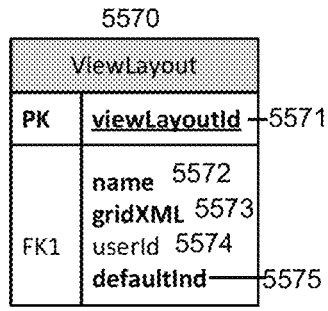

Figure 75

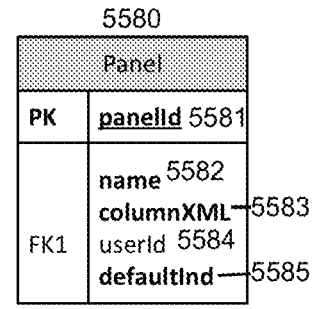

```
<view>
  <panels> 5590
    <panel>                    5593
      <panelId></panelId>  5594
      <position></position> <!-- Based on Flow Style: left, right, top, bottom, center -->
5595— <stacked></stacked> <!-- true,false – if true, creates tabs -- >
      <moveability></moveability> <!-- fixed, adjustable -->
    </panel>              5596
  </panels>
  <tabs> — 5591   /5597
    <position></position> <!-- left, right, top, bottom -->
    <tab>
      <panelId></panelId> 5598
      <order></order> 5599
    </tab>
  </tabs>
</view>
```

Figure 78

```
<panel>
  <columns> 5601
    <column>
      <name></name>5602
      <source></source> 5603
      <width></width> 5604
      <order></order> 5605
    </column>
  </columns>
</panel>
```

DATA COMMAND CENTER VISUAL DISPLAY SYSTEM

BACKGROUND

As technology advances, users of computer systems are asked to read and respond to an ever increasing amount of data. In complex systems, it is often difficult to present all of the data needed for decision-making in a way that facilitates quick decision-making that takes into account all of the relevant data. For example, physicians (interchangeable with "doctors" as used herein) are often called upon to make rapid life and death decisions based on a patient's conditions in the context of a medical history as presented in an Electronic Medical Record ("EMR"). However, the visual display systems for conventional EMRs are often difficult to understand and require the user to move through multiple screens, interfaces, and pop-up screens to obtain the disparate information needed to make a care decision. This is problematic when caring for multiple patients in a busy practice and is particularly problematic in a critical care setting.

Conventional EMR systems provide computerized interfaces between medical professionals and their staff and patients and are designed to facilitate and streamline the business of medical care. EMR systems allow a medical provider to track the delivery of medical care, access a patient's medical records, track billing for services provided, and follow a patient's progress. However, conventional EMR systems have mostly not met their promise because they typically include complex interfaces that require users to navigate through multiple layers, folders and/or windows to access even basic patient information. As a result, a HIMSS survey showed that 40% of physicians would not recommend their EMR to a colleague, 63.9% said note writing took longer with electronic health records, and 32% were slower to read other clinician's notes. A recent study by Medical Economics indicated that 67% of physicians are displeased with their EMR systems. Moreover, the complex interfaces are particularly problematic at the point of care as they slow physicians down and distract them from meaningful face time caring for patients. As a result, many physicians defer their interaction with the EMR systems until after the patients have been treated. A recent study reported in the Annals of Internal Medicine reported that physicians are spending almost half of their time in the office on EMR and desk work and spend just 27% on face time with patients, which is what the vast majority of physicians went into medicine to do. Once the physician gets home, they average another one to two hours completing health records. Thus, the complex interfaces of current EMR systems have led to diminished quality of the physician's practice of medicine, diminished patient quality of care, and negatively impacted physicians' job satisfaction. More user-friendly interfaces enabling physicians with ready access to the information accessible through EMR systems at the point of care would improve the physician-patient interactions and would be particularly useful in avoiding medical errors and missed diagnoses and increase compliance with insurance billing rules and regulations.

An underlying driver of physician's dissatisfaction with EMR systems is that medical knowledge is doubling every five years, diagnostic tests and procedures are exploding, and documentation requirements for payments are increasing. Physicians are becoming burdened with documentation and administrative tasks rather than spending their time as medical providers. As a result, the EMR system has created a barrier between the physician and patient, where physicians have to turn their back to the patient to input their findings, and have to navigate through multiple screens to do so rather than interact directly with the patient. The potential for medical errors, over ordering or under ordering of diagnostic tests, and other related mistakes generally, occurs because information is missed or buried in the electronic medical record and/or because information does not get transferred from the paper chart or copied from an earlier EMR entry. Important laboratory results or reports from other physicians can be lost or are difficult to access. Therefore, rather than reducing opportunities for potential medical errors, in many cases the electronic medical records systems themselves have created possibilities for error that did not exist with paper based medical files.

Communication of medical findings between physicians seeing patients treated by multiple health care providers has become more difficult. Now, rather than a phone call, simple fax or one page dictated medical summary, physicians are now sending voluminous amounts of information as the EMR gets stuffed with insurance documentation requirements and cut and paste options from "previous visits." Some medical conditions, such as diabetes, require multiple medical personnel to treat the patient. A single patient may have an eye doctor, family physician, endocrinologist, podiatrist, cardiologist, nephrologist, dietician/exercise physiologist, and diabetes education program coordinator. Primary care physicians can be audited and, if the annual report from a consultant is not in the chart, they can be financially penalized. The most important person in the team is the patient. A tool, such as the Command Center described herein, is desperately needed that provides one summary page, with one entry per visit, that can be used by all of the care providers who can share care and see results. All can be alerted to a critical occurrence such as a hospital admission. Finally patients and their physicians can have a one page cliff note summary of the patients' visits with all of their physicians. Even a message can be sent to any or all who are sharing care. A tool is desired where physicians referring patients or sharing surgical and post-operative care (for instance a cataract surgeon co-managing with an optometrist) are able to share visits while looking at the entire patient's conditions.

A simplified method of sharing of pre- and post-operative care is desirable where a simple one page summary can be printed out and handed to the patient with future appointments on one line that can later be filled in. This will help with patient compliance and increase the likelihood that the patient will keep appointments. On this one page should include the results and the medications the patient is supposed to take, reminding a patient and the co-managing physician what was prescribed and for how long. A tool is also needed to stop duplication of diagnostic tests and to improve referring physician communication. If one physician (an optometrist, for instance) takes a photograph of an eye on a particular day and sends the patient to a physician (ophthalmologist) for a second opinion, it is desired that the exam of the referring physician be incorporated into a table whereby the consultant sees the results of the physician's (optometrist's) exam and diagnostic test (photos) on one line and does not need to repeat the photo. It is further desired that the findings of the consultant be shared with the referring physician whereby patients have one shared table for all of their physicians. This improves communication, reduces the likelihood of medical errors, and reduces the cost of healthcare, as fewer repetitive diagnostic tests are performed for physicians in different practices. Now, physicians can share information and patient histories in quick cliff note-like fashion. Through advancing technologies and telemedicine a shared diagnostic test can be looked at by multiple parties all instantly seeing previous examinations and the patient's medical history.

Another set of problems for users of EMR systems revolve around finance. Physicians are trained to treat disease and are typically not trained to manage their practices and be business people. As a result, physicians increasingly rely on technicians, assistants, and other staff, often not qualified or properly trained to input information. Improper documentation or billing can occur, which the physician is held accountable for. Many current EMR systems require significant administrative overhead, and are prone to user error that can result in a discrepancy between billing, claims and payment for professional services and patient procedures. Physicians rarely know if what they had previously authorized to bill was in fact billed correctly, and rarely do physicians know if what they were paid was, in fact, correct.

In addition, there is a great demand for managing costs in the healthcare system. In recent years, health care networks have put in place systems for population health management and for revenue cycle management by providing software systems that enable healthcare providers to better track patient care and payment for healthcare services. However, it has been particularly difficult to involve the physicians directly into the revenue cycle management process. With so many priorities demanding the physicians' attention, few take the time to think about finances for an individual patient. Nine out of ten physicians cited shifting reimbursement models and the financial management of practices as their top challenges, according to a 2013 Wolters Kluwer Health Survey. Physicians typically make treatment decisions independent of cost factors and are unaware of the actual costs of the requested treatment. Providing such information to a physician at the point of care is desirable to enable the physicians to make informed decisions and is an excellent opportunity to get physicians involved on an individual patient basis in revenue cycle management. Unfortunately, providing such data to the physicians at the point of care would function to further clutter the EMR interfaces and require the physicians to spend more time interacting with the EMR system than interacting with the patient unless an efficient tool is designed.

To compound the physician's challenge, insurance companies and federal insurance programs such as Medicare and Medicaid hold physicians personally liable for what is billed, paid, and documented. Severe penalties and even criminal charges can occur when errors are made. The government has collected $2.5 billion for "wrongful under and over billing and inadequate documentation" (see https://www.justice.gov/opa/pr/departments-justice-and-health-and-human-services-announce-over-278-billion-returns-joint). Most physicians are not even aware that the government has written local coverage determinations (LCDs) (i.e. billing requirements) that are different across regions of the country and every insurance company has its own documentation frequency of tests and billing rules. Physicians, even if they are aware of the existence of LCDs, rarely have read the voluminous rules and regulations that without notice to a physician can change at any time, yet the physician is held liable. If a physician moves to another state, the rules and regulations can be entirely different. A tool is desperately needed that at the point of care can briefly present to the physician, based on the patient's insurance, the rules and regulations for whatever a physician orders, and what needs to be documented or performed.

Overall, while EMRs were meant to reduce costs and improve quality of care, the opposite has occurred. Dr. Steven Stack, president of the American Medical Association, addressed this issue when he said: "Imagine, in a world where a 2-year-old can operate an iPhone, graduated physicians are brought to their knees by electronic health records. When you have more than a quarter million physicians being penalized by the Government by a single program, I think that most people will understand the math. It is not that 250,000 plus physicians are the problem, it is most likely the single program they are being punished by." The Government has collected substantial sums of money from physicians and hospitals annually for either under or over billing, or wrongful billing. Physicians need a tool that helps them meet all insurance regulations and make certain that charges are billed correctly.

The overarching problem is that data input and currently available user interfaces are not aligned with the way physicians practice medicine. As Gary Botstein, MD of Dekalb Medical Center in Decatur, Ga., said at a Break the Red Tape Town Hall: "It's very easy to record large amounts of data and click-off boxes. So the emphasis is really on data collection, but what physicians ought to be doing is data synthesis. They ought to be taking that data, putting it together and coming up with a differential diagnosis and then figuring out what the best diagnosis is and then the best treatment . . . EMR was in front of me, I had 280 data points . . . to complete. To do this voluminous review of systems that was irrelevant to my patient's visit, it was like looking for a needle in a haystack. Once all this data was collected, you couldn't even find it." Dr. Puppula, of Alliance Pain and Spine Centers in Atlanta stated at the same Break the Red Tape Town Hall: "Most systems today are not (designed around clinical care). They are set to comply with the federal regulations with policy makers as opposed to actual physician care, and the concern is we're basically being turned into data miners in order to spend all of our time and effort on documentation as supposed to the key issue of medical decision-making." A simple, elegant solution is needed that helps the physician synthesize information and populate and document the chart when they see a patient on one screen, not on multiple tabs.

In current EMR systems numerous fields and data entry must occur on many different screens describing physician's findings. It takes a tremendous amount of time for data entry. A wrong click of a mouse can insert the wrong information. This is a difficult task for a busy physician and is often handed off to technicians to handle. A tool is desperately needed that will help a physician modify and review a summary of the patient's history on one screen. Further, a tool is desired that would act like a switchboard and enable auto-population of data, where information is documented in a patient's chart when the patient is evaluated. Most EMR systems separate each patient visit by tabs representing each date of service. Critical historical information related to patient testing, diagnosis, surgical histories, and complications, are often dispersed on multiple pages, without any visual markers to identify which page houses the information that a clinician needs to review. These cumbersome formats in the EMR cause significant delay in evaluating a patient and can lead to medical mistakes, as information is lost in the confusing formatting. An improved system would provide a snapshot of the critical medical data along with the billing and clinical guidelines related to the patients' treatment, which is unique to existing EMR formats. In combining these critical data into one comprehensive format, the improved system would increase efficiency and accuracy of the patient evaluation process.

There is also a significant need for a tool that allows a physician to identify medical problems through data visualization, where data is presented and displayed in an intuitive, easy to read manner and which enables the rapid identification of billing and collections. Since physicians are typically time constrained, the tool should allow the physician to access information while examining a patient in order to quickly identify potential billing and or reimbursement problems, as well as medical problems, so that issues can be resolved with the patient in real time. The tool would thus enable the physician to be involved with revenue cycle management, while simultaneously double-checking documentation and reducing medical errors.

A tool is needed to help a physician order diagnostic tests, procedures and medications while seeing on one screen all of the patient medical situation and having a bird's eye overview of what has been ordered/performed in the past and the results and costs. Physicians can get distracted as they are forced to multi-task. A tool is desperately needed that puts the pertinent information at the fingertips of the physician and that can be ordered directly from the screen including the patient's medical information. Yet, physicians often are blindfolded when it comes to knowing requirements of a particular patient's insurance that may require a patient to go to a particular location to obtain a diagnostic test or the cost of that test for the hospital, practice or patient. The same holds true in regards to ordering medication or a procedure. A tool is desired that will enable physicians to discuss options with the patient at the point of care and alter the plan if necessary.

Physicians also need a tool that will enable them to collect and evaluate their own clinical outcomes. This is important because pay for performance models are increasingly being implemented and compensation will be based on clinical and cost savings outcomes, rather than for services and procedures provided. At the heart of all pay for performance models is data analysis. Tinsley suggests "that tracking clinical data is essential in preparing for pay for performance models. Even if a small practice can participate in large scale, value-based model, it can surely implement measures that track and reward quality patient management. There is always more money behind knowing the clinical outcomes and data behind physicians' requests. A lot of physicians are saving payers money and not getting a piece of the pie." A tool is desperately needed that can provide the physician with a summary of results of their medical care. This will then enable them to improve care and to negotiate rates with insurance carriers, and will help them in establishing cost saving methods for delivering care and determining if the care they provide meets set standards.

A tool is desperately needed to help physicians document better and more quickly, identify errors and make suggestions by incorporating artificial intelligence and adaptive learning engine techniques into patient care to, for example, find discrepancies in payments, to alert physicians about inconsistent medical documentation or improper orders, to speed up the process of complying with regulations, or to alert the physician that a plan or order is inconsistent with a preferred practice plan for a patient.

A tool is also needed to alert the physician of important messages, letters and laboratory results that are not readily accessible in current EMRs, so they do not miss important findings and so that the physician may learn about important reports while they are examining a patient. In many cases, these reports may just have been received in the mail or by fax and a clerk just scans it and it becomes buried within the EMR without alerting the physician. Physicians rely on surrogates, like technicians or receptionists to document information on each visit such as a chief complaint. Important alerts that the staff wishes to send to a physician on the day the physician is examining the patient should be communicated on the same page so that everything relating to a patient can be seen at once and nothing important missed. Further, in some cases such alerts should be removed at the end of the day, because they are no longer relevant, thus reducing information clutter allowing the physician to focus on what is important and relevant.

A tool is further needed that allows a physician to make important notations, or that reminds the physician of changes or allows the physician to make a brief note that the physician understands and to help the physician rapidly guide decision making to care for the patient that is not just for chart documentation alone. The note should be able to be changed at any time if it is just for the physician to remind themselves of how to care for the patient. Insurance companies want complete, accurate and understandable notes to justify payment. Physicians are often forced to do meaningless documentation. A tool is needed just for the physician that allows shorthand reminders for the physician to best care for the patient without regard to what "the insurance company will police."

Most EMR systems are highly proprietary and do not communicate well with each other. This lack of interoperability presents a barrier to the transparent communication of health information. A tool is needed that can grab and summarize data from multiple sources and EMR systems. In particular, a tool is needed that will conform to new interoperability standards proposed and allow for a complete patient history, no matter what EMR system is used. The interface should also be flexible so that the information presented may be customized to the needs of the user.

Thus, there is a significant need for a data presentation tool that allows for the capture and presentation of large amounts of disparate data to a user such as a physician in a way that facilitates informed efficient decision-making. In the case of an EMR interface, the tool should allow physicians to rapidly detect potential problems, inconsistencies, medical changes, potential billing errors, review diagnostic tests and navigate through the entire patient chart history, and document within the chart with minimal navigation so that the data may be readily accessed at the point of patient care with minimal distraction from caring for the patient. The data command center described herein, is designed to address these and other needs in the art.

SUMMARY

The above and other needs in the art are addressed by a data command center visual display system and associated methods for displaying data on a display screen from multiple data sources and allowing navigation amongst the data without leaving the display screen of the visual display system. Numerous technical issues rooted in computer technology must be solved for the data to be presented to the visual display system so that the data may be displayed in the command center without leaving the display screen. For example, the visual display system must provide access to the requisite health information systems and third party support services whereby the data may be accessed, processed, and presented without unacceptable delay. Also, the display data must be collected and ordered to facilitate the various combinations of the data into respective display panels that may be navigated on the display screen. For example, it is desirable for the data to be configured in a task-based or specialty-specific display configuration for used by physicians, for example. To do this, various features in prior art systems needed to be acquired and combined in a new way to facilitate access to the features without having to navigate away from the display screen. For example, conventional EMR systems provide interfaces to third party prescription ordering systems but require the user to navigate to another system and away from the EMR interface. Accessing ordering screens without leaving the display screen becomes particularly difficult where the display screen space is limited, as is the case for many physicians who use portable display devices such as iPads™ and other mobile computers. The structural embodiments described herein address these technical issues to generate the command center visual display system embodiments described herein.

In exemplary embodiments, such a data command center visual display system includes a patient database that stores patient identification information, patient insurance information, and patient medical history information, a computer readable storage medium having stored thereon instructions thereon, and processor that executes the instructions to perform operations including creating a plurality of adjustable display panels configured to display predetermined combinations of the patient identification information, patient insurance information, and patient medical history information, and creating a patient flowsheet that integrates the patient medical history information into a table that presents the patient's medical history by visit to at least one physician with respective procedures or actions performed during each visit represented as first icons identifying the procedure or action performed and second icons enabling selection of a new procedure or action, where the first and second icons provide links to associated patient medical history information and ordering display panels that may be accessed without leaving the display screen. In response to selection of the second icon by a user of the visual display system, an ordering display panel is presented to the display screen in addition to the adjustable display panels and patient flowsheet. The desired procedures or actions may be ordered from the ordering display panel while relevant portions of the patient's medical history are still visible on the display screen. The scope of the claims also contemplates corresponding methods performed by the visual display system and users thereof.

In exemplary embodiments, the ordering display panel comprises an ePrescribing panel for ordering medication or a medical procedure ordering panel for ordering a medical procedure. By way of example, the medical procedure ordering panel for ordering a medical procedure may further provide a link to quality reporting panel that displays quality reporting metrics and/or peer data related to the procedure that is being ordered. All of such ordering display panels are configured in the context of the screen display to save real estate so that the ordering display screen may be displayed while still being able to view the medical history data, for example.

In other exemplary embodiments, the ordering display panel comprises an imaging order panel for ordering a medical image of the patient or a lab order panel for ordering a lab test of the patient. In still other embodiments, instructions are provided that when executed create an image icon in an adjustable display panel and/or the patient flowsheet that, when selected by the user of the visual data system, opens a display window for viewing of one or more images without leaving the display screen.

In other exemplary embodiments, the visual display system incorporates financial data with the patient medical history data into the display panels. Such a visual display system includes a patient database that stores patient identification information, patient insurance information, patient medical history information, and patient payment information, a computer readable storage medium having stored thereon instructions thereon, and a processor that executes the instructions to perform operations including creating a plurality of adjustable display panels configured to display predetermined combinations of the patient identification information, patient insurance information, patient medical history information, and patient payment information, and creating a patient flowsheet that integrates the patient medical history information and patient payment information into a table that presents the patient's medical history by visit to at least one physician with respective procedures or actions performed during each visit represented as first icons identifying the procedure or action performed and second icons indicating whether the procedure or action has been paid for in part or in full, the first and second icons providing links to associated patient medical history information and/or patient payment information. In response to selection by a user of the visual display system, the adjustable display panels and patient flowsheet are moved into a task-based or specialty-specific display configuration such that the patient identification information, patient insurance information, patient medical history information, and patient payment information may be accessed without leaving the display screen. The task-based or specialty-specific display configuration is then presented to the display screen. In exemplary embodiments, selection of the first icons or second icons open display windows to associated medical history data and/or financial data and overlay a portion of the display screen with the display windows whereby the associated medical history data and/or financial data may be viewed by the user of the visual display system while the adjustable display panels and the patient flowsheet are displayed in a background on the display screen. Throughout this description, it will be appreciated that all financial data in the system, including costs to patient, is compartmentalized such that no user may see financial details for users or organizations not authorized in accordance with applicable policies and law. Also, the scope of the claims also contemplates corresponding methods performed by the visual display system and users thereof.

The visual display system includes a number of features that enable accessing information on the display screen. For example, third icons are provided in the patient flowsheet or display panels that include links to compliance information about compliance with insurance guidelines and/or good clinical practice guidelines for a procedure or action associated with each third icon. In exemplary embodiments, the compliance information includes aggregated medical treatment guidelines and an overview outlining similarities and differences amongst different medical treatment guidelines making up the aggregated medical treatment guidelines. The aggregated medical treatment guidelines may include information related to recommended follow-up with the patient, information related to procedures permitted or prevented by the patient's insurance or contra-indications, and information relating to proper billing for the procedure or action associated with a third icon selected from the patient flowsheet or display panels. In exemplary embodiments, the visual display system provides access to a clinical decision support system that uses a rules engine and/or natural language processing to aggregate the medical treatment guidelines and to generate the overview outlining similarities and differences amongst different medical treatment guidelines making up the aggregated medical treatment guidelines. The clinical decision support system and/or natural language processing system may further compare medical data to notice patterns, errors and anomalies in different entries or notes, find discrepancies in payments, alert the user of the visual display system about inconsistent medical documentation or improper orders, speed up the process of complying with regulations, alert the user of the visual display system that a plan or order is inconsistent with a preferred practice plan for a patient, or warn the user of the visual display system that billing certain procedures might not be covered. The natural language processing system may also be accessed parse notes in the patient flowsheet or display panels for potential ICD10 codes or alternative diagnosis.

The visual display system also includes a display configuration that enables users of the visual display system to order medications, diagnostic tests, images, procedures, and the like directly from the patient flowsheet or display panel. For example, an icon or link in the patient flowsheet or display panel may include an ePrescribing panel for ordering medication or a medical procedure ordering panel for ordering a medical procedure. The medical procedure ordering panel may further include a link to a quality reporting panel that displays quality reporting metrics and/or peer data related to the procedure that is being ordered. In other embodiments, an icon or link in the patient flowsheet or display panel may include an imaging order panel for ordering a medical image of the patient or a lab order panel for ordering a lab test of the patient. In still other embodiments, an image icon is provided in an adjustable display panel and/or the patient flowsheet that, when selected by the user of the visual data system, opens a display window for viewing of one or more images without leaving the display screen. In other embodiments, an alert icon is provided in an adjustable display panel and/or the patient flowsheet that, when selected by the user of the visual data system, opens an alert message without leaving the display screen. In still other embodiments, one of the display panels may be configured to accept today's visit notes from the user of the visual display system in connection with a patient visit for storage for access with other data of the one display panel.

Other novel features in exemplary embodiments include a moveable note icon for association with context information in a corresponding one of the adjustable display panels and/or the patient flowsheet. The note icon moves with the context information as the context information is moved on the display screen. When the note icon is selected, the user of the visual display system may enter a note relating to the context information.

In still other embodiments, data input by the user of the visual display system may trigger auto-population of information in the adjustable display panels and patient flowsheet and auto-population of the patient's medical record in an electronic medical record system. In the exemplary embodiments, the auto-population occurs without the user of the video display system leaving the display screen.

In other embodiments, new clinical information for the patient is provided to a diagnosis evaluation algorithm for comparison of the new clinical information with previous corresponding clinical information for the patient to determine whether the new clinical information is indicative of an improvement or worsening of the patient's medical condition. The visual display system further generates diagnosis indicators providing a visual representation of an improvement of a medical problem, disease, or symptom, or a worsening of a medical problem, disease, or symptom as a result of taking a particular medication or undergoing a particular medical procedure and displays the diagnosis indicators in the adjustable display panels and/or the patient flowsheet.

Other embodiments of the visual display system allow for increased speed of data presentation by a local database that stores a subset of patient identification information, patient insurance information, patient medical history information, and patient payment information, where the subset includes the patient identification information, patient insurance information, patient medical history information, and patient payment information for patients having an appointment within a predetermined time window.

The visual display system in exemplary embodiments includes interfaces to an external health information system and third party service systems. In exemplary embodiments, the external health information system includes at least one of an electronic medical records system, a practice management system, a health information exchange, a picture archive and communications system, a clearing house/billing system, and a laboratory system. On the other hand, the third party service systems may include one or more of an ePrescribing system, an insurance verification/referral/preauthorization system, a system for establishing medical necessity by verifying that a procedure or medication is associated with a correct ICD10 code supporting its use, a clinical services pricing and location system, a claim status checking system, services in support of the National Correct Coding Initiative, services to proactively ensure claims are coded correctly to prevent issues in billing, claims compliance services that evaluate claims against National Coverage Determination (NCD) and Local Coverage Determination (LCD) guidelines as well as local insurance regulations to establish and document medical necessity, a natural language processing system, and artificial intelligence/cognitive systems that provide clinical decision support.

In exemplary embodiments, the patient identification information, patient insurance information, patient medical history information, and patient payment information is stored in the patient database in transactional tables that capture clinical and billing data and reporting tables where data is aggregated for a particular physician, practice, health system or other entity. Each table uses a surrogate primary key that is a unique value within the table used to identify a row that is not directly tied to data in that row. In the exemplary embodiments, XML code moves and stores different display panel and flowsheet views. The XML code further identifies a collection of panels and tabs, wherein within each panel is a panel ID that links the panel to a tab, the panel's position, and whether or not the panel is stacked with another panel. The XML code may also set up the display panels and patient flowsheet on the display screen by, for example, identifying a collection of columns and, for each column, a name of the column along with a data source. The display panels so configured are presented to the display screen for selection and display panel frames on the display screen are manipulated for receiving selected display panels.

In other exemplary embodiments, the patient flowsheet is organized around patient medical information corresponding to a particular disease state and/or procedures and/or insurance coverage and/or actions for treating the particular disease state.

The patient database may also be adapted to include patient medical history information from a plurality of medical providers whereby the patient flowsheet may be adapted to include medical history information from more than one medical provider in order to provide shared treatment of the patient in the patient flowsheet. In other embodiments, a summary table may be provided that illustrates everything the user of the visual display system has done for each patient in a particular time frame or for each patient having a particular disease state or a particular insurance in a particular time frame. The summary table may also include information from other medical providers who are providing shared treatment of the patient. If financial data, cost, charge, payment is on the summary table with the medical data, this data is compartmentalized such that no user may see financial details for users or organizations not authorized in accordance with applicable policies and law.

DESCRIPTION OF THE DRAWINGS

FIG. 2 illustrates a medical record window of the medical record system of FIG. 1 that is useful for deploying or launching embodiments of the invention in accordance with the first embodiment.

FIG. 4A illustrates a medical record dashboard in accordance with the first embodiment of the invention.

FIG. 4C illustrates a portion of the medical record dashboard of FIG. 4A in accordance with the first embodiment of the invention.

FIG. 4D illustrates a portion of the medical record dashboard of FIG. 4A in accordance with the first embodiment of the invention.

FIG. 5A depicts a medical summary update process in accordance with the first embodiment of the invention.

FIG. 5B illustrates a notes update process in accordance with the first embodiment of the invention.

FIG. 6 illustrates a user action record access process in accordance with the first embodiment of the invention.

FIG. 8 illustrates a medical record and diagnosis update process in accordance with the first embodiment of the invention.

FIG. 10A illustrates a medical record update marker process in accordance with the first embodiment of the invention.

FIG. 10B illustrates a medical record update marker process in accordance with the first embodiment of the invention.

FIG. 11 illustrates a portion of the medical record dashboard of FIG. 4A including a scrolled display in accordance with the first embodiment of the invention.

FIG. 12A illustrates a portion of the medical record dashboard for a glaucoma practice in accordance with the first embodiment of the invention.

FIG. 12D illustrates a portion of a medical record dashboard for display as a function of patients seen by a gastrointestinal physician during a certain period of time with CPT codes performed on patients on a particular day in accordance with the first embodiment of the invention.

FIG. 12E illustrates a portion of a medical record dashboard for display as a function of patients with a specific disease ICD in accordance with the first embodiment of the invention such that many patients may be compared at the same time, which can be useful for clinical research or for tracking clinical outcomes.

FIG. 13A illustrates a medical record dashboard in accordance with the first embodiment of the invention.

FIG. 13B illustrates a ledger window accessible from the medical record dashboard of FIG. 13A in accordance with the first embodiment of the invention.

FIG. 20 illustrates the Patient Information panel for displaying high level information about the patient in accordance with the second embodiment of the invention.

FIG. 21 illustrates the Patient Insurance panel for displaying the patient's insurance information in accordance with the second embodiment of the invention.

FIG. 23 illustrates the Problems tab displaying a patient's problem list as imported from the EMR in accordance with the second embodiment of the invention.

FIG. 25 illustrates the Surgeries tab that displays information about the patient's surgeries in accordance with the second embodiment of the invention.

FIG. 25A illustrates an exemplary embodiment of a Data Command Center for use with an EMR system customized for shared care between an optometrist and an ophthalmologist.

FIG. 25B illustrates a summary of symptoms selected from the Data Command Center of FIG. 25A.

FIG. 25C illustrates a summary of exam findings selected from the Data Command Center of FIG. 25A.

FIG. 25D illustrates the billing summaries selected from the Data Command Center of FIG. 25A.

FIG. 26 illustrates the Allergies tab that displays a patient's allergy information in accordance with the second embodiment of the invention.

FIG. 27 illustrates the Medications tab that displays medication information in accordance with the second embodiment of the invention.

FIG. 28 illustrates the Labs tab that displays lab information in accordance with the second embodiment of the invention.

FIG. 29A illustrates the Physician tab that displays information about the patient's other physicians and provides a listing of letters sent to the patient's other physicians in accordance with the second embodiment of the invention.

FIG. 30 illustrates the Letters/Document tab that displays letters and documents transferred from the EMR system in accordance with the second embodiment of the invention.

FIG. 32A illustrates an exemplary embodiment of the Retina Flowsheet illustrated in FIG. 15 in accordance with the second embodiment of the invention.

FIG. 33B illustrates an example popup display window illustrating abnormal test results over time.

FIG. 36 presents a flowsheet for diabetes in accordance with the second embodiment of the invention.

FIG. 37 illustrates an exemplary Financial Flowsheet in accordance with the second embodiment of the invention.

FIG. 45 illustrates the Medication Alternatives (Suggested) sub panel of the six sub panels illustrated in FIG. 44.

FIG. 54 illustrates the Locations/Costs sub panel of the sub panels illustrated in FIG. 51.

FIG. 75 illustrates the ViewLayout table that stores the panels and tabs that make up the view and how they are positioned in accordance with the invention.

FIG. 76 illustrates the Panel table that stores references to the data displayed within a panel in accordance with the invention.

FIG. 77 illustrates the view XML that provides means for moving and storing the different display panel and flowsheet views in exemplary embodiments of the invention.

FIG. 78 illustrates the panel XML that provides means for setting up the display panels and flowsheets in exemplary embodiments of the invention.

DETAILED DESCRIPTION

Figure 1:
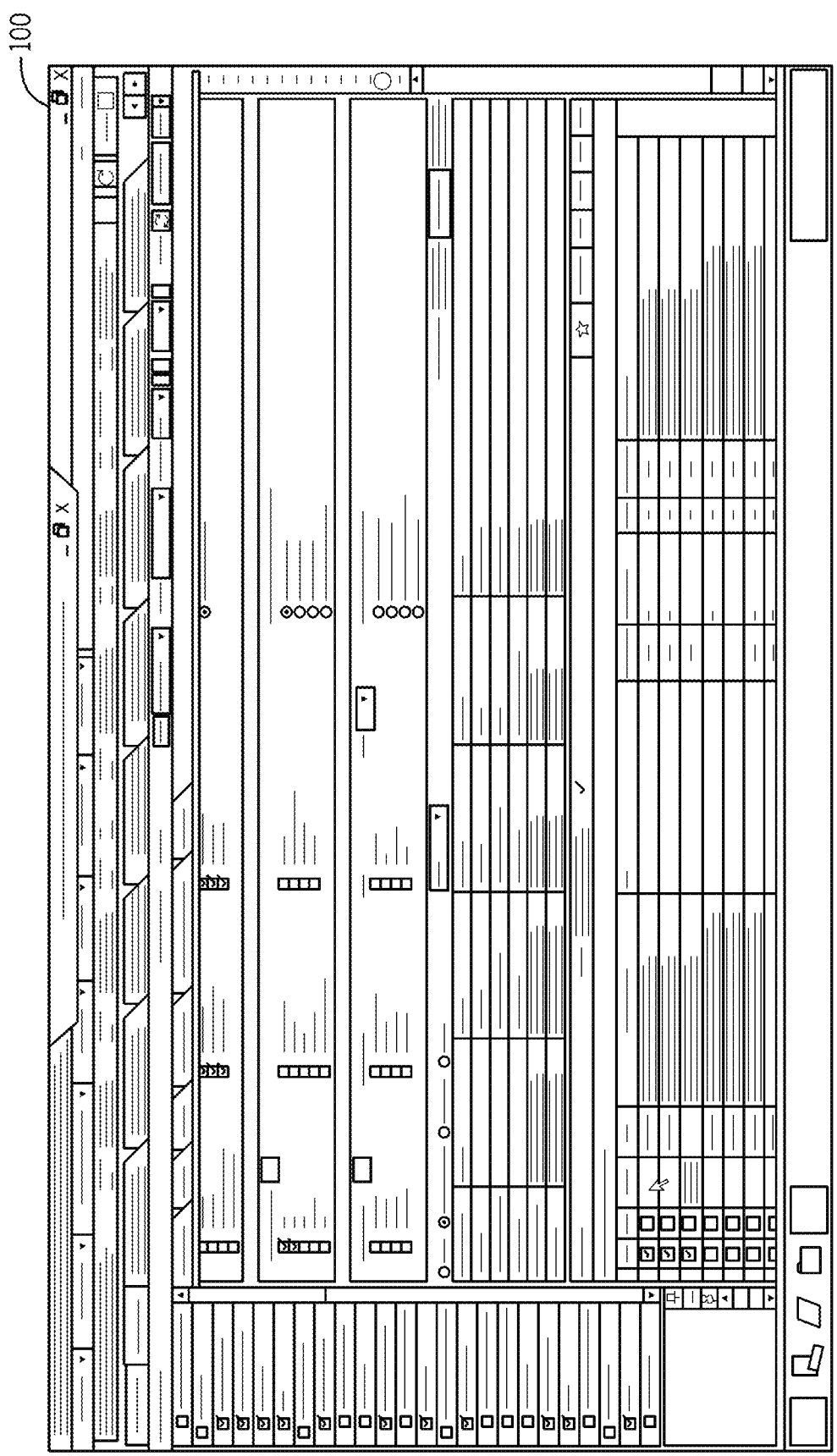
FIG. 1 illustrates an exemplary embodiment of a Data Command Center for use with an EMR system customized for a Retina Ophthalmology practice in accordance with a first embodiment of the invention.

Exemplary embodiments of a Data Command Center in accordance with the invention are described below with respect to FIGS. 1-79. Those skilled in the art will appreciate that the illustrated embodiments described are for exemplary purposes only and are not limited to the specific process and interfaces described.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. For example, though the invention is described for use with an EMR system in an exemplary embodiment, those skilled in the art will appreciate that the systems and methods described herein may be used for numerous other applications where much data is presented to the viewer, including, for example, interfaces to stock tracking and purchasing software, industrial monitoring systems, and the like. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

Some embodiments herein provide one or more technological solutions in the realm of one or more of data assimilation and recordation with real-time communications across a network, computers, or the Internet to improve the performance of, and technology of, data assimilation and recordation, communication and messaging software, systems and servers by providing automated functionality that effectively and more efficiently manages data assimilation and recordation and related automatic triggering of new computing events in the network based on the data gathered during an actual event in ways that cannot effectively be done, or done at all, manually. For example, some embodiments herein provide one or more technological solutions to processing a user interface including a single page quick review "summary sheet" that is rendered by pulling key data points from EMR interactive notes allowing a physician to provide the best possible care. Further, the improved assimilation and recordation, communication and messaging software, and systems and servers enable centralized collection and review of information and two-way auto-population of the user interface from billing or other parts of local and remote electronic medical record systems that can reduce human error, and can cut down on medical errors. This technology can allow a physician or other healthcare worker to quickly access and review critical medical and procedure data using consistent data visualization field formats. This technology can automatically summarize each patient visit on one line on one page that can be seen and through pattern recognition, and rapidly visualized. This technology can allow a physician to instantly evaluate a patient's situation, and catch potential billing errors.

Some embodiments herein provide one or more technological solutions to providing a user interface that functions as a "command center" for the physician's decision-making. Using data collection, assimilation and recordation with real-time communications across a network, computers, or the Internet, some embodiments of the invention described herein provide an information hub where the lifetime of a patient's medical and surgical history, diagnostic tests results, and prescribed medications can be accessed. Further, the user interface can provide alerts regarding the reasons for the patient's visit, and can include messages from staff that can be programmed to self-delete and not be viewable after it has been removed.

Some embodiments of the invention provide a user interface that can function as an epicenter for physician care allowing medical synthesis of the problems confronting the patient. To make the best decisions, the physician needs to understand the entire picture of a patient's life, while being able to hone in on any detail. Some embodiments of the invention can function as an EMR similar to how a ganglion cell is to the brain or the spinal cord to the body. Some embodiments of the invention provide the ability for the findings of a physician during "today's visit" to be rapidly entered into the relevant fields/tabs/screens within an EMR, streamlining data entry required for documentation and interpretation. Some embodiments of the invention can provide a starting point for caring for a patient, where new orders can be placed or messages can be sent. Using a summary review table, the physician can navigate and interact with the entire EMR for the patient without the need to access multiple screens, and can be interoperable to enable extraction of pertinent information from other sources.

Medical sub-specialization, information overload, and increased complexity of reimbursements for service all conspire to remove the physician from caring for a patient. Some embodiments of the invention can save the physician time that can be used for time with the patient rather than time used with a computer screen and a mouse. Finally, presented here is the new tool that makes the computer age successfully replace the paper age in properly caring for patients. Some embodiments of the invention can allow the physician and hospitals to comply with insurance companies and the government which demand that they comply and be responsible for their billing. Some embodiments of the invention can help transform the mindset of a physician from being a medical provider without any knowledge of business or finance, to a physician able to participate in revenue cycle management. Some embodiments of the invention can, therefore, insert the physician back into being the quarterback of the healthcare system. Some embodiments of the invention can give the physician the time to be a healer while at the same time rapidly synthesizing information that can cut costs and improve outcome quality. In an ever-expanding interoperable complex world, some embodiments of the invention can function as a physician's genie and magic carpet that seamlessly transports the physician though the maze of data entry and provides the overview needed for medical synthesis.

Some computerized or electronic medical record ("EMR") systems provide computerized interfaces between medical professionals and staff and one or more medical records databases. Some embodiments of the invention disclosed herein include a command center visual display system and method that can be linked to or otherwise accessed from a conventional EMR system. In some other embodiments, any conventional EMR system can be coupled or linked with the command center visual display system and method described herein.

Some embodiments of the command center visual display system and method can be interfaced with a variety of systems including but not limited to EMRs, Health Information Exchanges (HIEs), Billing Clearinghouses, Insurance Companies, Picture Archiving and Communication Systems (PACS) as well as third party services to provide information and services used in data presentation.

Some embodiments of the invention include a command center visual display system and method that can be included as an add-on software package to a conventional medical record system. In some embodiments, tasks associated with an add-on software program can be seamlessly linked and/or incorporated into one or more core software tasks or modules of the conventional medical record system. In some embodiments, a message-based interface can be used to connect and transmit data between one or more software modules of the command center visual display system and method, and one or more conventional medical records systems and/or one or more patient records and/or databases comprising patient records. In some embodiments, application programming interfaces (hereinafter "APIs") can be used to connect and transmit data between one or more software modules of the command center visual display system and method, and one or more conventional medical records systems and/or one or more patient records and/or databases comprising patient records. For example, in some embodiments of the invention, the command center visual display system and method can be configured to receive patient data from a health information exchange or a medical provider. In some further embodiments, the command center visual display system and method can auto-populate various data fields (including information fields, tables, or windows) from a variety of sources. The sources can include electronic, physical (paper records), and human input. In some embodiments, an electronic dataflow can be established between the command center visual display system and method and one or more computer systems of servers that comprise patient information (e.g., electronic medical records). In some embodiments, the dataflow comprises a one-way flow from the source to the command center visual display system and method. In some other embodiments, the dataflow comprises a two-way flow from the source to the command center visual display system and method, and from the command center visual display system and method to the source. This information can be any medical diagnosis information prepared by a medical practitioner, any medical procedures or services provided to the patient, including procedures or services by claims made, or billings or payments including billing signed off by a physician as detailed above, billings, payments, or other information from anywhere in the EMR chart not limited to treatment summaries, and/or diagnosis summaries, and/or patient feedback summaries, and/or other physician summaries, patient outcome summaries, and so on. For example, in some embodiments, the command center visual display system and method discussed below can display and/or auto-populate with at least one of a patient's prior medical procedures, diagnostic tests, surgeries, current medications, current illnesses, treated illnesses, and so on.

In some further embodiments, new software features of the command center visual display system and method can be added to an existing application without modifying the existing code of the existing application. In some other embodiments, the command center visual display system and method can function as an independent application, not linked, overlaid, or otherwise interfaced with any conventional medical record system.

First Embodiment of Data Command Center

Figure 2:
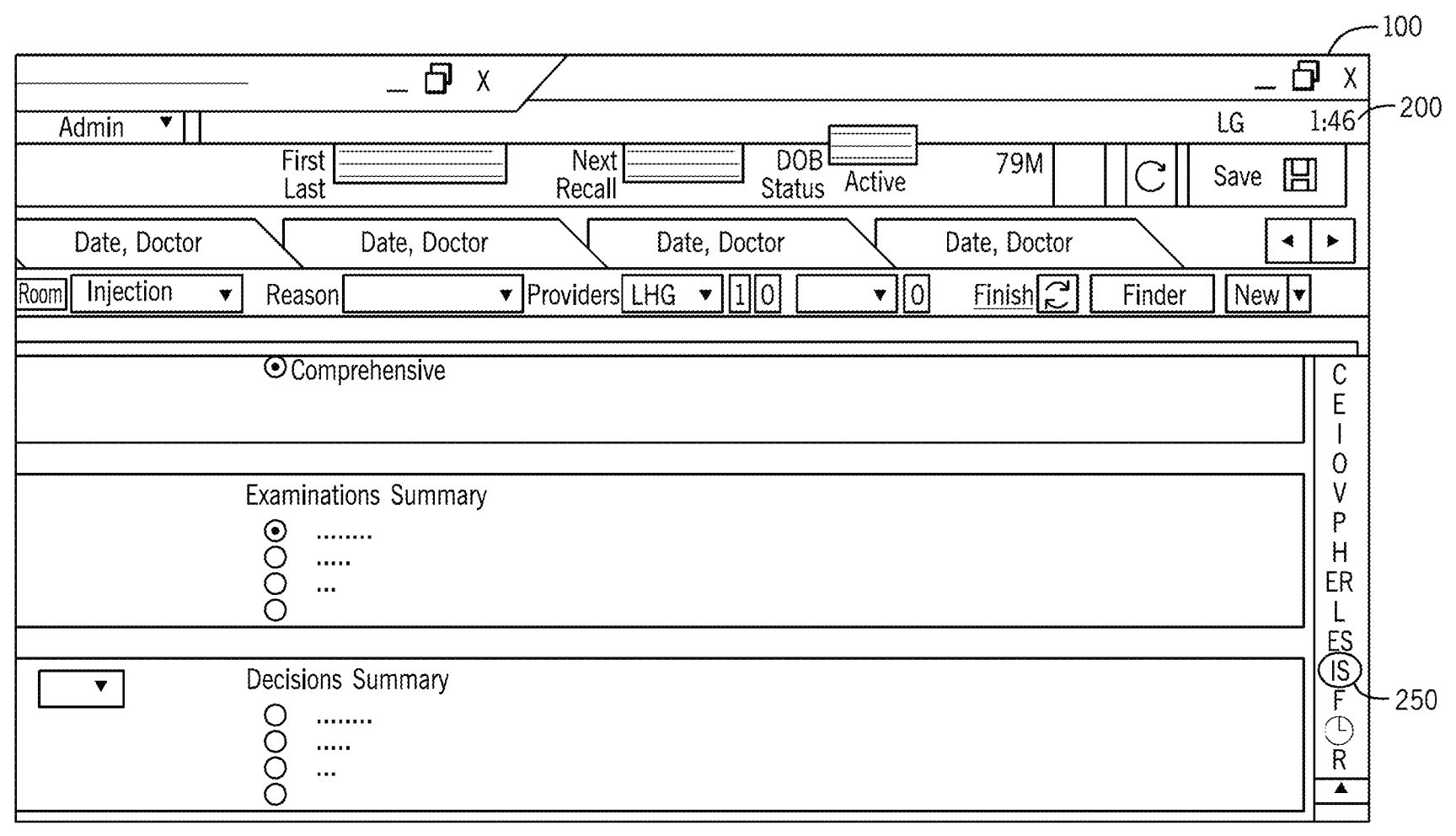

FIG. 1 illustrates an embodiment of a Data Command Center (CC) implemented as a data interface to a medical record system 100 in accordance with a first set of embodiments of the invention. In accordance with the first set of embodiments, a user, such a medical practitioner, can utilize a conventional medical record system to launch or enter a command center visual display system that can display information dashboards, tables, charts, windows, as tailored by a user. FIG. 2 illustrates a medical record window 200 of the medical record system 100 in accordance with a first set embodiments of the invention described herein. In some embodiments, the medical record window 200 of a conventional medical record system can include a command center visual display system launch icon 250 to facilitate access to and/or launch of one or more embodiments of the command center visual display system and method. It will be appreciated that the "icons" used herein are graphical elements with links to associated dynamic or static data in the same system or a remote system. Of course, the icons may simply be links. For the ease of description, whenever the text refers to "icons" such "icons" may be graphical elements with links or simply links to associated dynamic or static data.

In some embodiments, a user can use the command center visual display system launch icon 250 or other displayed icon or display element to access or launch the command center visual display system and method described herein. In some further embodiments, the launch icon 250 can be used to temporarily halt the medical record system 100 and access or launch the command center visual display system and method. In some other embodiments, the launch icon 250 can be used to access or launch the command center visual display system and method while the medical record system 100 continues to run in parallel, continues to run in a background mode, and/or is switched to an idle mode.

Figure 3:
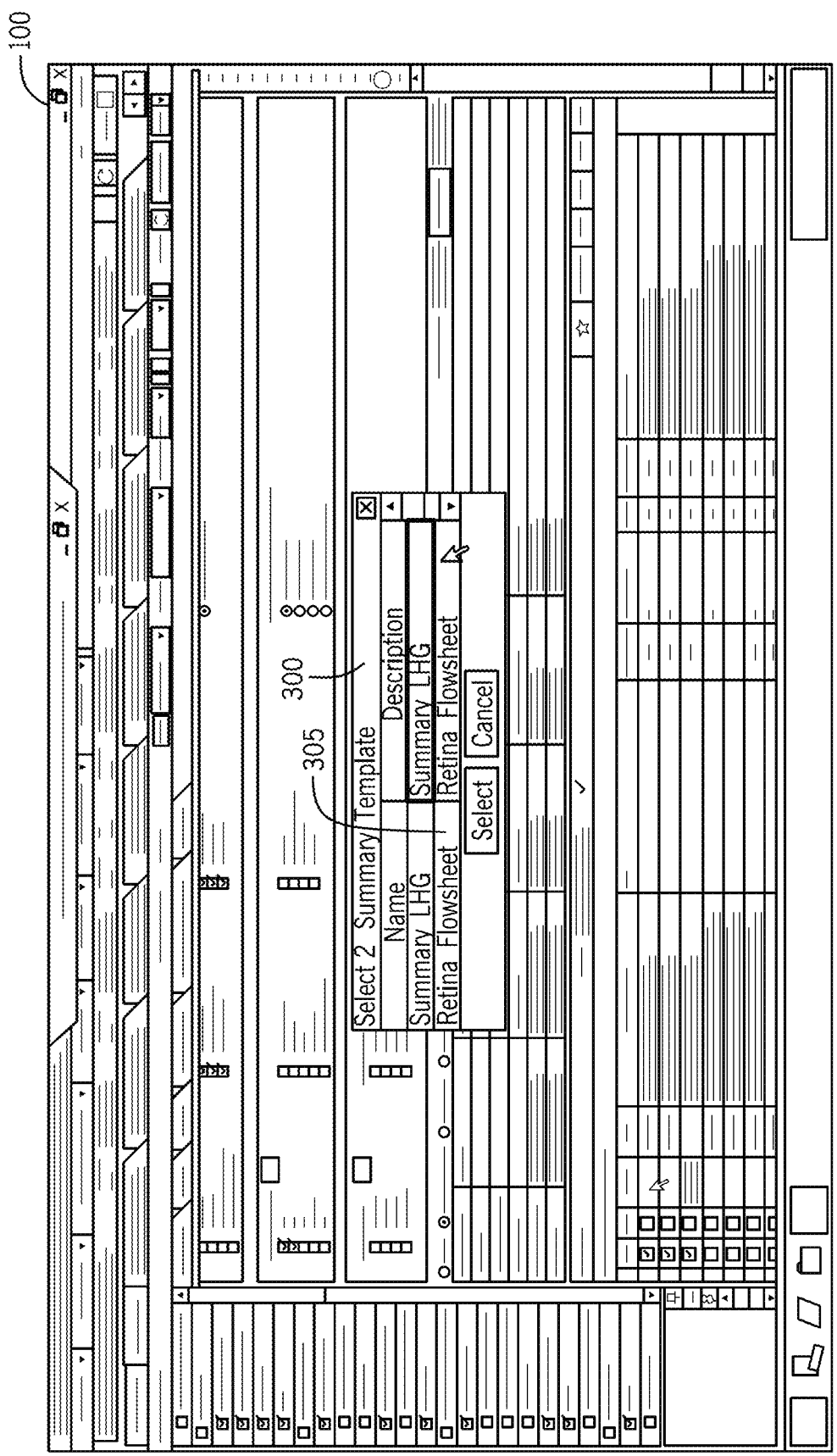
FIG. 3 illustrates a medical record dashboard selection window useful for selecting and launching embodiments of the invention in accordance with the first embodiment.

Referring to FIG. 3, illustrating a medical record dashboard selection window useful for selecting and launching embodiments of the invention described herein. In some embodiments, after a user selects or clicks the launch icon 250, a medical record dashboard selection window 300 can be displayed. The medical record dashboard selection window 300 can include one or more selectable medical record dashboards from which a user can select to access at least one medical record dashboard. For example, in one non-limiting example embodiment, the user can select "Retina Flowsheet" 305 to access and/or launch a medical record dashboard including a retina flowsheet. In some further embodiments, the at least one medical record dashboard can include any number of selectable medical records for any medical condition, and/or any medical diagnosis, and/or any medical treatment.

Figure 4A:
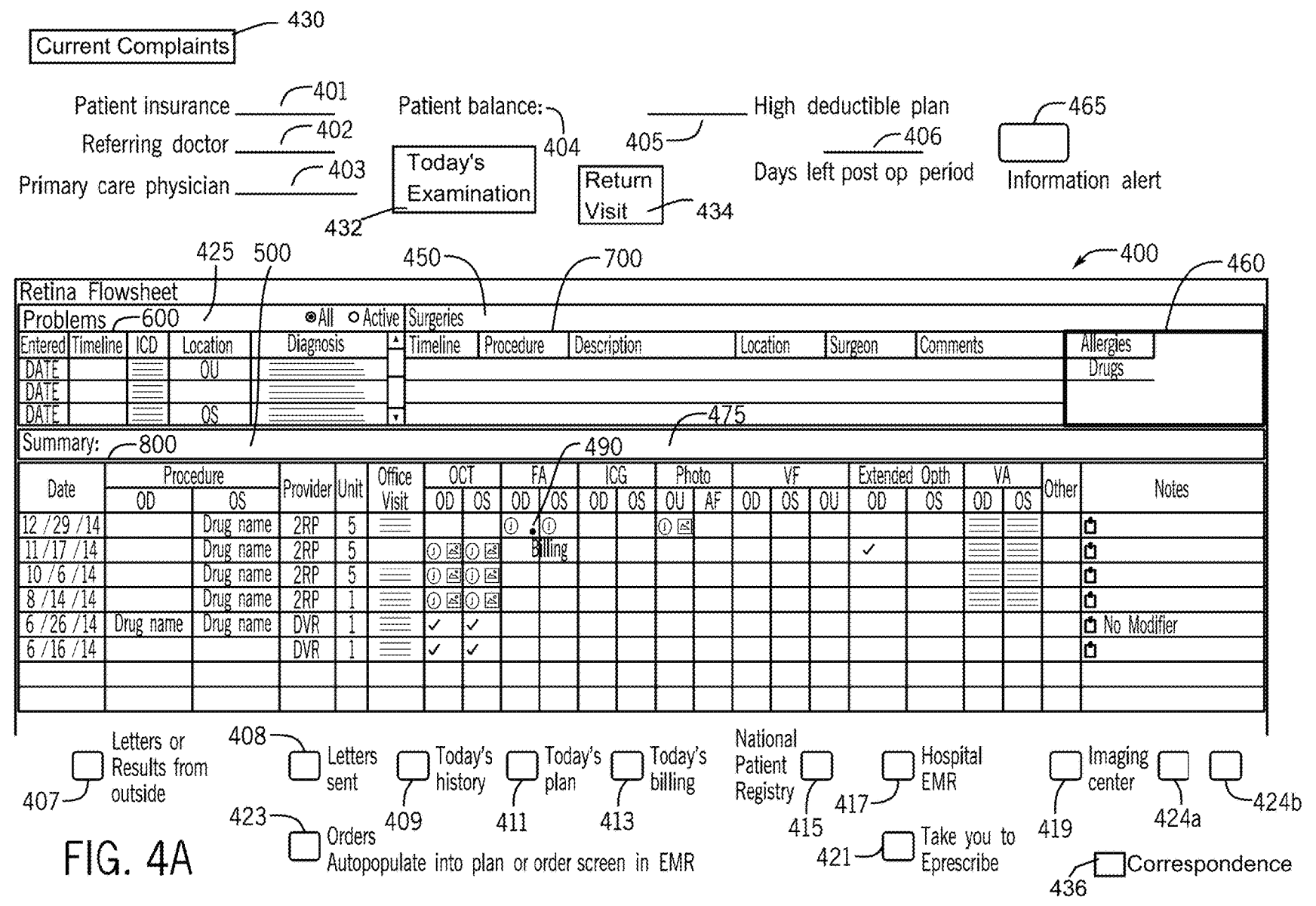

Some embodiments of the invention comprise one or more displayed tables and/or dashboards that function as a Data Command Center. The Data Command Center can enable a user to work with a single display that can be configured as a central medical record entry, access, update, recording, and archival site. For example, FIG. 4A illustrates a medical record dashboard 400 in accordance with a first embodiment of the invention. In some embodiments, the medical record dashboard 400 can be displayed by the user following the user's selection of at least one medical record dashboard from the medical record dashboard selection window 300. In some embodiments, the medical record dashboard 400 can display data from one or more medical records, and/or track medical procedures and services based on claims made or billing signed off by a physician for one or more delivered medical procedures or services. Some embodiments of the invention include a command center visual display system and method that can dynamically link to various external databases comprising patient information that can be displayed in the medical record dashboard 400. For example, in some embodiments, the command center visual display system and method can function as a portal to patient information prepared by the user or patient information from other sources. Further, in some embodiments of the invention, the medical record dashboard 400 can be auto-populated as a function of claims made or billing signed off by a physician. In this instance, any data displayed within the medical record dashboard 400 is derived from one or more claim records that have been billed for one or more procedures or services have previously been provided to the patient. In some other embodiments, auto-population can be enabled in both directions interacting as a switchboard between the entire EMR and the medical record dashboard 400 along with what is added to any window, sub-window, column or entry in the medical record dashboard 400 being automatically added to the appropriate part of the chart for documentation before finalizing the encounter.

In some embodiments, the medical record dashboard 400 can display information related to any medical procedures or services in relation to care of a patient. For example, in some embodiments, the medical record dashboard 400 can display information related to medical procedures or services in relation to retinal eye medical care of a patient. In some embodiments, the medical record dashboard 400 can display information including components where there is a summary of the patient's problem list that a user can input patient information and constantly update and change. Further, this information can be auto-populated with the touch of a button into a designated location such as the current plan documenting the patient's current visit (thus aiding documentation for the current visit). Further, whatever is important for a user to input into the day's visits for documentation can be initially inputted in the table, and then permanently into the day's patient visits. Further, the summary section of the medical record dashboard 400 can be constantly fluid, and can be changed at every visit rather than being written to an unchangeable document or file (e.g., such as a PDF). Further, any patient data that is inputted, received, analyzed, or created can be auto-populated into any portion of the dashboard 400, and/or can form a dataflow out of the medical record dashboard 400 to another electronic system or server, or another user, observer, or other $3^{rd}$ party.

In some embodiments, the medical record dashboard 400 can display various windows and sub-windows based on a user preference and/or current or previous user interaction with the medical record dashboard 400. For example, in some embodiments, the medical record dashboard 400 can display a problems window 425 and/or a surgeries window 450 where information related to a patient's medical problems and surgeries can be displayed in information columns 600, 700 respectively. Further, in some embodiments, patient information related to allergies and drugs can be displayed within the allergies/drug section 460. This information can be auto-populated from a variety of sources, or inputted by a user.

In some embodiments, the medical record dashboard 400 can include a summary window 475 enabling a user to view and edit summary information related to the patient, any details of care provided to the patient, and/or and any medical diagnosis information prepared by a medical practitioner. Further, in some embodiments, the medical record dashboard 400 can also display detailed information related to any medical procedures or services provided to the patient, including procedures or services that are auto-populated by claims made, or billings or payments including billing signed off by a physician as detailed above. For example, in some embodiments, the medical record dashboard 400 can display a command center visual display window 500 including information columns 800 that can be auto-populated by claims made or billings signed off by a physician. The auto-population can include billings, payments, or other information from anywhere in the EMR chart. For example in some embodiments, the information that is auto-populated can include treatment summaries, and/or diagnosis summaries, and/or patient feedback summaries, and/or other physician summaries, and so on. For example, in some embodiments, the command center visual display system and method can display and/or auto-populate at least one field, table, or window with at least one of a patient's prior medical procedures, diagnostic tests, surgeries, current medications, current illnesses, treated illnesses, and so on. The command center visual display system and method can auto-populate various data fields via an electronic dataflow established between the command center visual display system and method and one or more computer systems of servers that comprise patient information (e.g., such as electronic medical records). The dataflow can comprise a two-way flow from the source of patient data to the command center visual display system and method, and from the command center visual display system and method to the source. In some embodiments of the invention, this information can be any medical diagnosis information, any medical procedures or services provided to the patient, procedures or services by claims made, or billings or payments including billing signed off by a physician as detailed earlier, any information from anywhere in the EMR chart including treatment summaries, and/or diagnosis summaries, the patient's prior medical procedures, diagnostic tests, surgeries, current medications, current illnesses, treated illnesses, and/or patient feedback summaries, and/or other physician summaries, patient outcome summaries, treatment summaries, and/or diagnosis summaries, and/or patient feedback summaries, and/or other physician summaries or treatments. Further, in some embodiments, the information that is auto-populated can include patient outcome summaries. For example, in some embodiments, the command center visual display system and method process a plurality of patient outcomes and display an analysis of patient outcomes based at least in part on patient information from treatment summaries, and/or diagnosis summaries, and/or patient feedback summaries, and/or other physician summaries or treatments. In some embodiments, the patient outcomes can include or comprise physician quality reporting system (PQRS) quality measures. In some embodiments, calculated or reported patient outcomes can include or comprise at least one PQRS measures code.

The medical record dashboard 400 can include miscellaneous information identifying the patient, information related to the patient's insurance plan, physicians and referring physicians, and the patient's current balance. Other information can relate to the patient's prior visit, prior diagnosis or procedure and any important information relevant to the next visit. Additional information can relate to the current visit, including history of illness and chief or current medical complaint, billing information, and retrievable medical information including pharmacy information. For example, in some embodiments, the medical record dashboard 400 can include a patient insurance entry 401, referring physician entry 402, and primary care physician entry 403. The medical record dashboard 400 can also include patient balance entry 404, and a high deductible plan entry 405. Important patient information related to a pending or current visit can include a "days left post op period" entry 406 and/or an information alert 465. In some embodiments, the information alert 465 can be auto-populated based on other information or entries in the medical record dashboard 400. In other embodiments, the information alert 465 can be set by any user to alert the user or other user of information relevant to the patient. In some embodiments, the information alert 465 can comprise a daily technician update, including information to medical information such as blood pressure, or whether the patient is pregnant, or any other urgent information with which a member of a health care team can alert another member. Further, this information can become permanent or can be deleted from the dashboard 400, and from any record or table accessible from the dashboard 400, including any medical record. Further, this information can serve as or be configured as a "sticky note" that can be removed from any of the above-mentioned records. For example, the "sticky note" can be an electronic sticky note riding on the dashboard or any record accessible from the dashboard. Further, the dashboard 400 can provide improvement as described where test interpretations and evaluation of patients, once documented and billed, usually become date stamped, and cannot be easily amended without applying a new date of amendment. In some embodiments, the command center visual display system and method can improve and follow care that not necessarily be used as part of a particular day's medical record. Therefore, months or years apart, physicians can add notes into the table when new findings, discoveries, or realizations warrant it without feeling encumbered that they are "changing past medical record" and a disclosure of such can be at the bottom of the dashboard 400. Allowing physicians and technicians to add and change notes within this dashboard 400 (rather than changing the patients EMR chart) can enable them to summarize critically important health/history/treatment data, which can then be used as a faster point of reference while examining the patient. Notes that sit on the table can flag or alert the physician to an important medical change, and can be used as an additional form of communication to strengthen lines of communication between technicians/clinic staff and physicians to better ensure that the physician is quickly directed to important medical information.

In some other embodiments, a daily technician update can be accessed or otherwise made visible to the user in at least one other portion of the dashboard 400. In some embodiments, the information alert 465 can be displayed in a specific color and/or with a specific graphic and/or animation. For example, in some embodiments, the information alert 465 can comprise a flashing red animation. To protect the physician during an audit, a statement on the dashboard 400 can be added that "notes on this table" are not necessarily added at the time listed as the date and not for documentation in a medical record, but as a rapid reminder medical decision making and cliff note reference tool. As another example, if this patient's records were ever sent to another physician or insurance company or were audited, this is critical information a physician is often not privy to and an icon on the table may alert the physician of this fact. By selecting this or another icon, the history of this audit or records release request or other occurrence can be seen. So, if an insurance company is requesting a medical necessity report or other information that is needed by a billing office or anyone else, the physician may be informed on the table so that the physician can instantly decide what is needed. A report can be dictated or chart information transmitted within or outside the practice in an expedited manner. Often just an office worker decides what to send in reply to an outside entity request. By using this tool at the point of care when a patient is being examined, the patient may be consulted by the physician to correct any information that needs clarification, and decisions and reports can most accurately be made. Additionally, physicians remotely can be alerted about requests and one summary table rapidly allows for more rapid and accurate communication.

Some embodiments include an alert or access to one or more letters or results from outside (icon 407) systems or third parties. Some further embodiments include an alert or access to letters sent 408. The letters can be written, typed, and/or one or more dictated letters from the user and/or another medical provider. Some embodiments include an entry or access to the current day's history, the current day's plan, and/or to the current day's billing. For example, some embodiments include a "Today's history" button or icon 409, a "Today's plan" button or icon 411, and a "Todays billing" button or icon 413. In some further embodiments, a correspondence button or icon 436 can be used to view, access, enter, and/or auto-populate correspondence related to a patient's care. This can include any medical record and/or any correspondence generated while the patient is under care by the user and/or any other physician or medical practitioner, medical services provider, and/or medical insurance company.

In some embodiments, the medical record dashboard 400 can display a summary of the patient's problem list that a user can input patient information and constantly update and change. For example, some embodiments include the ability to enter or access current complaints of the patient (button 430). In some embodiments, a user can add or update one or more entries of the patient's chief or current complaints, and/or a user can view one or more entries of the patient's chief or current complaints using the button 430. In some embodiments, if a user activates (e.g., by clicking using a cursor) the button 430, information related to the patient's current medical problems or complaints can be shown and/or displayed and/or updated by any user or user's assistant. In some embodiments, the information can be auto-populated into the medical record dashboard 400 and/or to any other accessible window displayed by the command center visual display system and method.

In some embodiments, the medical record dashboard 400 can display a today's examination access button 432 that a user can use to view and/or input patient information, patient examination results, tests, notes, or any information relevant to the medical care of the patient. In some embodiments, a user can add or update one or more entries of the today's examination, and/or a user can view one or more entries of the examination. In some embodiments, if a user activates (e.g., by clicking using a cursor) the button 432, information related to the patient's examination including medical problems or complaints patient information, patient examination results, tests, notes, etc., can be shown and/or displayed and/or updated by any user or user's assistant. In some embodiments, the information can be auto-populated into the medical record dashboard 400 and/or to any other accessible window displayed by the command center visual display system and method. In some embodiments, any stored or displayed patient's examination can be cleared from the medical record dashboard 400 following some time period once the patient visit is complete. In some embodiments, the medical record dashboard 400 can remove display or access to a previous patient's examination details once the patient visit has ended. In some other embodiments, the medical record dashboard 400 can remove display or access to a previous patient's examination details later in the day of the patient's visit, or before the following day, or at any time selectable by the user or user's assistant. In some embodiments, the information can be auto-populated into the medical record dashboard 400 and/or to any other accessible window displayed by the command center visual display system and method. In some embodiments, the information can be auto-populated into any EMR system for recordation into one or more EMR's of the patient. In some embodiments of the invention, for any auto-populated information that includes technical information without any associated professional interpretation, the command center visual display system and method can provide a visual and/or audible alert to enable a user to provide an update for auto-population to an EMR system.

In some embodiments, the medical record dashboard 400 can also include at least one link to information from external databases, providers, hospitals (e.g., such as a discharge summary), clinics and/or testing laboratories, etc., (e.g., where the information can include the overall diagnostic imaging center of the practice for certain pieces of equipment and into the machine to actually see all of the study). In the latter example, the medical record dashboard 400 can receive information from at least one database and/or server and/or controller coupled to receive data from the diagnostic equipment. Further, some embodiments may include an entry or access to the National Patient Registry or other kind of registry (link 415), hospital EMR (link 417), imaging center 419 (including accessing software imaging and diagnostic management systems to handle many diagnostic images and studies or specific diagnostic equipment), and ePrescribe link 421.

In some embodiments, the user can access at least one ePrescribe database, server, and/or website directly from the dashboard 400 using the ePrescribe link 421. Further, in some embodiments, orders can be auto-populated into the plan or order screen of EMR ("Orders" link 423). For example, in some embodiments, during or after completion of a patient examination, any medical service, medical test or diagnostic, or other medical service can be auto-populated into an order section of the chart. In some embodiments, any recommendation for a return visit can be viewed, accessed, and/or auto-populated using the return visit button or icon 434. For example, in some embodiments, the recommendations can be any advised next steps in the patient's care, any diagnosis, prescriptions, tests, etc. In some embodiments, the aforementioned "Today's plan" button or icon 411 can be used to view, access, and/or auto-populate details and systems including for a day's activities for the patient examination.

In some embodiments, a single button or icon entitled "Imaging Center" (button 424a) can take a user (e.g., a physician) instantly or immediately to the piece or pieces of diagnostic equipment that were used that or another day for testing so the physician can now measure and enter the findings. This can be internal in the user's practice so that any diagnostic equipment can be accessed. In some embodiments, the same or another button can provide a link in the major table to an image or diagnostic management software system. In this way, some embodiments can handle the tremendous amount of diagnostic equipment and images, and unlike prior art tables that just provide access to a PDF, these embodiments provide access to not just one single piece of diagnostic equipment but all of them and the complete study, not just a "slice", can be evaluated and comparison of changes over time made.

Once entered, the data can be auto-populated into the dashboard 400 (e.g., such as a retina flowsheet) under other column 1200 (FIG. 4C), where each clinical research study would have other factors followed such as central macular thickness ("CMT"), or ischemic index ("ISI"). Further, the second button (button 424*b*) can take the user to either the company sponsoring the clinical research website (sometimes a pharmaceutical company and other times a company that invented a device). The clinical researcher could immediately go to this website and input any data that was obtained from that visit from the diagnostic equipment button 424*a*, and/or to a research spreadsheet where the user (e.g., a clinical researcher in this example embodiments) can input the data, or where the data can be auto-populated (e.g., from the other column 1200 or into the other column 1200).

Figure 4B:
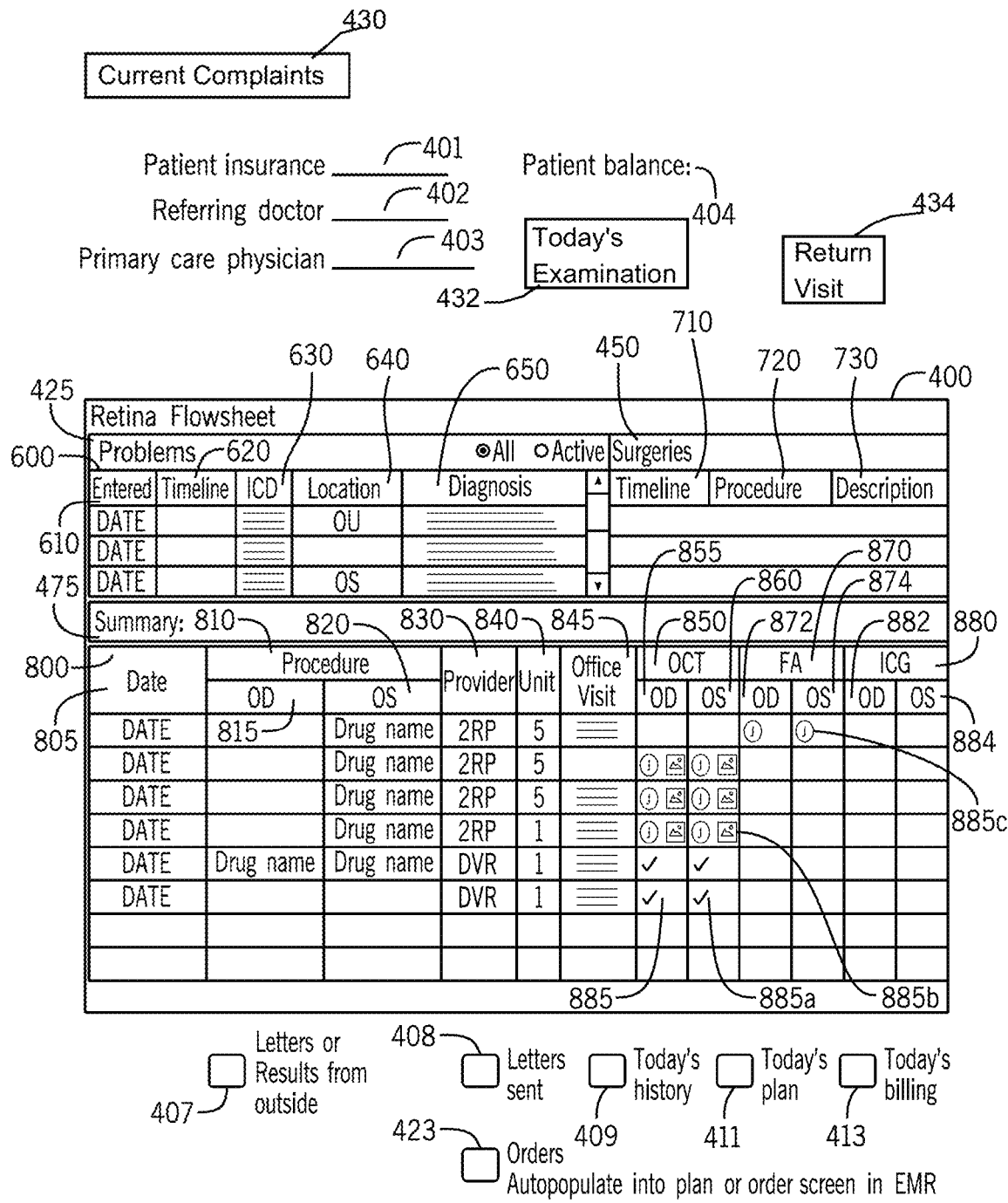
FIG. 4B illustrates a portion of the medical record dashboard of FIG. 4A in accordance with the first embodiment of the invention.
Figure 4D:
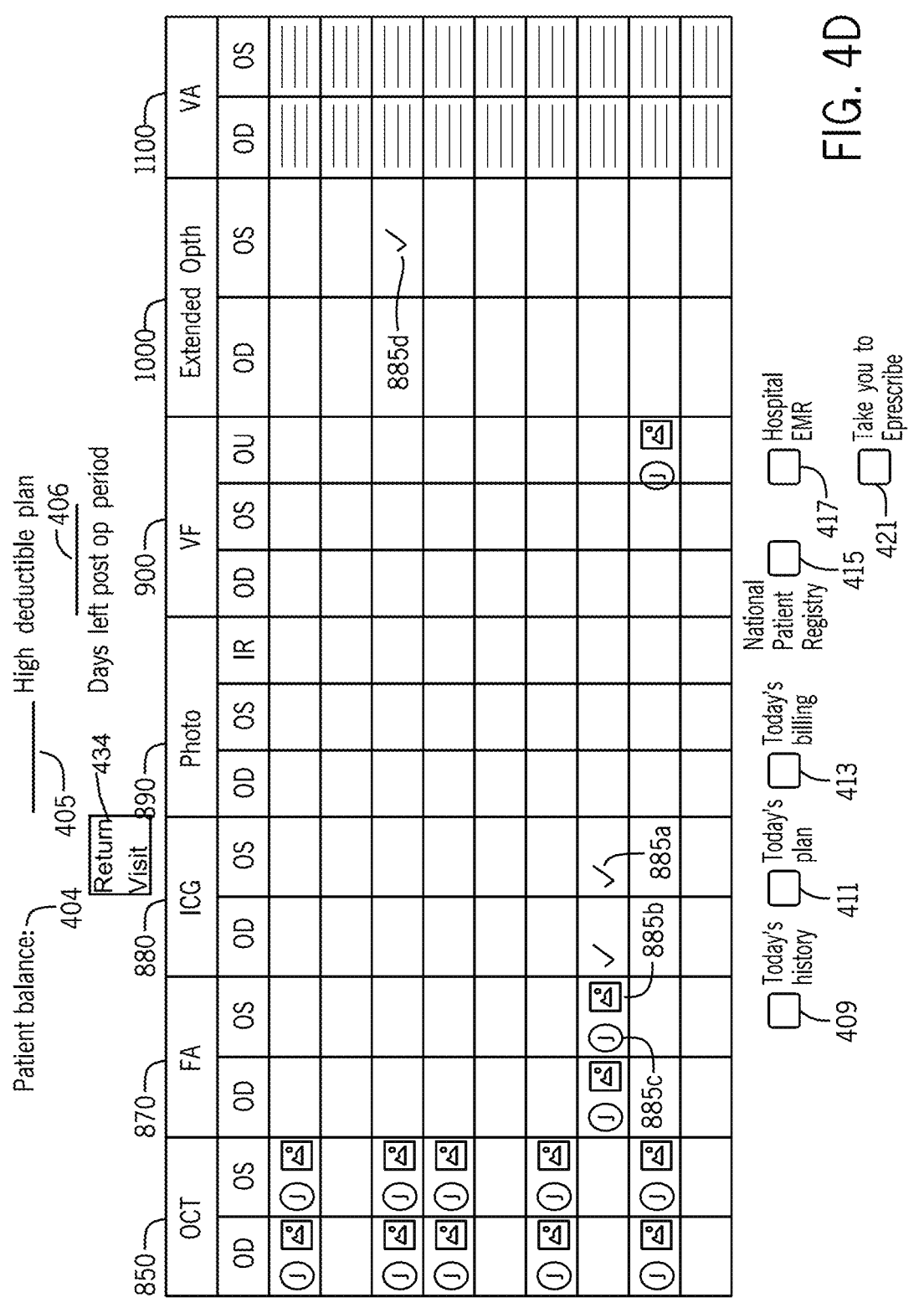

Further details of the problems window 425, surgeries window 450, and command center visual display window 500 and are provided in FIGS. 4B-4D illustrating enlarged views of portions of the medical record dashboard 400. For example, FIG. 4B illustrates a portion of the medical record dashboard of FIG. 4A in accordance with some embodiments of the invention. As illustrated, in some embodiments, the information columns 600 of the problems window 425 can include a date and time information in entered date column 610, a timeline column 620, an "ICD" column 630 for international classification of disease codes including international classification of disease codes version 9 or version 10 (hereinafter collectively referred to as "ICD code") information, location of the problem or disorder (shown as "OD", "OS", "OU" identifying right eye, left eye, both eyes), or from any part of the body, and a diagnosis column 650 for detailing information related to an initial diagnosis or final diagnosis of a patients problem or disorder that can be auto-populated or inputted. Further, in some embodiments, the information columns 700 of the surgeries window 450 can include information related to services or procedures that were provided to the patient (procedure columns 720), a description of the services or procedures performed (description columns 730), and when the services or procedures were provided (timeline columns 710). Referring to FIG. 4C, in some embodiments of the invention, the surgeries window 450 can include location information 740, surgeon or physician information 750, and a comments section 760.

Referring to the command center visual display window 500, the information columns 800 can include a date column 805, and a procedure column 810 illustrating or providing access to information detailing one or more procedures performed on the patient. Further, the procedure column 810 can include an "OD" column 815, and "OS" column 820 providing right and left eye procedure information, or could be a body part (i.e., orthopedic surgery limb versus spine). In some embodiments, information related to the medical provider, the location where the procedure was performed, and office visit information can be provided to the user in the provider column 830, and unit column 840, and office visit column 845.

In some embodiments of the invention, the user can view information related to tests and procedures performed on the patient. For example, in some embodiments, these can include information related to one or more medical imaging procedures such as an optical coherence tomography ("OCT"), or fluorescein angiography ("FA"), and/or indocyanine green chorioangiography ("ICG"), or any current procedural terminology code (hereinafter "CPT code"), including any CPT code found in the American Medical Association CPT 2015 professional edition or other edition, the entire contents of which is incorporated by reference. Moreover, the user can view information related to tests and procedures performed on the patient based on an ICD code. Other clinical vocabularies such as Systematized Nomenclature of Medicine (hereinafter "SNOMED codes") can be used in other embodiments as the system is not limited.

In some embodiments of the invention, the user can compare patient clinical information, such as labs and vitals, before and after a selected medication has been prescribed or a procedure has been performed to better understand the effect of the medication or procedure on the patient. Similarly in other embodiments, the user can examine how the current patient compares against other patients in the practice and population in general to better understand outcomes.

In some embodiments, medical procedures performed (including any of the aforementioned medical imaging procedures) that have been billed and claimed can be viewed or accessed by a user within any of the "OCT" column 850 (split as an "OD" column 855 and "OS" column 860), an "FA" column 870 (split as an "OD" column 872 and "OS" column 874), and/or "ICG" column 880 (split as "OD" column 882 and "OS" column 884).

Referring to FIG. 4C, illustrating a portion of the medical record dashboard of FIG. 4A in accordance with some embodiments of the invention, the information columns 800 can include a photo column 890 configured to enable a user to access any photographic images of the patients eyes including optical and auto-fluorescent images of the eyes ("OU" column 892 and "AF" column 894). In some embodiments, if visual function tests were performed, information can be viewed or accessed in the visual field "VF" column 900 (including an "OD" column 910, "OS" column 920, and/or "OU" column 930). Some embodiments also include an extended ophthalmology column 1000 (including "OD" column 1050 and "OS" column 1070), and a visual acuity column ("VA" column 1100, including "OD" column 1150, and "OS" column 1170). In some embodiments, as described earlier, other details of various tests, procedures or services can be viewed or accessed in the other column 1200. Further, information associated with any of the user-accessible tests, procedures or services or other notes provided by the user and/or medical provider can be viewed or accessed in the notes column 1300 using one or more notes access icon 1350 and/or by viewing a note entry 1375 (e.g., and/or any note entered using the note entry window 1305). The information can also be auto-populated into the EMR plan pages. The command center visual display system and method can auto-populate various data fields of the medical record dashboard of FIG. 4A via an electronic dataflow established between the command center visual display system and method and one or more computer systems of servers that comprise patient information (e.g., such as electronic medical records). The dataflow to and from the medical record dashboard of FIG. 4A can comprise a two-way flow from the source of patient data to the command center visual display system and method, and from the command center visual display system and method to the source.

Some embodiments of the invention include visual cues, icons, or markers representing and/or enabling access to detailed information related to medical services, procedures or tests provided to the patient. Further, by employing data visualization techniques to train the user's eye to quickly identify these icons or markers can increase the efficiency of user accessing key medical indicators such as test results and surgical histories. For example, in some embodiments, medical services, procedures or tests performed or provided can be assigned a visual code, icon, or graphical marker. For example, FIG. 4B at least shows visual cues, icons, or markers 885 representing medical services, procedures or tests performed or provided to the patient. In some embodiments, the information columns 800 within the command center visual display window 500 can include at least one "test done, no image attached" icon 885a, one or more "see image in order viewer" icon 885b, at least one "view order interpretation" icon 885c, and/or at least one "procedure billed or claims made" icon 885d, where an appearance in the medical record dashboard 400 represents a claim was made, and a change in color or other method (italics, bold, etc. can represent whether the bill was paid. Further, FIG. 4D illustrates another portion of the medical record dashboard 400 of FIG. 4A in accordance with some embodiments of the invention and shows example of "test done, no image attached" icon 885a, "see image in order viewer" icon 885b, "view order interpretation" icon 885c, and "procedure billed or claims made" icon 885d, where an appearance in the medical record dashboard 400 represents a claim was made, and a change in color or other notification method can represent whether the bill was paid. Data visualization icons and markers housed in the table can be used to quickly identify billing or coding errors, and thus can empower the physician to be proactive and thorough in areas of compliance with insurance guidelines. The use of these icons to identify potential errors in coding can provide an additional level of protection and proofing to reduce and prevent potential billing and/or malpractice errors.

Figure 5A:
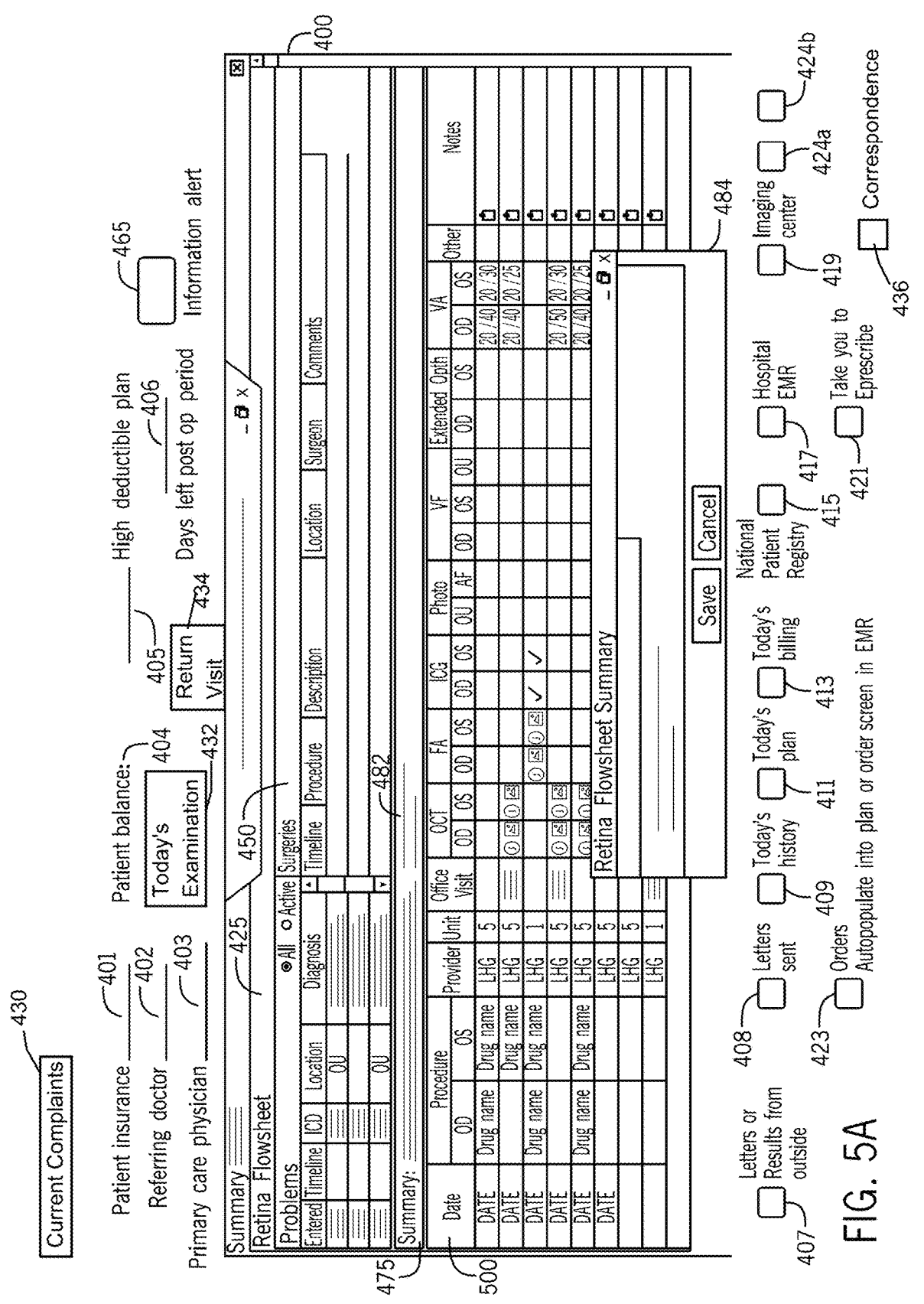

In some embodiments of the invention, the medical record dashboard 400 can provide a text summary of any aspect of the medical record dashboard 400. As described earlier, the summary window 475 can enable a user to view and edit summary information related to the patient, any details of care provided to the patient, and/or and any medical diagnosis information prepared by a medical practitioner. In some embodiments, the user can add and/or edit the summary information. For example, FIG. 5A depicts a medical summary update process in accordance with some embodiments of the invention. In some embodiments, the medical record dashboard 400 including the problems window 425, surgeries window 450, summary window 475, and command center visual display window 500 can include summary comments 482 that can be entered, updated, expanded using the summary input window 484. In some embodiments, a user can enter information within the summary input window 484 for entry into the summary window 475.

Figure 5B:
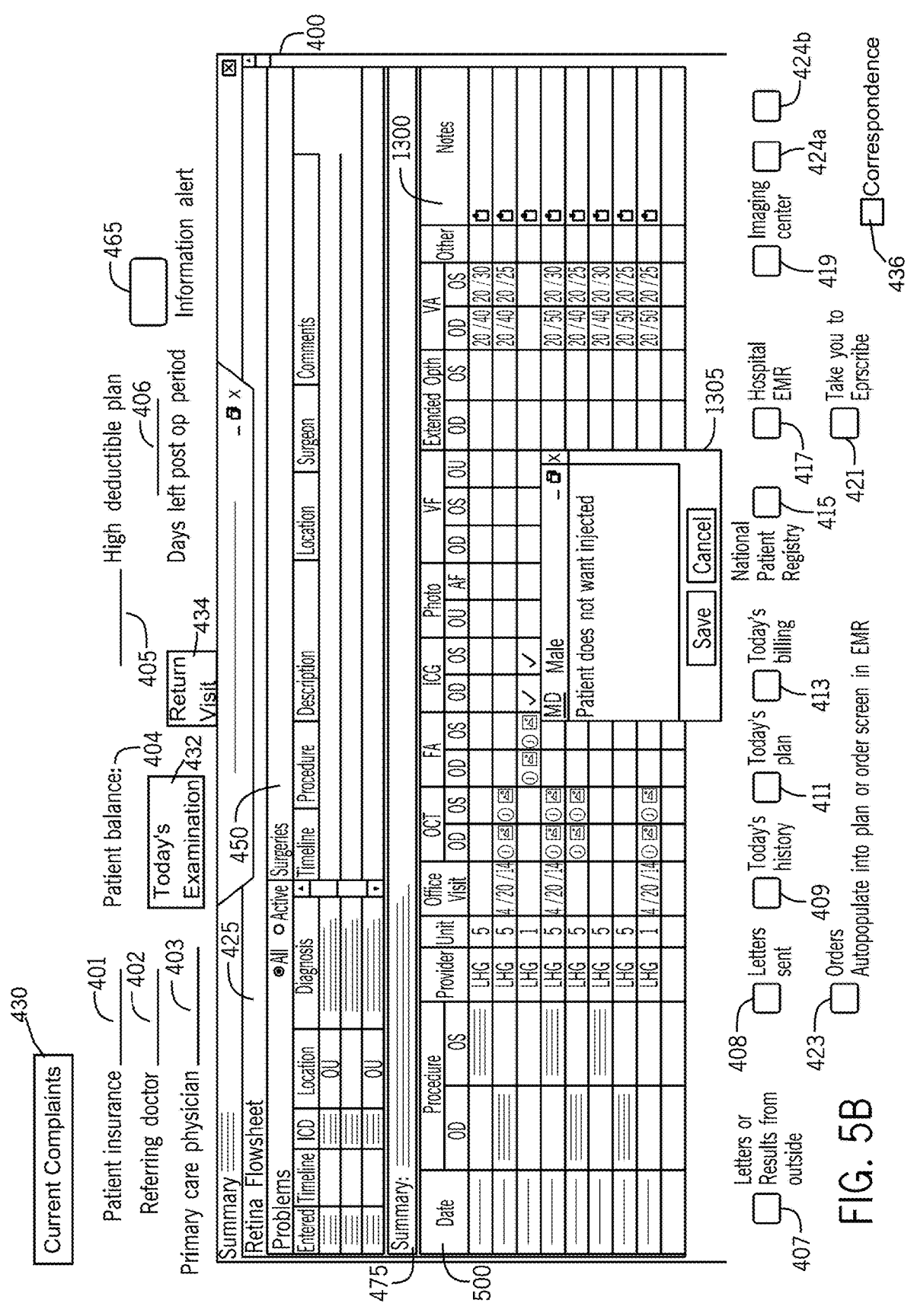

In some embodiments of the invention, the user can add or update information associated with any of the user-accessible tests, procedures or services or other notes provided by the user and/or medical provider in the notes column 1300. For example, FIG. 5B illustrates a notes update process in accordance with some embodiments of the invention. In some embodiments, the medical record dashboard 400 comprising the problems window 425, surgeries window 450, summary window 475, and the command center visual display window 500 with notes column 1300 can be updated with one or more notes using the note entry window 1305. In some embodiments, placement or viewing functions can be toggled using a left or right mouse click function. For example, in some embodiments, following an initial impression or diagnosis, a right click can be updated or shown in a note (e.g., through note entry window 1305), and/or a left click can show in the summary (e.g., summary window 475 as summary comments 482). Further, a right-click for instance or other method can insert what is typed in the table into the corresponding area of the medical chart (e.g., the plan), whereas a left click would insert only into the table and not any other location within the EMR.

Regarding the visual cues, icons, or markers 885 (referred to above and shown at least in FIG. 4B), in some embodiments, a user can access underlying information linked to the visual cues, icons, or markers 885. For example, using a single click or mouse-over, a user can use the command center visual display window 500 of the medical record dashboard 400 to access and view any information auto-populated within the command center visual display window 500 and/or other windows or sub-windows of the medical record dashboard 400. For example, FIG. 6 illustrates a user action record access process in accordance with some embodiments of the invention. In some embodiments, a user action 887 (depicting a user click or mouse-over of a cursor) can enable a user to access and view information (in this example, information lined to "see image in order viewer" icon 885b). In some further embodiments, a user can use a single click or mouse-over to user can access and view any information within any portion of the medical record dashboard 400. Further, in some embodiments, a user can use left and right mouse clicks to navigate from one portion of the medical record dashboard 400 to another. Furthermore, in some embodiments, a right-click mouse function update the user and/or display any important information in the medical record dashboard 400, and a left-click can bring the user back to another portion of the medical record dashboard 400.

Figure 7:
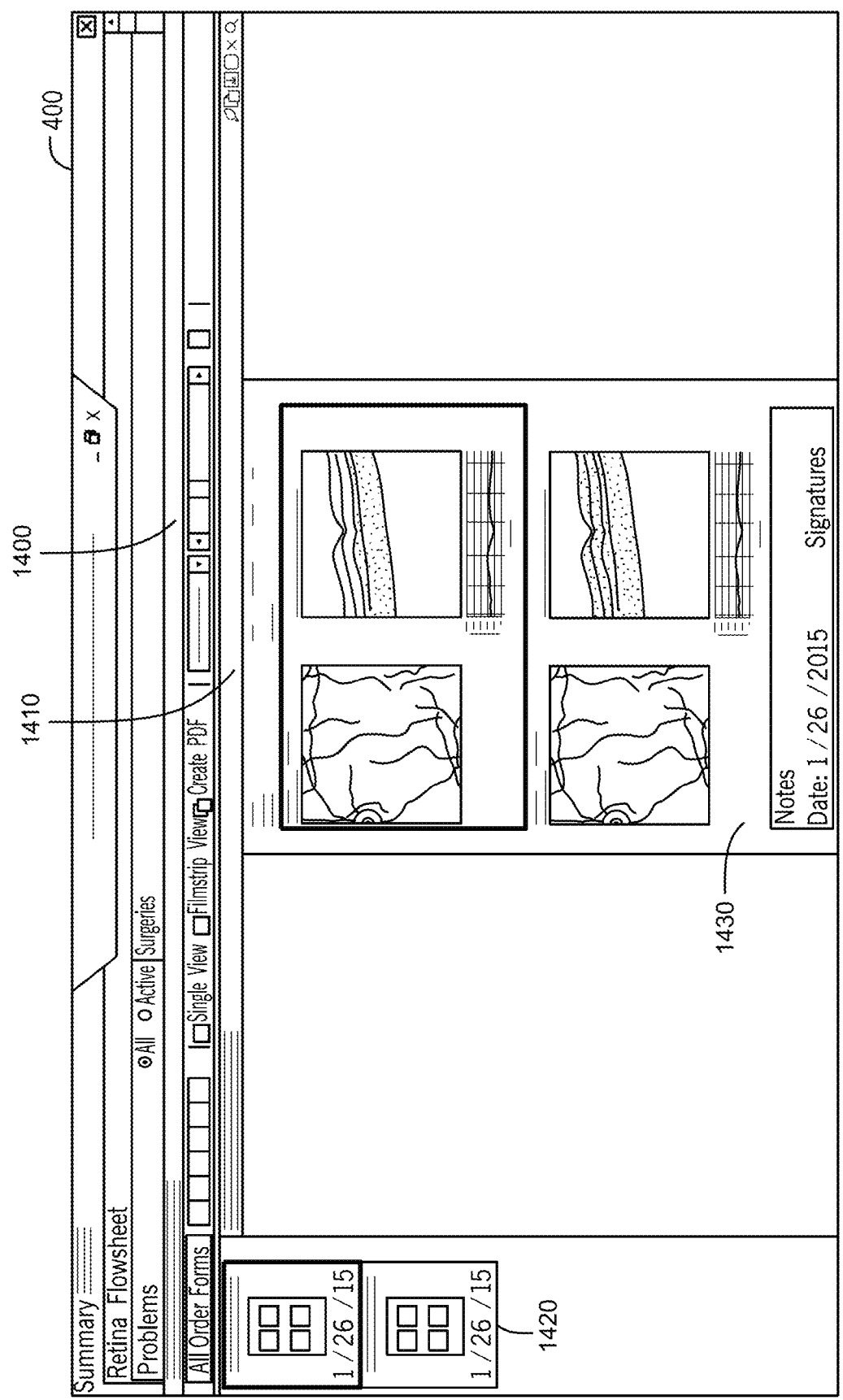
FIG. 7 illustrates a medical records access window in accordance with the first embodiment of the invention.

As an example embodiment of the invention, the command center visual display system and method can display at least one medical record as a result of the user action 887. For example, FIG. 7 illustrates a medical records access window 1400 in accordance with some embodiments of the invention. In some embodiments, the user's action (represented by user action 887) can direct the command center visual display system and method to display the medical record access window 1400 including a medical record display 1410. Further, in some embodiments, at least one medical record 1430 can be selected from the medical record list 1420 for viewing in the medical record display 1410. As illustrated in FIG. 7, in some embodiments of the invention, the at least one medical record 1430 can include an image or photograph such as an optical and/or fluorescein angiogram image. In other embodiments, the at least one medical record 1430 can comprise an X-ray image. In some further embodiments, the at least one medical record 1430 can include an MRI scan or any report or anything ordered or performed by the physicians. In some embodiments, the at least one medical record 1430 can comprise one or more dictated letters from the user or another medical provider. Further, in some embodiments, the at least one medical record 1430 can comprise a record or any portion of a correspondence from another medical provider.

In some embodiments of the invention, the command center visual display system and method can enable a user to access underlying information linked or related to diagnostic codes. In some other embodiments, the command center visual display system and method can enable a user to access underlying information linked or related billing codes. For example, in some embodiments, using a single click or mouse-over, a user can use the command center visual display window 500 of the medical record dashboard 400 to access and view any information related to diagnostic and/or billing codes. In some embodiments, the diagnostic and/or billing code information and payment history can be displayed in a separate document or window. In some other embodiments, diagnostic and/or billing code information can be display overlaid onto the medical record dashboard 400 (e.g., as a pop-up window or transient text and/or graphics).

In some embodiments, at least one medical record 1430 can comprise a transition of care document (hereinafter "CCD"). In some embodiments of the invention, the command center visual display system and method can be configured to receive one or more CCDs from one or more medical providers for display to the user. In some embodiments, command center visual display system and method can be configured to extract information from the CCD for display to the user. For example, in some embodiments, information from a received CCD can be extracted and used to populate one or more data columns or fields of the medical record dashboard 400 and/or one or more linked data columns or fields of the medical record dashboard 400. In some other embodiments, the command center visual display system and method, enabled by the system 30, can be configured to receive direct messaging information. The command center visual display system and method can be configured with standards and profiles required for interoperability and document-based health information exchange with other healthcare organizations. These can include IHE profiles, CDA and CCD, NwHIN Direct, HL7v2, HL7v3, DICOM, X12, ITK (UK), DMP (France), and NEHTA (Australia), etc. For example, in some embodiments, the system 30 can include an HL7 message router and schemas for exchange of direct messages including a graphical editor for transforming messages and data.

Figure 8:
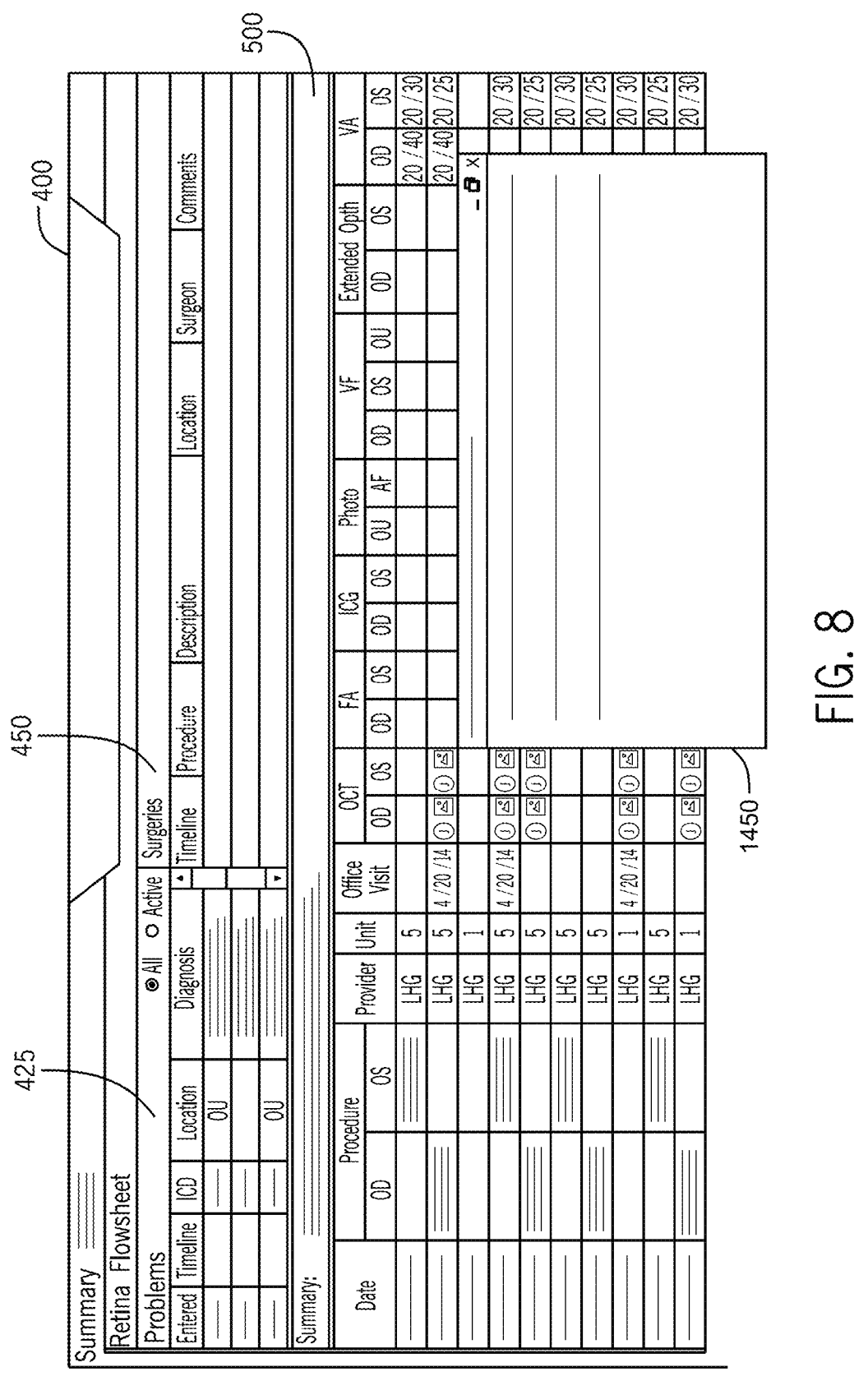

In some embodiments of the invention, the user can retrieve and/or update information related to a medical diagnosis. For example, FIG. 8 illustrates a medical record and diagnosis update process in accordance with some embodiments of the invention. In some embodiments, the medical record dashboard 400 including problems window 425, surgeries window 450, summary window 475, and command center visual display window 500 can include an option to enable a user to update or enter at least one medical diagnosis using a medical record/diagnosis window 1450. In some embodiments, multiple medical diagnoses can be provided or updated by a user. In some embodiments, the user providing the medical diagnosis can be any medical practitioner providing the service or procedure to the patient. In some other embodiments, the medical record/diagnosis window 1450 can be updated by a user other than the medical practitioner providing the service or procedure to the patient.

Further, in some embodiments, information can also be auto-populated into the EMR plan pages. The command center visual display system and method can auto-populate various data fields related to information in any one of the problems window 425, surgeries window 450, summary window 475, and record/diagnosis window 1450 via an electronic dataflow established between the command center visual display system and method and one or more computer systems of servers that comprise patient information (e.g., such as electronic medical records). The dataflow can comprise a two-way flow from the source of patient data to the command center visual display system and method, and from the command center visual display system and method to the source.

Figure 9:
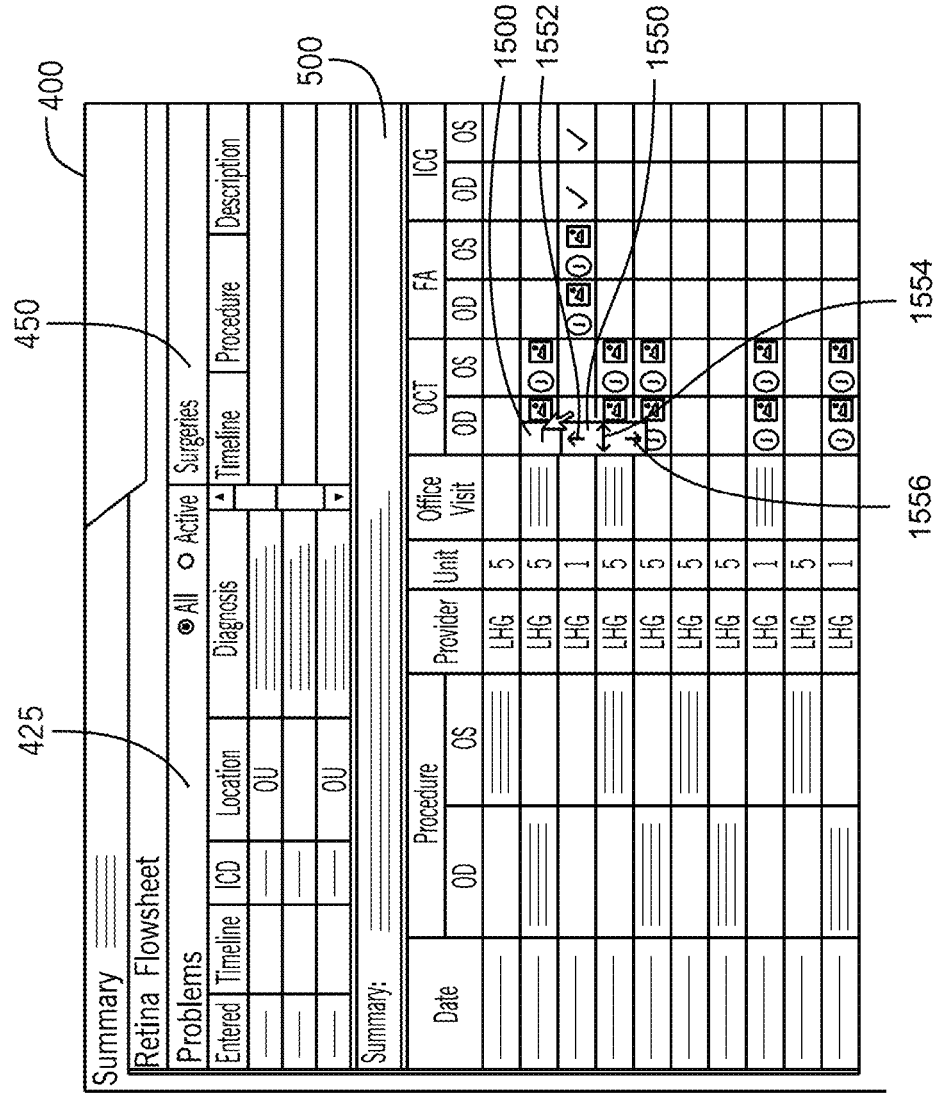
FIG. 9 illustrates a medical record update marker process in accordance with the first embodiment of the invention.

In some embodiments, the command center visual display system and method can enable a user to update information displayed in the command center visual display window 500. For example, in some embodiments, a user can update information related to a medical diagnosis and/or information related to a medical test or other service or procedure. For example, FIG. 9 illustrates a medical record update marker process in accordance with some embodiments of the invention. The medical record dashboard 400, including problems window 425, surgeries window 450, and summary window 475 is shown with a record update marker 1500 being accessed by a user and displaying a update marker selection tab 1550. In some embodiments, the update marker selection tab 1550 can include a user-selectable marker or icon. For example, in some embodiments, update marker selection tab 1550 can include a selectable diagnosis indicator 1552, a selectable diagnosis indicator 1554, and/or a selectable diagnosis indicator 1556. In some embodiments, the selectable diagnosis indicators 1552, 1554, 1556 can provide a graphical representation of a medical diagnosis, outcome, or test. For example, in some embodiments, the diagnosis indicators 1552, 1554, 1556 can provide a visual representation of an improvement of a medical problem, disease, or symptom, or a worsening of a medical problem, disease, or symptom. Further, in some embodiments, the diagnosis indicators 1552, 1554, 1556 can provide a visual representation of a medical problem, disease, or symptom that is stable or substantially unchanged. In some embodiments, the diagnosis indicators 1552, 1554, 1556 can provide a visual representation directly related to one or more variables of a physical test. For example, in the field of ophthalmology, some imaging tests can provide an analysis of the thickness of the retina related to an eye disease such as macular degeneration. In some embodiments, an increase in thickness can represent a worsening of the condition, whereas a decrease in thickness can represent an improvement. A stable or unchanged thickness can indicate the disease is responding to treatment or is in remission. Further, by using data visualization techniques such as by using a color change or other method (e.g., such as using italics, bold text, and/or underlined text), a particular important change in a test can be marked for internal reference alerting a physician to the tests or procedures that are important and to take note for future reference. Further, in some embodiments, the diagnosis indicators 1552, 1554, 1556 can comprise a color and/or graphical change providing a visual representation of items billed, items not billed, or tests needing reports or interpretations are required. A color change or data visualization method (e.g., such as using italics, bold text, and/or underlined text) can also tell a physician if a test or procedure was billed, rejected, or if an interpretation needs to be made.

As an example embodiment, the diagnosis indicators 1552, 1554, 1556 can provide a visual representation of the status of a patient with an eye disease such as macular degeneration. For example, in some embodiments, the diagnosis indicators 1552, 1554, 1556 can be selected from the update marker selection tab 1550 when the user intends to indicate a worsening of the condition (e.g., where the thickness of the retina is increasing). In some embodiments, any of the diagnosis indicators 1552, 1554, 1556 can be color-coded to represent a status or provide a visual indicator of a medical condition, test, or diagnosis linked to the diagnosis indicators 1550. For example, in some embodiments, the diagnosis indicator 1552 can be color coded red and the diagnosis indicator 1556 can be color-coded green. Further, the diagnosis indicator 1554 can be color-coded blue or black. In some other embodiments, the diagnosis indicator 1552 can be color coded green and the diagnosis indicator 1556 can be color-coded red. In other embodiments, other graphical markers or icons can be used, and/or other colors can be used to differentiate the diagnosis indicators 1552, 1554, 1556. Further, in some embodiments, in addition to or in place of using a color differentiation between the diagnosis indicators 1552, 1554, 1556, one or more of the diagnosis indicators 1552, 1554, 1556 can flash or pulsate.

Figure 10A:
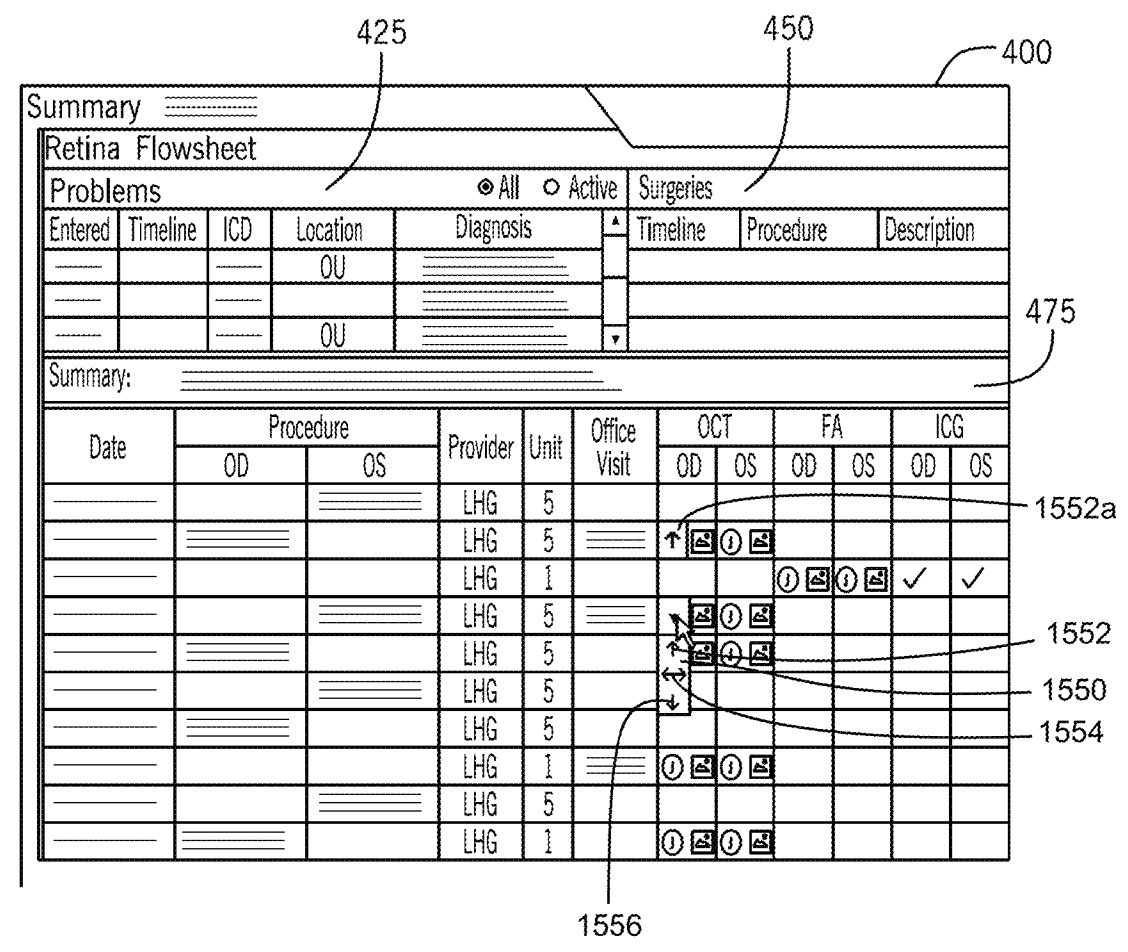

In some embodiments, the command center visual display system and method can enable a user to provide a plurality of updates to information displayed in the command center visual display window 500. For example, in some embodiments, a user can update information related to a medical diagnosis and/or information related to a medical test or other service or procedure, and subsequently provide further updates to the same information or to other information. For example, FIG. 10A illustrates a medical record update marker process in accordance with some embodiments of the invention including medical record dashboard 400, with problems window 425, surgeries window 450, summary window 475, and command center visual display window 500. The command center visual display window 500 depicts diagnosis indicator 1552a representing previously updated information. The command center visual display window 500 also illustrates a user updating information with a process described above using the update marker selection tab 1550 comprising a selection of diagnosis indicator 1552, diagnosis indicator 1554, or diagnosis indicator 1556.

Figure 10B:
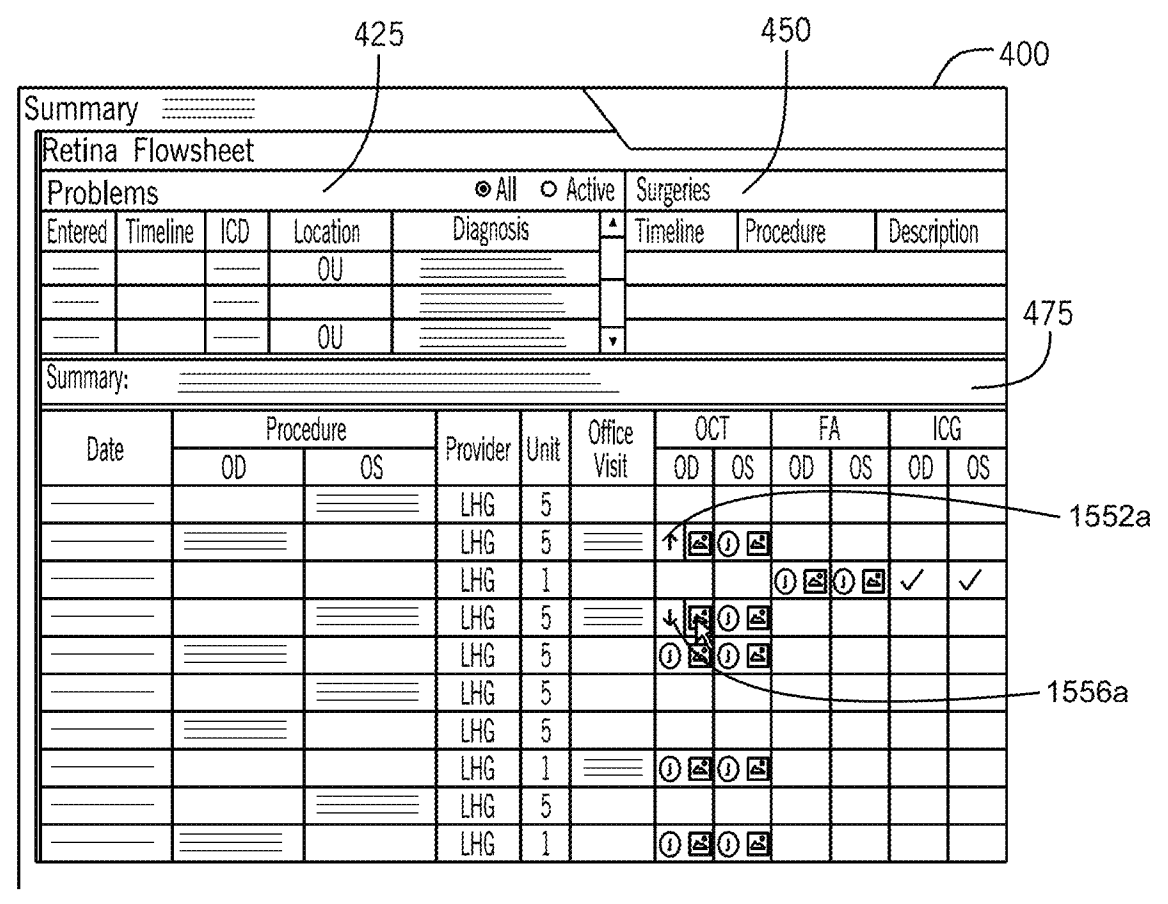

Further, FIG. 10B illustrates a medical record update marker process in accordance with some embodiments of the invention. Following the medical record update marker process shown in FIG. 10A, in some embodiments, the medical record dashboard 400 including medical record dashboard 400, with problems window 425, surgeries window 450, summary window 475, and command center visual display window 500 can display diagnosis indicator 1552a and diagnosis indicator 1556a indicative of updated information or status of a patient and/or a patient's disease, test, or medical condition. Further, any ICD, SNOMED or similar code can be inserted.

FIG. 11 illustrates a portion of the medical record dashboard 400 of FIG. 4A including a scrolled display in accordance with some embodiments of the invention. In some embodiments, the medical record dashboard 400 including problems window 425, surgeries window 450, summary window 475 can include a command center visual display window 500 that comprises a scroll display 505. In some embodiments, any information displayed in the command center visual display window 500 can be scrolled by the user to bring non-visible portions of the command center visual display window 500 into view. This procedure can enable the user to view the entire history of the patient independent of the number of years of history that is on record.

Figure 12A:
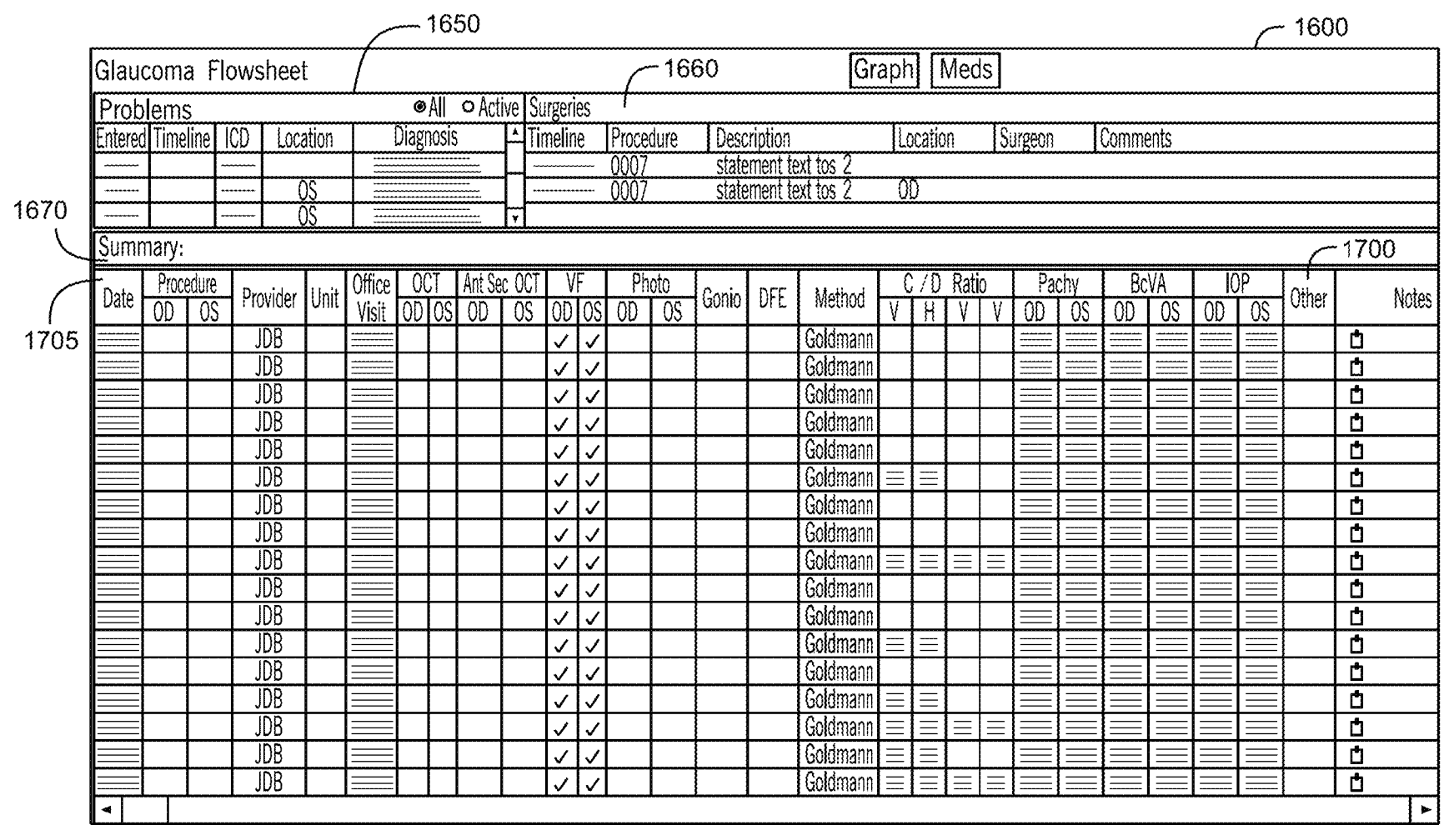

FIG. 12A illustrates a portion of the medical record dashboard 1600 in accordance with another embodiment of the invention. In some embodiments, the medical record dashboard 1600 can display data from one or more medical records, and/or track medical procedures and services based on claims made or billing signed off by a physician for one or more delivered medical procedures or services. Further, in some embodiments of the invention, the medical record dashboard 1600 can be auto-populated as a function of claims made or billing signed off by a physician, auto-populated from any portion of a selected chart. In this instance, any data displayed within the medical record dashboard 1600 can be derived from one or more claim records that have been billed for one or more procedures or services have previously been provided to the patient. In reference to the medical record dashboard 1600 and/or the previously described medical record dashboard 400, in some embodiments of the invention, auto-populating visits by actual claims made or billings signed off by a physician, by definition occurs after the visit with the patient. In some embodiments, the command center visual display system and method can auto-populate the some information at the time the patient is seen, or shortly thereafter, or even before in preparation for a visit (i.e., lab results), so that even if a patient is not seen on a particular day, the user (e.g., medical provider) can view the displayed information in the table for information. For example, in some embodiments, information related to vision can be made with the current date at the time patient is seen. In some embodiments, a user or user's assistant can update the command center visual display system and method with medical tests or test results (e.g., a vision test) as they are performed or shortly thereafter (i.e., on the same day). In this example, this information can immediately trigger the current date and auto-populate the vision column. This information can then be immediately viewed by a user and/or medical provider, and can be updated with notes or comments or other information as the user and/or medical provider is attending to the patient. Further, after the claim has been made for any diagnostic tests or examinations or procedures that have not yet been billed, the date may then auto-populate in the future with the other related columns. In some embodiments, while examining a patient, important information and/or certain parameters that are critical to follow can be immediately updated to the command center visual display system and method. Using these procedures, the command center visual display system and method can enable the medical provider to review the patient's medical history, treatment history, and instantly see items of importance on the day they're examining a patient. For example, the user and/or medical provider can be enabled by the command center visual display system and method, on the day the patient is examined, to review information such as a vision or glaucoma table, intraocular pressure, blood pressure, blood sugar, etc. When billing claims are made, further information is filled to complete the billed claims record. As a further example, a patient may be seen a few days apart and the diagnostic tests etc. and claims have not yet been made, however the command center visual display system and method can be configured to show that the patient was seen that day (e.g., with a vision, pressure test, etc.), and the command center visual display system and method can enable a user (such as a physician) to interpret and/or add special notes on the day they see a patient or before they see the patient rather than waiting to make some notes when a claim is actually generated.

In some embodiments, a medical office wishes to communicate results or a test (e.g., a pathology result or test) a blinking cursor can appear to alert a lab physician to confirm done or other correspondence can be auto-populated into other portions of the EMR. Also any written or type correspondence or any links to dictated information using voice recognition coupled to or integrated with the command center visual display system and method. The display can include information including components where there is a summary of the patient's problem list that a user can input patient information and constantly update and change. Further, this information can be auto-populated with the touch of a button into a designated location such as the current plan documenting the patient's current visit (thus aiding documentation for the current visit). Further, whatever is important for a user to input into the day's visits for documentation can be initially inputted in the table, and then permanently into the day's patient visits. Further, the summary section of the medical record dashboard 2100 (FIG. 13A) can be constantly fluid, and can be changed at every visit rather than being written to an unchangeable document or file (e.g., such as a PDF). Any patient data that is inputted, received, analyzed, or created can be auto-populated into any portion of the dashboard 2100. The command center visual display system and method can auto-populate in a one-way or two-way direction in various data fields related to information in any patient information via an electronic dataflow established between the command center visual display system and method and one or more computer systems of servers that comprise patient information (e.g., such as electronic medical records). The dataflow can comprise a two-way flow from the source of patient data to the command center visual display system and method, and from the command center visual display system and method to the source including another electronic system or server, or another user, observer, or other 3rd party.

By following a patient on the day of delivery (e.g., for a vision intraocular pressure or anything else) the Command Center visual display system and method can enable the user and/or medical provider to see the diagnostic test on same day even though it has not been billed. Further, this procedure can enable the medical provider to optionally add a note (as described earlier) and allow free hand typing at the end of the line.

In some embodiments, medical information populated within the command center visual display system and method (e.g., shown as visual cues, icons, or markers 885 representing medical services, procedures or tests performed or provided to the patient) can include a visual marker such as a red dot. In some embodiments, the command center visual display system and method can display the red dot until a claim is actually made at which time the command center visual display system and method can display can display a green dot (i.e., the command center visual display system and method can convert the red dot to a green dot). In some embodiments, by clicking on the dot, the user can toggle between the payment screen and the command center visual display window 500, 1700. This can allow medical providers to improve patient care, to review the actual picture of a diagnostic test that is displayed within the command center visual display window 500, 1700, to review other diagnostic tests results, and to compare to what happened on other days. In some embodiments, at any time, a medical provider can click on the dot to access a display where the claim is billed, and any payment that was made can be displayed. This process can help to reduce medical errors enabling medical providers to quickly review the billings and claims made or billings signed off by a physician and payment portions of the command center visual display system and method. Further, this procedure serves as an additional tool to minimize coding, compliance with insurance guidelines, and medical treatment errors, as the command center visual display system can provide a quick reference tool that can pull all critical medical and procedure data from the patients EMR chart into a concise and clear table.

In some embodiments, the medical record dashboard 1600 can display information related to medical procedures or services in relation to care of a patient with glaucoma. In some embodiments, the medical record dashboard 1600 can display various windows and sub-windows based on a user preference and/or current or previous user interaction with the medical record dashboard 1600. Some embodiments include a medical record dashboard 1600 that comprises information columns 1640 including a problems window 1650 and/or a surgeries window 1660 where information related to a patient's medical problems and surgeries can be displayed. In some embodiments, the medical record dashboard 1600 can include a summary window 1670 enabling a user to view and edit summary information related to the patient, any details of care provided to the patient, and/or and any medical diagnosis information prepared by a medical practitioner. Further, the medical record dashboard 1600 can also display detailed information related to any medical procedures or services provided to the patient, including procedures or services that are auto-populated by claims made or billing signed off by a physician as detailed above or other method. For example, in some embodiments, the medical record dashboard 1600 can display a command center visual display window 1700 including a plurality of information columns 1705. In some embodiments, the command center visual display window 1700 can be scrolled by the user to display other portions of the command center visual display window 500.

In some embodiments, the medical record dashboards 400, 1600 can also display detailed information related to notification of payment of any medical procedures or services provided to the patient, including procedures or services that are auto-populated by claims made or billing signed off by a physician as detailed above or other method. Moreover, the medical record dashboards 400, 1600 can enable a user to access and/or track the status of the billing and payment process at any point in time. For example, in some embodiments, the medical record dashboards 400, 1600 can access and view any patient encounter form (i.e. a superbill), any claims made to a clearing house, any updates on accepted or rejected bills from the clearing house, any claims made to an insurance company, and/or any payments received for any claims made.

Figure 12B:
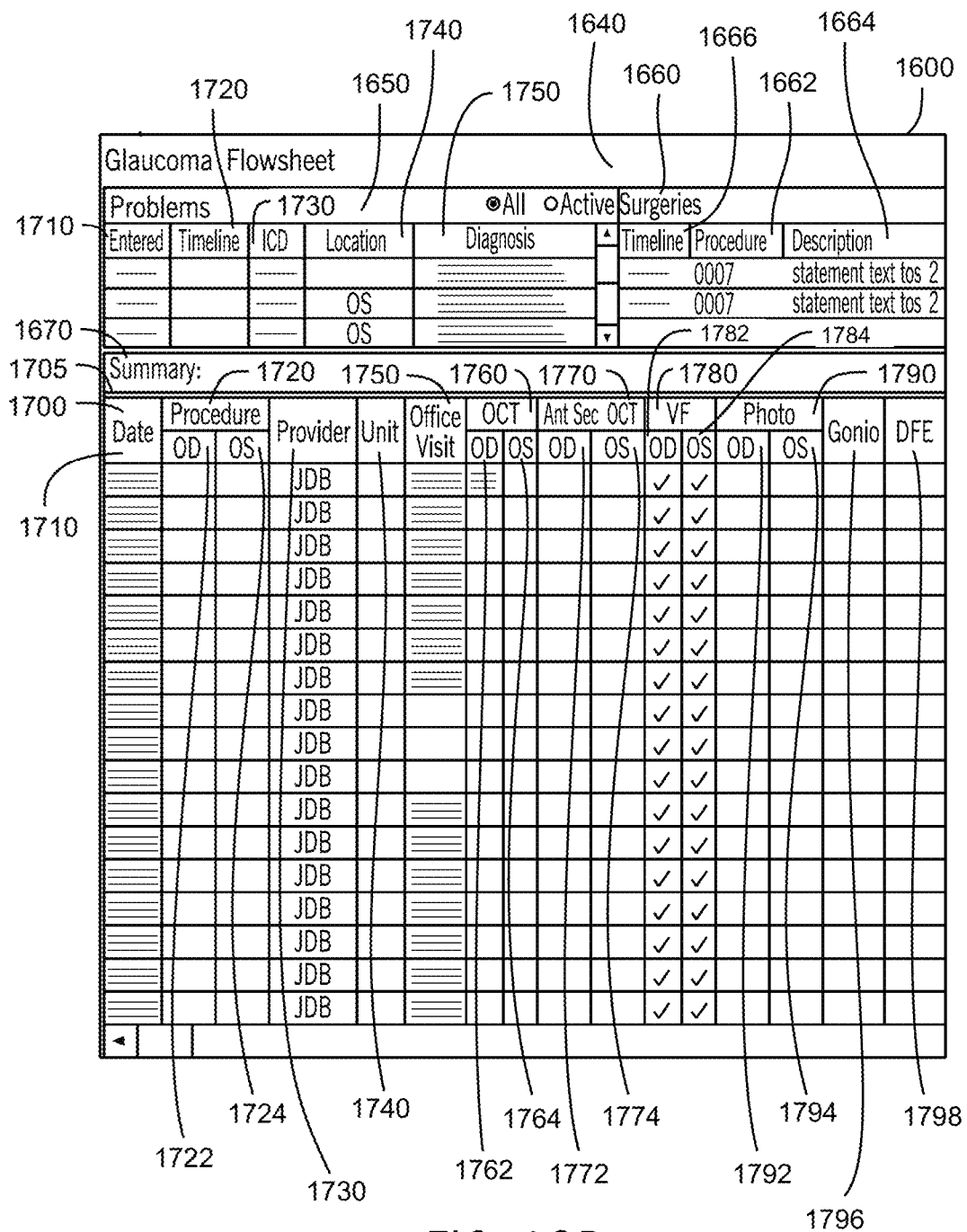
FIG. 12B illustrates a portion of the medical record dashboard of FIG. 12A in accordance with the first embodiment of the invention.

FIG. 12B illustrates a portion of the medical record dashboard 1600 of FIG. 12A in accordance with some embodiments of the invention. As shown, the problems window 1650 can include a date and time information in entered date column 1710, a timeline column 1720, an "ICD" column 1730 for ICD code information, location of the problem or disorder (shown as "OD", "OS", "OU" identifying right eye, left eye, both eyes) (column 1740), and a diagnosis column 1750 for detailing information related to an initial diagnosis or final diagnosis of a patients problem or disorder. Further, the surgeries window 1660 can include information related to services or procedures were provided to the patient (procedure columns 1662), a description of the services or procedures performed (description columns 1664), and when the services or procedures were provided to the patient (shown as timeline columns 1666), and can include a surgical report that can be brought up and viewed by the user.

Referring to the command center visual display window 1700 of dashboard 1600, the information columns 1705 can include a date column 1710, and a procedure column 1720 illustrating or providing access to information detailing one or more procedures performed on the patient. Further, the procedure column 1720 can include an "OD" column 1722, and "OS" column 1724 providing right and left eye procedure information. In some embodiments, information related to the medical provider, location where the procedure was performed, and office visit information can be provided to the user in the provider column 1730, and unit column 1740, and office visit column 1750.

In some embodiments of the invention, the command center visual display window 1700 can enable a user to view information related to tests and procedures performed on the patient including, but not limited to one or more medical imaging procedures such as an optical coherence tomography ("OCT"), or fluorescein angiography ("FA"), and/or indocyanine green chorioangiography ("ICG"). In some embodiments, medical procedures performed (including any of the aforementioned medical imaging procedures) that have been billed and claimed can be viewed or accessed by a user within any of the "OCT" column 1760 (shown split as an "OD" column 1762 and "OS" column 1764), an "Ant Seg OCT" column 1770 (split as an "OD" column 1772 and "OS" column 1774).

In some embodiments, if visual function tests were performed, information can be viewed or accessed in the "VF" column 1780 (including an "OD" column 1782, and/or an "OS" column 1784. Some embodiments include a photo column 1790 configured to enable a user to access any photographic images of the patient's eyes including optical and/or auto-fluorescent images of the eyes ("OD" column 1792 and "OS" column 1794). Further, some embodiments include a Gonio column 1796 providing access to gonioscopy data and/or information related to a dilated fundus examination ("DFE" column 1798). In some embodiments, the surgeries window 1660, can include location column 1642, surgeon column 1644, and a comments column 1646 (shown in FIG. 12C).

Figure 12C:
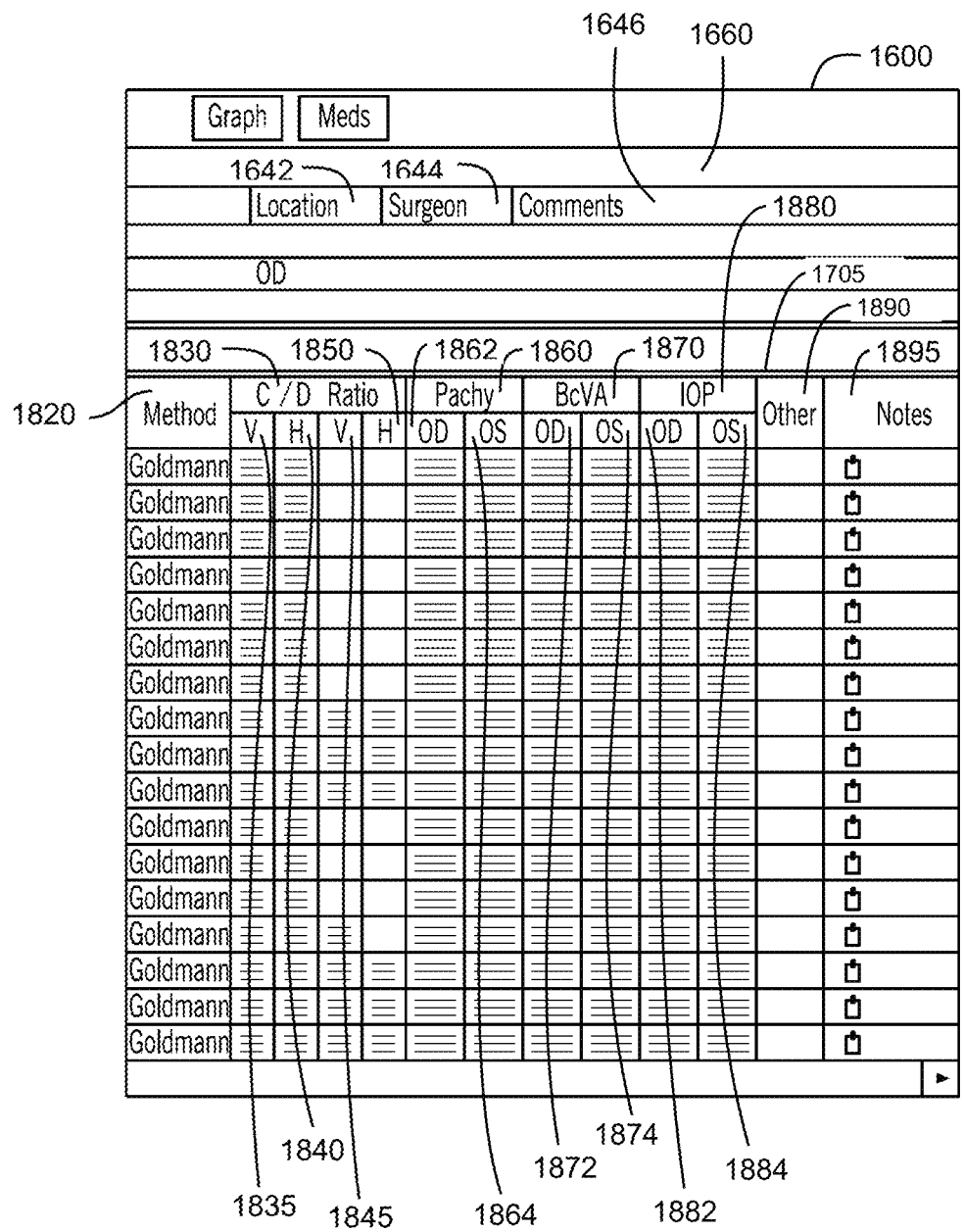
FIG. 12C illustrates a portion of the medical record dashboard of FIG. 12A in accordance with the first embodiment of the invention.

In some embodiments of the invention, the command center visual display window 1600 can enable a user to view information related to tests and procedures performed on the patient including a cup-to-disc ratio ("C/D") to assess the progression of glaucoma, Pachymetry data ("Pachy"), refraction test information such as best-corrected visual acuity ("BCVA"), and/or intraocular pressure (IOP) data. For example, FIG. 12C illustrates a portion of the medical record dashboard of FIG. 12A in accordance with some embodiments of the invention and shows method column 1820, "C/D ratio" column 1830, "Pachy" columns 1860, "BcVA" columns 1870, and "IOP" columns 1880. In some embodiments, the "C/D ratio" column 1830 includes "V" column 1835, "H" column 1840, "V" column 1850, and "H" column 1850. Further, in some embodiments, the "Pachy" columns 1860 includes "OD" column 1862, and "OS" column 1864. In some embodiments, the "BcVA" columns 1870 includes "OD" columns 1872, and "OS" columns 1874. Some embodiments include "IOP" columns 1880 including "OD" columns 1882, and "OS" columns 1884. In some embodiments, other columns 1890 can be used to add additional test information. Further, the command center visual display window 1700 can also include a notes column 1895 for accessing and updating notes related to tests and medical diagnosis. In some embodiments, the command center visual display window 1700 can be updated with comments and notes as described earlier with respect to command center visual display window 400.

In some embodiments of the invention, the command center visual display system and method can display and auto-populate the medical record dashboard 400 and/or the medical record dashboard 1600 with more than one patient information. For example, in some embodiments, any windows, sections, or columns of the medical record dashboard 400, 1600 can display information related to a plurality of patients. Any patient data that is inputted, received, analyzed, or created can be auto-populated into any portion of the dashboard 400, 1600, where the command center visual display system and method can auto-populate in either a one-way or a two-way direction. Thus, data fields related to information in any patient information can be communicated via an electronic dataflow established between the command center visual display system and method and one or more computer systems of servers comprising patient information (e.g., such as electronic medical records).

Further, in some embodiments of the invention, any information displayed by the command center visual display system and method can display and auto-populate the medical record dashboard 400 and/or the medical record dashboard 1600 as a function of patients seen during a specified time period. In some other embodiments of the invention, the command center visual display system and method can display and auto-populate the medical record dashboard 400 and/or the medical record dashboard 1600 as a function of a specified disease and/or diagnosis. For example, in some embodiments, the command center visual display system and method can display and auto-populate the medical record dashboard 400 and/or the medical record dashboard 1600 as a function of a diagnosis or procedure or prescribed medication or lab or imaging test from input received from a physician or other medical practitioner or provider. For instance, every patient who has the diagnosis of diabetes with their name and the date last scene is auto-populated. Certain parameters that may need to be followed by the user from all of their patients with this condition can be auto-populated. For example, in the case of patients with diabetes, parameters can include how often they've missed appointments, blood sugar, hemoglobin A1C, medications, major new medical complications such as heart attack, stroke, amputations, blindness, each of which can be auto-populated and followed to enable the user to see how all their patients are doing. In some embodiments, input and the ability to display data can be based on single values or on complex multi-variate input (i.e. patients with diabetes, taking metformin and seen by the practice in the last 30 days).

In some embodiments, the user can receive a daily report on all the patients they have seen, what the diagnosis codes are and what CPT, ICD, or office visit billing codes were done whether they have been billed or not. In some embodiments, the user can view a report of patients for a specific day or week based on appointments or other data such as referrals. With this functionality, at the end of the day physicians can see all of their activity or the practice's activity and using data visualization techniques can realize what activity still needs to be completed or was not entered properly. The user can then review the same information in a few days' time and weeks or months later to insure that the proper billing and collections has occurred. In some embodiments, any report or diagnostic test can be sent to a patient portal, to an email server, and/or as a fax. Further, the user can be alerted when the claims go out and when they are actually paid. For example, in some embodiments, the above described methods of display can provide a mechanism for determining payments to the user, and if claims are being made for each patient seen in any particular day, week or month.

In some embodiments, any report, note, letter, referral or diagnostic test can be sent to an EMR, patient portal, a messaging platform to an email server, and/or as a fax. Messages can be transmitted to a patient or another practice focused on appointment reminders, medication prescriptions and/or refills, and good care management guidelines. It should be recognized the data interoperability and messaging are not limited to the examples provided but apply to any information within the Command Center.

Examples of the aforementioned examples of displayed data sorted and viewable by patient, disease time period, physician, etc., are shown in FIGS. 12D and 12E. For example, FIG. 12D illustrates a portion of a medical record dashboard 1900 for display as a function of disease or patient in accordance with some embodiments of the invention. Further, FIG. 12E illustrates a portion of a medical record dashboard 2000 for display as a function of patients or physician or disease state in accordance with some embodiments of the invention. In some embodiments, the medical record dashboards 1900, 2000 can be displayed overlaid on a previously viewed dashboard such as medical record dashboard 400, 1600. For example, in some embodiments, the medical record dashboards 1900, 2000 can be displayed in the command center visual display window 500. In other embodiments, the medical record dashboards 1900, 2000 can be displayed independently from the medical record dashboard 400, 1600, and the user can toggle a display of any of the medical record dashboards 400, 1600, 1900, 2000.

Referring to FIG. 12D, including providing a list of patients 1905, within column 1910, an entire day of patients listed by date or by insurance coverage can be provided or the list can comprise a single patient with multiple visits. For example, in some embodiments, within column 1920, an office visit and any items billed for a routine examination day and any other CPT codes billed that day can be displayed. Some specialties may have many CPT codes during an office visit (e.g. Ophthalmologists, whereas others (e.g., Gastroenterologists) may have four during an office visit. In some embodiments, column 1930 can include the procedures that a physician may perform, and are usually not on the same day as the exam (these are GI physicians examples). In some further embodiments, the column 1940 can include various important parameters that can be followed for a specific patient. Some embodiments include column 1950 that includes where a physician writes notes about patient care issues. In some embodiments of the invention, column 1960 can takes the user to that patient's personal EMR or review table and can also send a message to the patient. In some embodiments, the column 1970 can takes the physician to the charge payment history of the patient, and also a message can be sent to the billing department from this table. Columns can be reconfigured such that all patients with a particular insurance company that have a particular diagnosis on any given date or over a prolonged period of time can have tests and procedure results, as well as payments compared, allowing on one screen anyone to rapidly move through this visual display system to empower rapid comparison of results and potential payment anomalies for the same insurance company for the same CPT codes but perhaps different ICD9 or 10 diagnosis and to see if there is a mismatch (e.g., through the use of artificial intelligence systems discovering insurance payment irregularities). In some embodiments, columns 1920, 1930 can be colored 'black' when a claim is made, and can be colored 'green' if paid, and can be colored 'yellow' if a payment is pending, and can be colored 'red' if payment denied by one rendition, e.g., physician reconciliation report of messages sent individuals for follow up, and/or a report of all the message activity from any given day.

Referring to FIG. 12E, including example embodiments related to patients with diabetes, the display for patients 2010 can include can include a variety of medical, billing, and insurance related information. FIG. 12E illustrates a portion of a medical record dashboard for display as a function of patients with a specific disease ICD, such that many patients may be compared at the same time, which can be useful for clinical research or for tracking clinical outcomes. This embodiment tracks all patients in a practice or a subset of patients and can compare, for example, particular diagnostic test results in patients with a particular condition, the results of a particular medication, how all the patients did who received a particular intraocular lens into the eye, etc. The information is put into each individual patients table, but all patients with that issue can also be called up on a single table such at that illustrated in FIG. 12E. This feature can compile and compare all patients with a particular insurance company that have a particular diagnosis and compare tests and procedure results, as well as payments, allowing a doctor on one screen to rapidly see results, changes, patterns and payment anomalies. This feature also allows the extraction of patients with similar conditions for referrals and clinical research, batch generation for cross-referrals (e.g. optometry for an ophthalmologist), etc. This medical record dashboard 2000 can be displayed as shown, or can be sorted based on any of the data columns. For example, the patients 2010 can be shown including information displaying insurance coverage 2020, date of diagnosis of diabetes 2030, the patient's age 2040, the patient's weight 2050, the patient's height 2060, their body mass index 2070, their initial presenting HbgA1C 2080, their most recent HbgA1C 2090, their hypertension status 2092, their recent blood pressure 2094, their All ICD diagnosis 2096 and their current or past medications 2098. In some embodiments, the medical record dashboard 2000 can be reconfigured to shown patients 2010 sorted by any of the columns 2020, 2030, 2040, 2050, 2060, 2070, 2080, 2090, 2092, 2094, 2096, 2098.

Those skilled in the art will appreciate that a summary table of the type illustrated in FIG. 12E enables the physician to put into one dashboard 2000 everything the physician has done in a particular time frame, such as a day. For instance, a line of information for the information entered into the chart for every patient for today's visit may be presented in the dashboard 2000. Whatever the technician records like the patient's vision and any diagnostic tests or laser procedures or injections in the eyes that were actually done that day come up on the dashboard 2000 for interpretation. Dashboard 2000 thus shows on one page literally everything a physician may have done from laser surgeries to injections to photos is all summarized for inspection and confirmation. The physician may also refer to the notes section such that physicians can write notes reminding themselves to do something like call the patient's family at night, check laboratories results, or remind physicians of items to do. Those type of messages can remain permanent or disappear if the physician chooses. The dashboard 2000 also serves as a double-check enabling the physician to check again (e.g. 48 hours later) when everything for that day should have already been billed or 60 days later when everything is paid and all dates queried can be compared. Also, the physician may call up all patients having a common insurance carrier to facilitate satisfaction payments from the insurance carrier.

In some embodiments of the invention, the command center visual display system and method can enable a user to update a medical record dashboard 400 and/or the medical record dashboard 1600 to be mark personalized to the next treating physician or patient to follow progression changed outcomes. This may be used to access quality of care and prove effectiveness and results resolution, and can be used for negotiating with insurance carriers or for performance research. For example, anything can be tracked or personalized to the needs of the treating physician or patient to follow progression, changes, and outcomes. This can be used to assess quality of care and prove effectiveness and results of treatment. Quality outcome measures are critical for all practices to start to follow as this improves patient care, and in the future, a physician's financial compensation from insurance companies, or any penalization may be determined based on the quality of care metric. Further, physicians who participate in clinical research must follow defined parameters over time as they learn whether a particular drug, or device, or other item being investigated actually improve changes or worsens particular parameters. As described earlier, in some embodiments, the information that is auto-populated can include patient outcome summaries. In some embodiments, the command center visual display system and method can process patient outcomes and display an analysis of patient outcomes based on patient information from treatment summaries, and/or diagnosis summaries, and/or patient feedback summaries, and/or other physician summaries or treatments. The patient outcomes can include or comprise physician quality reporting system (PQRS) quality measures, and calculated or reported patient outcomes can include or comprise PQRS measures codes.

By way of example in FIG. 4C, vision is followed in column 1100, and in the other column 1200, many different parameters that may change over time can be added. For example, as described earlier with respect to participation in clinical research studies, other factors followed such as central macular thickness ("CMT"), or ischemic index ("ISI") (% and a scan in millimeters) can be followed. Therefore, every time the patient comes in to be examined, the table can serve the multi-purpose of treating the patient, and for inputting research data from the office visit right into the table. This can then auto-populate into another portion of the EMR or derive these numerical values and place them into the research Excel spreadsheet. Also it could go the other way, where if the Excel research spreadsheet can be also have the data inputted into the review table.

In some embodiments of the invention, the command center visual display system and method can enable a date alert or self-destruction of any information or data entered or auto-populated in the medical record dashboard 400 and/or the medical record dashboard 1600. For example, in some embodiments, any message, or note, or summary, or any medical data can include a date alert and/or a self-destruct function that can instruct the command center visual display system and method to remove and/or delete information from the medical record dashboard 400 and/or the medical record dashboard 1600. In other embodiments, the historical date and/or an alert or warning can be provided with any auto-populated or user-summoned information to assist the user with an assignment of relevancy to any data being reviewed prior to, during, or after a patient visit or examination. In some embodiments, this feature can optimize the standard of care being delivered by the user. For instance, this feature can help monitor preferred practice patterns or serve as a reminder on information needed for clinical review.

Figure 13A:
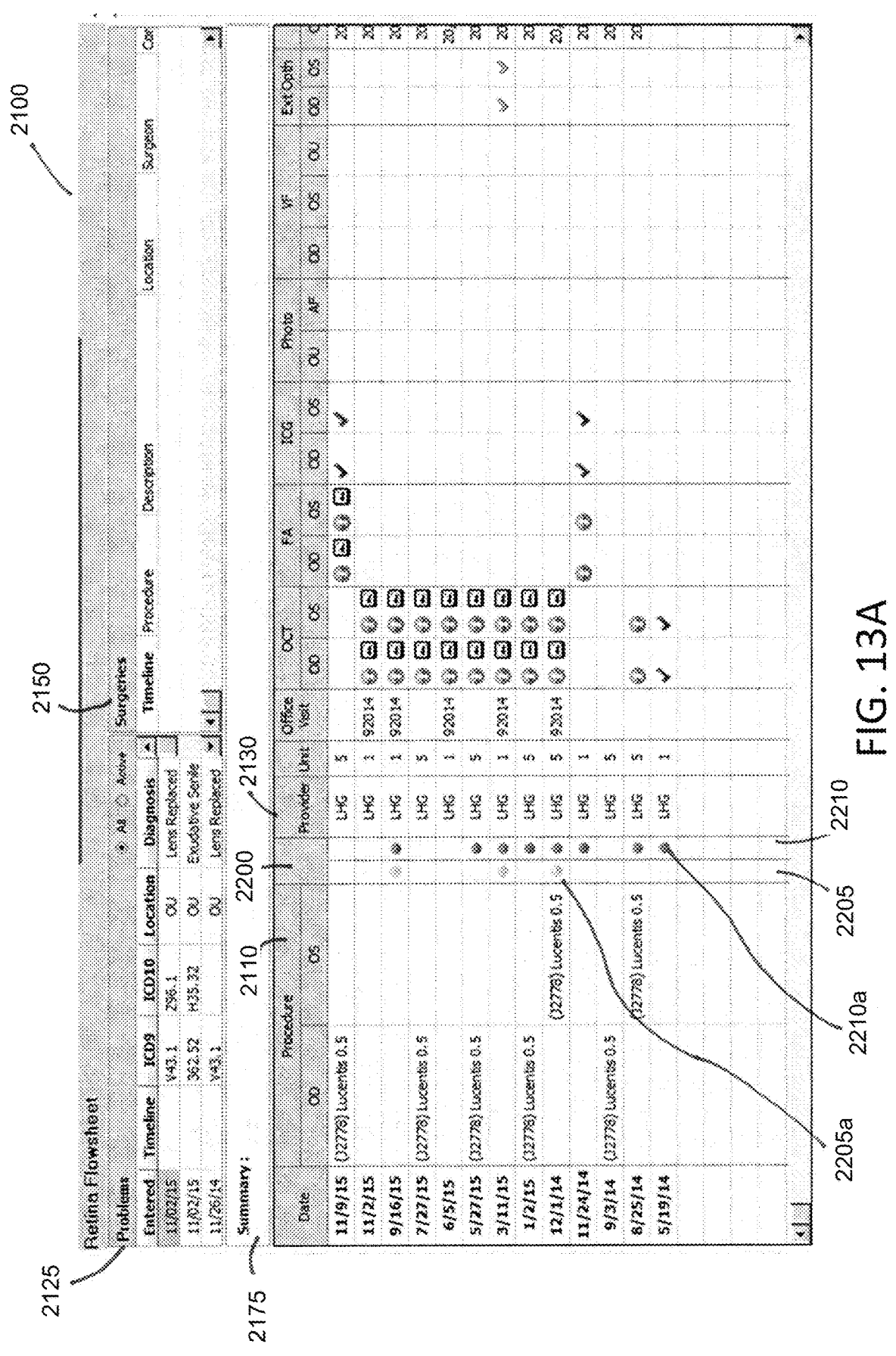

In some embodiments of the inventor, the command center visual display system and method can enable a user to access a detailed ledger comprising financial information related to one or more procedures. In some embodiments, the ledger can be accessed from a medical record dashboard. Further, in some embodiments, the dashboard can include at least one visual indication of a payment for services provided, where detailed information of the charges, payments, write-offs, adjustments, and balances can be accessed and displayed. For example, FIG. 13A illustrates a medical record dashboard 2100 in accordance with some embodiments of the invention. In some embodiments of the invention, the medical record dashboard 400 illustrated in FIG. 4A can comprise, include, or be replaced by the medical record dashboard 2100. In some embodiments, the medical record dashboard 2100 can be access as described for the medical record dashboard selection window of FIG. 3. In some embodiments, the medical record dashboard 400 can be displayed by the user following the user's selection of at least one medical record dashboard from the medical record dashboard selection window 300. For example, in some embodiments, the user can select "Retina Flowsheet" 305 to access and/or launch the medical record dashboard 2100.

In some embodiments, the command center visual display system and method display a medical record dashboard 2100 including a display of data from one or more medical records, and/or track medical procedures and services based on claims made or billing signed off by a physician for one or more delivered medical procedures or services. Some embodiments of the invention include a command center visual display system and method that can dynamically link to various external databases comprising patient information that can be displayed in the medical record dashboard 2100. For example, in some embodiments, the command center visual display system and method can function as a portal to patient information prepared by the user or patient information from other sources. Further, in some embodiments of the invention, the medical record dashboard 2100 can be auto-populated as a function of claims made or billing signed off by a physician. In this instance, any data displayed within the medical record dashboard 2100 is derived from one or more claim records that have been billed for one or more procedures or services have previously been provided to the patient. In some other embodiments, auto-population can be enabled in both directions interacting as a switchboard between the entire EMR and the medical record dashboard 2100 along with what is added to any window, sub-window, column or entry in the medical record dashboard 2100 being automatically added to the appropriate part of the chart for documentation. In some embodiments, the medical record dashboard 2100 can display information related to medical procedures or services in relation to retinal eye care of a patient. In other embodiments, the medical record dashboard 400 can display information related to medical procedures or services in relation to any kind of medical care of a patient.

In some embodiments, the medical record dashboard 2100 can display various windows and sub-windows based on a user preference and/or current or previous user interaction with the medical record dashboard 2100. For example, in some embodiments, the medical record dashboard 2100 can display a problems window 2125 and/or a surgeries window 2150 where information related to a patient's medical problems and surgeries can be displayed.

In some embodiments, the medical record dashboard 2100 can display information including components where there is a summary of the patient's problem list that a user can input patient information and constantly update and change. Further, this information can be auto-populated with the touch of a button into a designated location such as the current plan documenting the patient's current visit (thus aiding documentation for the current visit). Further, whatever is important for a user to input into the day's visits for documentation can be initially inputted in the table, and then permanently into the day's patient visits. Further, the summary section of the medical record dashboard 2100 can be constantly fluid, and can be changed at every visit rather than being written to an unchangeable document or file (e.g., such as a PDF). For example, in some further embodiments, the medical record dashboard 2100 can include a summary window 1670 enabling a user to view and edit summary information related to the patient, any details of care provided to the patient, and/or and any medical diagnosis information prepared by a medical practitioner. Further, the medical record dashboard 2100 can also display detailed information related to any medical procedures or services provided to the patient, including procedures or services that are auto-populated by claims made, or billings or payments including billing signed off by a physician as detailed above. All of the features of the medical record dashboard 400 as described earlier can be provided in the medical record dashboard 2100.

Some additional features include the dashboard 2100 displaying at least one visual indication of a payment for services provided on the dashboard 2100. Further, the user can be provided with access to a detailed ledger comprising financial information related to one or more procedures. For example, in some embodiments, the dashboard can comprise a payment indicator column 2200 including one or more indicator and/or access icons. For example, in some embodiments, the payment indicator column 2200 can comprise a column 2205*a* that can be populated with one or more indicator icons. In other embodiments, the column 2205*b* can be provided with one or more indicator or access icons. In some embodiments, the one or more indicator or access icons can comprise icons of color such as yellow or green.

The payment indicator column 2200 can be positioned anywhere on the dashboard 2100. In the example embodiments of FIG. 13A, the payment indicator column 2200 can be positioned between the procedure column 2110 illustrating or providing access to information detailing one or more procedures performed on the patient, and information related to the medical provider, provider column 2130, that can display the location where the procedure was performed, and office visit information.

Figure 13B:
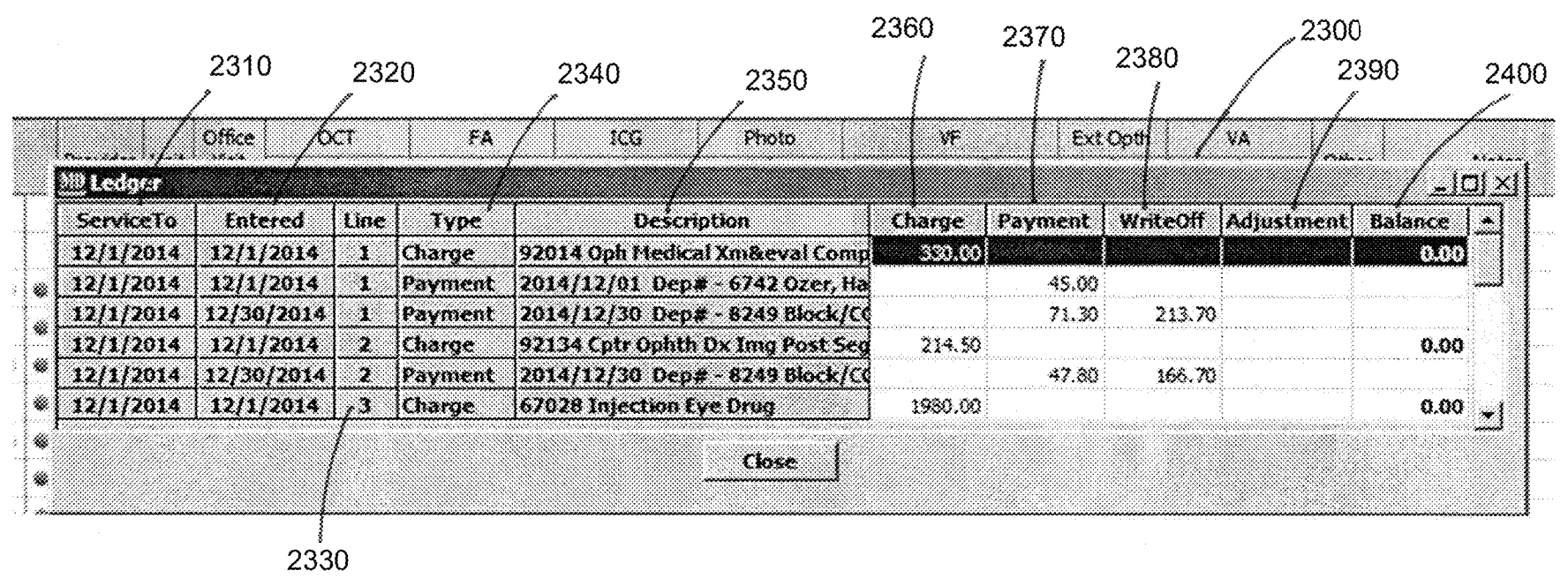

In some embodiments, one or more of the icons of the payment indicator column 2200 can be accessed by the user to initiate the command center visual display system and method displaying more detailed financial information. An example embodiments is illustrated in FIG. 13B illustrating a ledger window 2300 accessible from the medical record dashboard 2100 of FIG. 13A. In some embodiments, the command center visual display system and method can display the ledger window 2300 overlaid onto the medical record dashboard 2100. In other embodiments, the ledger window 2300 can be displayed in place of the medical record dashboard 2100. In other embodiments, the ledger window 2300 can be displayed with the medical record dashboard 2100.

In some embodiments, the ledger window 2300 can include information processed by the command center visual display system and method including information related to the date of procedure, description of the procedure, dates entered, a charge type, etc. For example, in some embodiments, ledger window 2300 can include the service to column 2310, entered column 2320, line column 2330, type column 2340, and description column 2350. Further, in some embodiments, the ledger window 2300 can include information related to payments and billing. For example, in some embodiments, the ledger window 2300 can include a display of a charge column 2360, payment column 2370, write-off column 2380, adjustment column 2390, and a balance column 2400. In some embodiments, the user can close the ledger window 2300 and return to the medical record dashboard 2100 at any time. In other embodiments, more than one ledger window 2300 can be displayed based on selections made by the user in the medical record dashboard 2100.

Figure 14:
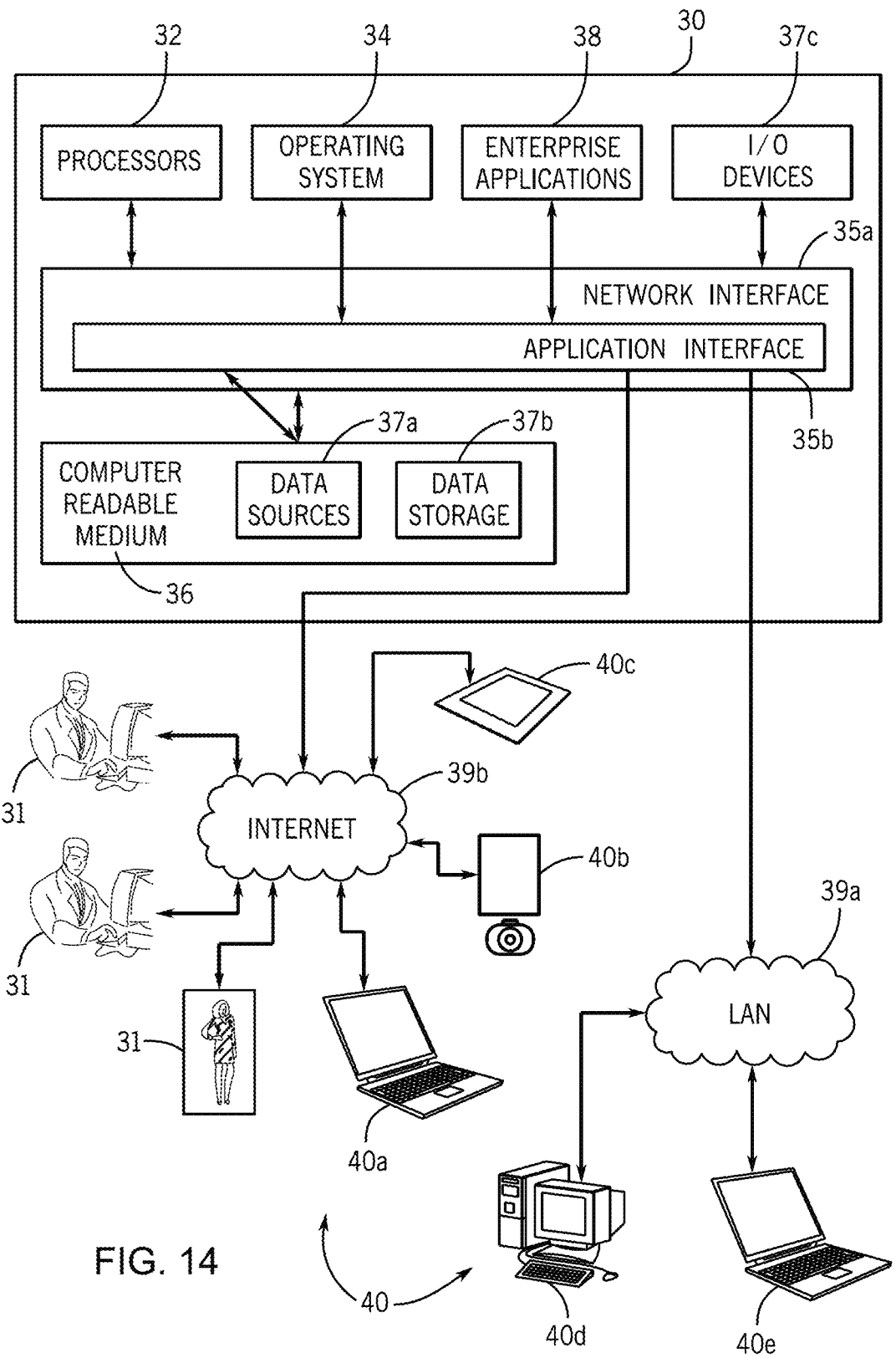
FIG. 14 illustrates a computer server system configured for operating and processing components of the data command center visual display system and method in accordance with the first embodiment of the invention.

FIG. 14 illustrates a computer system 30 configured for operating and processing components of the command center visual display system and method in accordance with some embodiments of the invention. In some embodiments, the computer system 30 can process one or more software modules of the aforementioned command center visual display system and method and display information related to medical services within at least one graphical user interface. Further, in some embodiments, using the computer system 30, the command center visual display system and method can manage the organization of data and data flow between the various components of the command center visual display system and method. For example, in some embodiments, the computer system 30 can be configured to process and display the medical record dashboard 400 and/or the medical record dashboard 1600. Further, in some embodiments, the computer system 30 can be configured to process and display auto-populated data within any portion of the medical record dashboards 400, 1600, including, but not limited to the command center visual display window 500 and/or the command center visual display window 1700.

In some embodiments, the system 30 can include at least one computing device, including one or more processors 32. Some processors 32 can include processors 32 residing in one or more conventional server platforms. The system 30 can include a network interface 35*a* and an application interface 35*b* coupled to at least one processors 32 capable of running at least one operating system 34. Further, the system 30 can include a network interface 35*a* and an application interface 35*b* coupled to at least one processor 32 capable of running one or more of the software modules (e.g., enterprise applications 38). Some embodiments of the invention also relate to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data are obtained over a network the data can be processed by other computers on the network, e.g. a cloud of computing resources.

With the above embodiments in mind, it should be understood that the invention can employ various computer-implemented operations involving command center visual display data stored in computer systems. Moreover, the above-described databases and models can store analytical models and other data on computer-readable storage media within the system 30 and on computer-readable storage media coupled to the system 30. In addition, the above-described applications of the command center visual display system can be stored on computer-readable storage media within the system 30 and on computer-readable storage media coupled to the system 30. These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated.

Some embodiments include the system 30 comprising at least one computer readable medium 36 coupled to at least one data storage device 37*b*, and/or at least one data source 37*a*, and/or at least one input/output device 37*c*. In some embodiments, the invention embodied by the command center visual display system can also be embodied as computer readable code on a computer readable medium 36. The computer readable medium 36 can be any data storage device excluding a modulated electrical signal that can store data, which can thereafter be read by a computer system (such as the system 30). Examples of the computer readable medium 36 can include hard drives, network attached storage (NAS), read-only memory, random-access memory, FLASH based memory, CD-ROMs, CD-Rs, CD-RWs, DVDs, magnetic tapes, other optical and non-optical data storage devices, or any other physical or material medium which can be used to tangibly store the desired information or data or instructions and which can be accessed by a computer or processor (including processors 32).

In some embodiments of the invention, the computer readable medium 36 can also be distributed over a conventional computer network via the network interface 35*a* so that the command center visual display system embodied by the computer readable code can be stored and executed in a distributed fashion. For example, in some embodiments, one or more components of the system 30 can be tethered to send and/or receive data through a local area network ("LAN") 39*a*. In some further embodiments, one or more components of the system 30 can be untethered to send or receive data through an internet 39*b* (e.g., a wireless internet). In some embodiments, at least one software application 38 running on one or more processors 32 can be configured to be coupled for communication over a network 39*a*, 39*b*. In some embodiments, one or more components of the network 39*a*, 39*b* can include one or more resources for data storage, including any other form of computer readable media beyond the media 36 for storing information and including any form of computer readable media for communicating information from one electronic device to another electronic device.

In some embodiments, the network 39*a*, 39*b* can include wide area networks ("WAN"), direct connections (e.g., through a universal serial bus port) or other forms of computer-readable media 36, or any combination thereof. Further, in some embodiments, one or more components of the network 39*a*, 39*b* can include a number of client devices which can be personal computers 40 including for example desktop computers 40*d*, laptop computers 40*a*, 40*e*, digital assistants and/or personal digital assistants (shown as 40*c*), cellular phones or mobile phones or smart phones (shown as 40*b*), or smart watch, pagers, digital tablets, internet appliances, and other processor-based devices. In general, a client device can be any type of external or internal devices such as a mouse, a CD-ROM, DVD, a keyboard, a display, or other input or output devices 37*c*. In some embodiments the display can be a heads-up or virtual display, such as a HoloLens available from Microsoft, that can only be seen by the user. In some embodiments, various other forms of computer-readable media 36 can transmit or carry instructions to a computer 40, including a router, private or public network, or other transmission device or channel, both wired and wireless. The software modules 38 can be configured to send and receive data from a database (e.g., from a computer readable medium 36 including data sources 37*a* and data storage 37*b* that can comprise a database), and data can be received by the software modules 38 from at least one other source. For example, as described earlier, in some embodiments of the invention, using the system 30, the command center visual display system and method can be configured to receive one or more CCD from one or more medical providers for display to the user 31. In some embodiments of the invention the command center visual display system and method can be configured to receive HL7 messages and or use Application Programming Interfaces (APIs) to send and receive data. Further, in some embodiments, patient data can be retrieved from one or more master patient index databases (e.g. a master patient database managed by a government entity and/or a third party provider such as insurance company or collective of insurance companies). In some further embodiments, data can be retrieved from the national register of drugs and pharmaceuticals. In some further embodiments, data can be retrieved from health information exchanges.

In some embodiments, at least one of the software modules 38 can be configured within the system 30 to output data to at least one user 31 via at least one digital display (e.g., to a computer 40 comprising a digital display). In some embodiments, the system 30 as described can enable one or more users 31 to receive, analyze, input, modify, create and send data to and from the system 30, including to and from one or more enterprise applications 38 running on the system 30. Some embodiments include at least one user 31 coupled to a computer 40 accessing one or more modules of the command center visual display system including at least one enterprise applications 38 via a stationary I/O device 37*c* through a LAN 39*a* or via a wireless connection. In some other embodiments, the system 30 can enable at least one user 31 (through computer 40) accessing enterprise applications 38 via a stationary or mobile I/O device 37*c* through an internet 39*a*.

In some embodiments, the software modules 38 can include a server-based software platform that can include command center visual display software modules suitable for hosting at least one user 31 account and at least one patient account or record. Further, some embodiments of invention includes the software modules 38 that can include at least one server-based software platform that can include command center visual display software modules suitable for hosting at least at least one patient account or record. In some embodiments, using the system 30, the command center visual display system and method can manage multiple user accounts and/or multiple patient accounts. In some embodiments, the software modules 38 can include a server-based software platform that can include command center visual display software modules suitable for hosting a plurality of user accounts accessible by multiple medical practitioners (e.g., physicians, surgeons, optometrists, ophthalmologists, podiatrists, dentists, etc.) In some embodiments of the invention, patient accounts can be accessible by the patient's medical practitioner and not shared with other medical practitioners holding one or more user accounts within the command center visual display system and method. In some further embodiments, one or more patient accounts can be accessible and shared by a user 31 associated with the patient account. For example, in some embodiments, a user 31 can grant access to at least one other user of the command center visual display system and method. In some embodiments, shared access can be at least partially restricted. For example, in some embodiments, shared access can be restricted to viewing at least a portion of the shared patient's account or record.

Second Embodiment of Data Command Center

Figure 15:
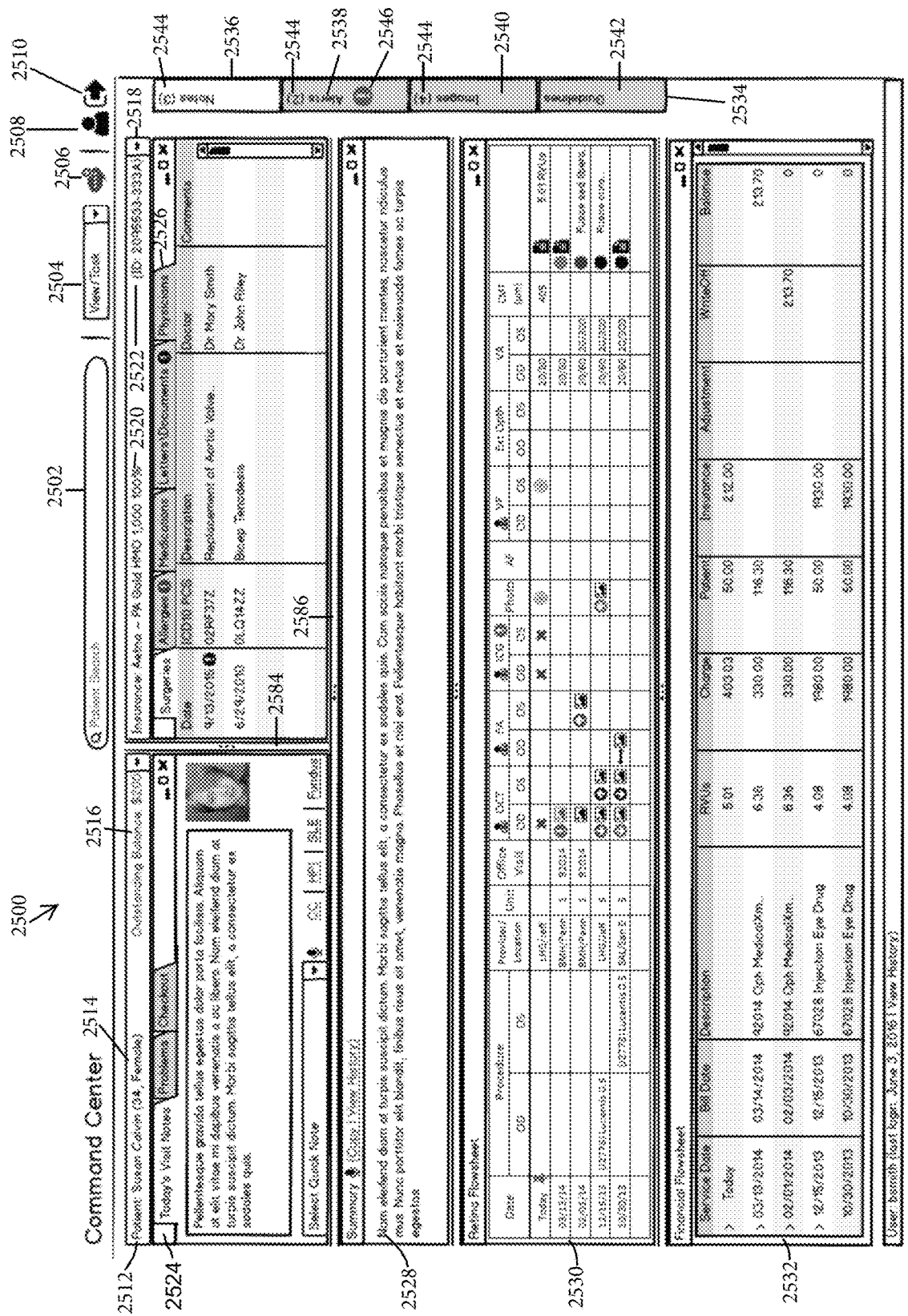
FIG. 15 illustrates an exemplary embodiment of a Data Command Center for use with an EMR system customized for an Ophthalmology Retina practice in accordance with a second embodiment of the invention.

FIG. 15 illustrates another embodiment of a Data Command Center (CC) 2500 implemented as a data interface to a medical record system useful for deploying or launching a second set of embodiments of the invention. The CC 2500 in the exemplary embodiment is designed to interact with a conventional EMR system although, as noted above, the CC 2500 may be used with other large data systems to present data to users in a meaningful way. In addition, the exemplary embodiment illustrates a CC 2500 for implementation in an Ophthalmology practice. Those skilled in the art will appreciate that the interface may be readily configured for other medical specialties. Indeed, one of the key features of the CC 2500 described herein is its flexibility to display data from multiple data sources in multiple different panels on a single interface. In the exemplary embodiment, the CC 2500 provides a comprehensive overview of the patient's clinical and financial history as well as providing a means to quickly order tests while retaining the ability to see previous medical history. Clinical and insurance guidelines as well as preferred practices are quickly accessible based on the patient's conditions, medications and procedures so that the physician may readily provide optimal care and be compliant with medical and billing requirements. The physician thus becomes a part of revenue cycle management for each patient in the physician's practice.

It will be appreciated by those skilled in the art that specific features of the first embodiment described above may also be included in the second embodiment, and vice-versa, and the descriptions of the features of the first embodiment above are incorporated into the following description by reference. For example, like the first embodiment described above, the Data Command Center 2500 described with respect to FIGS. 15-56 may incorporate self-deleting staff messages that are presented to the Command Center 2500. For example, a staff person can send a message about a patient to the physician that appears in a display window in the Command Center 2500 with a message such as "the patient has been waiting over an hour and is upset" or the "patient has previously filed a malpractice complaint" that do not become part of the patient's medical record. The message may be programmed to be deleted once the patient's visit is billed.

FIG. 15 illustrates an exemplary embodiment of a Data Command Center (CC) 2500 for use with an EMR system customized for an Ophthalmology practice. As illustrated, across the top of the page the user has the ability to search for patients at 2502, select different views of the data at 2504, add sticky notes at 2506, access user information at 2508, and logout at 2510. Immediately below that on the upper left-hand side of the CC 2500 is the Patient Information Bar 2512, which contains the patient's identifying information 2514 so the user knows they are looking at the correct patient record. The Patient Information Bar 2512 also notifies the user of patient's outstanding balance 2516. To the right of the Patient Information Bar 2512 is the Patient Insurance Bar 2518, which provides the patient's insurance information 2520, including the ID number 2522 for the patient's primary insurance. Below the Patient Information Bar 2512 is a collection of tabs 2524 displaying different sets of information about the selected patient. A different collection of tabs 2526 is found underneath the Patient Insurance Bar 2518. Under tabs 2524 is the Summary panel 2528 where the user can enter notes about the patient (e.g. patient did not show up for missed appointments). The next section, the Retina Flowsheet 2530, is an encounter driven panel that summarizes key clinical and financial information in chronological or reverse chronological order at a glance, allows the user to order new Procedures and Imaging tests, and provides assistance complying with insurance regulations, as will be described in more detail below. Below the Retina Flowsheet 2530 is the Financial Flowsheet 2532 providing a summary of the financial information related to the patient and this is adapted to provide the user with the ability to drill down into individual transactions. On the right side of the CC 2500 are a series of vertical tabs 2534 that when individually clicked slide out to provide more information to the user. The Notes Tab 2536 expands to display patient notes, while the Alerts Tab 2538 expands to display patient alerts (e.g. patient's chart was requested by insurance company or sent for a second opinion). The Images Tab 2540 expands to display images for the patient and the Guidelines Tab 2542 expands to display clinical practice and insurance guidelines along with preferred practice patterns where applicable. On each tab, displayed next to the tab title is the count of the new items 2544 since the last time the user accessed the patient record. Once the tab is expanded, the new count may be removed because the user has seen the information. If important or critical data exists within the tab, a special alert icon 2546 is displayed on the tab. Once viewed, the alert icon 2546 is removed. As will become apparent from the following description, the layout of the CC 2500 permits access by the user to all of the relevant information within one click of the mouse and without having to steer to other screens that would take the user away from the CC 2500. For example, the information is either available in a display window, behind a tab, or available via a pop-up window; accordingly, the user does not have to leave the display screen to access the information.

Figure 16:
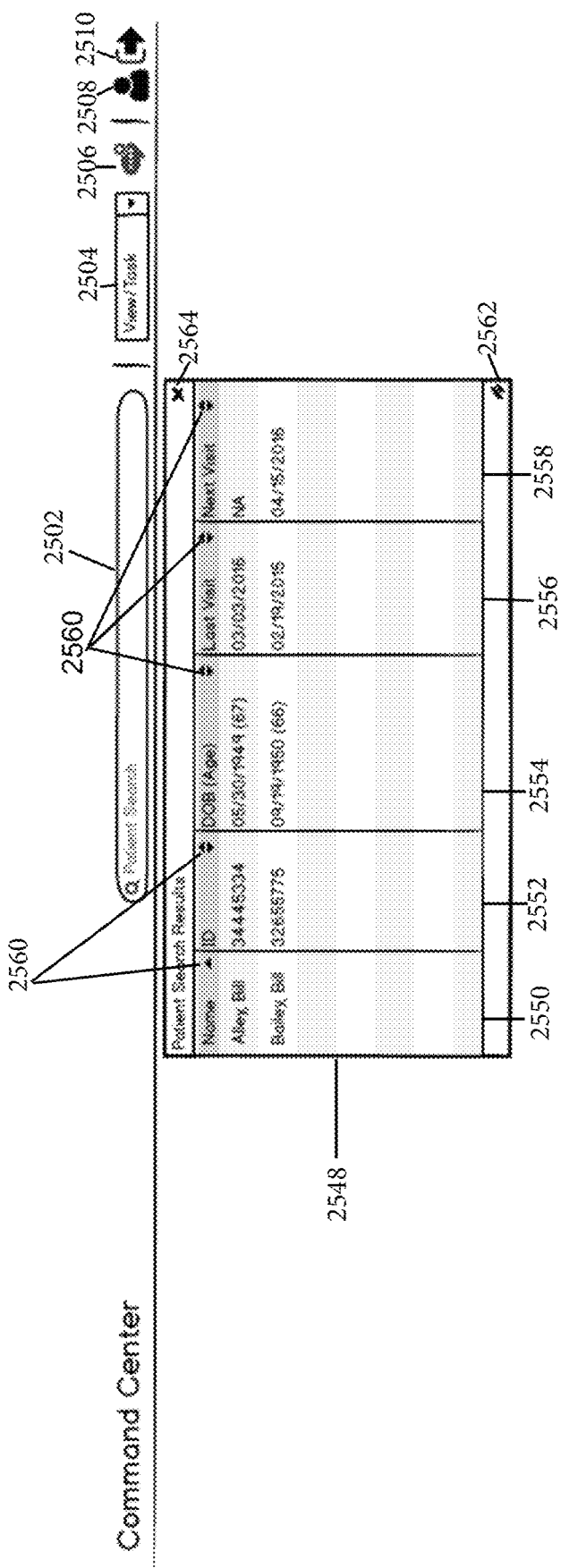
FIG. 16 illustrates the search results of a patient search input into the patient search field in accordance with the second embodiment of the invention.

FIG. 16 illustrates the search results 2548 of a patient search input into the patient search field 2502. To search for a patient, the user types in the Patient Search field 2502. After the user types the third character in the field, the search results 2548 appear matching the criteria. As the user enters additional characters, the search results are refreshed. The search criteria looks for any patients where the sequential string of characters entered matches the same sequential string of characters in either the patient's first or last name. For example, entering 'sam' matches Sammy Smith, Isamra Turek, Bill Samson, Michelle Bosam, but not Silas Amhearst. In an exemplary embodiment, the results 2548 display the following fields: Name 2550 (Last, First), Patient ID 2552, Date of Birth and age 2554, Last Visit (Date) 2556, and Next Visit (Date) 2558 if scheduled. The results are sorted alphabetically by last name, then first name, followed by date of birth, but the user can change the search order by clicking the sort icons 2560 at the top of each column. This sorting capability is available through the Command Center 2500 when viewing lists. The user may select a patient by clicking on the row in the results list 2548. When a patient is selected, the results panel 2548 closes and the patient record is retrieved. The user may control the size of the panel by clicking and holding the icon 2562 in the bottom right of the panel 2548. The user can close the results panel 2548 by clicking the close icon 2564.

Figure 17:
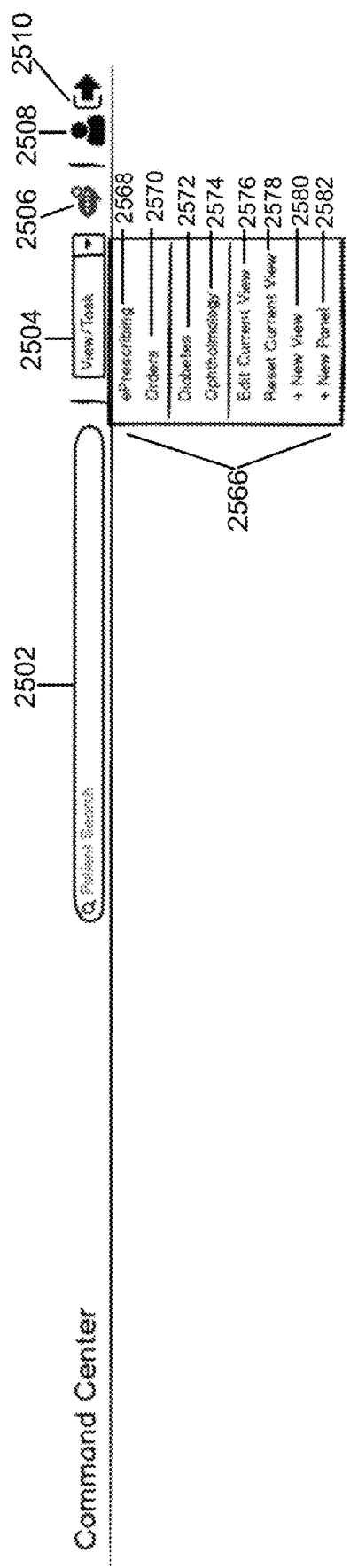
FIG. 17 illustrates a user control panel that displays views for selection by the user in accordance with the second embodiment of the invention.

A key feature of the Command Center 2500 is that it allows the user to control the layout of the screen and to create different views or layouts of the information based on their needs. FIG. 17 illustrates a user View control panel 2566 that displays views for selection by the user. As illustrated, the user may select one of several Views 2568-2574. Views ePrescribing 2568 and Orders 2570 are examples of task based views, while Diabetes 2572 and Ophthalmology 2574 are examples of condition or specialty specific views. In an exemplary embodiment, the system has several pre-configured views but more can be added over time by deploying new versions of the system or by user modification. The user may edit the Current View 2576, Reset the Current View 2578 to its default configuration, create a new View 2580, or create a new Panel 2582. If the user selects a new view from options 2568-2574, the screen layout is changed to reflect the selected view for the current patient. Referring back to FIG. 15, it should be noted the dimensions of the different panels can be resized by changing the location of the vertical sliders 2584 and horizontal sliders 2586. This allows the user to control how much real estate (space/area) on the screen is used for each panel. As the user adjusts the sliders 2584 and 2586, the dimensions are remembered so when the user returns to the view at a later time the system remembers the dimensions. The user also can reset the view to its default dimensions by clicking the Reset Current View 2578 option in the view control panel 2566. The entire view also resizes based on the dimensions of the user's monitor and the size of the browser displaying the CC 2500.

Figure 18:
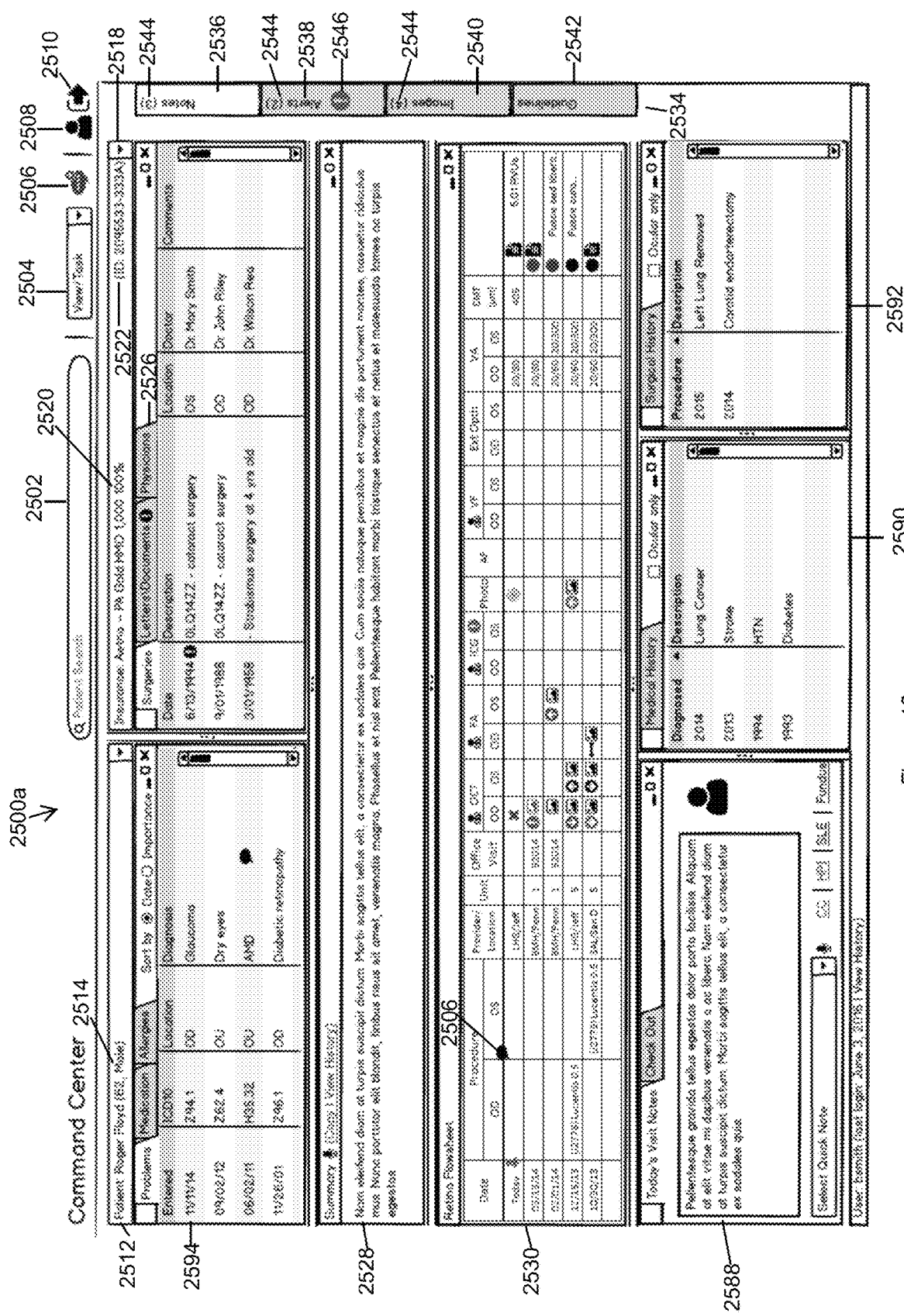
FIG. 18 is an example of a new view created by the user for their personal use in accordance with the second embodiment of the invention.

FIG. 18 is an example of a new View 2500a created by the user for their personal use. In this View 2500a, the financial flowsheet 2532 of FIG. 1 is replaced by panel 2588 for receiving today's visit notes (moved from the top left-hand side of CC 2500 in FIG. 15), a panel 2590 for illustrating the patient's medical history, and a panel 2592 for illustrating the patient's surgical history. Also, a medication panel 2594 is inserted in place of the panel for today's visit notes illustrated in FIG. 15. As described above, the user can change views by using the View Selection control 2504 at the top of the FIGS. 15 and 18.

Figure 19:
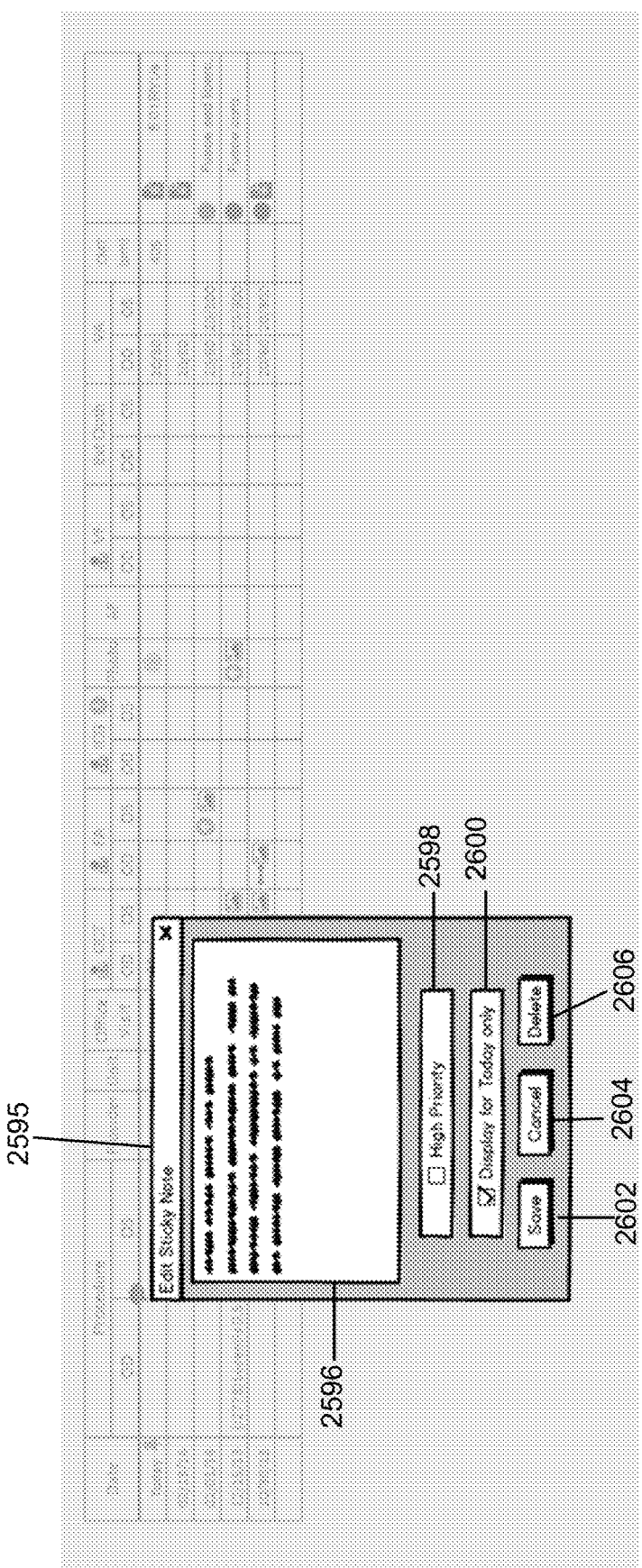
FIG. 19 illustrates the panel presented when the add sticky notes icon in FIG. 15 is selected.

FIG. 19 illustrates the panel 2595 presented when the add sticky notes icon 2506 in FIG. 15 or FIG. 18 is selected. As illustrated, the user may click and drag the icon 2506 to any location on the page and drop it where they want it placed. This allows the user to place the note in context of the information to which it refers. The icon 2506 then stays in place and is associated with dynamic data until deleted by a user or it expires based on the note settings. When the icon 2506 is placed, the Edit Sticky Note control panel 2595 is displayed. The Edit Sticky Note control panel 2595 can also be displayed if a user selects the icon 2506. Once the Edit Sticky Note control panel 2595 is opened, the user can enter a note in field 2596, select if the note is high priority 2598, select if the note should only be displayed today 2600, in which case after the date it is entered the note may no longer display. The user can save the note by clicking the Save Button 2602 or cancel the action by clicking the Cancel Button 2604. The user can delete the note by clicking the Delete button 2606 at which point the action is confirmed before deleting. When a user moves the mouse over the note icon 2506, the note text is displayed next to it in a tooltip. The note icon is colored, e.g., black if it is not high priority and, e.g., red if it is high priority or can flash or be highlighted in any other manner. A note icon 2506 is shown in context in the retina flowsheet 2530 in FIG. 18. If the note is deleted or expires, the note icon 2506 displayed on the page is removed. All deleted or expired Sticky Notes along with the location and duration where they are displayed are preserved for purposes of legal discovery but not accessible to the user as a general practice.

With reference back to FIG. 15, when the user selects the user profile icon 2508, a panel (not shown) is presented to allow the user to edit typical user information including their name, address, phone numbers, email address and password. The user can also select their preferred email or phone number or other method for communications sent by the Command Center.

When the user selects the Logout icon 2510, if any data is not saved, the user may be prompted to save data before closing the system. If the user answers positively that they want to save unsaved data, the user is not logged out. Once all data is saved, the user is prompted to confirm their desire to logout. If confirmed, the user is logged out.

The Patient Information Bar 2512 illustrated in FIG. 15 displays high level information about the patient. The user can click on the Patient Information Bar 2512 and the Patient Information Panel 2610 shown in FIG. 20 is displayed underneath the Patient Information Bar 2512. Clicking the bar a second time or anywhere else on the page may close the Patient Information Panel 2610. The Patient Information Panel 2610 contains the patient's date of birth 2612, race 2614, phone number 2616, the date when the patient was first seen 2618, the referring physician 2620, and interesting facts to remember 2622. Information in the Patient Information Panel 2610 can be edited in place by clicking on the item to be changed. When clicked, the field may change to a text field allowing the value to be changed with a Save button displayed next to it (not depicted). Clicking Save will save the data. Clicking a Cancel button (not shown) will not save the data leaving the value unchanged and the control may revert to static text. Below these fields is a Revenue Summary 2624 for the patient. The Revenue Summary 2624 displays patient totals for each year 2626 as well as grand totals 2628 for the total amount billed 2630, amount paid by insurance 2632, amount paid by the patient 2634, amount written off 2636, and the adjustments 2638 for each year.

Figure 21:
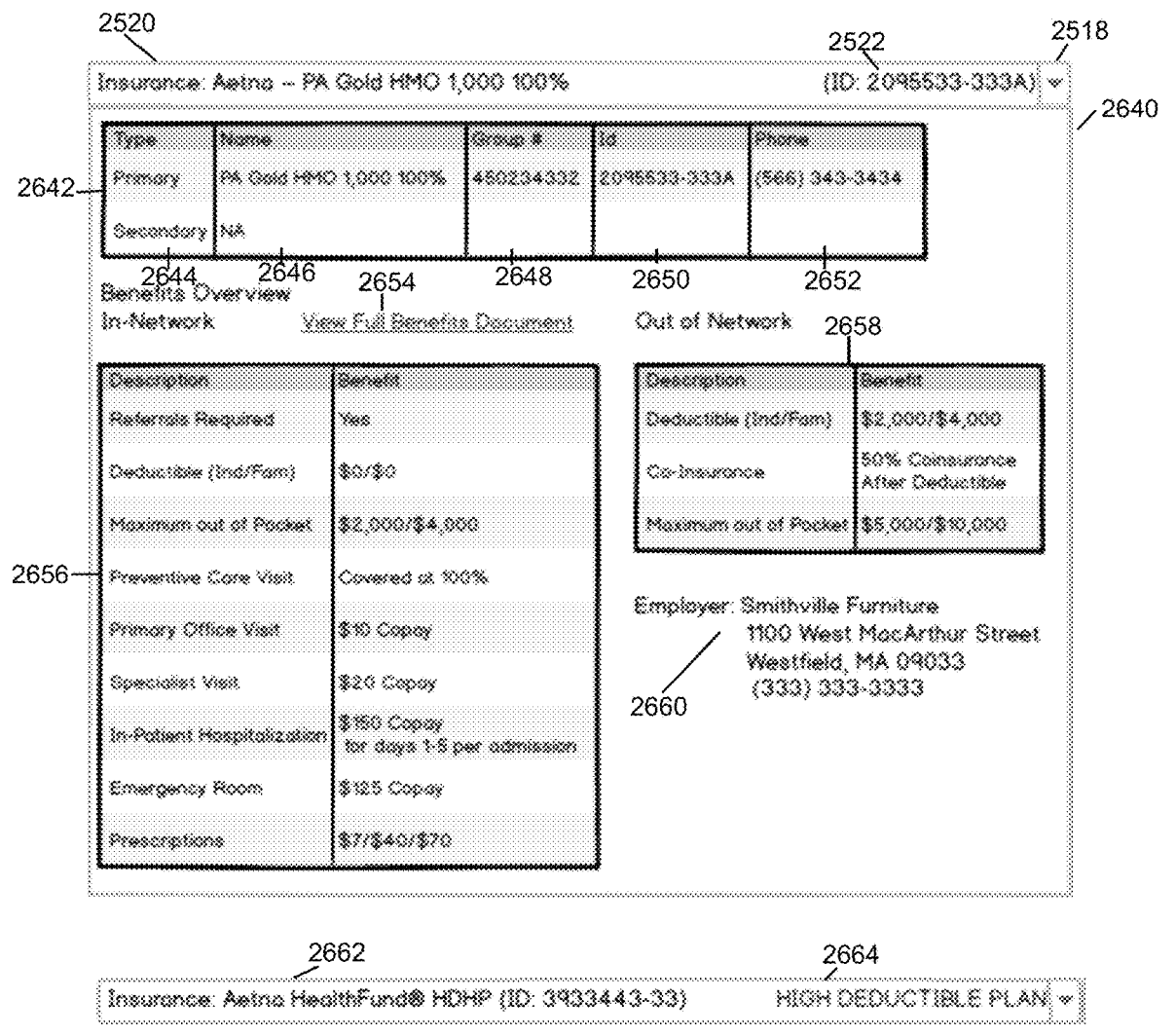

To the right of the Patient Information Bar 2512 in FIG. 15 is the Patient Insurance Bar 2518. The user can click on the bar and the Patient Insurance Panel 2640 illustrated FIG. 21 is displayed underneath the Patient Insurance Bar 2518. Clicking the Patient Insurance Bar 2518 a second time or anywhere else on the page may close the Patient Insurance Panel 2640. The Patient Insurance Panel 2640 contains information about the patient's insurance 2642 including the type 2644, name 2646, group number 2648, insurance ID number 2650, and phone number 2652 for each insurance company. A link to the patient's benefit document 2654 is provided as well as an overview of the patient's in-network benefits 2656 and out of network benefits 2658 as provided by the patient's insurance company. The values illustrated as 2656 and 2658 are provided for example purposes and may vary based on the data provided by insurance companies. The patient's employer's address and contact information 2660 is also displayed for convenience. Item 2662 displays an alternative embodiment of the Patient Insurance Bar 2520. In this case, the patient has a high deductible plan and this fact is displayed at 2664 in red in the Patient Insurance Bar 2520 to be sure the physician is aware that, in this case, the patient has a high deductible plan.

Figure 22:
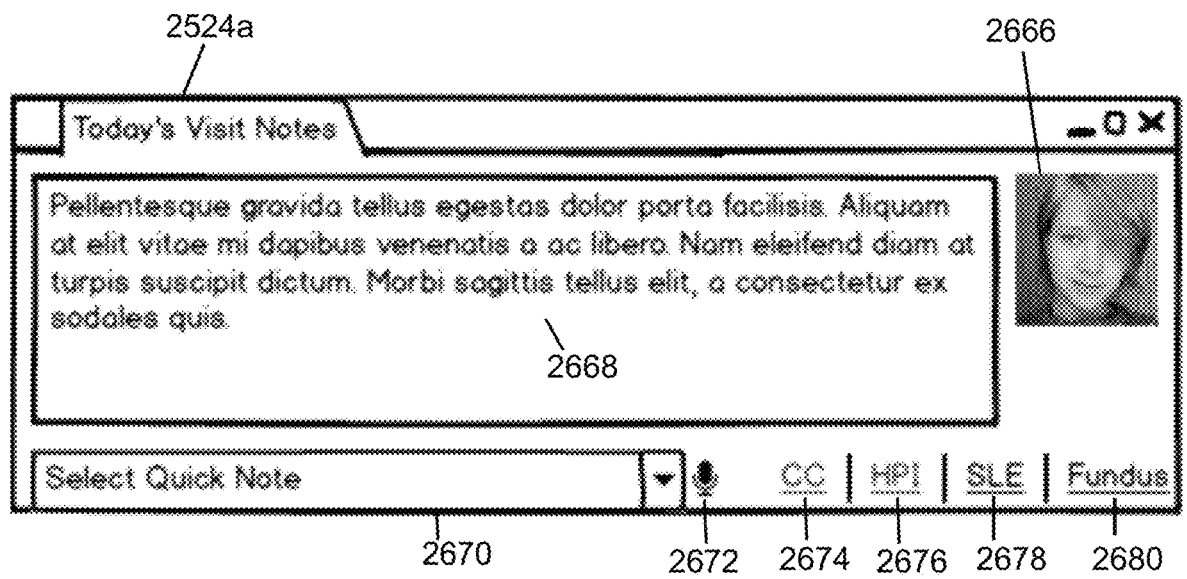
FIG. 22 illustrates Today's Visit Notes tab containing elements related to capturing information about notes specific to today's visit in accordance with the second embodiment of the invention.

Today's Visit Notes tab 2524a as illustrated in FIG. 22 contains elements related to capturing information about notes specific to today's visit. The tab 2524 contains a photo 2666 of the patient, free form text notes 2668, a control allowing the user to select pre-configured notes 2670, an icon 2672 that triggers a dictation feature allowing text entry into free form text notes 2668 via voice recognition, and a set of links 2674-2680 that are reminders to complete important aspects of an encounter in the EMR. The patient image 2666 is imported from the EMR and text notes 2668 can also be imported from the EMR through the Command Center CCOW Implementation described below. Items 2674-2680 display the status of the chief compliant (CC) 2674, history of present illness (HPI) 2676, slit lamp exam (SLE) 2678, and Fundus photograph 2680. This status is also provided to the Command Center via the CCOW implementation. Items 2674-2680 are displayed in red until complete at which time they are displayed in black. Based on EMR access and functionality, items 2674-2680 are links back to the specific area in the EMR. In an exemplary embodiment, the physician may dictate or type notes into the Today's Visit Notes tab 2524a that automatically generates a letter to a referring physician or another physician alerting that physician about something important in the patient's medical history. Beneficially, the referring letter may be generated while the patient's medical history is on the display screen in the Command Center interface.

The Problems tab 2524b as illustrated in FIG. 23 displays a patient's problem list as imported from the EMR. The following fields are displayed in this embodiment but can be configured to display other fields: date entered 2682, associated ICD10 code 2684, body location 2686, and diagnosis 2688. The user can manually order the list in order of severity or importance by clicking and dragging the rows. Sort by Date 2690 sorts the list in reverse chronological order and Sort by Importance 2692 sorts the list using the user's manual ordering. If the user has not adjusted the order of Problems, it may display in reverse chronological order. The default sort order is by Date 2690, but the user's last selection is remembered and automatically selected when the user returns to the application. The Sticky Note icon 2506 is another example of how a Sticky Note can be dropped anywhere on the page as previously seen in FIG. 18.

Figure 24:
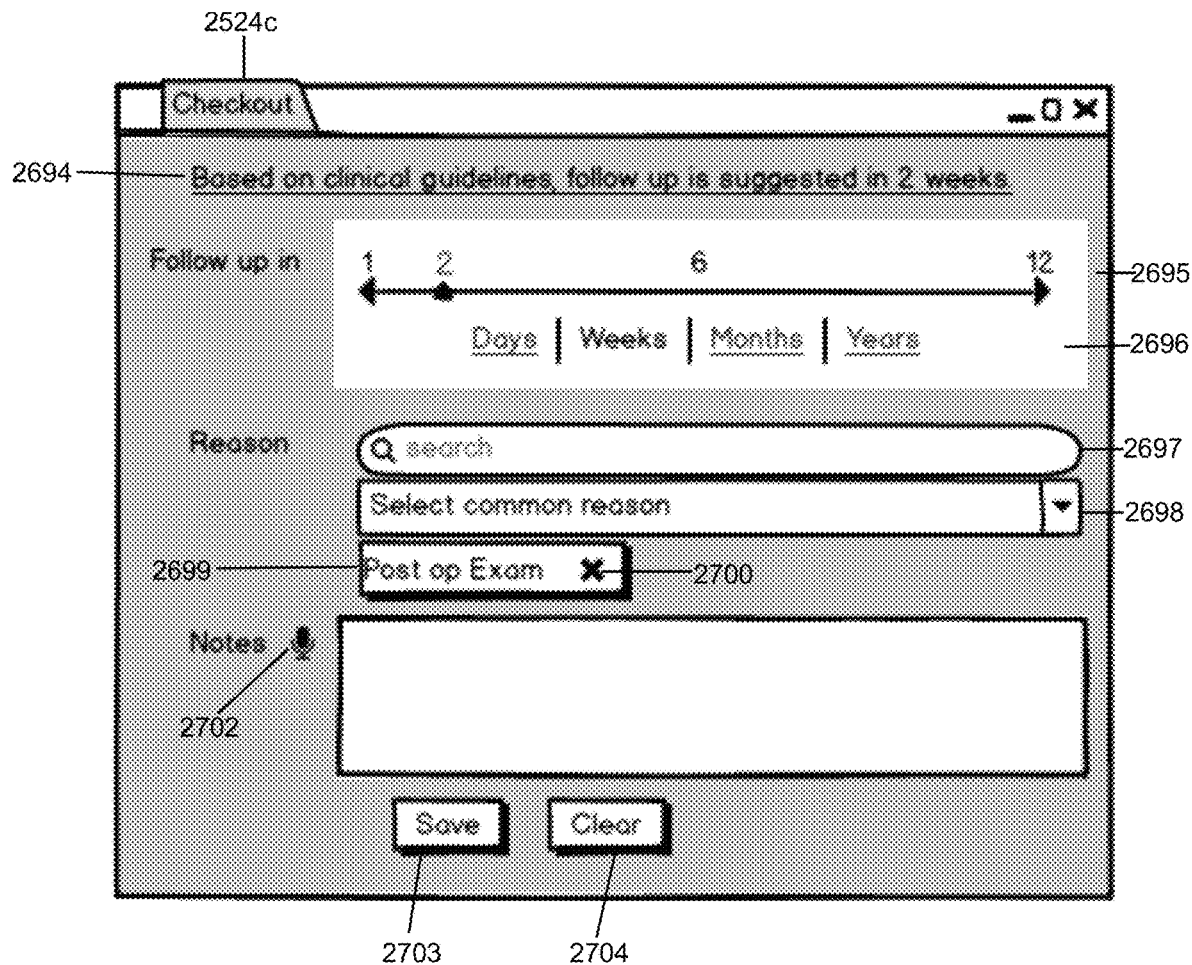
FIG. 24 illustrates the Checkout tab that is used to determine when a patient should return to the practice in accordance with the second embodiment of the invention.

The Checkout tab 2524c as illustrated in FIG. 24 is used to determine when a patient should return to the practice. This can also be used for a return visit to a shared physician's office which would then also in some embodiments populate a shared care medical table (FIG. 25A) that can be given to a patient for a future reminder of appointment. The Checkout tab 2524c displays the recommended clinical guideline 2694 based on the Command Center's Clinical Decision Support algorithms. The follow up timeframe 2695, 2696 is defaulted to the recommendation but can be overridden by the user. The user selects a count 2695 and a period 2696 to generate a time period in which the patient should return. The user can search for a reason using the search field 2697 or select a common reason 2698 from the control. The search feature 2697 implements basic type-ahead, search and results listing allowing the user to select an item. In the case of either the search 2697 or drop down 2698 the selected item is listed underneath at 2699. The user has the ability to delete the item by clicking the associated delete icon 2700. The user can also enter a free form text note 2701 or use dictation by selecting icon 2702. When complete, the user may click the Save button 2703 to save the Checkout information and send it to the EMR or clear the information by clicking the Clear button 2704.

Figure 25:
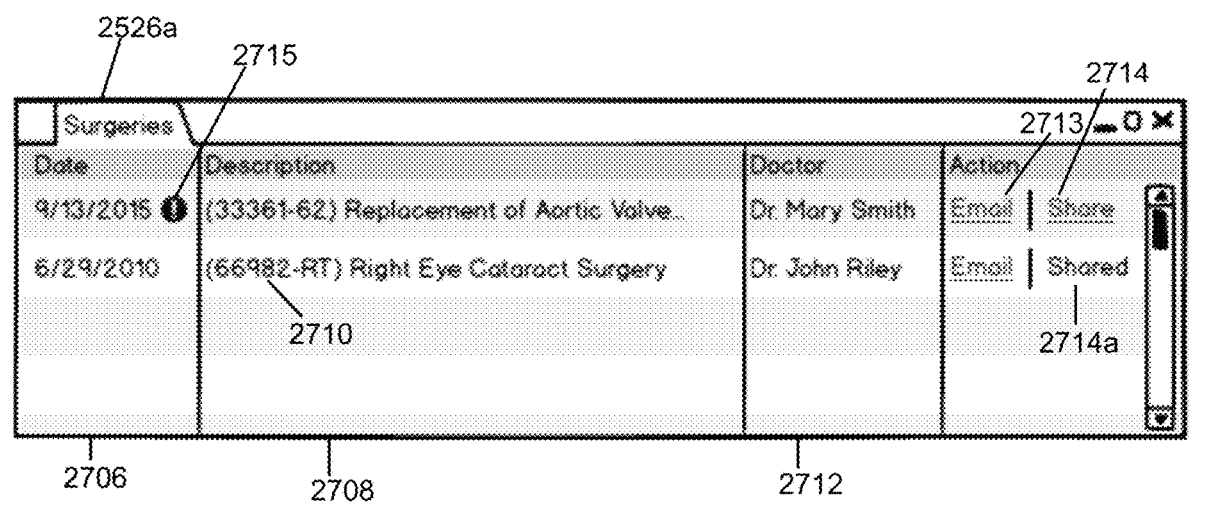

The Surgeries tab 2526a as illustrated in FIG. 25 displays information about the patient's surgeries. The Surgeries tab 2526a displays the date of surgery 2706, the description 2708 including the billing (ICD10) code 2710, the primary physician 2712, and several actions including the ability to email 2713 or share 2714 the patient record with another physician. The shared notation 2714a signifies that the patient record has already been shared with the other physician. A notes column (not shown) displays the first few characters or words based on available space of an associated note. Moving the mouse over the specific note displays it in a pop up. In the case of some surgeries, a hospital or physician may not be paid if readmitted in 30 days. In these cases, if a surgery has been performed in the last 30 days a black circle with an exclamation point 2715 may be displayed next to the date. Moving the mouse over the icon displays a message stating how many days are left until the patient can be readmitted. An associated note 2506 (FIG. 18) may also indicate that the patient is participating in a capitated plan where anything the physician orders for the patient may not be reimbursed.

When a patient record is shared with another medical professional, if the professional does not have access to the Command Center 2500, the other medical professional may receive an email to register for access to the Command Center 2500 (not depicted). If the professional does have an account but a new patient is being shared, the physician may receive an email notification. The new external user may only have access to the specific patients that are shared. Such sharing of patient medical records amongst the patient's physicians better enables the physicians to work together to follow preferred practice patterns for patient treatment as may be required by insurance companies and/or the government. This process is particularly helpful for managing patients with certain chronic diseases like diabetes where a nephrologist, podiatrist, ophthalmologist, endocrinologist, and family physician need to see each other's results. Another example is shared care before and after cataract surgery where optometrists and ophthalmologist need to see each other's results. Another example is shared care before and after cataract surgery where optometrists and ophthalmologist need to see each other's results.

Figure 25A:
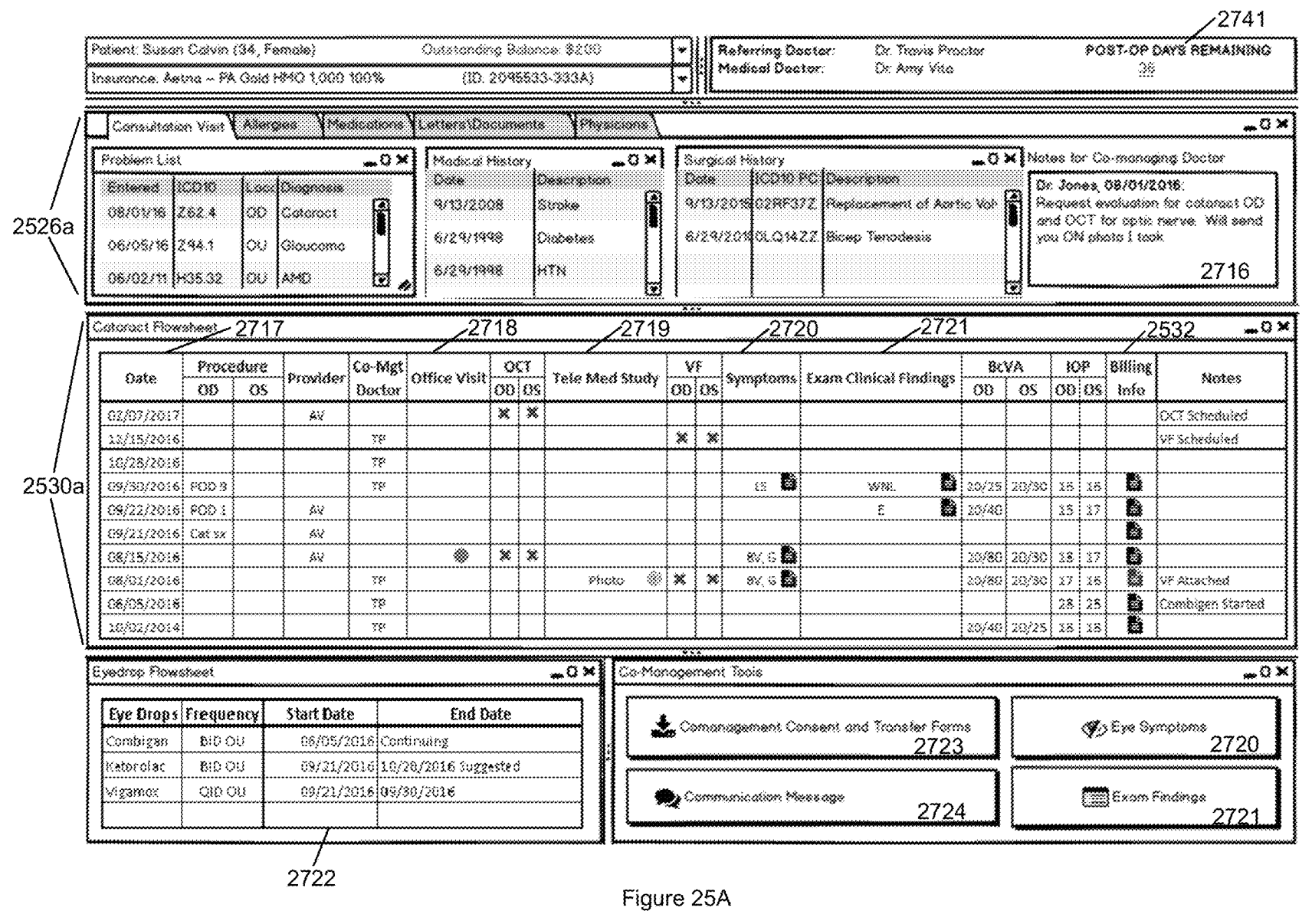
Figure 25B:
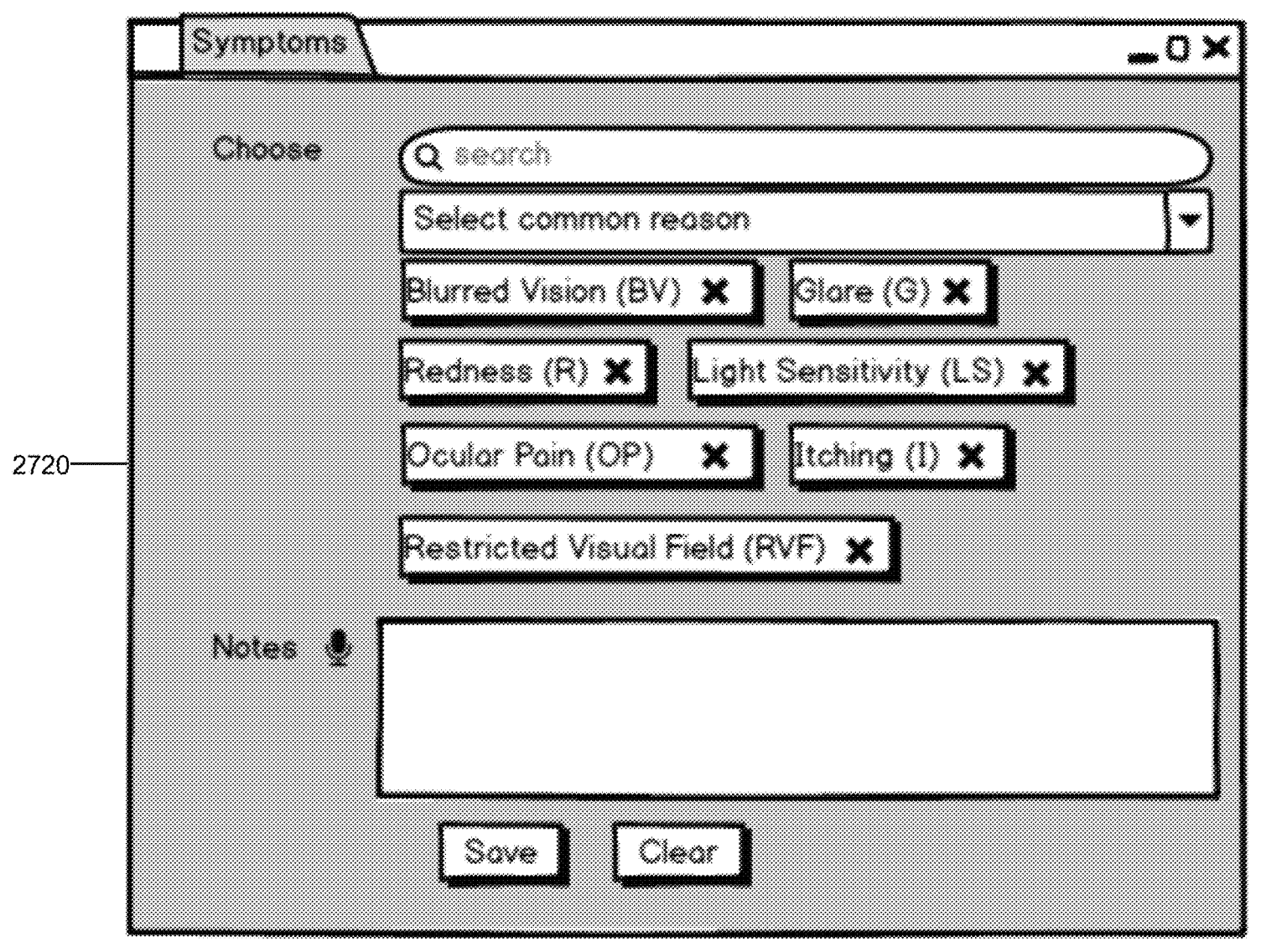
Figure 25D:
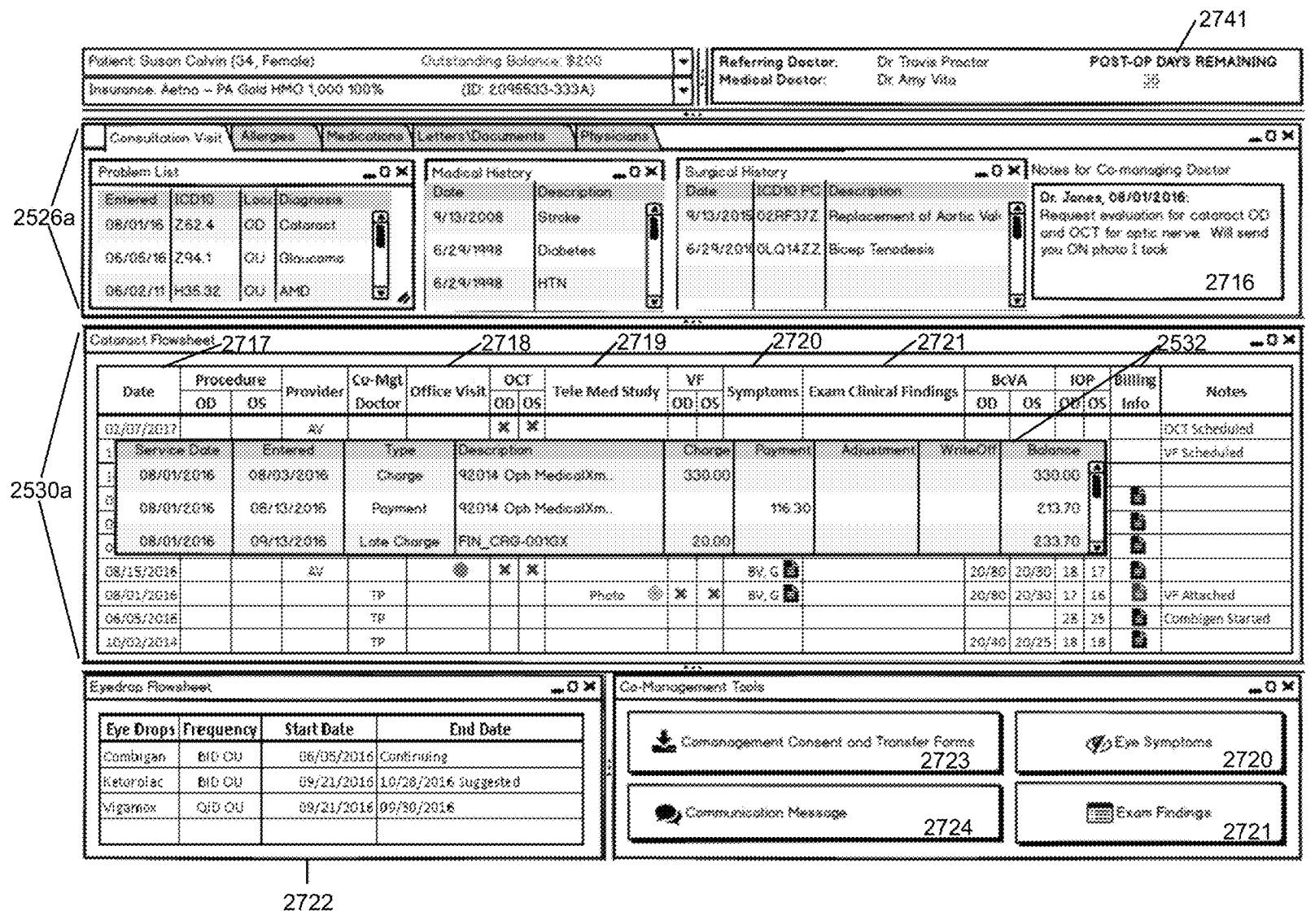

FIG. 25A presents an embodiment of a co-managed patient record in the Data Command Center (CC). In this example, an optometrist and an ophthalmologist share (co-manage) a patient's cataract surgery then share treatment of the patient's glaucoma. A notes field 2716 in the Consultation Visit display panel 2526a presents a mechanism to facilitate contextual content surrounding the co-managed procedure(s). A Cataract Flowsheet 2530a (purpose optimized dynamic panel) is presented with structured data elements designed to facilitate the identified procedure as conducted by multiple care givers. The Cataract Flowsheet 2530a is arranged by interaction dates 2717 and tracks office visits 2718 (both scheduled and realized) including sending reminders to patients and alerts when an appointment is missed (not shown), provides means to review and issue concurrence or dissent with diagnostic tests 2719, a summary of symptoms 2720 (clicking opens FIG. 25B), and a summary of exam findings 2721 (clicking opens FIG. 25C). Where available, billing summaries 2532 are presented in the Cataract Flowsheet 2530a as well. Clicking the billing summary 2532 may open a new billing window such as that illustrated in FIG. 25D to show billing details and the correct modifier at 2532. Eye drops after cataract surgery and/or glaucoma treatment is tracked on the Eye Drop Flowsheet 2722 (another purpose optimized dynamic panel). There is panel of co-management tools that provide the user with a means to download relevant forms 2723, and to send direct messages to the co-managing physician using button 2724 to access a co-management message center. An indication of the number of postop days remaining 2741 may also be provided. All financial data in the system, including costs to patient, is compartmentalized such that no user may see financial details for users or organizations not authorized in accordance with applicable policies and law.

To co-manage a patient using the interface embodiment illustrated in FIG. 25A, when a referring physician outside the practice wants a consultation, he or she can connect to the practice they are referring to and send information by opening the Cataract Flowsheet 2530a. The referring physician may manually insert or auto-populate information from any previous visit of the patient, and provide an annotation 2717 giving the reason for the consultation. When the receiving consultation physician examines the patient, the Cataract Flowsheet 2520a is auto-populated with the physician's findings. Co-management forms can be downloaded from the table at 2718 either at the time of the referral or after the consulting physician fills out the paperwork and the patient signs a consent form by selecting co-management forms or by visiting the referring physician's website. A message is sent to the referring physician to open the Cataract Flowsheet 2530a and the consent or other forms can be clicked upon and the referring physician can read or sign any forms needed. The "co-management consent" can change color or be distinguished in some other fashion when received back from referring physician. Every time the surgeon sees the patient, the Cataract Flowsheet 2530a automatically includes the date and findings. Then, post-operatively the co-managing physician, consultation physician or optometrist, when they see the patient in their office, auto-populates or fills out on the Cataract Flowsheet 2530a and shares any results.

The headers in the table in FIG. 25A may be selected to generate drop down menus for communicating results between the consulting physicians. For example, symptoms 2722 may be selected so that the surgeon can determine if there are new symptoms (FIG. 25B) or exam clinical findings 2723 may be selected so that the surgeon can determine if there are any new exam findings (FIG. 25C). In co-managing situations where one office does a diagnostic test but wants to share it with another office, instantly through telemedicine or other methods, including if the physician wants to fax the report or scan it to the EMR of the other physician, a report (e.g., "telemedicine study") 2721 may be selected for a demonstration of the diagnostic tests performed elsewhere. By selecting telemedicine study 2721, the surgeon/consulting physician can review the diagnostic tests and then send a message if he or she agrees with the interpretation of the physician who performed the diagnostic test.

Notes may be communicated between the physicians by selecting "communication message" 2724 to determine if there is any information that needs to be shared for office visits. The date column 2719 and office visit column 2720 are tied together. Some of the columns are left blank until the patient actually shows up for a future visit. For instance, after a surgery or consultation, the consulting physician, just as they would normally give an appointment card to a patient can actually give a co-management medical summary table where it shows the date of the future appointment at the referring or sharing physician's office, and when that date arrives the patient is seen and everything is auto-populated so the surgeon can see the results that the co-managing physician found. The findings are auto-populated by the optometrist/referring physician/co-managing sharing physician. If the appointment date is missed, the table can link up with a missing appointment report or send an alert to the patient themselves, the surgeon, the referring physician, business managers or anyone else as appropriate.

Figure 35:
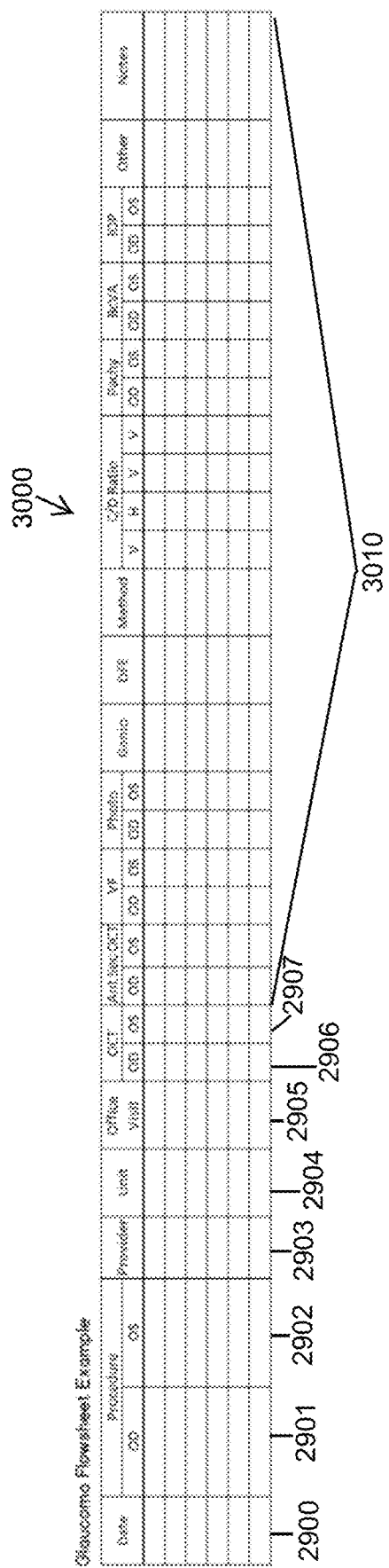
FIG. 35 illustrates a possible flowsheet for glaucoma in accordance with the second embodiment of the invention, which is similar to that presented above in FIG. 12A with respect to the first embodiment of the invention.

FIG. 25A provides an example also of how shared medical care may be provided in management of common conditions besides cataracts, such as glaucoma. An optometrist/general ophthalmologist can manage interval visits after the glaucoma specialist establishes a plan of care. For example, after initial consultation, the plan is shared with the referring or co-managing provider. At a subsequent examination, the referring provider accesses patient data, executes plan and enters the data into Cataract Flowsheet 2530a and/or a Glaucoma Flowsheet 3000 as illustrated in FIG. 35. An alert is sent to the glaucoma specialist confirming that the action plan is being carried out. This facilitates care of the patient by the plan. The glaucoma specialist can follow up every year or two while sharing interval visits with the referring optometrist/general ophthalmologist. Multiple benefits of such an arrangement include excellent care, appropriate supervision, reduced cost, improved quality of care of the patient without undue distance traveled. At any point of execution of the treatment plan, treatment can be altered based on clinical data available to the patient, glaucoma specialist as well as referring provider at all times.

Of course, other fields of medicine and industry have similar examples. For example, orthopedic surgeons share care with podiatrists and family physicians share care with all medical specialists. A prime example is shared care with multiple healthcare providers caring for a patient with a chronic disease, state such as diabetes. One patient can have an eye doctor, podiatrist, primary care doctor, endocrinologist, nephrologist, dietician, exercise physiologist, all who need to share care. Different providers may order the same or different tests. If they are in separate health systems, they may not know each other's diagnostic tests, but through this shared medical care table they can avoid duplication of ordering tests, thereby, reducing costs and delivering better care. They can share important data. FIG. 36 demonstrates parameters that could be shared among providers (in this case, participating in the care of diabetes patients) and, if so, the physicians sharing care would have a column next to perhaps the date listing the name of the physician and the healthcare provider office or medical practice/hospital they work. As previously noted, all financial data in the system, including costs to patient, is compartmentalized such that no user may see financial details for users or organizations not authorized in accordance with applicable policies and law.

Referring now to FIG. 26, the Allergies tab 2526b from display panel 2526 in FIG. 15 displays allergy information. The Allergies tab 2526b displays the date of diagnosis 2725, the ICD10 code 2726, and the description of the allergy 2727. This Allergies tab 2526b also has an option 2728 to show only Ocular related allergies. In other embodiments, different filters may be applied.

The Medications tab 2526c as illustrated in FIG. 27 displays medication information. The Medications tab 2527c displays the prescription date 2729, the medication name 2730, the dosage 2731, the frequency 2732, quantity 2734, last time it was filled and the number of refills remaining 2736, and who prescribed the medication 2738. The medications may be filtered by active medications 2740 and/or ocular medications 2742. The tab also includes a link to order new medications 2744. When the new medication link 2744 is clicked it opens the New Prescription overlay (FIG. 44) so that the existing medications can be seen when prescribing any new ones.

The Labs tab 2526*d* (not shown in FIG. 15) as illustrated in FIG. 28 displays lab information. The Labs tab 2526*d* displays the lab date 2746, the lab panel 2748, the lab name 2750, the result and unit of measure 2752, whether or not it is an abnormal lab result 2754, and any associated notes 2756. The notes column only displays the first few characters or words based on available space. Moving the mouse over the specific note displays it in a pop up. The tab includes filters for displaying only current labs 2758, only abnormal labs 2760, and the ability to select any individual lab 2762. The Labs tab 2526*d* also includes a link to order new Labs 2764. When the Order Lab link 2764 is clicked it opens the Order Lab overlay (FIG. 46) so that the existing labs can be seen when ordering new ones. The declining health icon 2766 and improving health icon 2768 are indicators so the user can quickly see how the patient is progressing or not progressing. These icons are determined on data import by Clinical Decision Support features of the Command Center as described below with respect to FIG. 63.

Figure 29A:
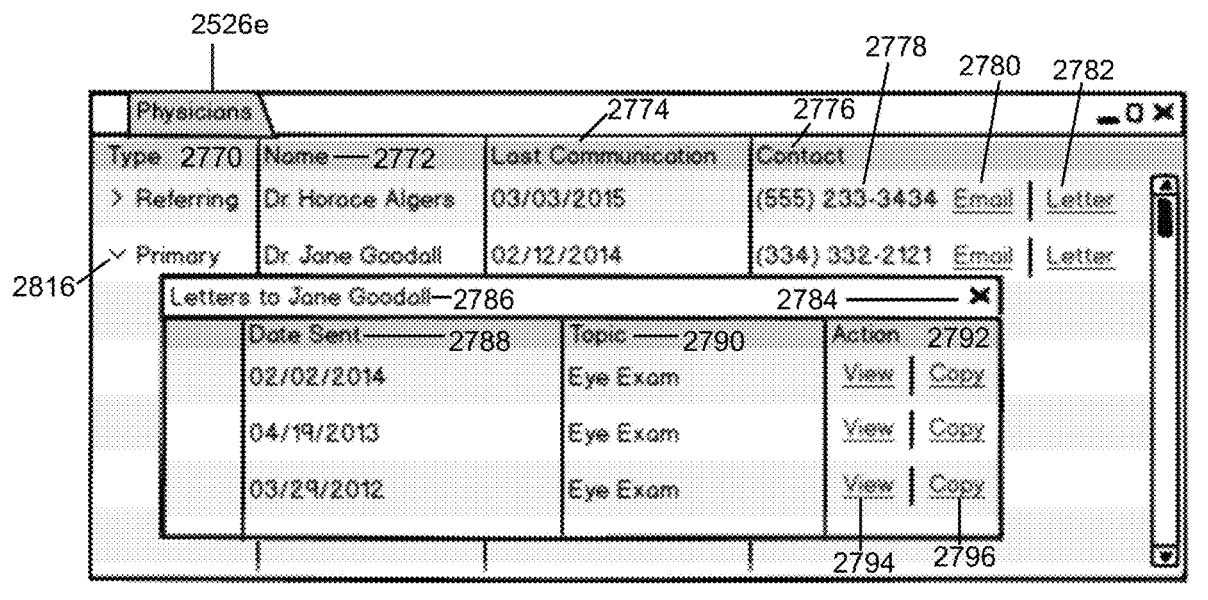
Figure 29B:
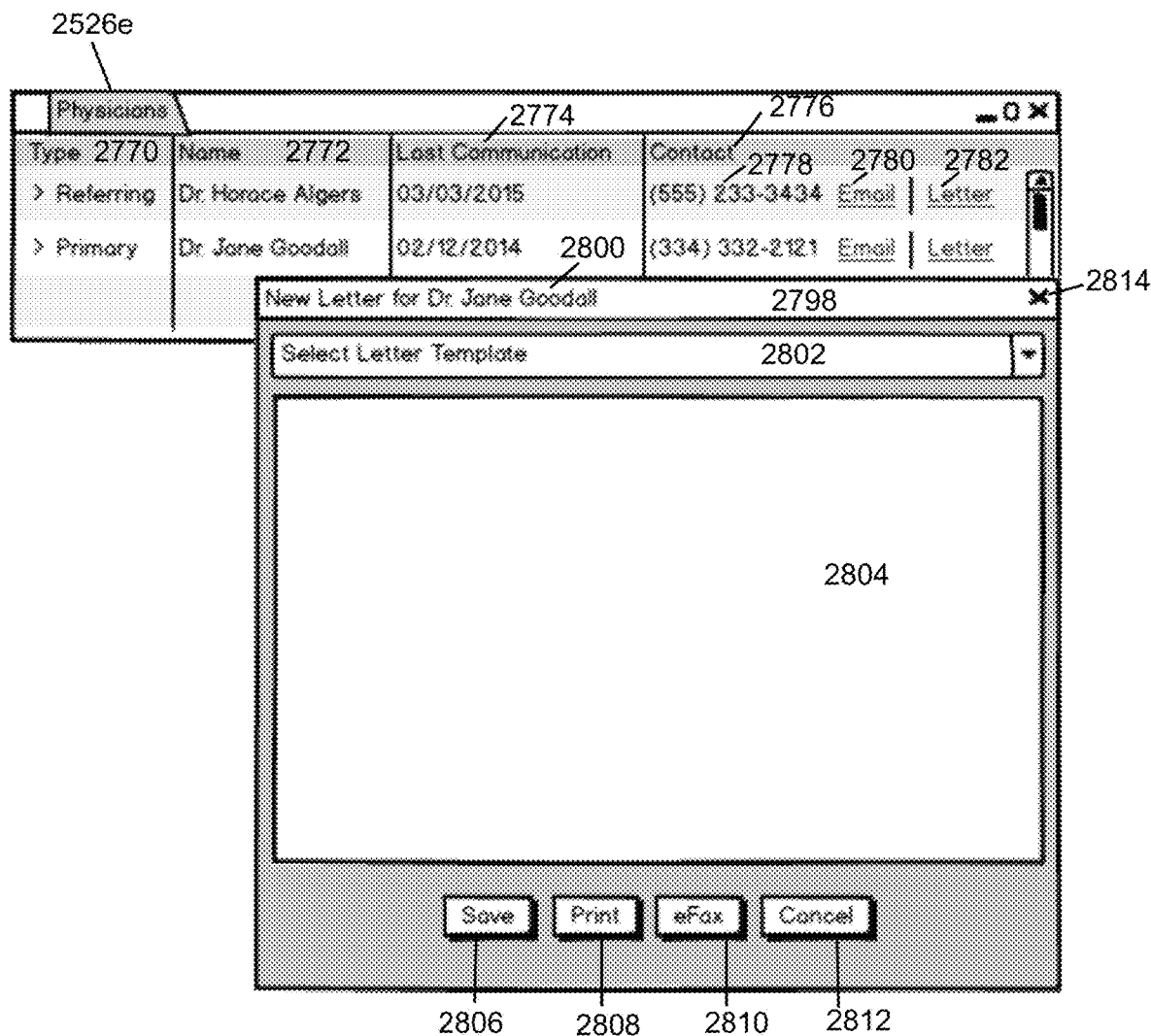
FIG. 29B illustrates the New Letter Popup when the letter link in FIG. 29A is selected in accordance with the second embodiment of the invention.

The Physician tab 2526*e* as illustrated in FIG. 29A displays information about the patient's other physicians and provides a listing of letters sent to the patient's other physicians. The Physician tab 2526*e* displays the type of physician 2770, the physician's full name 2772, the last time communication was officially recorded 2774, and the physician's contact information 2776 with the phone number 2778, link to email 2780, and a link to create a new letter 2782. Clicking the email link 2780 opens a window to email the physician using a secure email client on the local computer used to access the Command Center 2500. Clicking the Letter link 2782 opens the New Letter Popup 2798 shown in FIG. 29B. The New Letter Popup 2798 displays the title including the name of the physician 2800 to whom the letter is being addressed, a list of letter templates 2802, a text area to draft the letter 2804, a Save button 2806, a Print button 2808, an eFax button 2810, a Cancel button 2812, and a Close Icon 2814. The user can select a letter template from the list of templates 2802 and the contents are populated in the text area 2804 where the user can edit the letter. Once complete, the user can save the letter by clicking the Save button 2806 in which case it is sent to the EMR. The letter can be printed by clicking the Print button 2808 and can be faxed electronically by clicking the eFax button 2810 in which case the letter is transmitted by an integrated $3^{rd}$ party fax service. If the user does not want to complete a letter, the user can close the New Letter Popup 2798 by clicking the Cancel button 2812 or clicking the Close Icon 2814. For each physician, selecting the icon 2816 displays a list of letters 2784 sent to that physician. Clicking the icon 2816 a subsequent time closes the list of letters 2784. The list of letters 2784 displays the title including the name of the physician for the list 2786 to insure context, and a list of letters including the date sent 2788, the topic 2790, and action column 2792 including View link 2794 and Copy link 2796. Clicking the View link 2794 displays the letter in a read-only format in a popup (not displayed) and clicking the Copy line 2796 opens the New Letter Popup 2798 of FIG. 29B with the copied letter content displayed in the text area 2804 for editing or printing by selecting Print button 2808.

Figure 30:
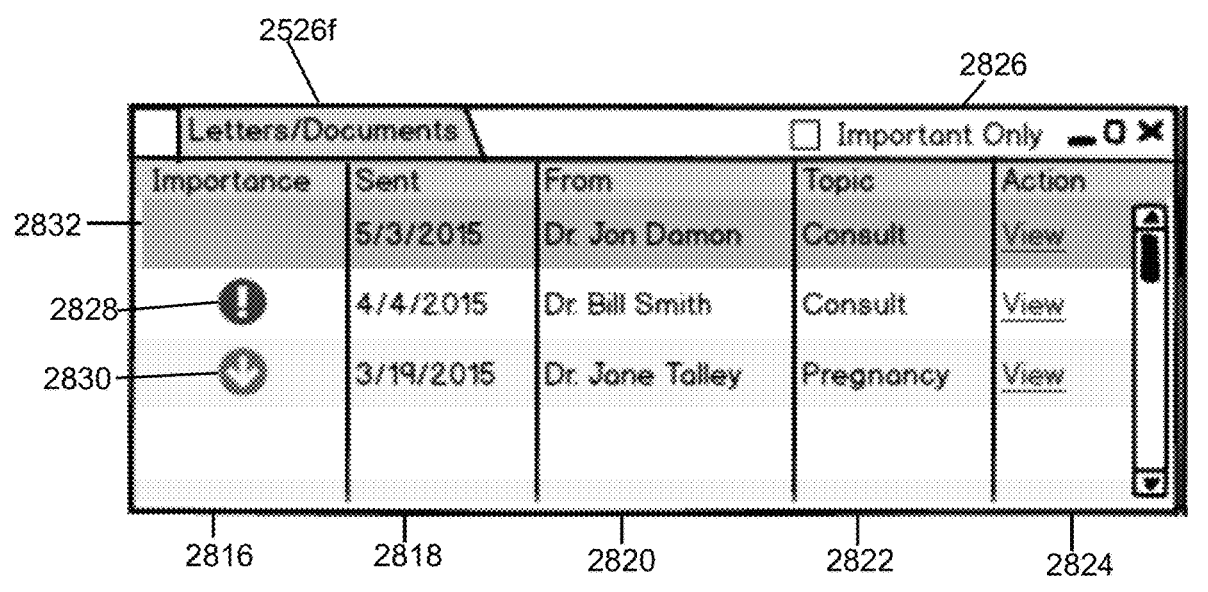

The Letters/Document tab 2526*f* as illustrated in FIG. 30 displays letters and documents transferred from the EMR system. The list of Letters and Documents displays a tabular list of items. The list includes a Level of Importance icon 2816, the date the letter was sent 2818, who the letter was from 2820, the topic of the letter 2822, and a link 2824 to View each document. Documents can also be filtered at 2826 so that only the important ones are displayed. The importance icon 2816 may either be blank, a red circle with an exclamation point 2828 if it is important (ex. cancer diagnosis letter the physician does not want to misplace) or a blue circle with a down arrow 2830 if it is low priority. If the user clicks the View icon 2824 for a document, the document is displayed in a popup (not displayed). The user can adjust the priority of a document by clicking on the Importance column and selecting a Level of Importance (not displayed). Letters that have not been viewed since the last appointment are also highlighted at 2832 to focus the user's attention on new items and after viewing the items they are no longer highlighted.

Figure 31:
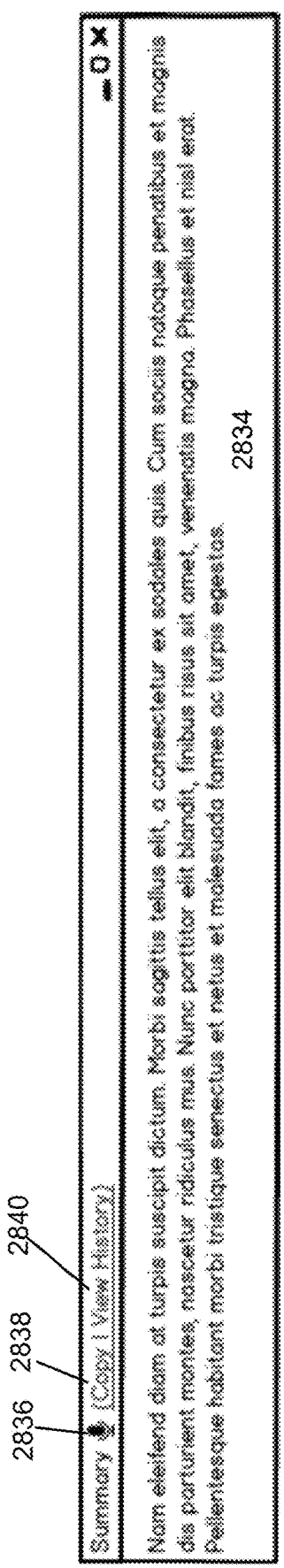
FIG. 31 illustrates the Summary panel that is a permanent note feature allowing the user to save and change the same note that is always visible when viewing the patient in accordance with the second embodiment of the invention.

The Summary Panel 2528 as illustrated in FIG. 31 is a permanent note feature allowing the user to save notes that are always visible when viewing the patient, so they do not get "lost" within general encounter notes. The Summary Panel 2528 includes a text area 2834 that when clicked enables in place editing (not displayed) and when complete the notes are saved. A dictation icon 2836 allows for note dictation, and the user can copy the notes at 2838 onto the operating systems copy area and by clicking the View History link 2840 the user can see a past history of edits and recover any of those previous edits (not depicted).

Figure 32A:
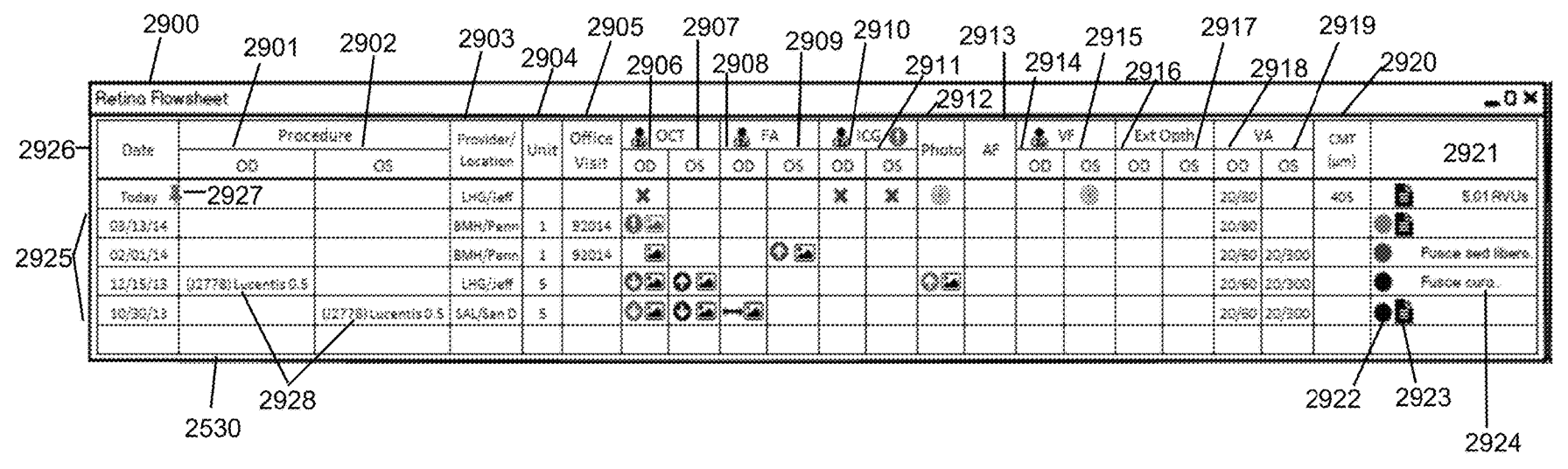
Figure 32B:
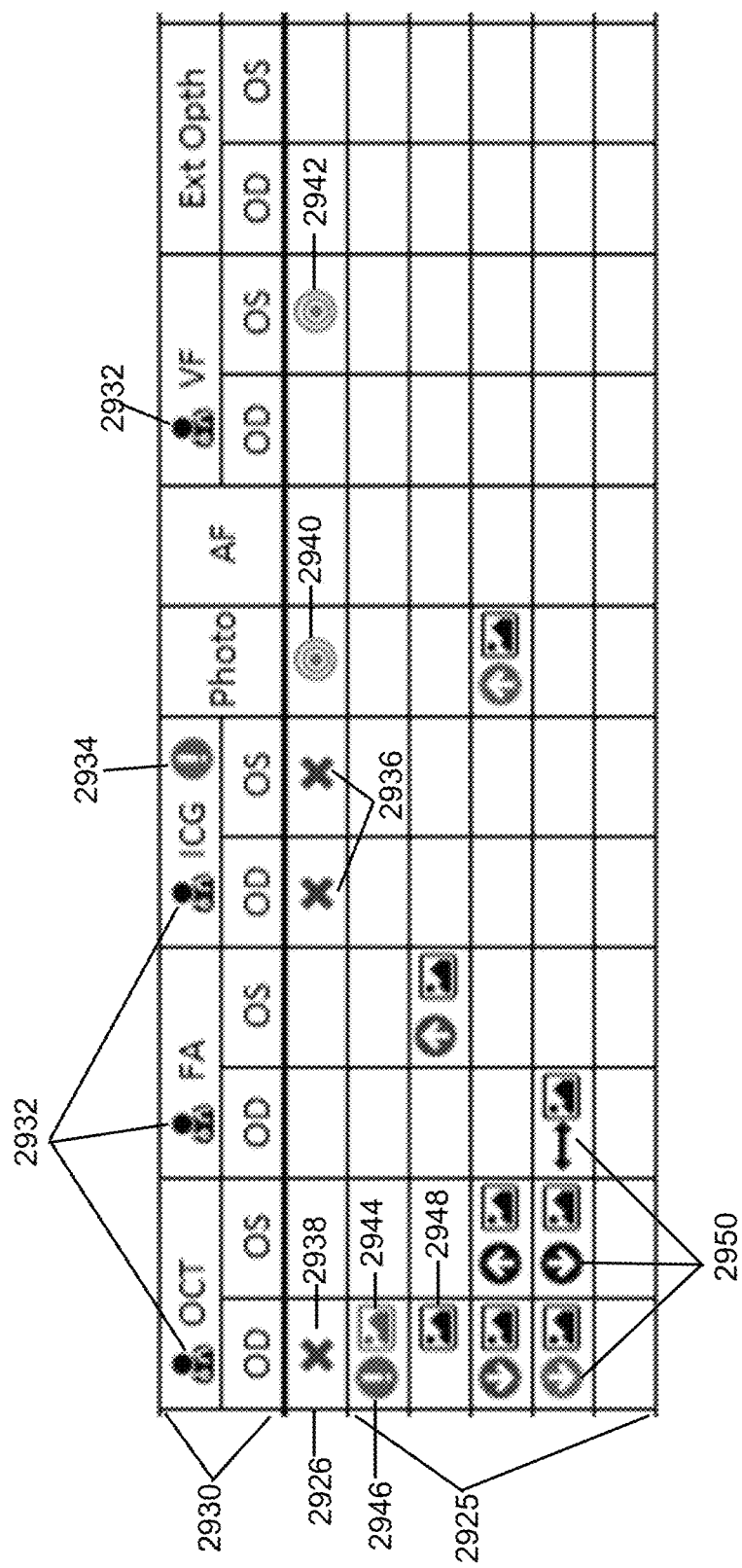
FIG. 32B illustrates the medical treatment information of the Retina Flowsheet of FIG. 32A in more detail.

The Retina Flowsheet 2530 illustrated in FIGS. 32A and 32B is the central focus of the Command Center. The Retinal Flowsheet 2530 is an embodiment of one implementation of how the Table can be configured. Like the embodiment illustrated in FIG. 4A, the Retina Flowsheet 2530 is based on implementation in an Ophthalmology practice, but can be easily configured for other medical specialties. The Retina Flowsheet 2530 provides a comprehensive overview of the patient's clinical 2900-2920 and financial 2922 history as well as providing a means to quickly order tests 2926 while retaining the ability to see past medical history as illustrated in FIGS. 23 and 25-29. As will be explained in more detail below with respect to FIG. 42, clinical, insurance guidelines and preferred practices are quickly accessible for each imaging modality.

The Retina Flowsheet 2530 displays the following columns in the illustrated exemplary embodiment: Encounter Date 2900, Procedure OD 2901, Procedure OS 2902, Provider and Location 2903, Unit 2904, Office Visit 2905, Optical coherence tomography (OCT) OD 2906, OCT OS 2907, fluorescein angiography (FA) OD 2908, FA OS 2909, indocyanine green (ICG) angiography OD 2910, ICG OS 2911, Retinal Photo 2912, Fundus auto fluorescence (AF) 2913, Visual Field (VF) OD 2914, VF OS 2915, Extended ophthalmoscopy (Ext Opth) OD 2916, Ext Opth OS 2917, Visual Acuity (VA) OD 2918, VA OS 2919, Central Macular Thickness (CMT) 2920, and Other 2921. The Other column 2921 includes a financial status icon 2922, a notes icon 2923 and note text 2924, if available.

The first row in the Retina Flowsheet 2530 represents the current visit 2926 and orders placed. The subsequent rows correspond to past encounters 2925. In the first row, if a pre-authorization is required for a procedure during today's visit, a tack icon 2927 is displayed. If a precertification is required and not available, the icon is red. If it is required and available it is green. If a precertification is not required, no tack is displayed.

The Procedure columns 2901, 2902 contain the procedure(s) performed 2928 on that date 2900. The full text may not fit in the field, so the data is truncated and when the user moves the mouse over the displayed text the full text is displayed in a tooltip (not depicted). Multiple procedures may be done on a single day and these would be visible in the tooltip. These may be concatenated into a single string and displayed as appropriate (not depicted). The Provider 2903 column contains the initials of the provider associated with the claim for that day and the location of the provider (as when the practice has more than one office). The Unit 2904 column contains the units of medication delivered, if applicable. The Office Visit 2905 column contains the office visit code, if one was billed for that day. In the VA columns 2918 and 2919 the Visual Acuity is entered either manually or through the CCOW interface (described below with respect to FIG. 60). The CMT 2920 column also is entered manually or through the CCOW interface. The user clicks on the appropriate row and it becomes a text field allowing entry of the data following standard browser editing data in place conventions. Hitting enter saves the data. Clicking on the value allows it to be edited (not depicted). The data is saved immediately and does not require a Save action. In the Other 2921 column the financial status 2922 icon is displayed. It is black if the claim is finalized, red if rejected or denied, and blue if it is in process. Clicking on a financial status icon 2922 may highlight the corresponding row in the Financial Flowsheet 2532 (FIG. 15) or if the Financial Flowsheet 2532 is not visible based on the user's configuration, it may open a popup (not depicted) that displays the Financial Flowsheet 2532 with the row highlighted. The notes 2923 icon may be clicked to enter a note (FIG. 32A) and if a note exists the text that fits in the field may display and when the user moves the mouse over the field it may display in a tooltip (not depicted).

FIG. 32B shows the medical treatment information of the Retina Flowsheet 2530 in more detail. As illustrated, a header 2930 embodies several unique features. For example, the header 2930 provides icons for easy access to clinical and insurance guidelines as well as preferred practices for each image modality (OCT, FA, ICG, and VF). Next to each image modality is a Physician icon 2932 and it links to the appropriate clinical and insurance guidelines as well as preferred practice guidelines for that imaging modality and the patient being viewed. The information is displayed on the Guidelines tab 2542 shown in FIG. 15, for example. In an exemplary embodiment, in addition to making the guidelines available, the Command Center 2500 provides an overview of the guideline to make information relevant to the patient condition more easily located and provides clinical decision support (CDS). These features help optimize the physicians' time with the patient and help them comply with insurance guidelines. An example of the CDS in this embodiment is the Alert icon 2934 and highlighted (e.g. red) X icons 2936. The alerts may be generated through data analysis (e.g. FIG. 63) or the alerts may be entered by technicians based on observations during the patient evaluation. For example, these icons may be used by a technician to tell the physician that the patient is allergic to the chemical compound used in performing the ICG imaging test, so the imaging test should not be performed. As another example of CDS, the X icon 2938 for the OCT image test in the right eye (OD) is highlighted (e.g. red). Insurance guidelines do not typically pay for repeat tests within 30 days, so this test cannot be ordered unless the physician overrides the process. Customized to the patient's insurance, this alert assists the physician in meeting insurance guidelines and helps the practice insure they will be paid for procedures they perform, but allow the provider to exercise clinical judgement and perform the test if medically necessary. Once a test is ordered, it appears as a blue bullseye 2940, 2942 icon until it is completed. Because of the placement of the bullseye icon 2940, 2942 the user can easily see which tests have been ordered for which eye.

In each imaging test column 2906-2919 in FIG. 32A, if an image was taken for a date, an image icon is displayed. If the image needs to be interpreted, it is colored red 2944 and an alert icon 2946—red circle with an exclamation point is displayed next to it. Clicking on the image icon 2944 or the alert icon 2946 displays the image on the Image Tab 2540 (FIG. 15). Once the image has been interpreted, it is displayed as a black image icon 2948 and the user can move the mouse over the image to see the interpretation (not depicted). The user also may select a Change in Status icon 2950 to signify if the patient is improving, declining or staying the same for each completed image by clicking on the space to the left of each image icon or, once selected, the Change in Status icon 2950. The available Change in Status icons 2950 in an exemplary embodiment are as follows:

Horizontal arrows (black)—no change.
Circle with Up arrow (red)—Negative increasing trend
Circle with Down arrow (red)—Negative decreasing trend
Circle with Up arrow (green)—Positive increasing trend
Circle with Down arrow (green)—Positive decreasing trend
Circle with Up arrow (black)—Increasing trend without comment on outcome
Circle with Down arrow (black)—Decreasing trend without comment on outcome.

Figure 33A:
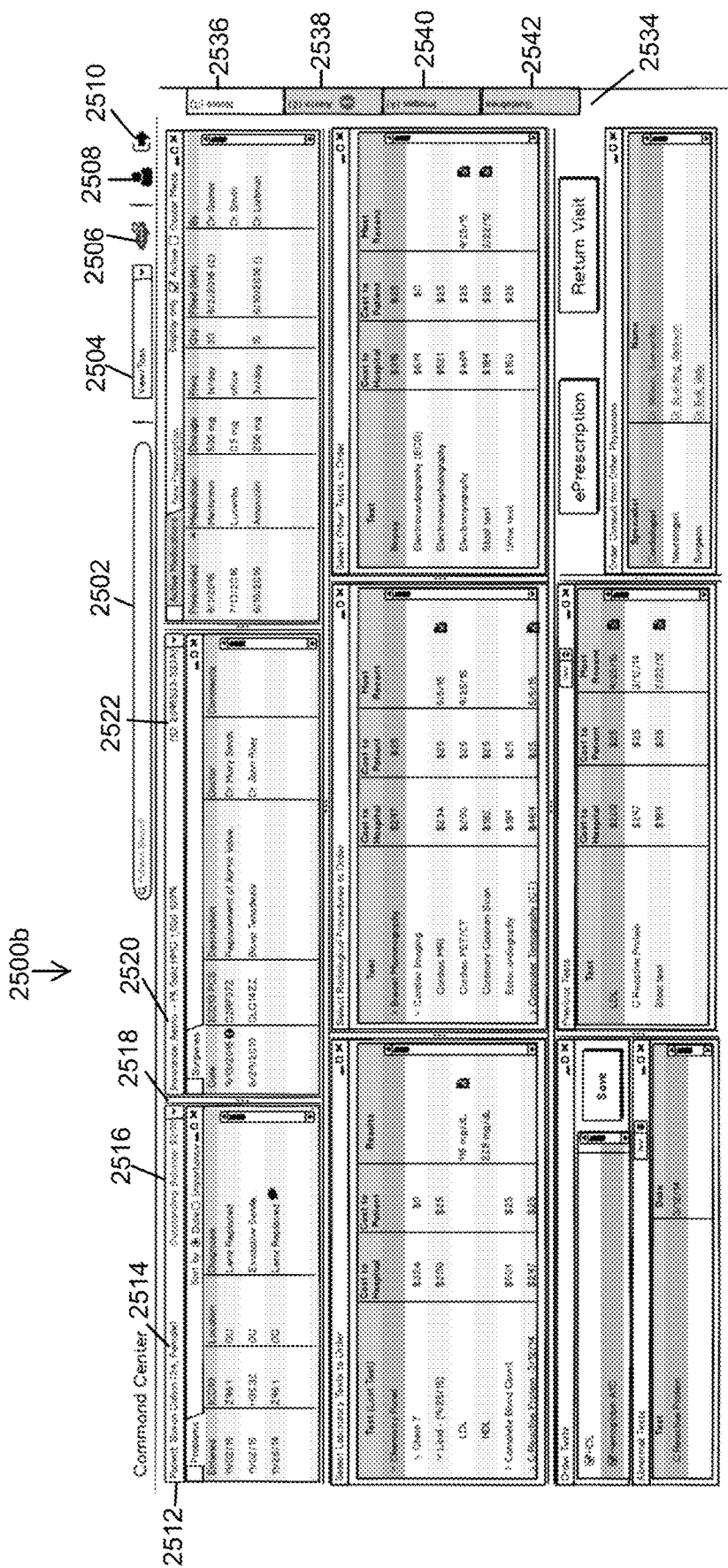
FIG. 33A illustrates a modified Command Center in which the display panels are replaced by panels for ordering clinical tests and procedures, diagnostic images, and medications in accordance with the second embodiment of the invention.

Several methods have been discussed by which the Command Center uniquely provides CDS to guide the physician to make better clinical and financial decisions. Physicians can also order tests and procedures directly from the Retina Flowsheet or via display panels in other embodiments of the Command Center 2500 without leaving the Command Center 2500 on the display screen. For example, the embodiment in FIG. 33A illustrates a modified Command Center 2500b in which the display panels are replaced by panels for ordering clinical tests and procedures, diagnostic images, and medications. This allows the user to see relevant tests, while further assisting the user in the decision-making process and reducing the cognitive burden imposed by other systems where the user must switch between results and order screens. In the exemplary embodiment, these tests are either ordered directly from the relevant portion of the Retina Flowsheet 2530 or the display panels are replaced by new tab or window popup display panels for ordering clinical tests and procedures, diagnostic images, and medications—all without leaving the display screen of the Command Center 2500, 2500a, or 2500b. As explained below with respect to FIGS. 56A and 56B, the configuration of display panels is flexible and may be set up and rearranged as desired by the user.

By way of example, one or more of the display panels in FIG. 33A may be adapted to present an overview of every laboratory test performed and display just the abnormal results. Such an additional panel 2951 is shown in FIG. 33B and may be adapted to enable a physician who is ordering a test to see in overview all that had been ordered in the past thereby tailoring what is needed to be ordered today, all without leaving the Command Center 2500b. Such display panels in the Command Center 2500b not just allows the physician to see the test that could be ordered while simultaneously knowing the medical conditions, but simultaneously on one screen shows all of the relevant tests ever ordered for this patient whether at the physician's particular practice or their institution or other institutions and in particular abnormal results and even trends that the physician wants to track and can be highlighted automatically or that the physician can highlight for their own future reference. Over time, the display panel of FIG. 33B may permit the physician to see everything that was ordered, look for a trend of improvement or decline, and help guide the physician establish what really is medically indicated to now order to help diagnose, manage and treat a patient's condition.

Figure 34A:
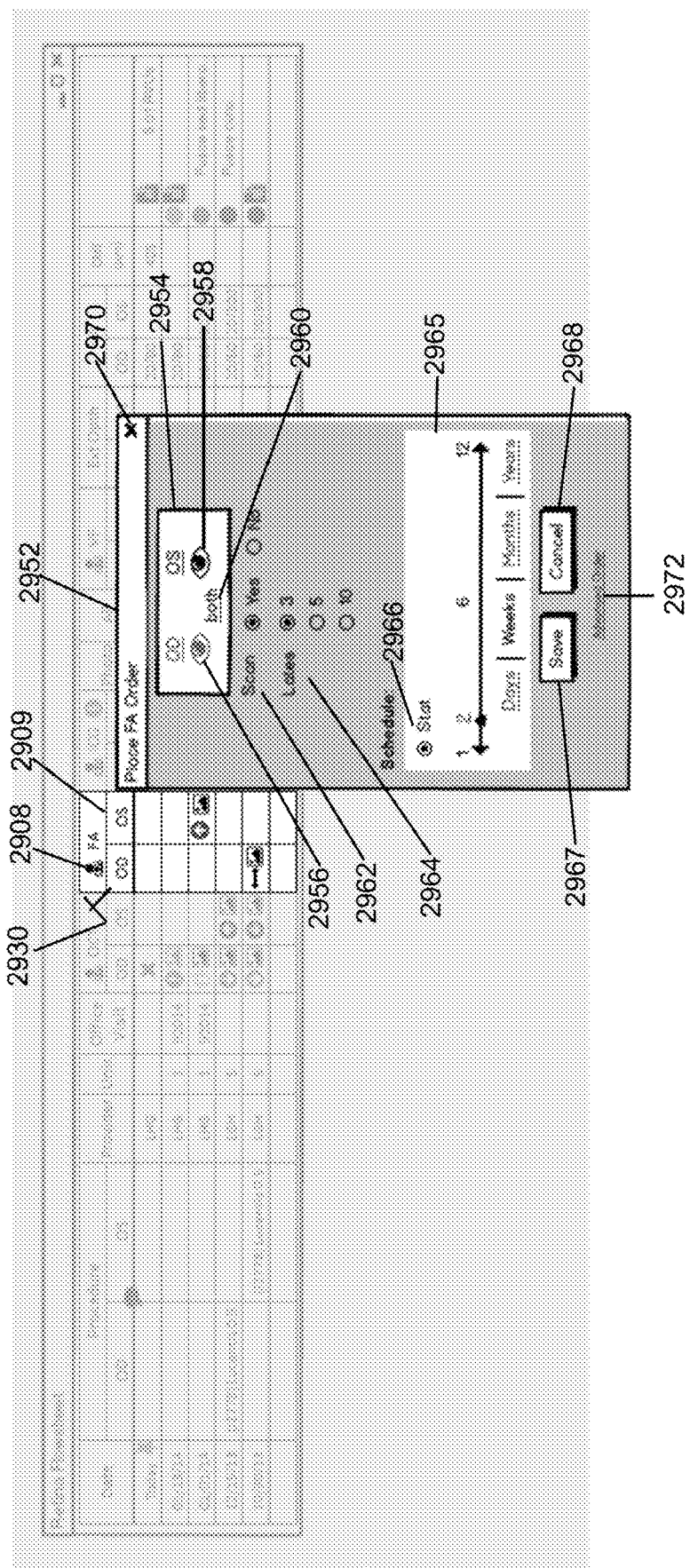
FIG. 34A illustrates the Place FA order dialog box that pops up when the user clicks the column header for the FA exam in accordance with the second embodiment of the invention.
Figure 34B:
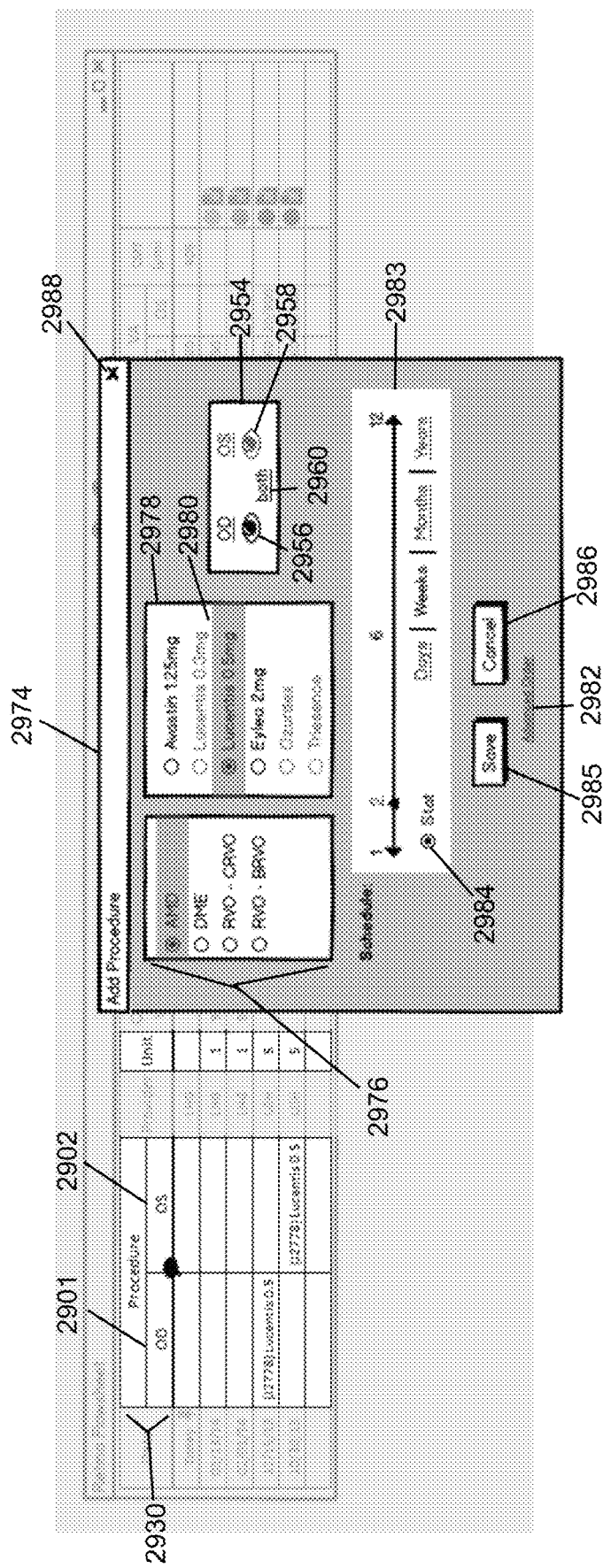
FIG. 34B illustrates another example of in situ ordering for the Procedure columns OD and OS in accordance with the second embodiment of the invention.
Figure 48:
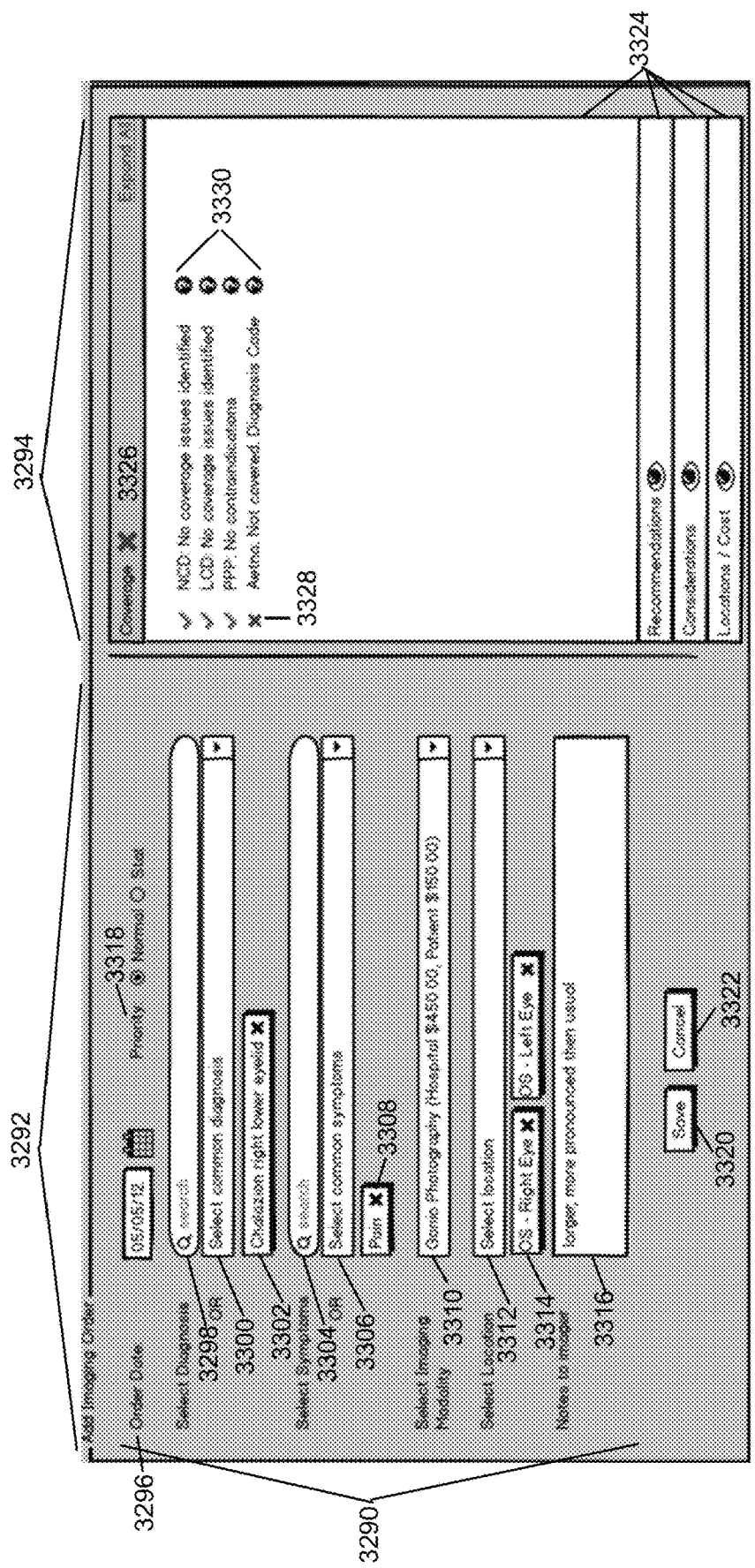
FIG. 48 illustrates a view of the Imaging Order panel in accordance with the second embodiment of the invention.

FIGS. 34A and 34B provide an example embodiment of the in situ ordering process using the Command Center of the exemplary embodiments whereby medications, diagnostic tests, images, procedures, and the like may be ordered directly from the display panels or patient flowsheet. As illustrated in FIG. 34A, the user clicks the column header 2930 for the FA exam 2908, 2909 and the Place FA Order 2952 dialog box is displayed. At this time, the portions of the page not including the FA columns 2908, 2909 are partially greyed out to focus the user's attention. In other words, the background is still viewable as it is critical to see the overview of the patient's medical conditions so that proper orders are made and mistakes are avoided. The dialog box contains a visual representation of the eyes 2954 allowing the user to visually select either the right OD 2956 or the left OS 2958 or both eyes 2960 by clicking the appropriate link. The user can select Scan 2962 and Lates 2964, schedule using the variable time frame slider 2965 or select stat 2966, and then click the Save button 2967 to save the order, which may place a blue bullseye or similar icon in the field based on the user's selections. The user can in the same dialog box 2952 or in an added dialog box specify the timing of the diagnostic test, e.g., now, ASAP, 2 weeks, x months, etc. The user can also cancel the order by clicking the Cancel button 2968 or the Close icon 2970. If a more complex order needs to be placed, the user may click the Advanced Order link 2972 to open the Advanced Order Display (FIG. 48). If a CPT code (required for billing and medical necessity testing) has not been provided, the Advanced Order Display (FIG. 48) is automatically displayed.

FIG. 34B illustrates another example of in situ ordering for the Procedure columns OD 2901 and OS 2902. As in FIG. 34A, the areas of the screen not associated with the order are partially greyed out and the Add Procedure dialog box 2974 is displayed. As in the FIG. 34A embodiment, the background is still viewable as it is critical to see the overview of the patient's medical conditions so that proper orders are made and mistakes are avoided. The dialog box 2974 allows the user to select a Condition 2976 to treat, a medication and dosage 2978 and the eyes upon which the procedure is to be performed. The Medication and Dosage control 2978 only allows the user to select the appropriate medications for the selected condition. For example, for treating AMD (Age-related Macular Edema) Lucentis 0.3 mg (2980) is not appropriate, so it is greyed out and not available for selection. If a more complex procedure needs to be performed, the user may click the Advanced Order link 2982 to open the Advanced Order Display (FIG. 48). The user may schedule the procedure using the variable time frame slider 2983 or select stat 2984. If a CPT code (required for billing and medical necessity testing) has not been provided, the Advanced Order Display is automatically displayed (FIG. 48). When finished, the user may click the Save button 2985 to save the order, which may place a blue bullseye in the field based on the user's selections. The user can in the same dialog box 2974 or in an added dialog box specify the timing of the procedure, e.g., now, ASAP, 2 weeks, x months, etc. The user can also cancel the order by clicking the Cancel button 2986 or the Close icon 2988. The in situ ordering is designed to provide a quick and easy method in context for a provider to order an exam, but allows flexibility for more complex needs.

While the above embodiments of the flowsheet have focused on managing Retina-related issues, other embodiments addressing other specialty practices can be easily created. Sticking with embodiments for ophthalmologists, FIG. 35 presents a possible flowsheet for Glaucoma, which is similar to that presented above in FIGS. 12A-12C. The Glaucoma Flowsheet 3000 shares columns 2900-2907 in common with the Retina Flowsheet 2530, but the group of columns 3010 is unique to this presentation. FIG. 36 presents a flowsheet for Diabetes. FIG. 36 shares the first column Date 2900 with the other flowsheets, but the remaining group of columns 3020 is unique to this presentation. The Meds column 3022 represents an example of further clinical decision support. With limited space, it is not possible to list all of the patient's medication, nor is it necessary in an overview. In this column 3022, the patient's diabetes medications may instead be categorized into an overall treatment approach. This could be Diet and Exercise (D&E), oral meds only (oral) or insulin therapy (insulin). At a quick glance the user can understand the progression of the patient's condition. This table of important results, tests, exams can also include cost of the labs, tests or procedures, as well as payments. In addition, this information is vitally important to all the healthcare providers caring for patients with chronic disease, in this case diabetes. Sharing care, as shown in FIG. 25A-D, allows all the patients providers to share information and to notify each other of changes. A column can be added next to the date listing each of the healthcare providers and their locations. As noted above, all financial data in the system, including costs to patients, is compartmentalized such that no user may see financial details for users or organizations not authorized in accordance with applicable policies and law.

Figure 37:
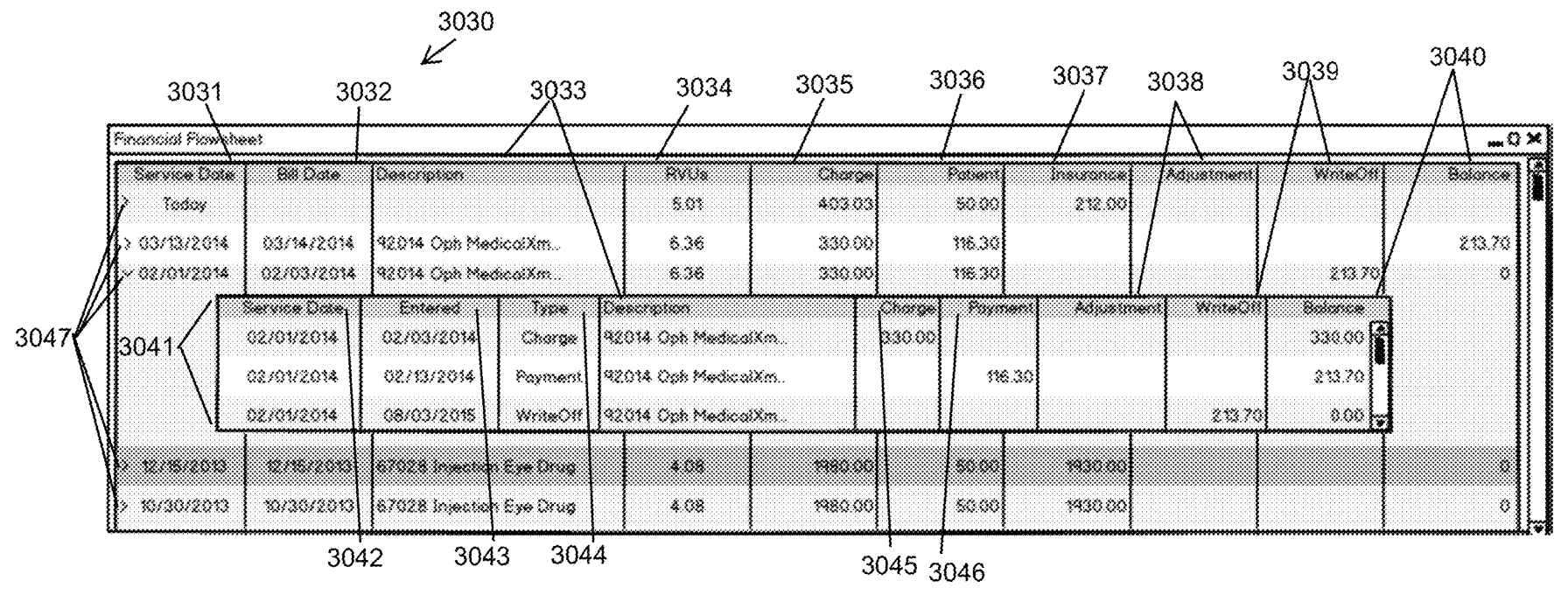

The Financial Flowsheet 2532 is illustrated in FIG. 37. The Financial Flowsheet 2532 contains a dynamic table 3030 of financial activity for the patient, as opposed to the physician's practice, as is usually the case with conventional EMR systems. As illustrated, an exemplary embodiment of the Financial Flowsheet 2532 includes the following fields: the Service Date 3031, Bill Date 3032, Service Description 3033, Relative Value Units (RVUs) 3034 that determine how a physician is paid in accordance with work effort, Gross Charges 3035, the Amount Due from the Patient 3036, the Amount Due from Insurance 3037, any Adjustments 3038, Write Offs 3039, and the outstanding balance 3040. Selection of the Encounter expansion control 3047 produces a second dynamic table 3041 within the first dynamic table 3030. The second table 3041 presents individual financial transactions associated with the encounter. In an exemplary embodiment, the second dynamic table 3041 contains: the Service Date 3042, Date Entered 3043, the Type of financial activity entered 3044, the Service Description 3033, the Charge or Amount Billed 3045, Payments 3046, Adjustments 3038, Write Offs 3039, and the outstanding balance 3040.

Figure 38:
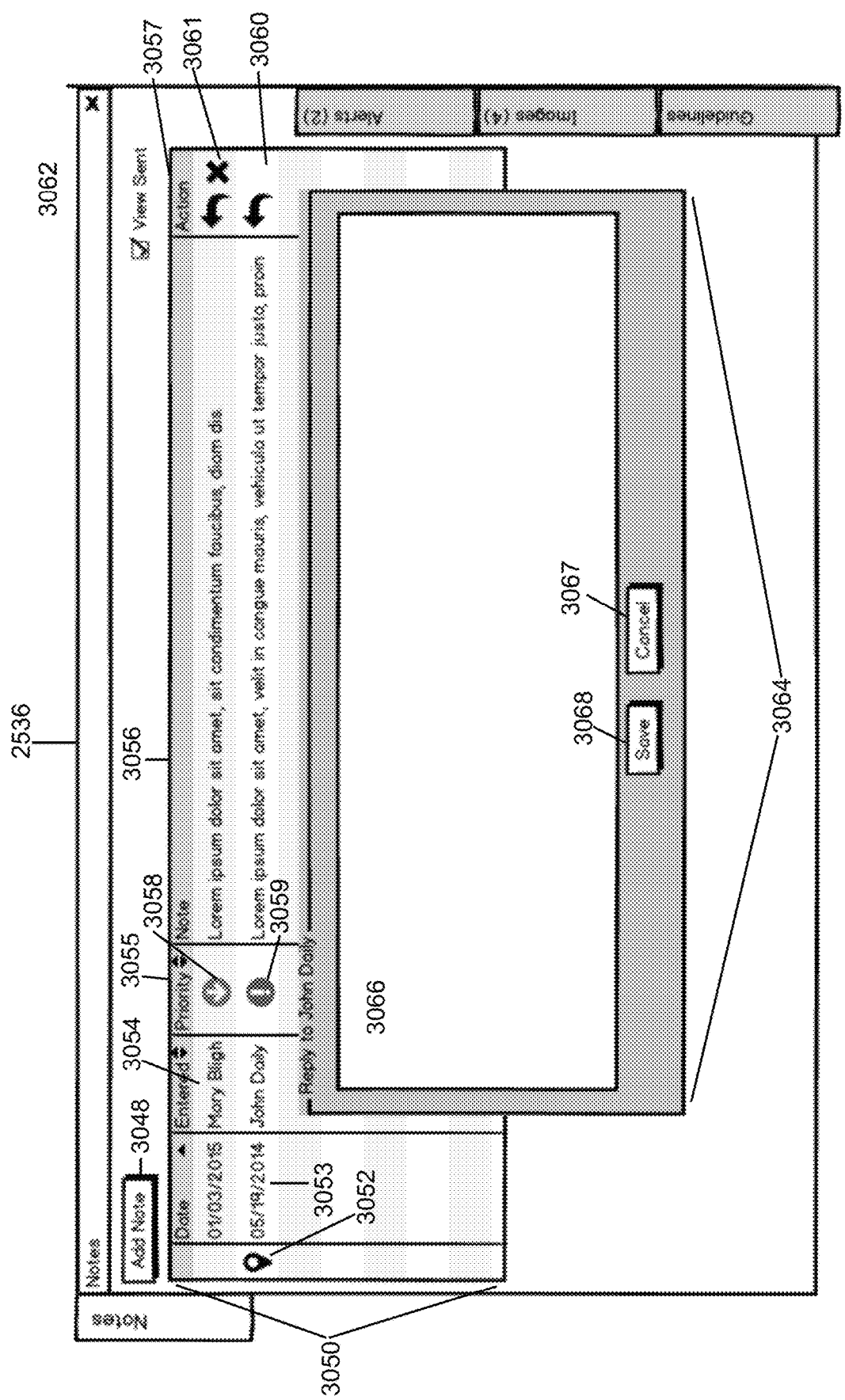
FIG. 38 illustrates a view of the Notes tab in accordance with the second embodiment of the invention.
Figure 39:
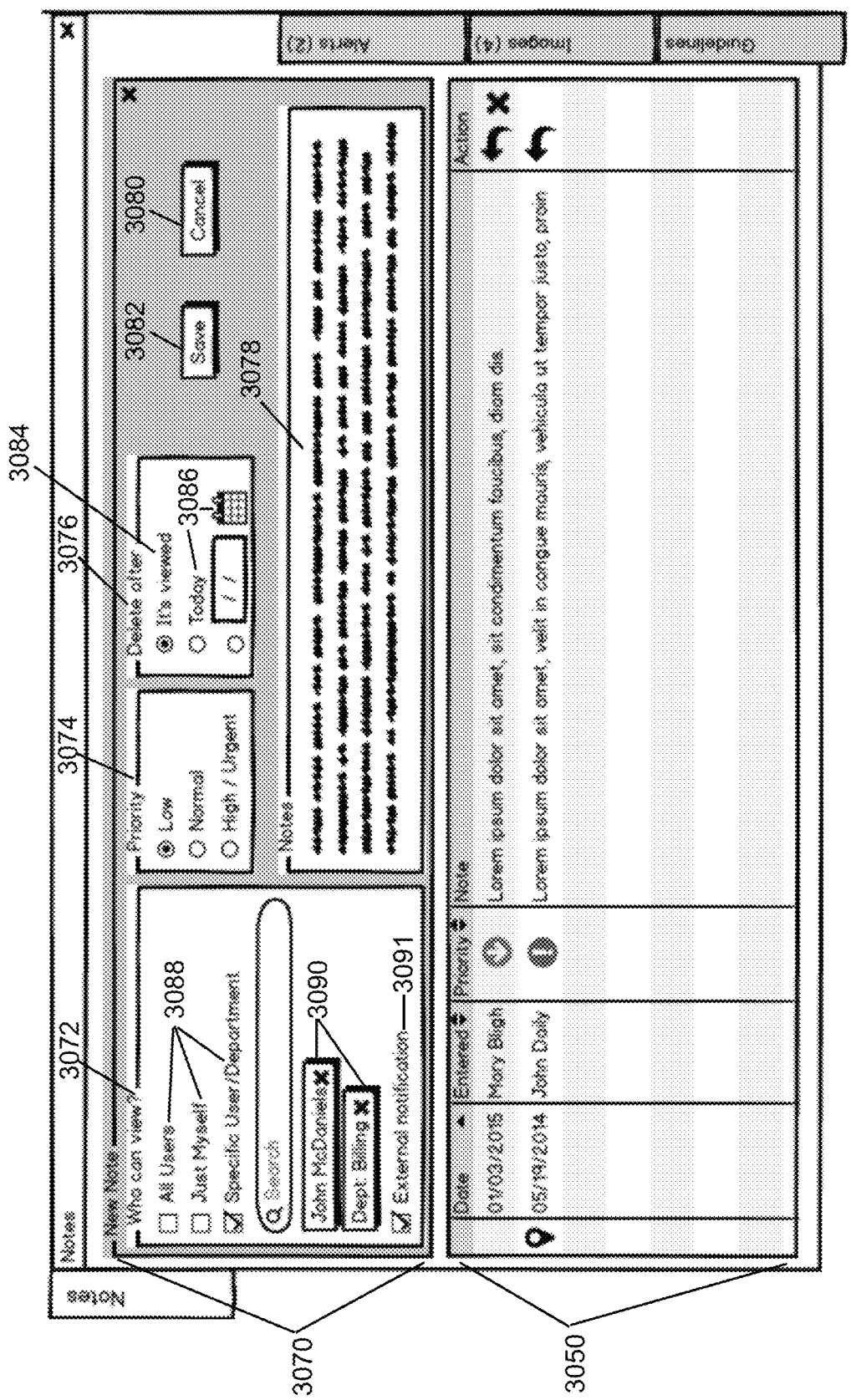
FIG. 39 illustrates how the Command Center enables the user to add notes in accordance with the second embodiment of the invention.

FIG. 38 presents a view of the Notes tab 2536. The Notes tab 2536 displays notes associated to the patient and may be used to create new notes. An Add Note button 3048 allows a user to create a new Note record (FIG. 39). A table 3050 presents the Note records previously created for this patient. The table contains several unique items, including: a map placement icon 3052 linking the record to a specified location in the system, the date the Note was created 3053, the user who created the Note 3054, the user specified priority of the note 3055, a preview of the note 3056, and the actions that the current user may perform 3057. The available priorities 3055 are low (3058), Normal (not shown), or High/Urgent (3059). Available actions may include the ability to reply to the Note (3060) or delete the Note (3061). The View Sent checkbox 3062 allows the user to select if the table filters records sent by the user from the list displayed in the table 3050. Selecting the reply object 3060 opens a new window 3064, which includes a free text entry field 3066, a Cancel button 3067, and a Save button 3068. Selection of the Cancel button 3067 causes the window to close without saving the text 3066. Selection of the Save button 3068 creates a new note.

FIG. 39 illustrates how the CC 2500 enables the user to add notes. The bottom of the page contains the table 3050 described in detail above with respect to FIG. 38. The top of the page displays the Add Note panel 3070 for creating a new note. The panel 3070 collects data for the note, including: the intended viewership 3072, the note's priority 3074, and the intended retention period of the note (3076). The panel 3070 also contains a free text entry field 3078, a Cancel button 3080, and a Save button 3082. The note's priority 3074 may be set to Low, Normal, or High/Urgent. The retention period 3076 of the note may be set to once It's viewed 3084 or after a given date 3086. The intended viewership 3072 may be restricted by the controls 3088. The list of approved viewers is presented as tags 3090. Selecting the External notifications checkbox 3091 may cause Command Center to send the note to the user's EMR. Selection of the Cancel button 3080 causes the panel to close without saving the text 3078. Selection of the Save button 3082 creates a new note.

Figure 40:
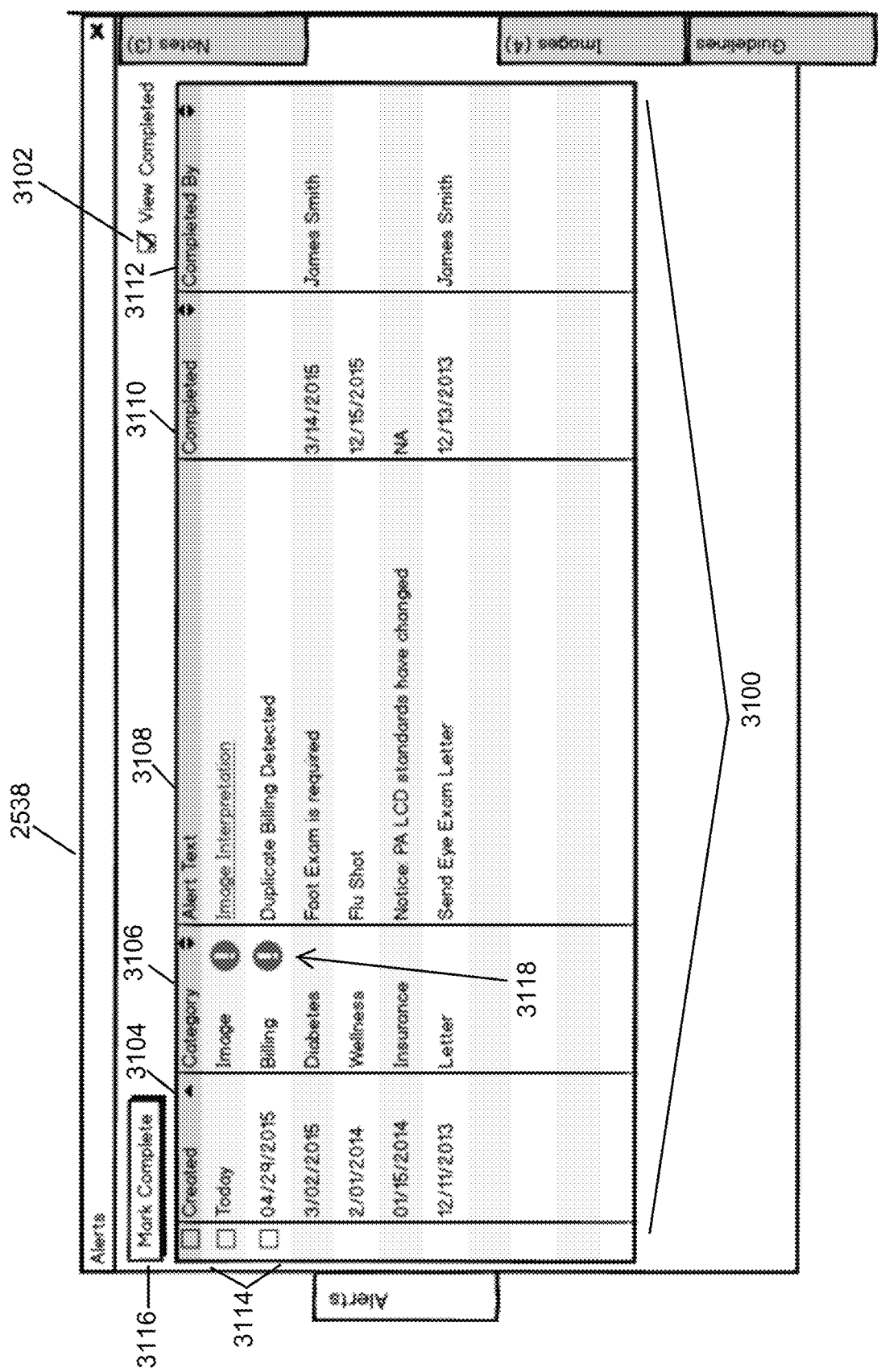
FIG. 40 illustrates a view of the Alerts tab notes in accordance with the second embodiment of the invention.
Figure 63:
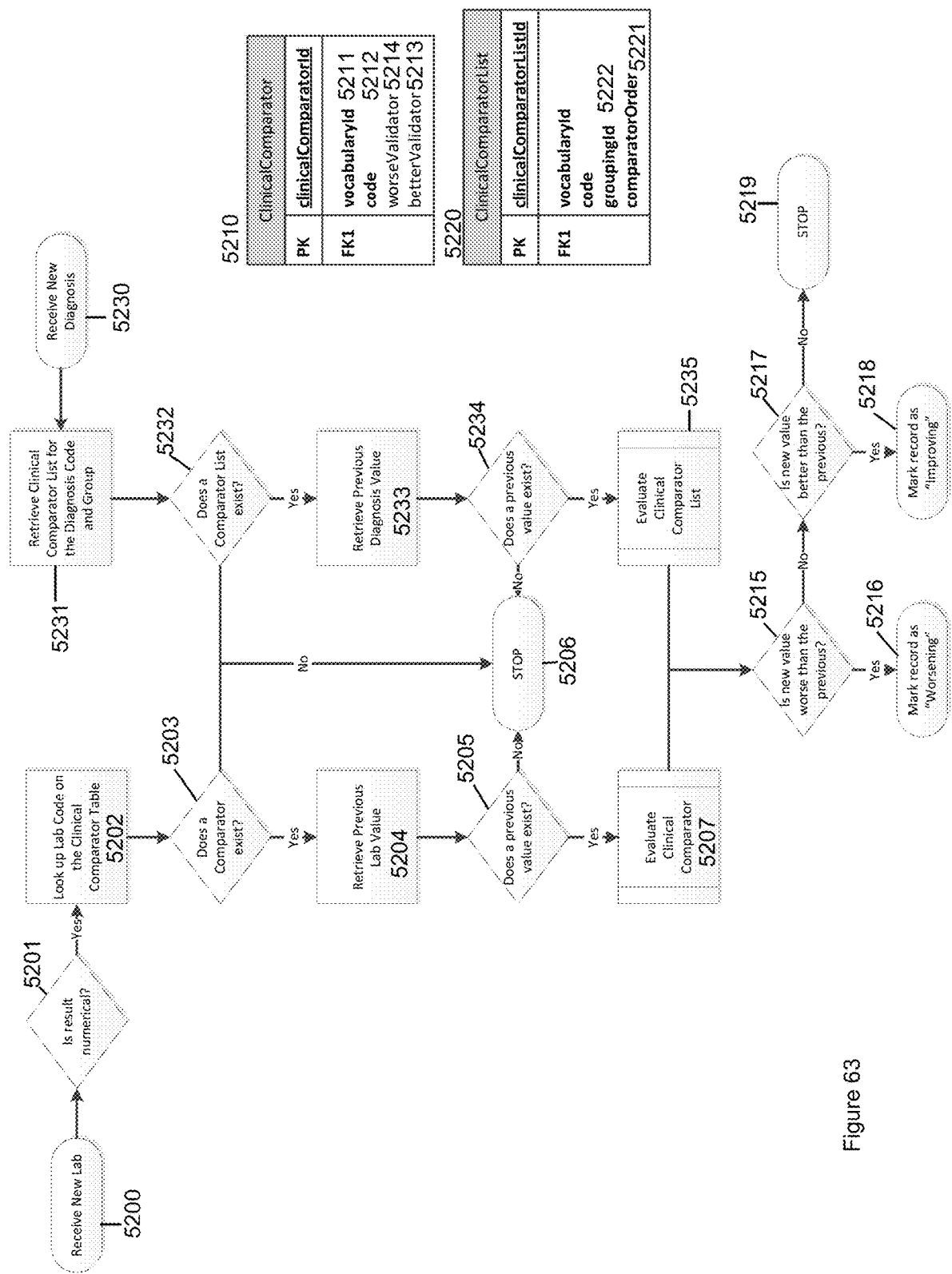
FIG. 63 illustrates a flowchart of the Clinical Evaluation Algorithm in accordance with the invention.

FIG. 40 illustrates a view of the Alerts tab 2538. The Alerts tab 2538 displays a table 3100 of Alerts created for this patient. The View Complete checkbox 3102 allows the user to select if the table filters completed records 3100. In an exemplary embodiment, the table 3100 contains: the date created 3104, the Alert category 3106, Alert subject 3108, date completed 3110 (if applicable), and the user who completed the alert (3112) (if applicable). Alerts are marked as complete by selecting the appropriate checkbox 3114 and the Mark Complete button 3116. Priority Alerts are designated by an icon 3118 in the Category 3106 column. Categories 3106 are driven by conditions, medications, procedures, or other process management algorithms. FIG. 63 described below details the Clinical Decision Support used to create the alerts.

Figure 41A:
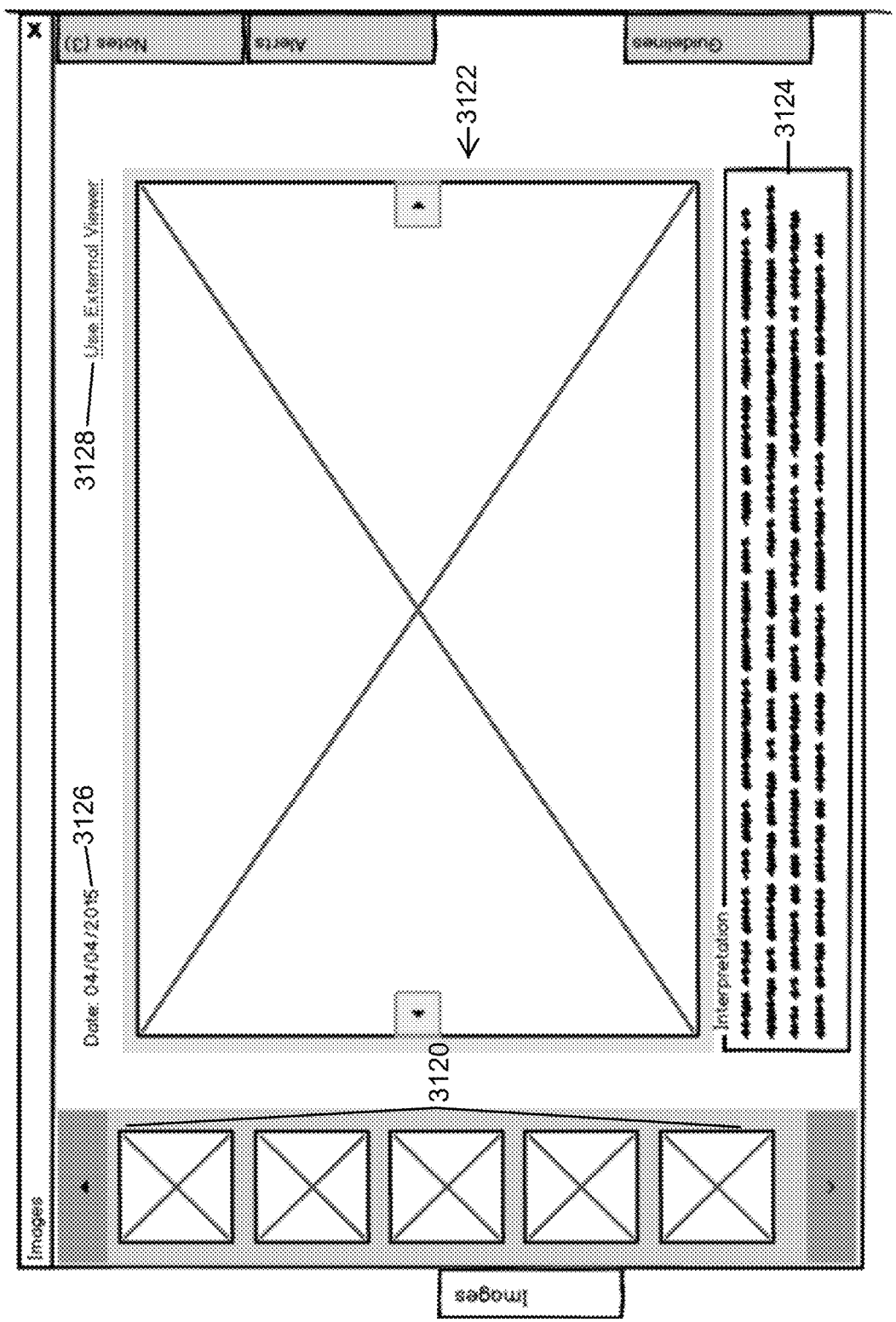
FIG. 41A illustrates a view of the Image tab in accordance with the second embodiment of the invention.

FIG. 41A illustrates a view of the Image tab 2540. A ribbon 3120 of patient images is displayed along the left side of the interface with a selected image 3122 enlarged for more detailed examination. Interpretation text 3124 associated with the image is presented along with the date 3126 the image was captured. A link 3128 opens the image with an external viewer.

Figure 41B:
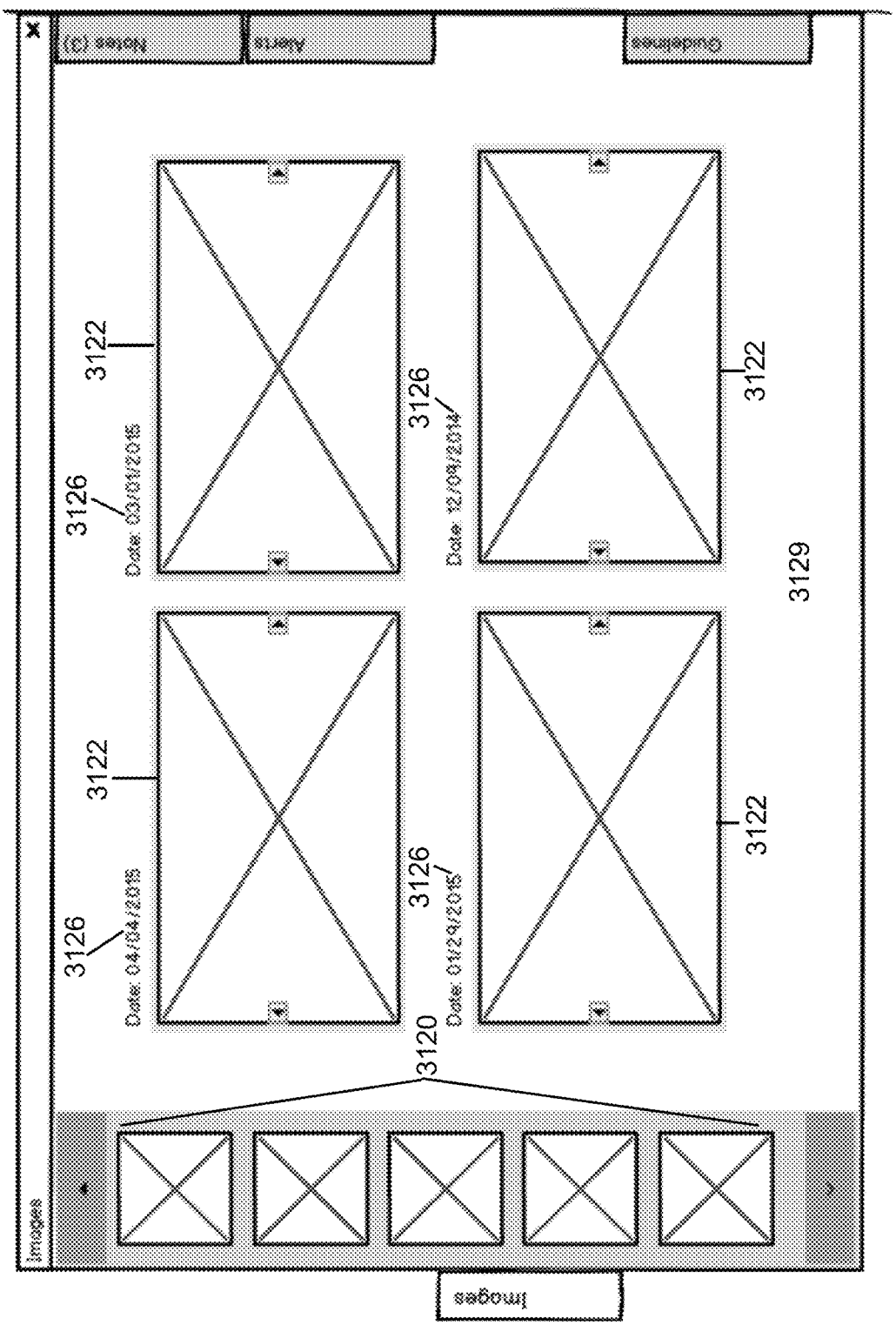
FIG. 41B illustrates an alternative presentation of the Image tab in accordance with the second embodiment of the invention.

In an alternative presentation of Image tab 2540 in FIG. 41B, users may drag multiple images onto the viewing area 3129 allowing the user to compare similar images to see changes over time or different image types for a more complete understanding of the body part imaged. The images 3122 may snap or be fixed to a grid layout by default but may also be specifically placed in the viewing area to improve the user's ability to interpret the images (not depicted). Images may be acquired through connectivity with a variety of diagnostic equipment and/or a PACS (Picture Archiving and Communication System) and the images displayed are either PDF representations or the DICOM (Digital Imaging and Communication in Medicine) images themselves allowing for complex image manipulation. As noted herein, such images may be ordered directly from the Retina Flowsheet 2530 by selecting an image icon within the flowsheet (FIG. 34A) or by opening the Add Imaging Order panel (FIG. 48 described below). It is noted that use of a third-party imaging vendor may require the user to navigate to a separate screen where the software of the third-party vendor would look at all diagnostic tests.

Figure 42A:
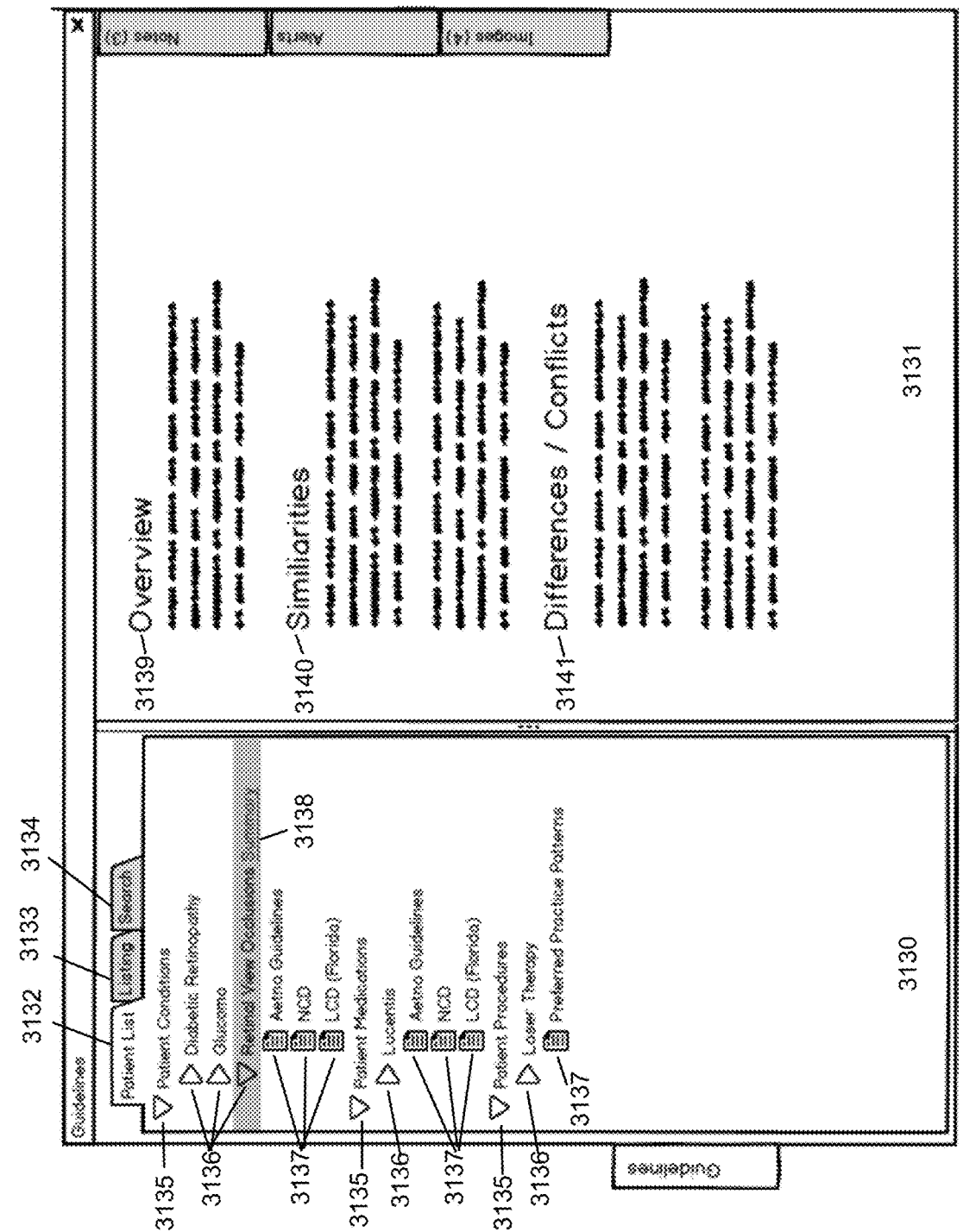
FIG. 42A illustrates a view of the Guidelines Summary tab in accordance with the second embodiment of the invention.

FIG. 42A illustrates a view of the Guidelines Summary tab 2542. There are two panels on this tab: a tabbed navigation panel 3130 and a content panel 3131. The navigation panel 3130 has three tabs, the Patient List tab 3132 which presents a patient-specific list based on the patient's identified insurance, conditions, procedures and medications, the Listing tab 3133 presents an indexed view of all available guidelines, and a Search tab 3134. The Patient List tab 3132 options are categorized into three lists 3135: conditions, medications, and procedures. Each list 3135 contains unique items 3136 and presents applicable guidelines 3137 for each item 3136. The content panel 3131 presents an amalgamated Summary 3138 of associated guidelines when an item 3136 is selected. The summary 3138 provides an Overview 3139 of the guidelines, presents areas where the guidelines agree as Similarities 3140, and areas where there is not agreement in the guidelines as Differences/Conflicts 3141. This allows a user to quickly understand complex insurance billing guidelines and clinical practices and optimizes their ability to make sound clinical judgements and accurately bill.

Figure 42B:
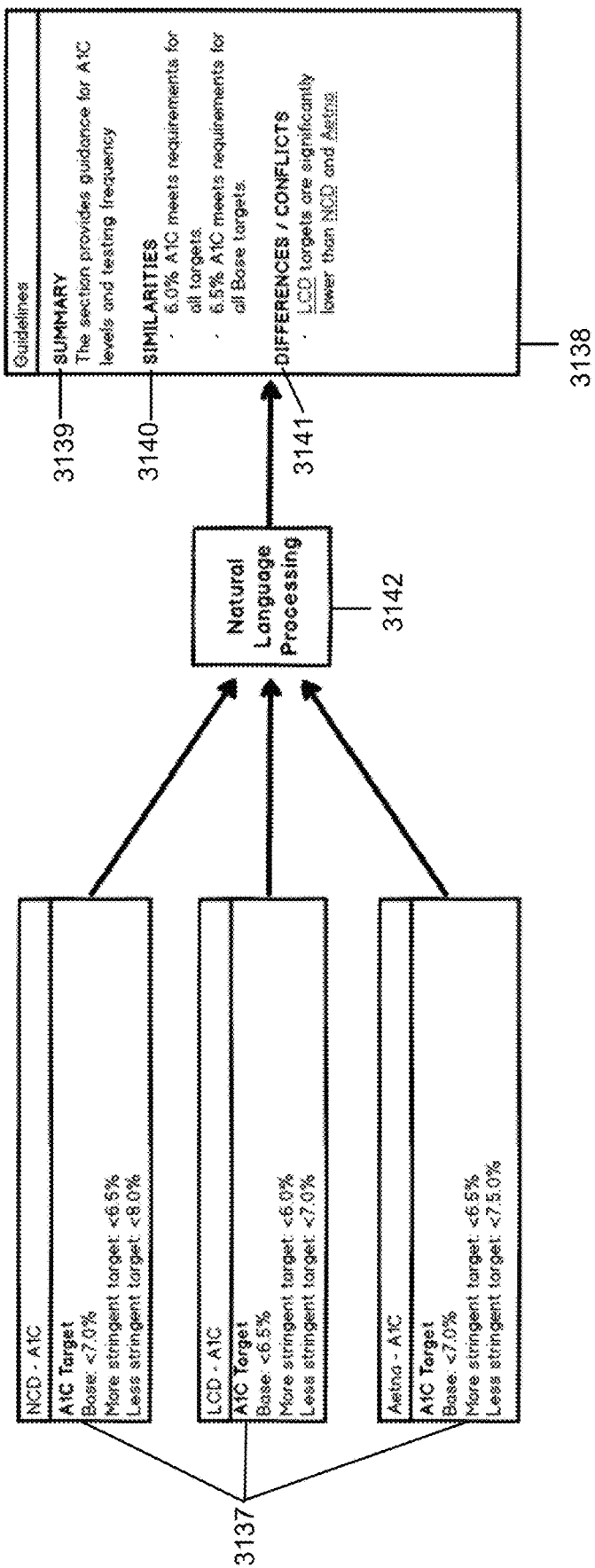
FIG. 42B illustrates an exemplary cognitive system enhanced clinical decision support system for providing cognitive enhanced guidance analysis and summary.

The Guidelines Summary may be enhanced using a cognitive system enhanced Clinical Decision Support ("CDS") system of type described below with respect to FIG. 72B to provide the summary 3138 shown in the content panel 3131 of associated guidelines illustrated in FIG. 42A. FIG. 42B presents a population process with disparate content encountered from various guideline jurisdictions 3137. Commercially available Natural Language Processing 3142 is used to contextually parse the language of the guidelines 3137 and to present the user with a unified summary 3138 including overview 3139, similarities 3140, and differences/conflicts 3141 described above. The cognitive system enhanced CDS thus augments the practitioner's judgement by representing a holistic view of relevant guidance.

Figure 43:
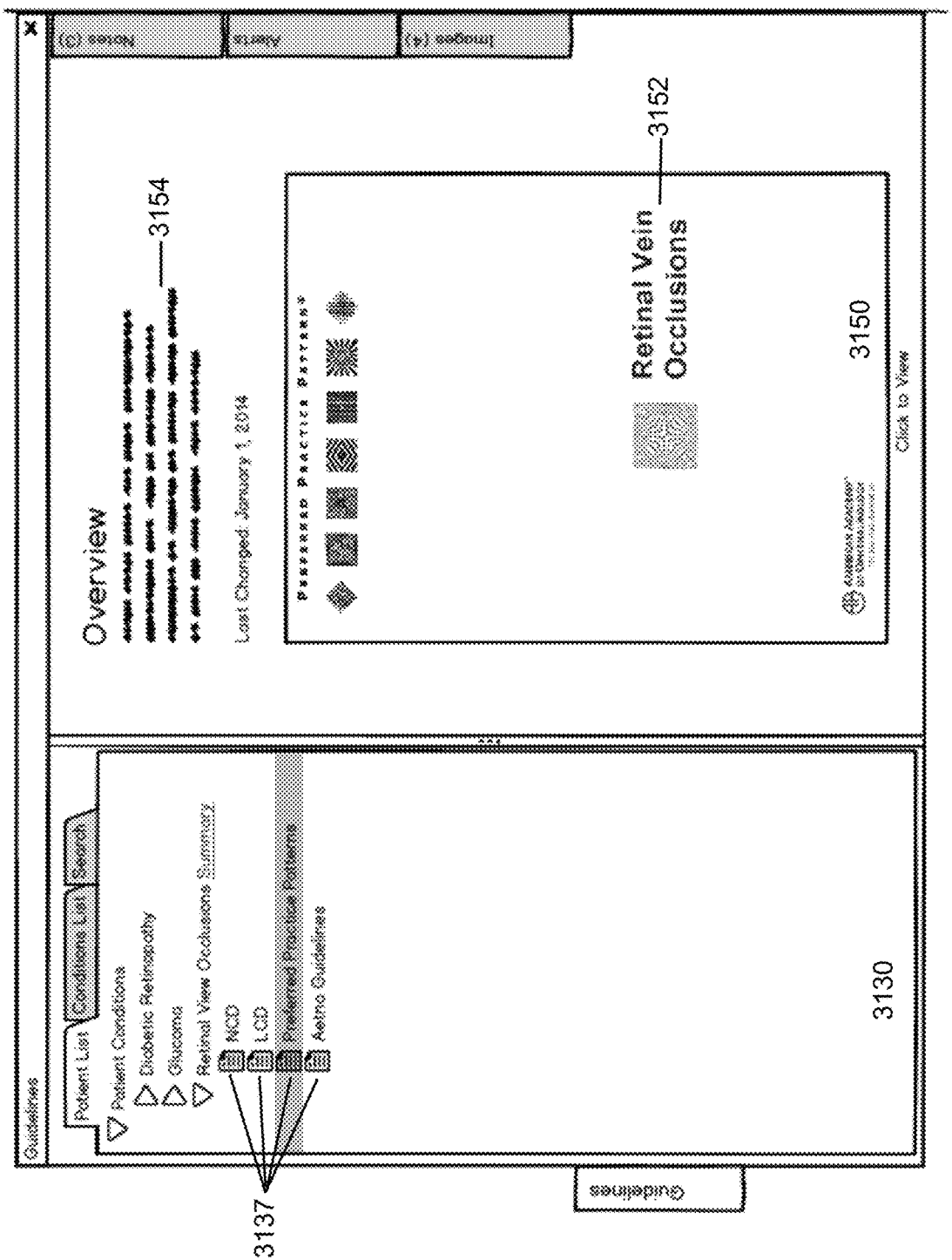
FIG. 43 illustrates a view of the Published Guidelines in accordance with the second embodiment of the invention.

FIG. 43 illustrates a view of the Published Guidelines, which may include Preferred Practice Patterns, and which may be accessed by selecting the physician icon 2932 in the header of the flowsheet (FIG. 32B), the guidelines tab 2542 (FIG. 15), and in each of the ordering panels for labs (FIG. 46), medications (FIG. 44), procedures (FIG. 51), and imaging (FIG. 48). The Smart Evaluation Panel in each of the order screens reference the Preferred Practice Patterns which may be used to track the physicians' activities. In FIG. 43, there are two panels: the tabbed navigation panel 3130 and a content panel 3150. The content panel 3150 presents a copy of the published guideline 3152 and an Overview 3154 of the guideline when that guideline 3137 is selected in navigation panel 3130. Clicking on the guideline 3152 opens the actual guideline.

The next few sections describe methods for ordering medications, labs, procedures, and imaging tests. Each unique panel has the ability to order the relevant items but also provides information about compliance with insurance guidelines, good clinical practice recommendations, provides cost-effective medically equivalent alternatives along with costs and pricing either in a hospital or outpatient setting allowing the clinical and patient may decisions that are both clinically and financially sound. These panels are presented as overlays or pop-up windows on the page allowing the user to easily see relevant medical information, critical notes, alerts and recommendations without leaving the ordering functions in the Command Center 2500. The user thus can understand the patient's complete medical history across institutions while placing a new order without having to switch contexts like within the typical EMR. By visualizing patterns and trends at the point of care, the user can better tailor the medications, labs, procedures, and imaging test they order to what is medically indicated.

Figure 44:
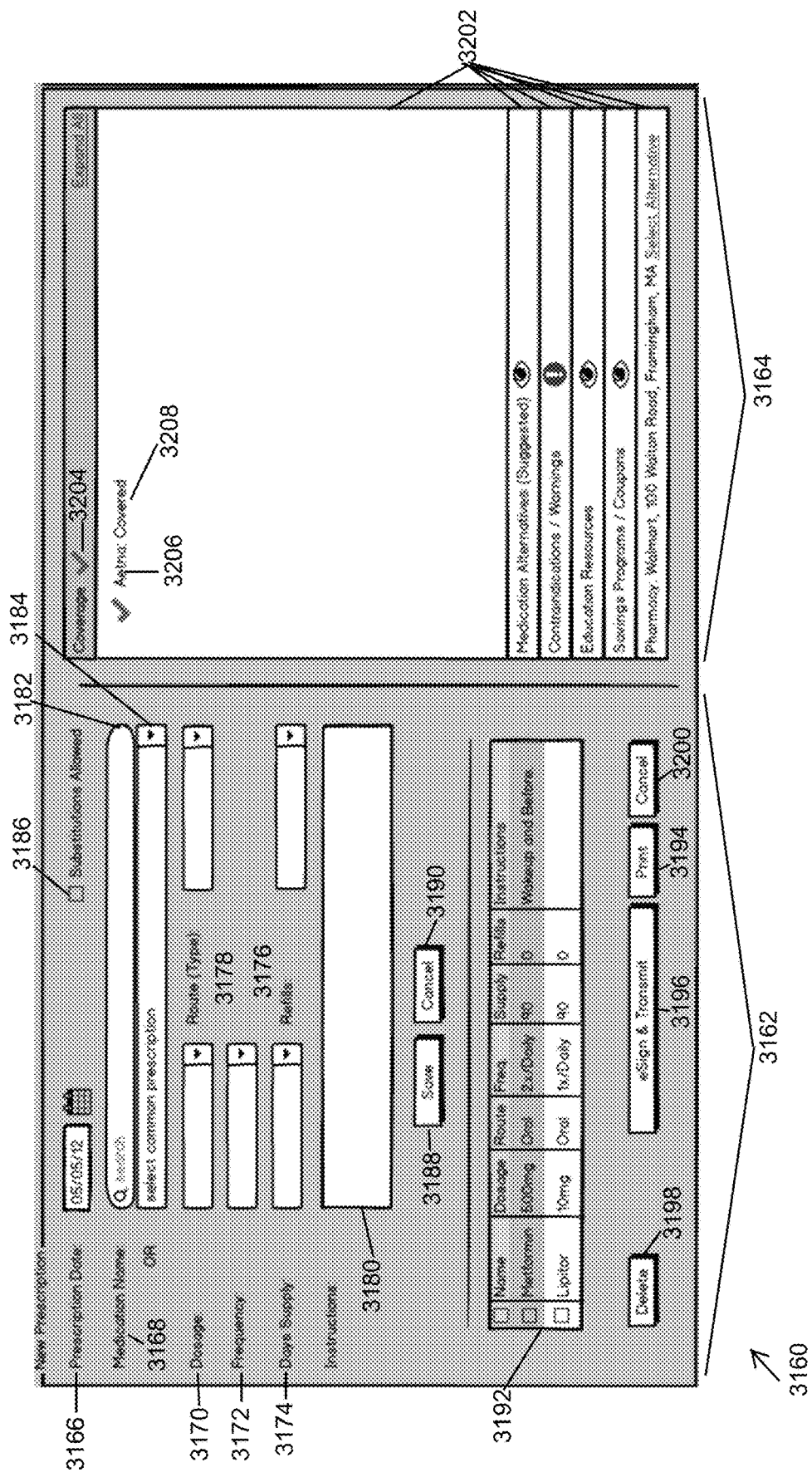
FIG. 44 illustrates a view of the Medication Order panel in accordance with the second embodiment of the invention.

FIG. 44 illustrates a view of the Medication Order panel 3160, which may be accessed from the Retina Flowsheet 2530 or may be provided as a separate display panel in the Command Center 2500. The Medication Order panel 3160 allows authorized users to order prescriptions for patients. There are two sections to the Medication Order panel 3160, a prescription section 3162 and a Smart Evaluation control section 3164. The prescription section 3162 allows the user to enter a prescription including: the prescription date 3166, medication name 3168, dosage 3170, frequency 3172, days' supply 3174, refills 3176, Route (Type) 3178, and text instructions 3180. The user can search for a medication using the search dialog 3182 or quickly select common prescriptions from the dropdown menu 3184. Allowing the pharmacist to make substitutions can be indicated with the checkbox 3186. The prescription can be saved 3188 or canceled 3190. Saved prescriptions are listed 3192 and they may be printed 3194, electronically transmitted 3196 to a selected pharmacy, or deleted using the associated checkboxes and Delete button 3198. The Cancel button 3200 may close the Medication Order panel 3160 and discard any unsaved work.

The Smart Evaluation control section 3164 contains six sub panels 3202 which may be toggled open and closed by the user. The Coverage subpanel 3204 presents the patient's insurer(s) 3206 and the coverage status 3208 of the selected prescription(s) 3192. In exemplary embodiments, the coverage status is determined by using third party services. The Smart Evaluation control section 3164 is a core aspect of combining clinical, financial, and insurance guidelines together into one display. The Smart Evaluation control section displays information related to insurance compliance, clinical guideline recommendations, recommendations for cheaper alternatives (drug cost advisor), pricing data from a hospital, practice and a patient's perspective all in the same display panel and all in the context of the patient's past medical history.

FIG. 45 illustrates the Medication Alternatives (Suggested) sub panel 3210 of the six sub panels 3202 illustrated in FIG. 44. The Medication Alternatives (Suggested) sub panel 3210 suggests alternative medications 3212 along with cautionary statements 3214 about its use. In exemplary embodiments, the alternative medication and pricing information are determined by using third party services.

Figure 46:
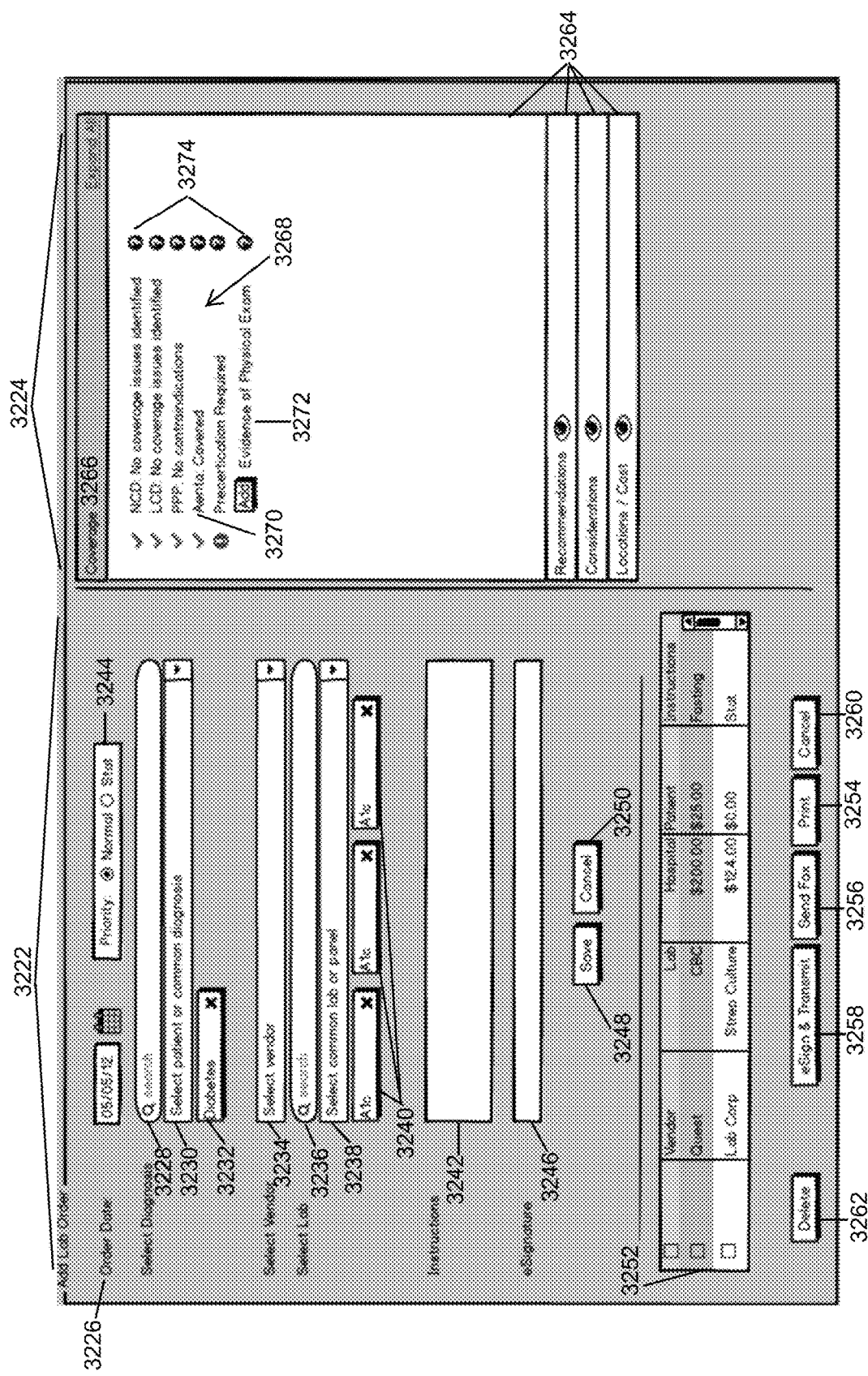
FIG. 46 illustrates a view of the Lab Order panel in accordance with the second embodiment of the invention.

FIG. 46 illustrates a view of the Lab Order panel 3220, which may be accessed from the Retina Flowsheet 2530 or may be provided as a separate display panel in the Command Center 2500. The Lab Order panel 3220 allows authorized users to order labs for patients. There are two sections to the panel, a Lab Activity section 3222 and the Smart Evaluation control section 3224. The Lab Activity section 3222 allows the user to enter a lab order including the order date 3226, associated diagnosis supporting the lab testing using either a search box 3228 or a drop down menu 3230, selected diagnosis as tags 3232, vendor selection 3234, and to search using a search box 3236 or to select commonly ordered labs from a drop down menu 3238, and a list of test ordered as tags 3240, along with instructions 3242. The priority is indicated with the checkbox 3244. An e-signature box 3246 is present for completing the lab order. Lab tests may be saved 3248 or canceled 3250 using the proper buttons. Selected lab tests 3252 may be printed 3254, electronically faxed 3256, electronically transmitted 3258 to a selected vendor, canceled 3260, or deleted 3262 with the associated buttons. The Cancel button 3260 may close the panel and discard any unsaved work.

The Smart Evaluation control panel 3224 contains four sub panels 3264 that may be toggled open and closed by the user. The Coverage subpanel 3266 presents an evaluation of whether or not the patient's insurance 3268 will cover 3270 the ordered tests 3252. Coverage subpanel 3266 also presents any precertification requirement 3272 and if a specific action is required. In the example demonstrated here, the patient primary insurance is Aetna and secondary insurance is Medicare. The Preferred Practice Guidelines are also evaluated. The question marks 3274 may also be activated to see more detail. In an exemplary embodiment, this evaluation is determined by using third party services.

Figure 47:
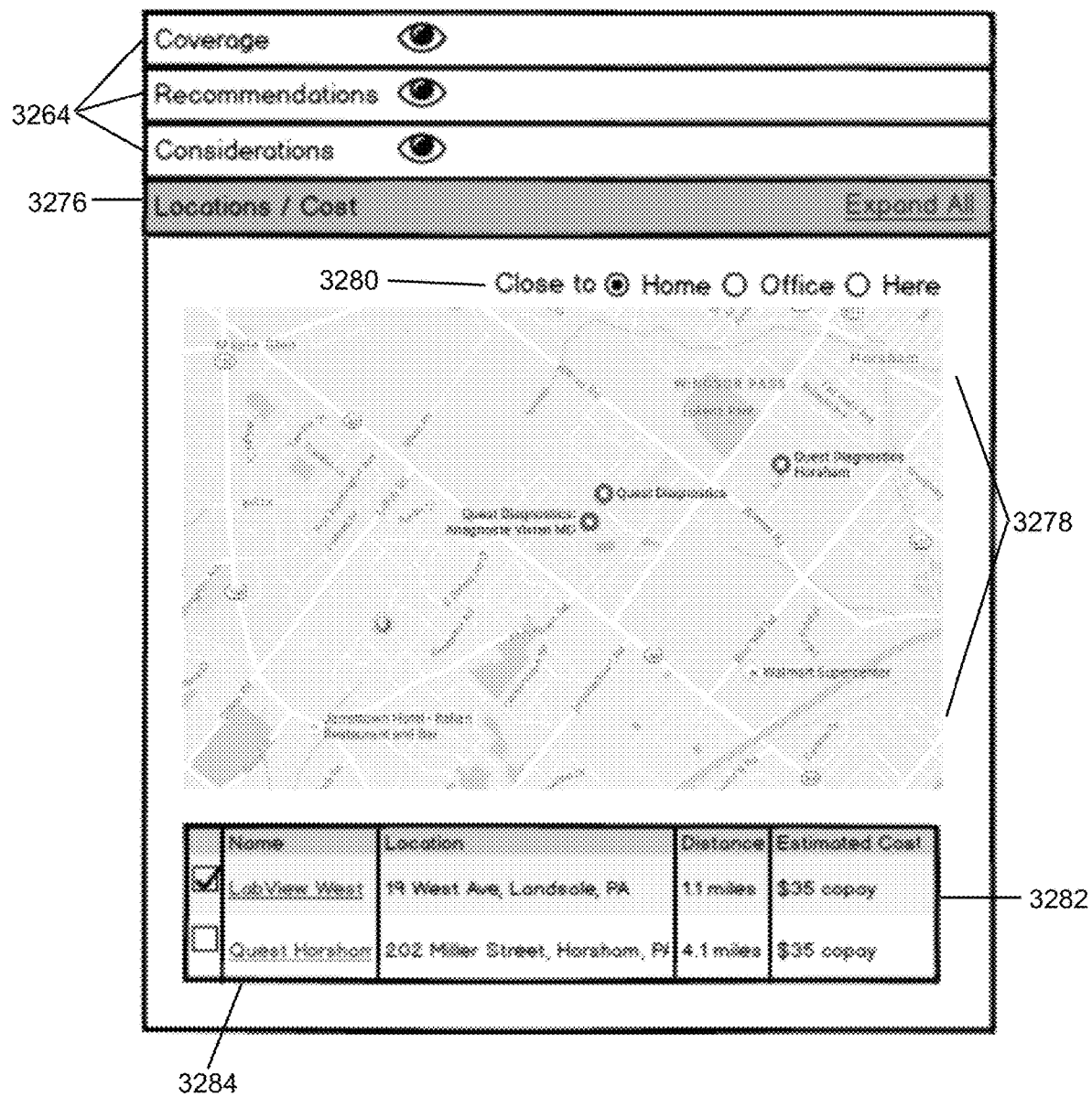
FIG. 47 illustrates the Locations/Costs sub panel of the sub panels of FIG. 46.

FIG. 47 illustrates the Locations/Costs sub panel 3276 of the sub panels 3264 of FIG. 46. The Locations/Costs sub panel 3276 provides a map 3278 with locations of vendors relative to selected locations 3280 (such as the patient's home, work, or provider's office). The Locations/Costs sub panel 3276 also displays the patient's costs (3282) for each vendor and address information in a map legend 3284. In an exemplary embodiment, this information is provided through a third party service.

FIG. 48 illustrates a view of the Imaging Order panel 3290. The Imaging Order panel 3290 allows authorized users to order Imaging for patients. There are two sections to the Imaging Order panel 3290, an Imaging activity section 3292 and the Smart Evaluation control section 3294. The Imaging activity section 3292 allows the user to enter an imaging order including the order date 3296, search using a search box 3298 or select a common associated diagnosis using drop down menu 3300 to supporting the imaging testing, select a diagnosis presented as tags 3302, search using search box 3304 or select common symptoms reported by the patient from a drop down menu 3306, select symptoms displayed as tags 3308, select the imaging modality 3310 with costs to the hospital and patient for each modality, select the location of the body to be imaged 3312 with supporting tags 3314, along with instructions 3316. The priority is indicated with the checkbox 3318. Imaging tests may be saved 3320 or canceled 3322 using the proper buttons.

The Smart Evaluation control panel 3294 contains four sub panels 3324 that may be toggled open and closed by the user. The Coverage subpanel 3326 is an evaluation of whether or not the patient's insurance will cover 3328 the ordered images 3310 and check medical necessity 3330 (per the relevant governmental and/or insurance guidelines).

Figure 49:
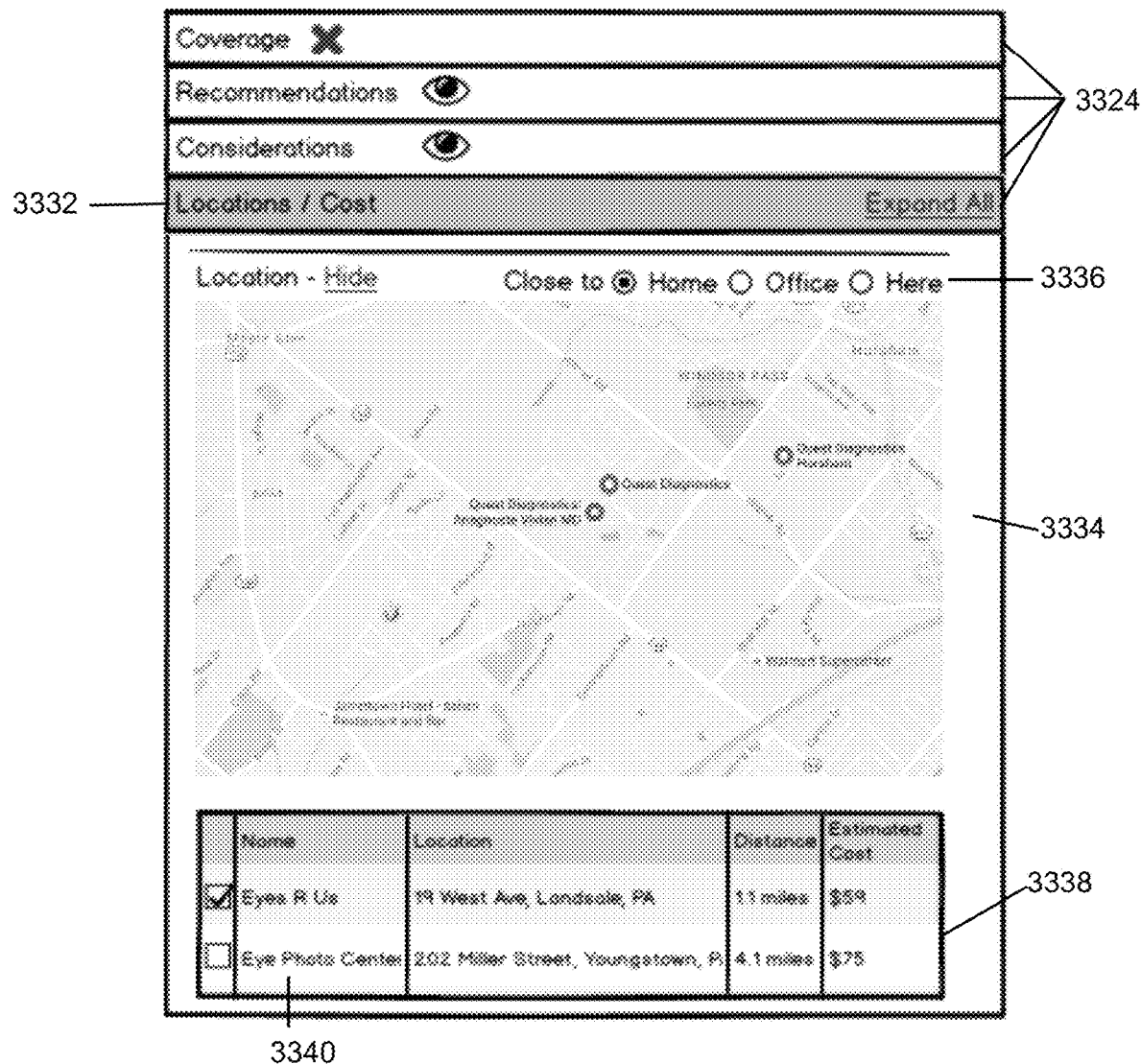
FIG. 49 illustrates the Locations/Cost sub panel of the sub panels illustrated in FIG. 48.

FIG. 49 illustrates the Locations/Cost sub panel 3332 of the sub panels 3324 illustrated in FIG. 48. The Locations/Cost sub panel 3332 provides a map 3334 with locations of vendors relative to selected locations 3336 (such as the patient's home, work, or provider's office). The Locations/Cost sub panel 3332 also presents the patient's costs (3338) for each vendor and address information in a map legend 3340. In an exemplary embodiment, this information may be provided through a third party service.

Figure 50:
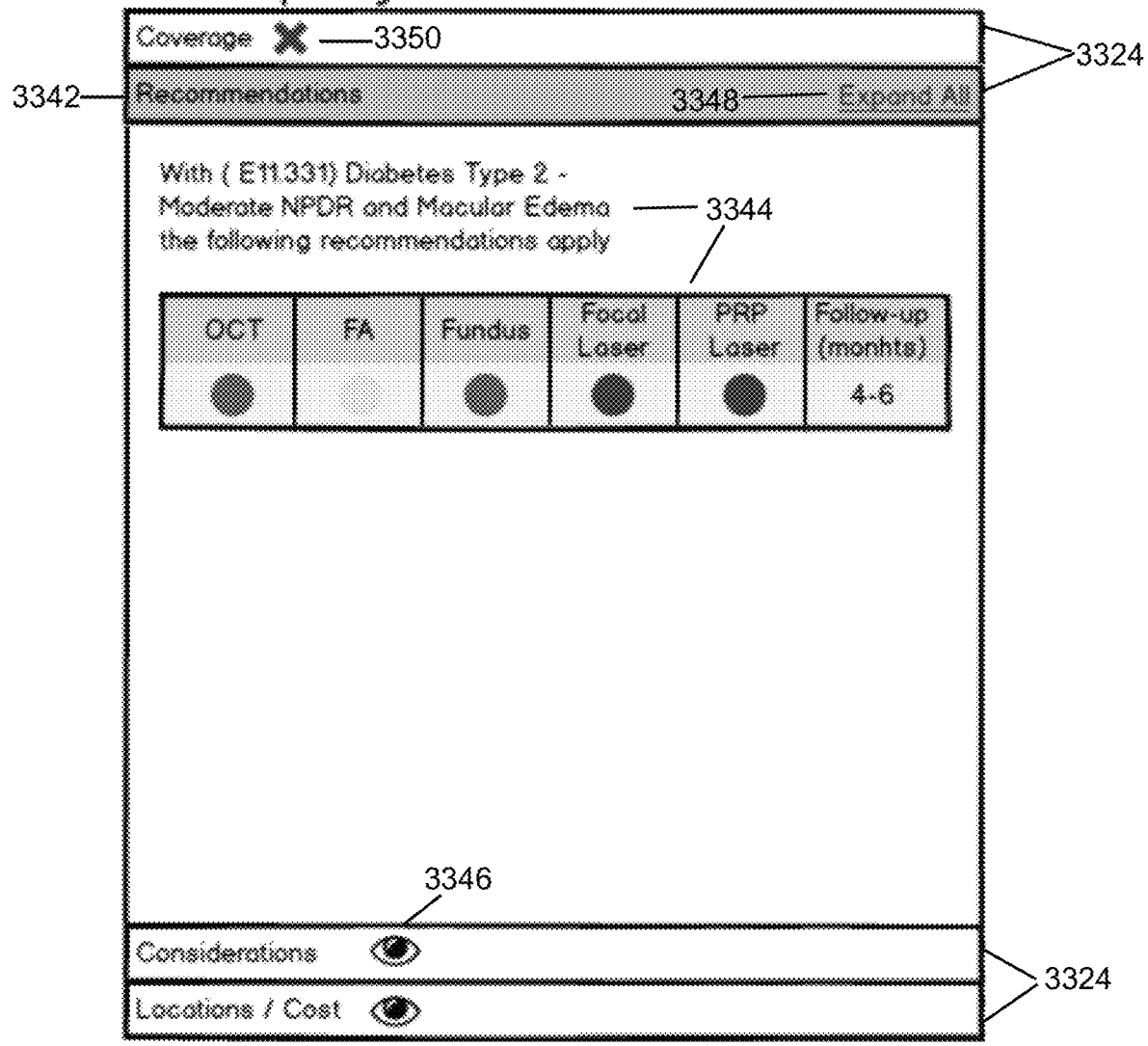
FIG. 50 illustrates the Recommendations sub panel of the sub panels illustrated in FIG. 48.

FIG. 50 illustrates the Recommendations sub panel 3342 of the sub panels 3324 illustrated in FIG. 48. In this example embodiment, the patient has Type 2 Diabetes, Moderate Non-Proliferative Diabetic Retinopathy and Macular Edema. The Recommendations sub panel 3342 provides recommendations for the proper imaging 3344 based on the patient's specified conditions and preferred practice guidelines. The eye icon 3346 on each of these panel headers signifies there is something on the tab. This prevents the user from having to click on each tab to see if anything exists. The user may expand all panels at the same time by clicking the Expand All link 3348 which is always displayed on the active tab. Once all panels are expanded, the active panel header displays a link to Close Other Panels (not depicted). The Coverage panel also displays a green checkmark or a red X icon 3350 to signify whether the selected diagnosis and imaging modality are covered under the patient's insurance.

Figure 51:
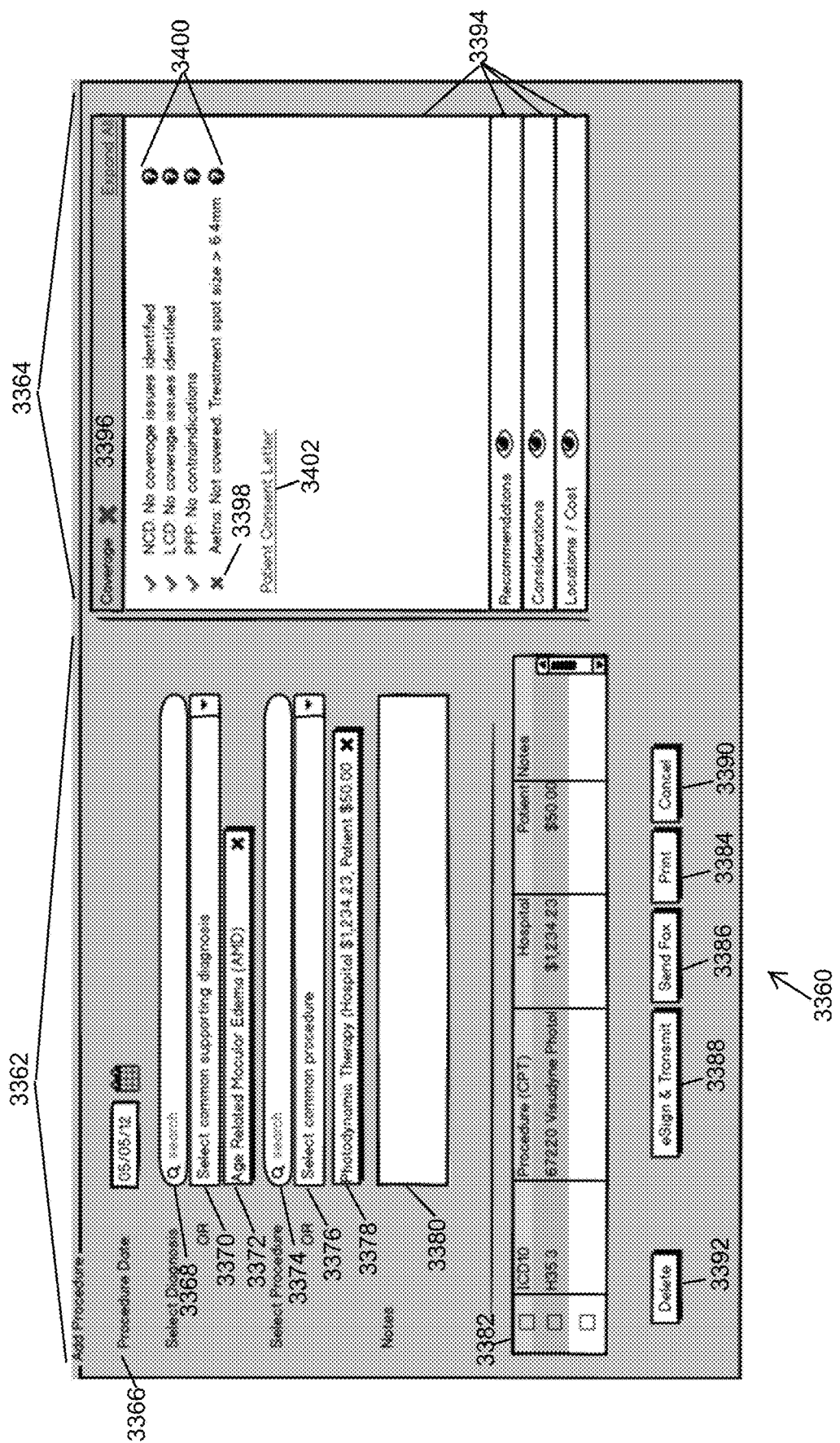
FIG. 51 illustrates a view of the Procedure panel in accordance with the second embodiment of the invention.

FIG. 51 illustrates a view of the Procedure panel 3360. The Procedure panel 3360 allows authorized users to order Procedures for patients. There are two sections to the Procedure panel 3360, a Procedure activity section 3362 and the Smart Evaluation control section 3364. The Procedure activity section 3362 allows the user to enter a Procedure including the order date 3366, search using a search box 3368 or select a common associated diagnosis using drop down menu 3370 to supporting the Procedure testing, select diagnoses presented as tags 3372, search using search box 3374 or select a common procedure using a drop down menu 3376, or select procedures displayed as tags 3378, along with notes 3380. The priority may be indicated with a checkbox (not shown). Selected Procedure(s) 3382 may be printed 3384, electronically faxed 3386, electronically transmitted 3388, canceled 3390, or deleted 3392 with the associated buttons. The Cancel button 3390 may close the panel and discard any unsaved work.

The Smart Evaluation control section 3364 contains four sub panels 3394 that may be toggled open and closed by the user. The Coverage subpanel 3396 presents an evaluation of whether or not the patient's insurance will cover 3398 the ordered procedures 3382 and check for medical necessity at 3400. Links 3402 are also presented to any documents that must be completed by the patient like a consent form. In an exemplary use, if a physician decided to schedule a laser treatment for a patient, the physician would input a plan of treatment by selecting the desired procedures from Procedure activity section 3362 and bring in all of the relevant cost data, effectivity, insurance restrictions, ability for the patient to choose care, etc. into Smart Evaluation control section 3364 for review before proceeding. Peer data (FIG. 55) may also be displayed to assist the physician in the decision-making process.

Figure 52:
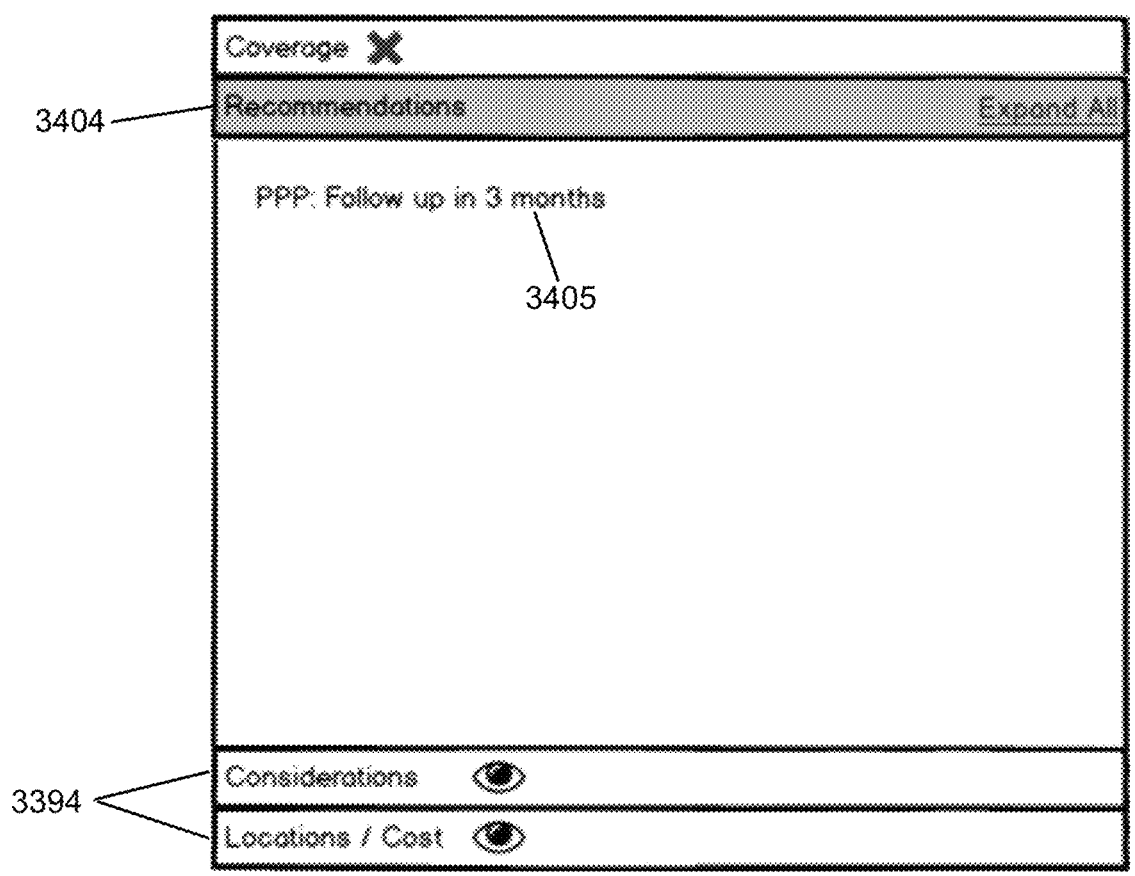
FIG. 52 illustrates the Recommendations sub panel of the sub panels illustrated in FIG. 51.

FIG. 52 illustrates the Recommendations sub panel 3404 of the sub panels 3394 illustrated in FIG. 51. The Recommendations sub panel 3404 provides recommendations 3405 based on the patient's specified conditions, selected procedures and clinical and insurance guidelines. Recommendations may be for alternative procedures based on the patient's condition, insurance regulations and or good clinical practice. Recommendations an also reflect necessary consults, for example rheumatology consult for uveitis. Alternatively, an automated consult request generator may generate prompts showing needed medical referrals based on various database inputs (e.g., rheumatology consult for uveitis). If the patient is already under the care of a rheumatologist, the system may alert the physician of the next scheduled appointment with a rheumatologist, who may, in turn, provide shared care as described with respect to FIG. 25A. In exemplary embodiments, this information is provided through a third party service.

Figure 53:
FIG. 53 illustrates the Considerations sub panel of the sub panels illustrated in FIG. 51.

FIG. 53 illustrates the Considerations sub panel 3406 of the sub panels 3394 illustrated in FIG. 51. The Considerations sub panel 3406 provides additional considerations 3407 a user may want to consider when evaluating procedures based on the patient's specified conditions and clinical and insurance guidelines. In exemplary embodiments, this information is provided through a third party service.

FIG. 54 illustrates the Locations/Costs sub panel 3408 of the sub panels 3394 illustrated in FIG. 51. The Locations/Costs sub panel 3408 is an embodiment of the panel as used in a hospital setting. The Locations/Costs sub panel 3408 provides a table 3409 with the associated costs and estimated reimbursement for the selected procedure to help the physician better understand the financial implications of providing the service. The Locations/Costs sub panel 3406 also presents the patient's estimated costs 3410. Where a medically equivalent but less costly alternative is available, it may be presented to the user (not depicted). In exemplary embodiments, this information is provided by the hospital itself from their charge sheet and accounting system and the patient costs from $3^{rd}$ party services.

Figure 55:
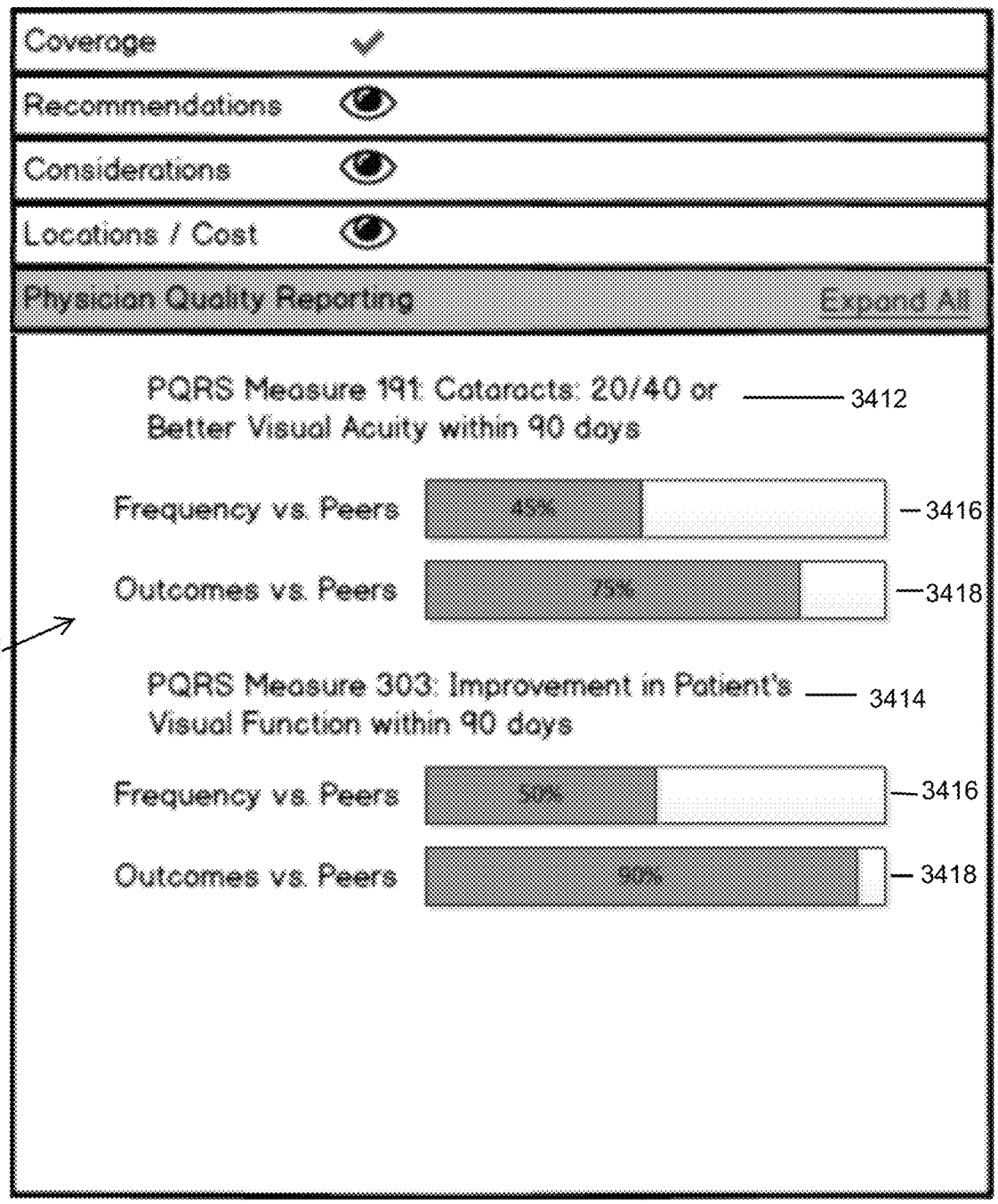
FIG. 55 illustrates a Physician Quality Reporting panel within the Smart Evaluation control panel.

FIG. 55 illustrates a Physician Quality Reporting panel 3411 within the Smart Evaluation control panel. The Physician Quality Reporting panel 3411 displays Physician Quality reporting metrics 3412, 3414 related to the procedure that is being ordered. Other quality reporting or peer data may be displayed. For each relevant metric, the Physician Quality Reporting panel 3411 displays the physician's frequency of performing the procedure in comparison to their peers 3416 as well as outcomes 3418.

Figure 56A:
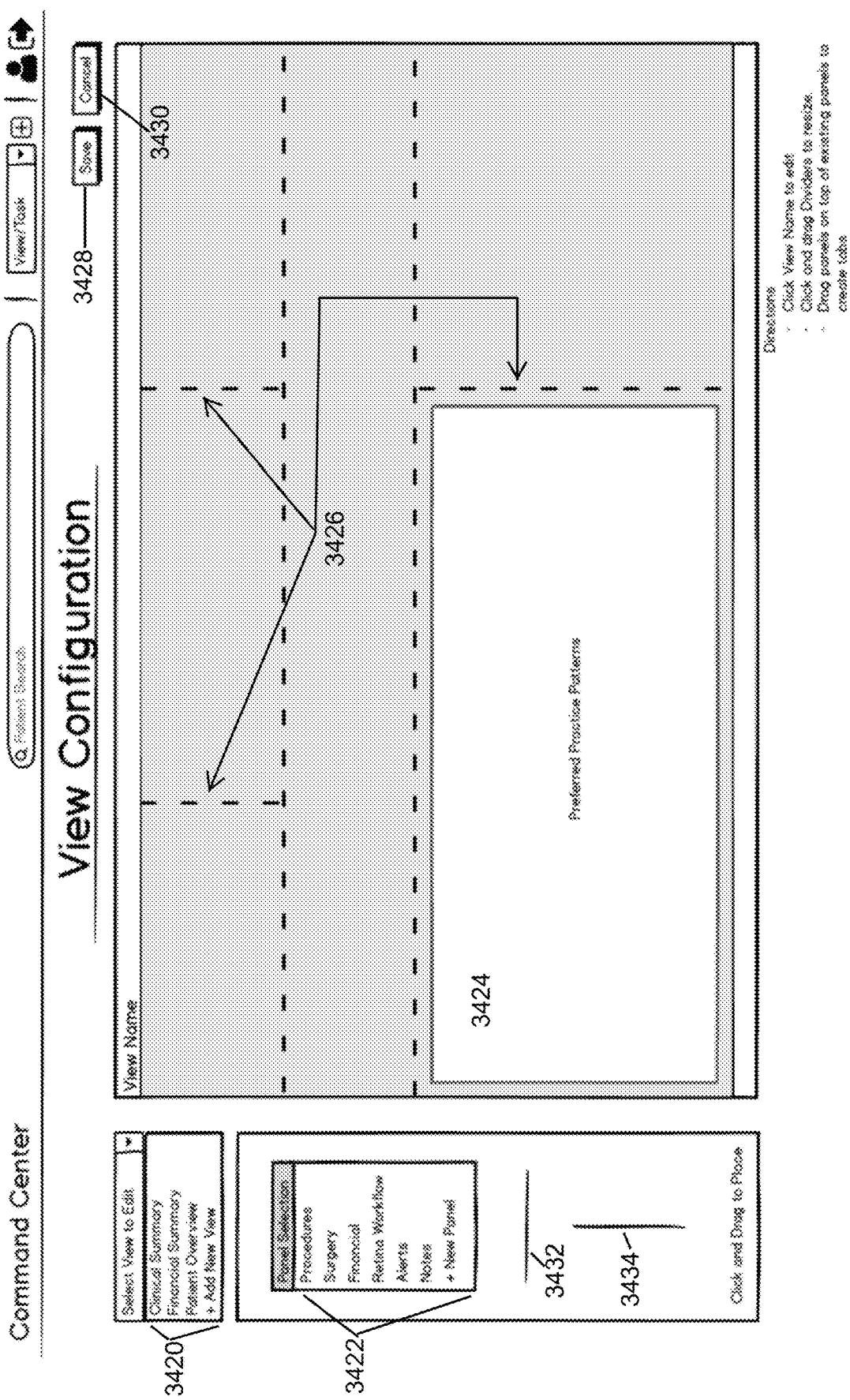
FIG. 56A illustrates the View Configuration page that provides the user a mechanism to create or modify dynamic dashboards to accommodate their unique requirements in accordance with the second embodiment of the invention.

The View Configuration page presented in FIG. 56A provides the user a mechanism to create or modify dynamic dashboards to accommodate their unique requirements. These dashboards are referred to herein as Command Center Views. The user identifies the view to be created or modified by selecting the appropriate option from the drop down menu 3420. Once the view has been selected, the user may select a panel to place in the view from the list 3422. Once the panel has been anchored in the View 3424, the dimensions of the panel may be adjusted by means for manipulating the panel frame(s) 3426. When the user is finished creating or modifying the view, the user may save (3428) or cancel (3430) their actions by selecting the associated buttons. Additional horizontal dividers 3432 and vertical dividers 3434 can be dragged and dropped onto the View in order to create new display panels. The dividers also can be removed by clicking on the desired divider and dragging it off the View.

Figure 56B:
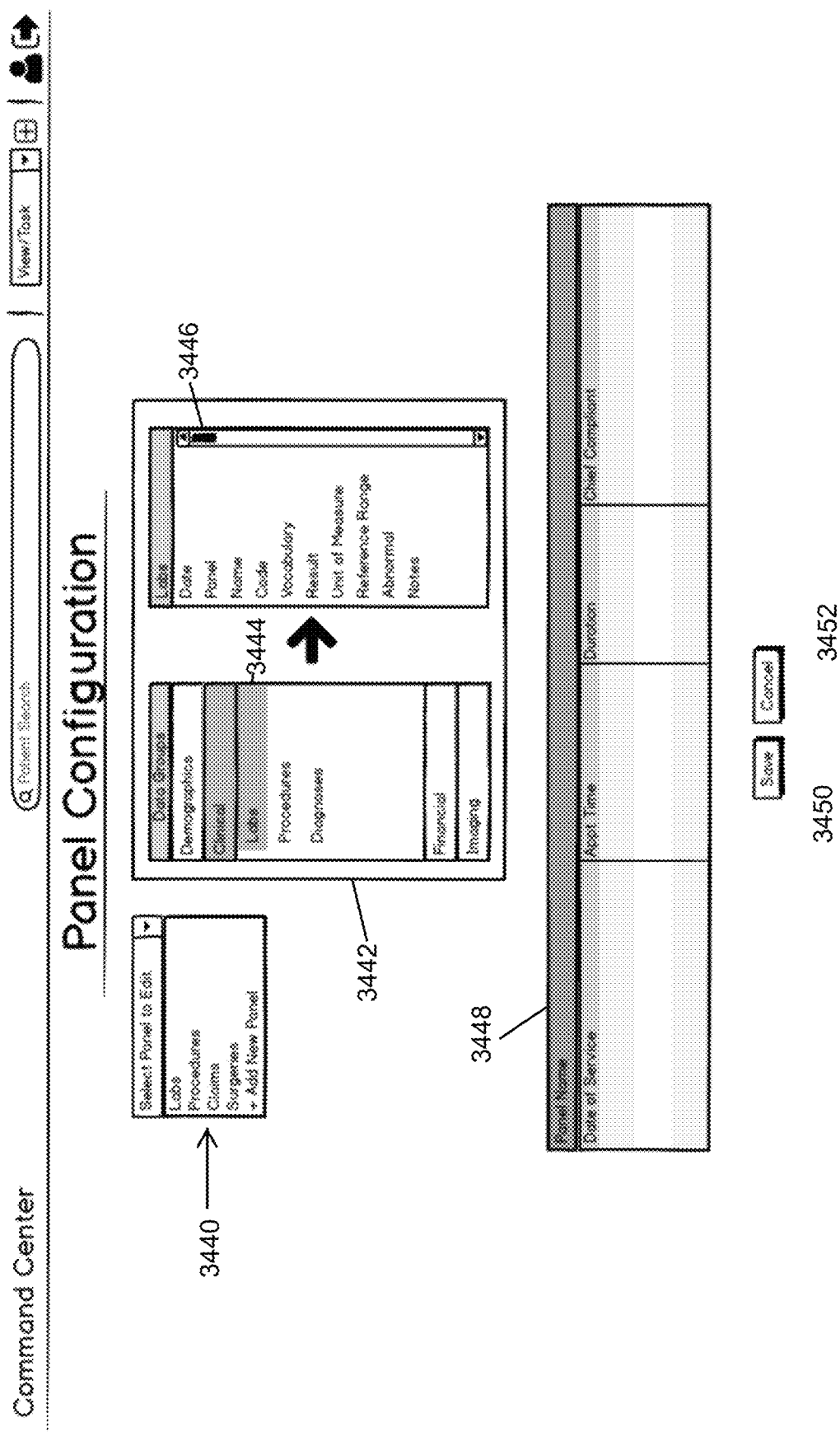
FIG. 56B illustrates the Panel Configuration page that provides the user a mechanism to create or modify display panels to use when populating the dynamic dashboards as described in FIG. 56A.

The Panel Configuration page presented in FIG. 56B provides the user a mechanism to create or modify display panels to use when populating the dynamic dashboards as described in FIG. 56A. The user identifies the panel to be created or modified by selecting the appropriate option from drop down menu 3440. The user then selects data to populate the panel from the Data Selector 3442. Available data 3444 is selected and migrated to the panel's Column List 3446. Users may also add custom fields allowing them to track any data relevant to the user. A preview of the panel 3448 is presented and updated as the user makes changes. When the user is finished creating or modifying the panel, the user may save 3450 or cancel 3452 their actions by clicking the associated buttons. The panels from the drop down menu 3440 thus may provide a template for creating a customized Command Center where all information desired by the user may be accessed without leaving the Command Center.

System Implementation

The Command Center user interface embodiments described above with respect to FIGS. 1-56 are characterized by their ability to present large volumes of dynamic data in a single screen whereby the data may be navigated without leaving the screen. For example, the data is either available in a display window, behind a tab, or available via a pop-up window and is thus accessible without leaving the display screen. To enable such processing to occur without unacceptable delay in data presentation, and to enable the display panels and flowsheet panels to reconfigured as described, a Command Center architecture has been designed that provides for flexibility in storage and presentation of dynamic data as well as dynamic caching techniques that allow for prompt presentation. As with the first embodiment described above, two-way auto-population techniques are also implemented whereby changes made in the Command Center are not only reflected in the screen display but also the associated electronic medical record is auto-populated as well without leaving the Command Center display screen. The system design will now be described starting with FIG. 57.

Figure 57:
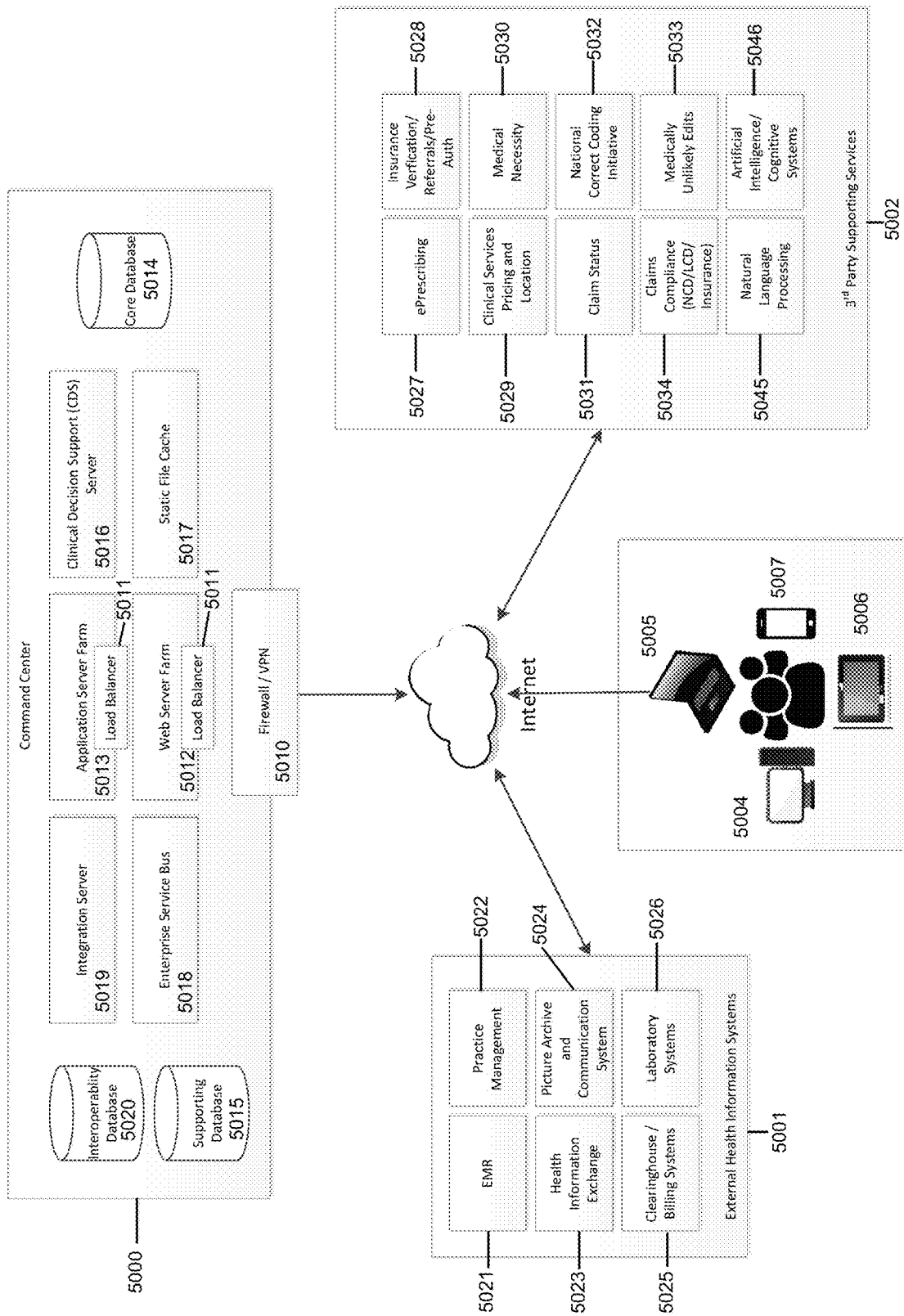
FIG. 57 illustrates the Command Center architecture and connectivity to external Health Information Technology systems and third party services in accordance with the invention.

FIG. 57 illustrates the Command Center architecture 5000 and connectivity to external Health Information Technology systems 5001 and third party services 5002. The Command Center architecture 5000 is a multi-tenant cloud-based web application. As known by those skilled in the art, multi-tenant means that the application is deployed once and all customers access the same server. Data is segregated by the application so that customers can only access their own data. The Command Center is accessible over the Internet via user platforms 5003 that implement a modern web browser (e.g. Internet Explorer 10, Google Chrome) on a desktop computer 5004, laptop 5005, tablet 5006, or a smartphone 5007 with internet connectivity.

The Command Center architecture 5000 illustrated in FIG. 57 is one embodiment of how the system can be configured to support a large user base. For security purposes, access to the cloud platform containing the Command Center is governed by a firewall and Virtual Private Networks (VPNs) 5010. Additionally, end to end encryption is an inherent part of the Command Center architecture 5000 as the Command Center architecture 5000 is optimized to meet the highest privacy and security expectations. Each component allows for both the application of current high strength encryption (ex. AES 256) as well as continuous implementation of evolving data protection and security best practices. The Command Center architecture 5000 configuration supports proven high-availability and disaster recovery practices, including fully encrypted off-site backup and redundant, geographically dispersed operations. Load balancers 5011 distribute the client requests to the most available web server in the web server farm 5012 to optimize response time. The web servers in the web server farm 5012 pass requests through the load balancer 5011 to the application server farm 5013 to continue processing the client requests. The application servers of the application server farm 5013 process the requests and access data from the core database 5014 and supporting database(s) 5015. Depending on the client request, the application servers may interact with the Clinical Decision Support Server 5016 where the primary business logic resides. Once processed, the web server returns the results of the client request back to the client for display. Static files are optimized for retrieval by residing on a dedicated server (static file cache) 5017 where they are cached and optimized for this purpose.

The exchange of information between external health information technology (HIT) systems 5001 and the Command Center 5000 is managed by dedicated servers designed to optimize system throughput and secure communications. All communications take place through a secure VPN 5010 connection. If the integration method is message-based, the sending HIT system 5001 may transmit messages to the Enterprise Service Bus 5018. However, if communication is based on an API standard, the sending HIT system 5001 may communicate with the Integration Server 5019. Both of these servers 5018, 5019 communicate directly with the Interoperability database 5020 and, in turn, with the core and supporting databases 5014, 5015. While communications with third party services 5002 are largely outbound from the Command Center 5000 to the services, it is possible to receive inbound communications. These third party communications may also be handled through the Enterprise Service Bus 5018 and the Integration Server 5019. As illustrated in FIG. 57, examples of HIT systems 5001 include Electronic Medical Records (EMRs) 5021, Practice Management Systems 5022, Health Information Exchanges (HIEs) 5023, Picture archiving and communication systems (PACS) 5024, claims-based systems such as Clearinghouses and Insurance Companies billing systems 5025, and Laboratory Systems 5026.

In exemplary embodiments, many third party supporting services 5002 are integrated to provide feedback and advice. Examples of these services include ePrescribing 5027, Insurance verification including referrals and pre-authorizations 5028, clinical pricing and location services 5029 used to find the best value on purchasing medications, procedures and imaging services, medical necessity checking 5030 to verify a procedure or medication is associated with a correct ICD10 code supporting its use, claim status checking 5031, services in support of the National Correct Coding Initiative 5032, Medically Unlikely Edits 5033 provided by Center of Medicare and Medicaid Services (CMS) to proactively ensure claims are coded correctly to prevent issues in billing, and claims compliance services 5034 which evaluate claims against CMS National Coverage Determination (NCD) and Local Coverage Determination (LCD) guidelines as well as local insurance regulations all in an effort to establish and document medical necessity and to document same in support of streamlined billing. Natural language processing program 5045 and artificial intelligence/cognitive systems 5046 may also be provided to, for example, provide the clinical decision support features described with respect to FIGS. 72A-72C. In exemplary embodiments, the NCD and LCD guidance is programmed into the Command Center 5000 so that alerts may be generated when a physician attempts to follow a treatment protocol that is non-compliant with the NCD and LCD guidance.

Those skilled in the art will appreciate that data latency may be improved by storing the data in the static file cache 5017 in the server of the distributed network of servers that is closest to the geographic location of the patient's appointment. In an exemplary embodiment, the server closest to the geographic location of the patient's appointment could contain data only for today's patients so that there is less data to query, thus improving the access speed for the data. Also, any data that is not stored locally may be cached locally after it has been accessed for the first time as it is more likely to be accessed a second time, thereby speeding up the data access. This architecture implements Proximity Request storage whereby data accessed most frequently is stored geographically closer to the user to reduce the time it takes to travel over the Internet. This approach is used by Netflix and others when hosting large movie files. In the present case, the most relevant patient data is stored within proximity of where it is stored. Relevant patient data is for patients that have been accessed in the past few days and any patients with an upcoming appointment. Having a smaller local subset of data makes the whole network operate more efficiently.

Figure 58:
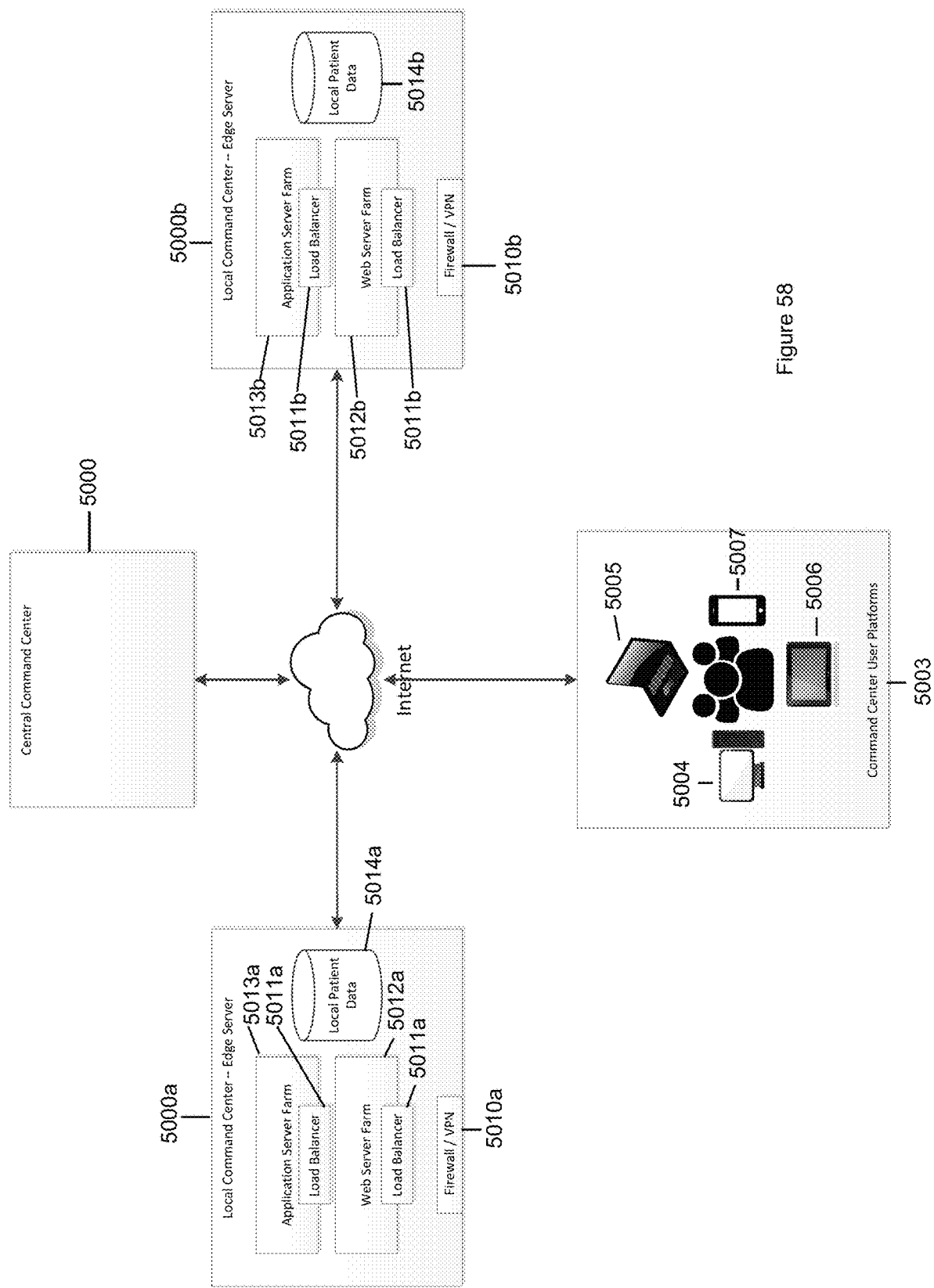
FIG. 58 illustrates the architecture of a central controlling server platform and multiple geographically distributed edge server platforms.

FIG. 58 illustrates the architecture of a central controlling server platform 5000 and multiple geographically distributed edge server platforms 5000a and 5000b. Each edge server platform 5000a, 5000b includes a firewall/VPN 5010a, 5010b, load balancers 5011a, 5011b, web servers 5012a, 5012b, application servers 5013a, 5013b, and a local Patient Database 5014a, 5014b. On a nightly basis, data for patients with appointments the next calendar day is transferred to the edge server located geographically closest to the user's primary access point as determined by IP address and stored in the local Patient Database 5014a, 5014b.

When a user requests data using platforms 5003, it is first attempted to be retrieved from the closest edge server 5000a, 5000b based on the user's location and proximity to the server. If the closest edge server 5000a, 5000b is not available, access to the central server 5000 is requested. In this configuration, the central server 5000 may be the closest geographically, in which case the user request is just processed on the central server 5000. If the data was only available on the central server 5000, in addition to returning the data to the user 5003, it is also made available on the geographically closest edge server 5000a, 5000b. This allows subsequent requests to be completed more quickly. Data is stored on the edge servers 5000a, 5000b for a pre-determined number of days after it has been last accessed because it is more likely to be accessed during this time period. After this time period has expired the data is purged from the local data storage 5014a, 5014b. All user entered data is always stored on the central server 5000 first and then propagated to the edge servers 5000a, 5000b.

This architecture has several advantages. In particular, the most likely data (patients with appointment during the current day and those that have been accessed in the past days) is made available at the closest geographic server. The response time to complete user's requests are completed faster because network latency is reduced due to a shorter physical distance, but also because queries resolve faster due to smaller datasets being stored on the edge servers. The distributed approach also makes the whole architecture more efficient, because requests handled by the edge servers 5000a, 5000b reduce the load on the central server 5000.

Figure 59A:
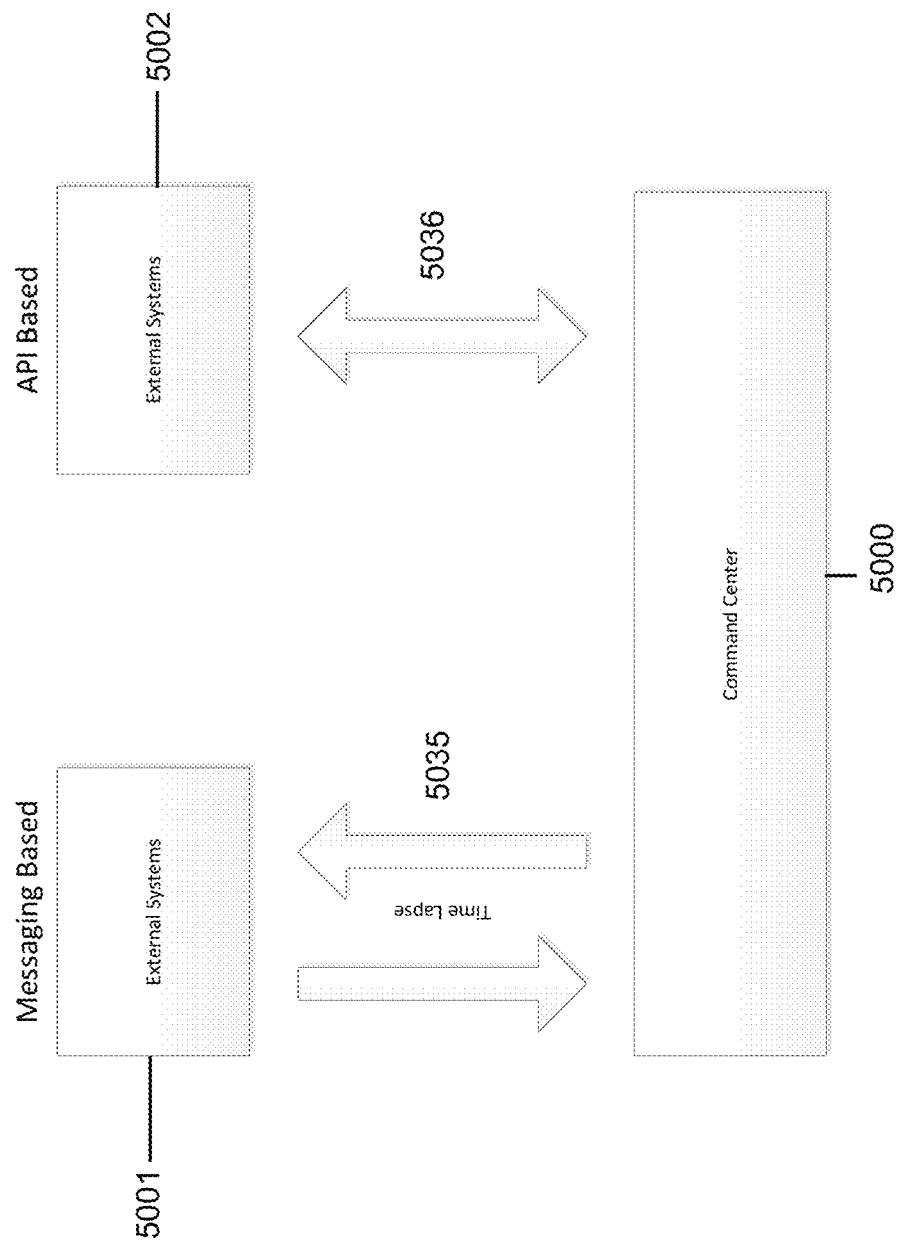
FIG. 59A illustrates integration of the Command Center with the user's existing Health Information Technology (HIT) and third party services using either industry standard message-based protocols or API-based methods in accordance with the invention.

As illustrated in FIG. 59A, the Command Center 5000 is designed to be integrated with the user's existing Health Information Technology (HIT) 5001 and Third party services 5002 using either industry standard message-based protocols 5035 or API-based methods 5036. The interconnection between systems is designed to be bi-directional, in that data can be sent and received from these external systems. Those skilled in the art will appreciate that these and all messages transmitted herein are transmitted in compliance with HIPAA requirements or other global privacy and security regulations using transmission media that enable such compliance.

Figure 59B:
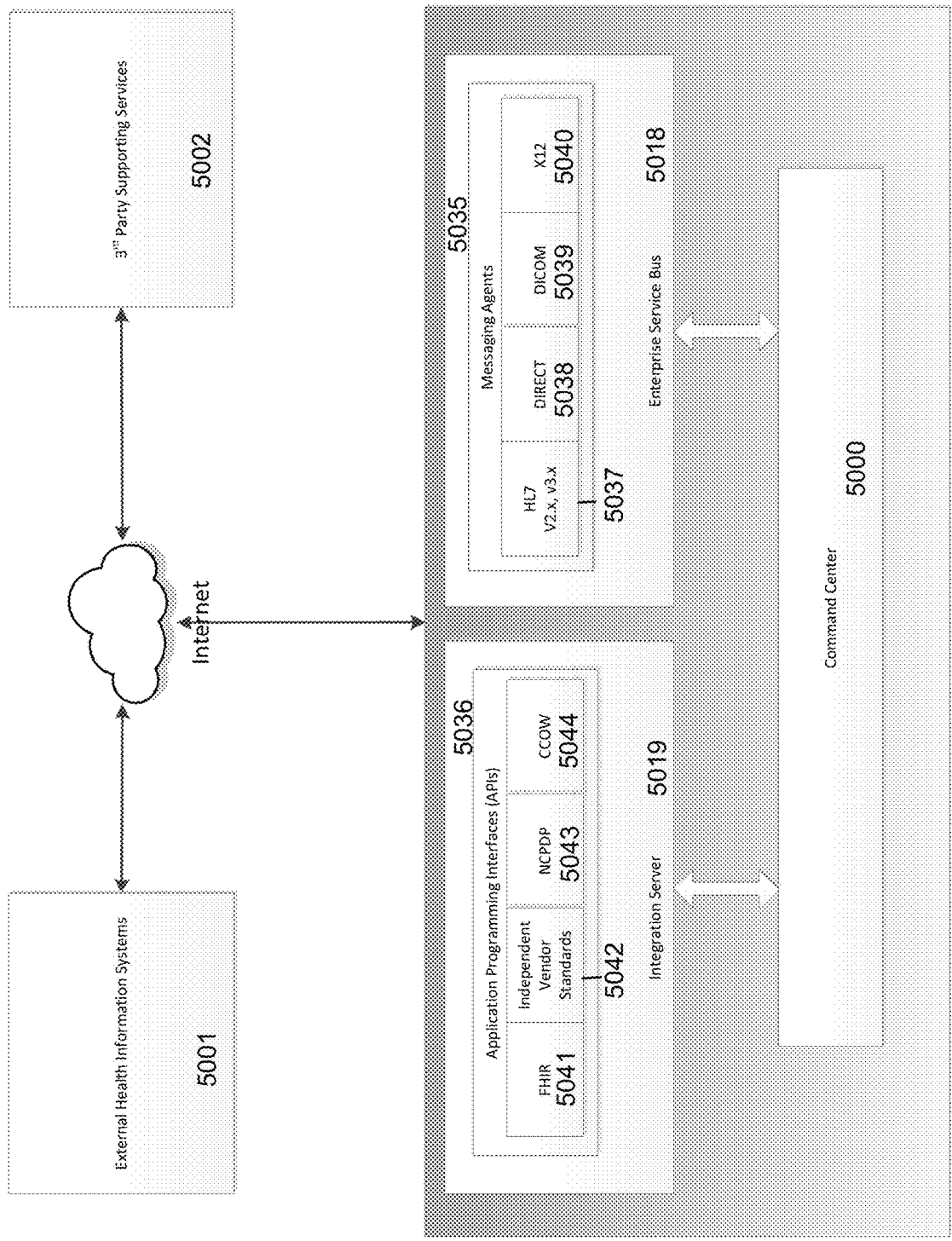
FIG. 59B illustrates systems integration standards used to communicate between the Command Center and external Systems in accordance with the invention.

Systems integration standards used to communicate between the Command Center 5000 and External Systems 5001, 5002 are depicted in detail in FIG. 59B. The external systems have been previously discussed, so the focus here is on communication protocols. Integration between systems uses a variety of industry standards methods. The integrations allow the external systems 5001, 5002 to share data with Command Center 5000.

Communication protocols can be grouped into two categories: message-based protocols 5035 and API-based protocols 5036. Message-based protocols 5035 are managed through an Enterprise Service Bus 5018. Enterprise Service Bus 5018 is designed to quickly and efficiently handle large volumes of messages ensuring that all of the messages are processed in order. Examples of message-based protocols 5035 are HL7 v2.x and v3.x (5037). V2.x is the most widely used healthcare integration standard and v3.x is similar to v2.x but uses the XML standard for encoding messages. DIRECT (5038) is a SMTP-based message protocol and is used for direct transmission of secure email messages. The Digital Archive and Communications in Medicine (DICOM) standard (5039) is used in tandem with a PACS system 5024 for processing images. The X12 standard (5040) is for the exchange of claims and billing data.

On the other hand, API-based messaging standards 5036 are managed by the Integration Server 5019. The supported standards include the Fast Healthcare Interoperability Resources (FHIR) standard 5041, several independent Vendor standards 5042, and the National Council for Prescription Drug Programs (DCPDP) standard 5043 used for ePrescribing. FHIR is the next generation method for integrating with HIT 5001 systems, specifically EMRs 5021 and (while not yet approved) is being widely adopted by EMR companies. Several vendors have also emerged that are extending FHIR and in some cases creating their own API-standards for achieving interoperability. Exemplary embodiments of the Command Center 5000 may incorporate each of these standards as they achieve critical mass in the market.

A major challenge in EMR integration is sharing context so that when the EMR user selects a patient other applications like the Command Center 5000 should display information about the same patient to prevent issues associated with accidentally viewing different patients. The Clinical Context Object Workgroup (CCOW) standard 5044 is designed to be used by separate applications to share this context. By using CCOW 5044, the EMR 5021 itself can communicate with the Integration Platform 5019 and the Command Center 5000.

Figure 60:
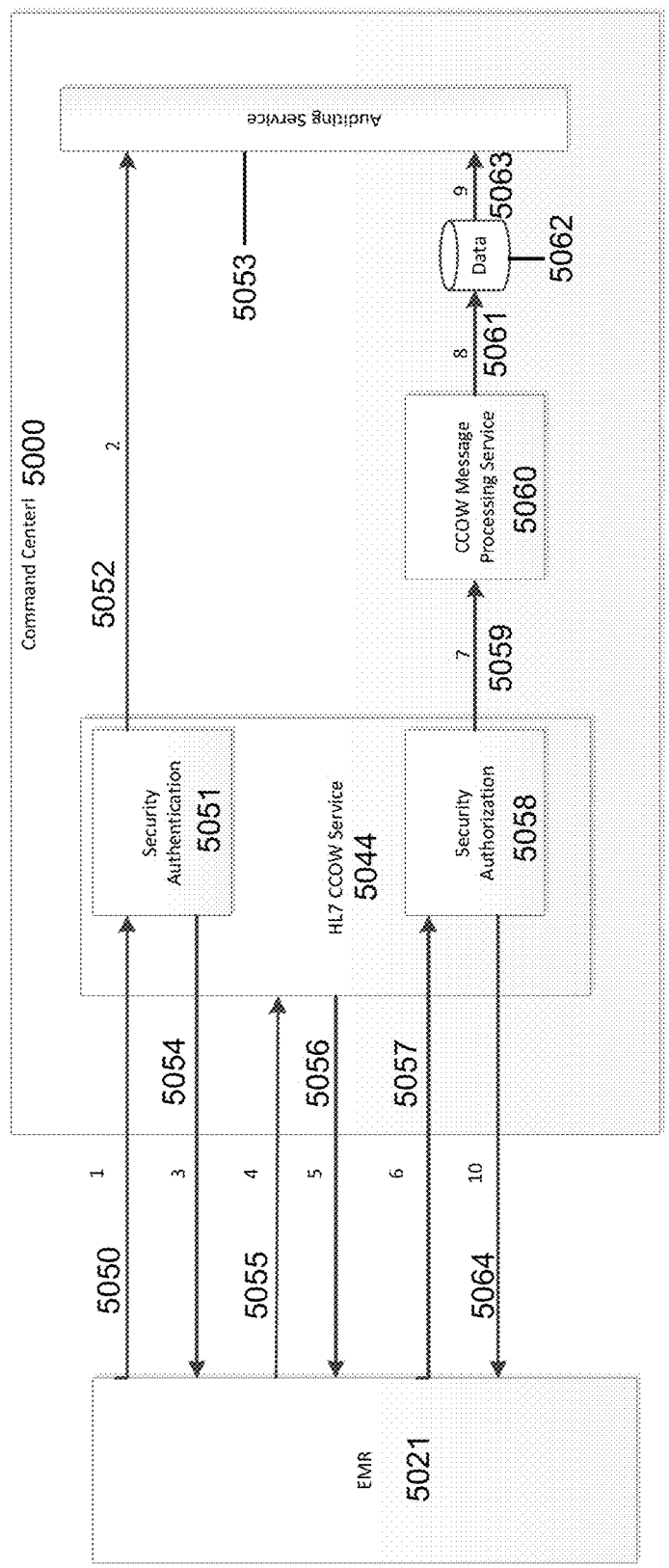
FIG. 60 illustrates an overview of the industry standard CCOW workflow and the various components involved in several transactions in accordance with the invention.

FIG. 60 illustrates an overview of the industry standard CCOW workflow and the various components involved in several transactions. As illustrated, the first step is sending authentication data 5050, typically a user account and password from the EMR 5021 to the Command Center CCOW Security Authentication Service 5051. The service 5051 authenticates the user and sends the request 5052 to the Command Center Auditing Service 5053 for long term storage. Once authenticated, the Security Authentication Service 5051 returns a token 5054 back to the EMR 5021 for use in further transactions. Once authenticated, if the user selects a patient, the Patient's identifying information along with the authentication token 5055 are sent to the Command Center 5000 using HTTP-based protocols. Once complete, the Command Center 5000 may now display the same patient as the EMR 5021. Upon a successful operation, CCOW Service 5044 may return a success message 5056. In the event new data is entered into the EMR 5021 that is required to be transferred to the Command Center 5000, it can be sent at 5057 via CCOW to the Command Center 5000. The first step is to check that the user is authorized for this action at 5058. If the user is not authorized, a denial of service message 5064 is returned to the EMR 5021. If the action is authorized, the message is forwarded at 5059 to the CCOW Message Processing Service 5060 where, upon processing, the message is sent at 5061 to the database 5062 where it is stored. The change in data is also sent at 5063 to the Auditing Service 5053 for long term storage. Upon successful completion of the transaction, a success message 5064 is returned to the EMR at 5064.

Figure 61:
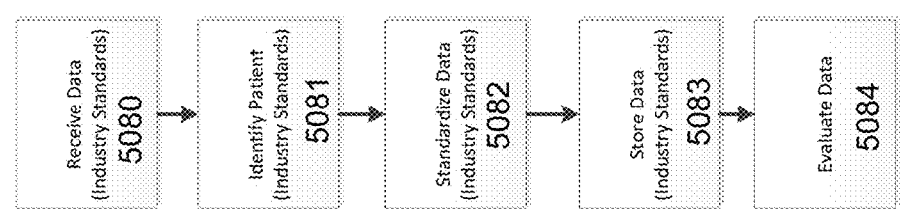
FIG. 61 illustrates a standard workflow when data is received from an external system through any of the messaging standards or API methods in accordance with the invention.

When data is received from an external system 5001 through any of the messaging standards 5035 or API methods 5036, a standard workflow is followed as depicted in FIG. 61. The first step (5080) is to receive data using the previously discussed standards. The message is parsed and the patient identifying information is extracted so the correct Patient can be identified (5081). Once the patient is identified, the data is standardized (5082) so it can be effectively used in the Command Center 5000 and then stored (5083). The last step in the process is to evaluate the data (5084) using a variety of mechanisms using advanced analytics as will be discussed below.

Figure 62:
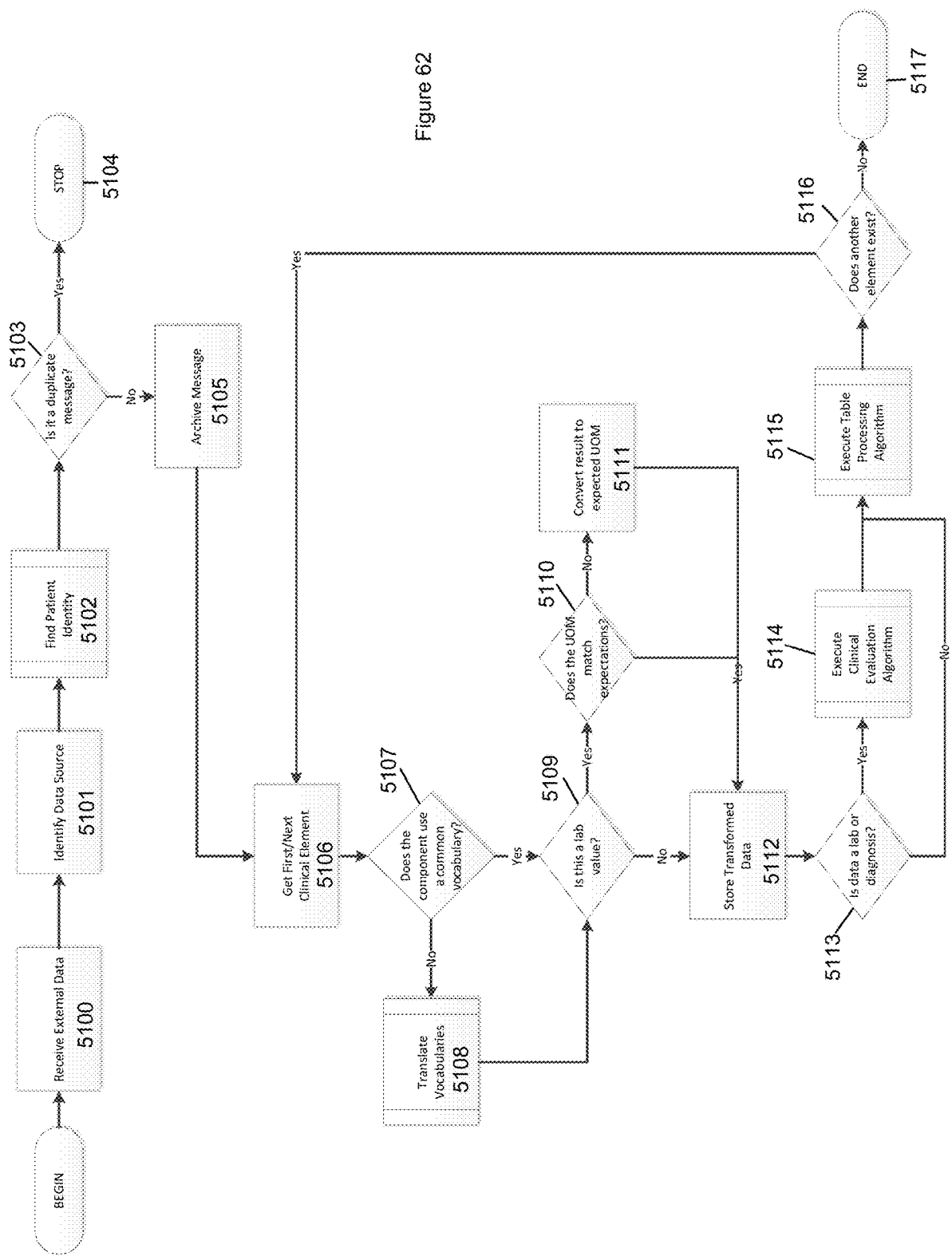
FIG. 62 illustrates a detailed flowchart of the data import process in accordance with the invention.

FIG. 62 illustrates a more detailed flowchart of the data import process. As illustrated, the process begins when External Data is received (5100). The first step is identifying the source of the data (5101) to ensure it is from a trusted source and allows the Command Center 5000 to associate it with the proper customer account. Next, the patient's internal identity must be located (5102) using industry standard mechanisms, such as a Master Patient Index. Once the customer and patient have been identified, it can be determined if the message is a duplicate (5013). If the message is a duplicate, the message may be abandoned (5104) because it has already been processed. This step is necessary to prevent duplicate data and reduce the number of messages processed because the Command Center 5000 cannot control what messages External Systems 5001, 5002 may send. If the message is not a duplicate message, the message can be stored for archival purposes along with a message digest to facilitate searching for duplicate messages (5105).

Messages can often contain multiple relevant pieces of information, so the Command Center 5000 selects the first data element for processing (5106) and then examines to see if the element is using a common vocabulary (5107). If it is not, using existing lookup and translation tables, the Command Center 50000 translates (5108) the element's code to the common vocabulary used by the Command Center 5000. These standards include ICD-10 (diagnoses), CPT (procedures), RxNorm (medications), and LOINC (labs) codes. Next, if this element is a lab value 5109, the Command Center 5000 checks (5110) to see if the unit of measure is the UOM used for this lab in the Command Center 5000. If it is not, the value is converted 5111 using basic math (ex. Converting 10 centimeters to 1000 mm or 6.1 mmol to 106 mg/dL). If the element is not a lab value or has been converted, the data is saved (5112) to the Command Center clinical tables in core database 5014, for example. The clinical tables are designed using common industry standards for storing relational clinical data. If the data is a lab or diagnosis 5113, the data is evaluated to see if the new data is an improvement or decline from the last similar value 5114 by executing the Clinical Evaluation Algorithm described below with respect to FIG. 63. After evaluating the data, the data is processed to see if the data should be added to a Command Center flowsheet (5115) (see Flowsheet description). Once these steps are complete, the processing algorithm looks for another element in the message (5116) and, if another element is present, the process starts over at step S106; otherwise the process terminates at 5117.

Lab and Diagnosis Data Evaluation

A key feature of the Command Center 5000 is its ability to evaluate lab and diagnosis data to determine if the patient is improving or getting worse based on a comparison of past lab data and diagnosis history and to present that information to the user in an easily recognizable way, using an icon such as health icons 2766, 2768 (FIG. 28), for example. This evaluation can then be used by the clinician to make faster decisions. FIG. 63 illustrates a flowchart of the Clinical Evaluation Algorithm. As illustrated, when a new lab value is received (5200), if the result is numerical (5201), the lab code is looked up in the ClinicalComparator table 5210 using the LOINC vocabulary and the lab code (5202). If a comparator exists (5203), the algorithm retrieves (5204) the most recent previous lab result of the same code for the same patient. If a comparator does not exist or no previous results exist (5205), the algorithm is complete (5206). If a previous value exists at 5205, the data is evaluated (5207). For example, the algorithm receives an A1c lab result of 6.7 mg/dL (we know the UOM is mg/dL because it was converted in FIG. 62 at steps S110 and S111). The algorithm searches the ClinicalComparator table 5210 using the search parameters Vocabulary=LOINC (5211), Code=4548-4 (5212). Since a Comparator is found, the previous result is retrieved at 5204, which in this example is 6.5 mg/dL. Each Comparator Record stores whether or not a lab result is getting better 5213 or worse 5214 based on if it is higher or lower than the previous value. In the example of an A1c lab test, the betterValidator=lessThan and the worseValidator=greaterThan. So the evaluation at step S207 determines the current value 6.7 is higher or greater than the previous value 6.5, which matches the worseValidator. Once the evaluation is complete, if the new value is worse (5215), the lab record is marked as "worse" (5216) and either "declining" or "rising" based on matching lessThan or greaterThan. On the other hand, if the new value is better (5217), the lab record is marked as "better" (5218) and either "declining" or "rising" based on matching lessThan or greaterThan. This pattern allows the use of four icons to better differentiate the patient's condition: better declining, better rising, worse declining, or worse rising. If the patient is neither improving nor getting worse, the evaluation is complete (5219) and the record is not marked or is marked as "no change." Those skilled in the art will recognize that this functionality can be expanded to include other clinical values measured and/or tracked within an office visit for example blood pressure and vision.

The Clinical Evaluation Algorithm can also be applied to certain Diagnosis codes where a pattern of progression is part of the patient condition. For instance, assume that a patient starts with no retinopathy and can then progresses to mild non proliferative diabetic retinopathy (NPDR) and then moderate NPDR and finally to severe NPDR. The ClinicalComparatorList table 5220 (FIG. 63) stores the information required to determine if a diagnosis is improving or not based on its position 5221 in the list signified by its grouping code 5222. In this scenario, where a new diagnosis code is received (5230), the Comparator listing is retrieved (5231). If a Comparator List exists (5232), the algorithm retrieves previous diagnosis codes (5233); otherwise it stops (5206). If previous values do exist (5234), the current diagnosis position in the list is compared against the position of the previous value in the list (5235). If the value is worse (lower) in the list (5215), the diagnosis is marked as "worse" (5216). If the new diagnosis is better (5217), the diagnosis is marked as "better" (5218). If neither is true, the evaluation is complete (5219) and the record is not marked or is marked as "no change." Thus, the output of the Clinical Evaluation Algorithm may be used to make decisions and to update the patient's medical record in the EMR accordingly.

Flowsheet

As noted above, the central focus of the Command Center 5000 is the flowsheet. In the exemplary embodiments described in detail above, the flowsheet is a Retina Flowsheet 2530 for ophthalmologists as illustrated in FIG. 15; however, those skilled in the art will appreciate that the flowsheet 2530 may be embodied in other formats (e.g., FIGS. 4, 35, and 36). As also noted above, the Command Center 5000 presents data to the screen in such a way that the user need not navigate away from the screen. So that the data may be presented without significant delay, the data is pre-processed and stored for display in the flowsheet. A frequent issue with EMR systems for a variety of reasons is slow response time. One of the reasons for the slow response is the need to retrieve data from a variety of sources, process the data, and then render it for display. The Command Center 5000 takes an improved approach. As data is received by the Command Center 500 from external sources, the Command Center 5000 dynamically determines if the data is applicable to the flowsheet, processes it and stores it in a simple database table structure described below that can be easily retrieved when requested.

Flowsheet—Images

Figure 64:
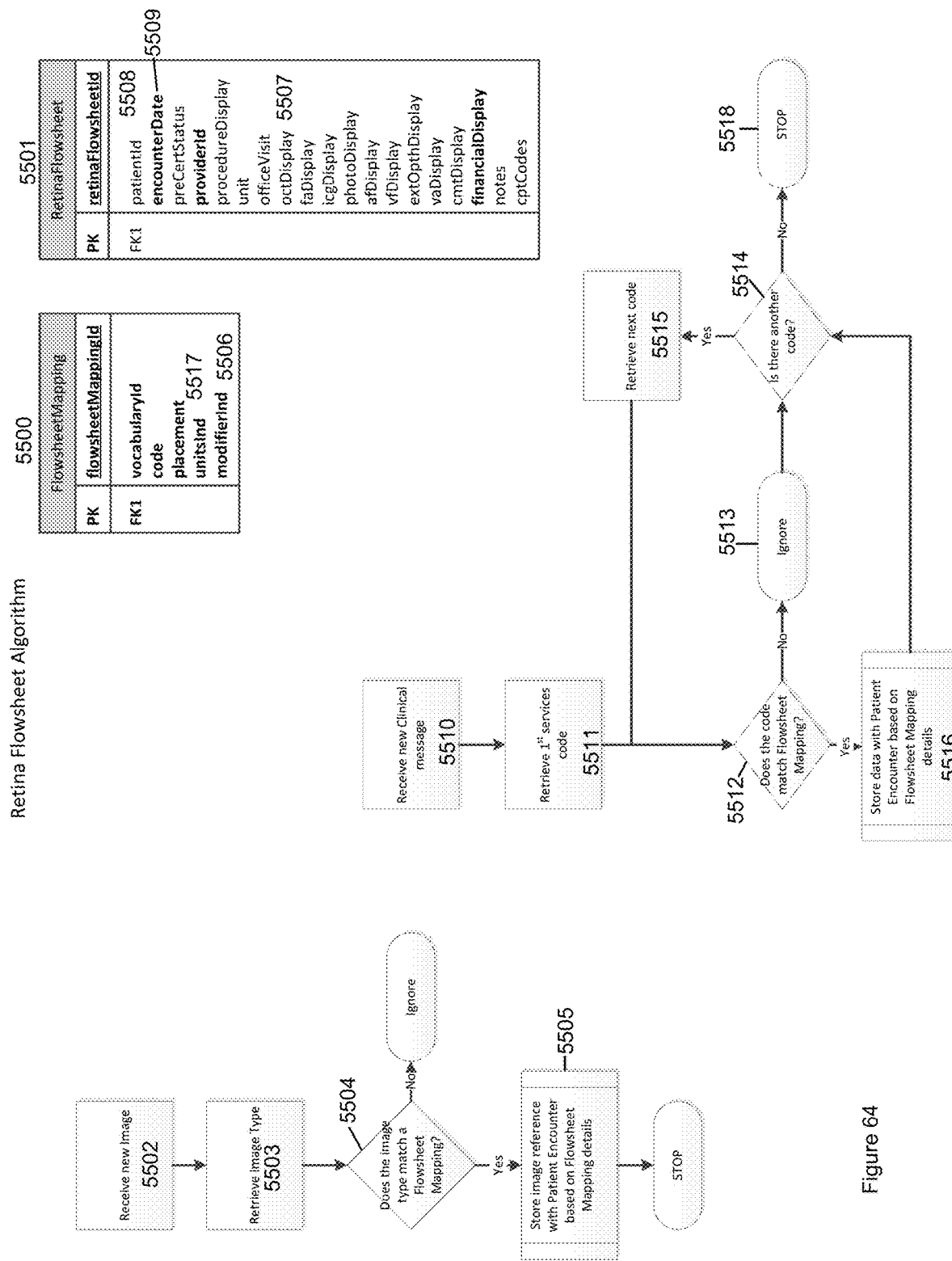
FIG. 64 provides a diagram of the tables used to determine if imported data is relevant to the FlowsheetMapping table and to store data for display on the in the flowsheet database fields in accordance with the invention.

FIG. 64 provides a diagram of the tables used to determine if imported data is relevant to the FlowsheetMapping table 5500 and to store data for display on the in the flowsheet database fields 5501. FIG. 64 also presents the logic used to process the imported data in reference to the flowsheet. For example, when new data is received by the Command Center 5000, the data includes either images or clinical data and it is determined whether the data received should be stored for display on the flowsheet. When a new image record is received (5502), the image type is extracted (5503) from the record and the FlowsheetMapping table 5500 is searched for the image type (Vocabulary—Images, Code=Image Type). If a match is found (5504), it means the image reference should be stored and displayed on the flowsheet (5505). If a match is not found at 5504, the image is ignored. In the case of eye images, the particular eye is important so the modifiedInd 5506 will equal 1, which means when the image reference is saved, it should be associated with the correct eye side which is part of the original image record per DICOM standards. For example, if an OCT image record for the left eye is received, the image type OCT is searched for on the FlowsheetMapping table (Code=OCT). Since the image type OCT is relevant to the Retina Flowsheet as well as the eye side, the image reference along with the eye side are stored in the RetinaFlowsheet table 5501 in the octDisplay column 5507. The placement field on the FlowSheetMapping Table 5500 is the location to where the data should be saved. Instead of having an OCTDisplayOD and OCTDisplayOS columns—one for each eye, the octDisplay column and other similar columns store structured data containing reference to multiple images based on eye side. The format for this column is "OD:image reference|OS:image reference" where image reference is the name and location of the image. If this is the first data for a particular encounter date, a new record is added to the RetinaFlowsheet 5501 and the patientId 5508 and encounterDate 5509 both found in the message are saved to the table.

Flowsheet—Clinical Messages

FIG. 64 further presents the logic used to process a received clinical message in the context of the flowsheet. As illustrated, when a clinical message (medications, procedures, diagnoses) is received (5510) it typically has multiple pieces of information in the same message, so each element is processed separately. The first element is selected from the message (5511) and evaluated (5512) to determine if it belongs on the Retina Flowsheet table 5501 based on finding a matching entry in the Flowsheet table 5501. For example, a procedure J2778 Lucentis 0.5 mg is received. A query is executed on the Flowsheet Mapping table 5500 where the Vocabulary=CPT and the code=J2778. If the procedure is not found in the table, the record would be ignored (5513) and if another element exists (5514) the next element would be selected (5515) for processing. If the procedure is found in the table, the procedure data is then stored (5516) in the RetinaFlowsheet 5501 where the column is specified by the placement field. In the case of a procedure, a medication may be administered, so the units are relevant. In this case, the unitsInd 5517 in the FlowsheetMapping table 5500 would be set to 1 signaling the algorithm to save the units associated with the record in the unit column of the RetinaFlowsheet 5501. If there is another code (5514), that code may be retrieved (5515) and the process starts over; otherwise the process is complete (5518).

Flowsheet—Financial Messages

Figure 65:
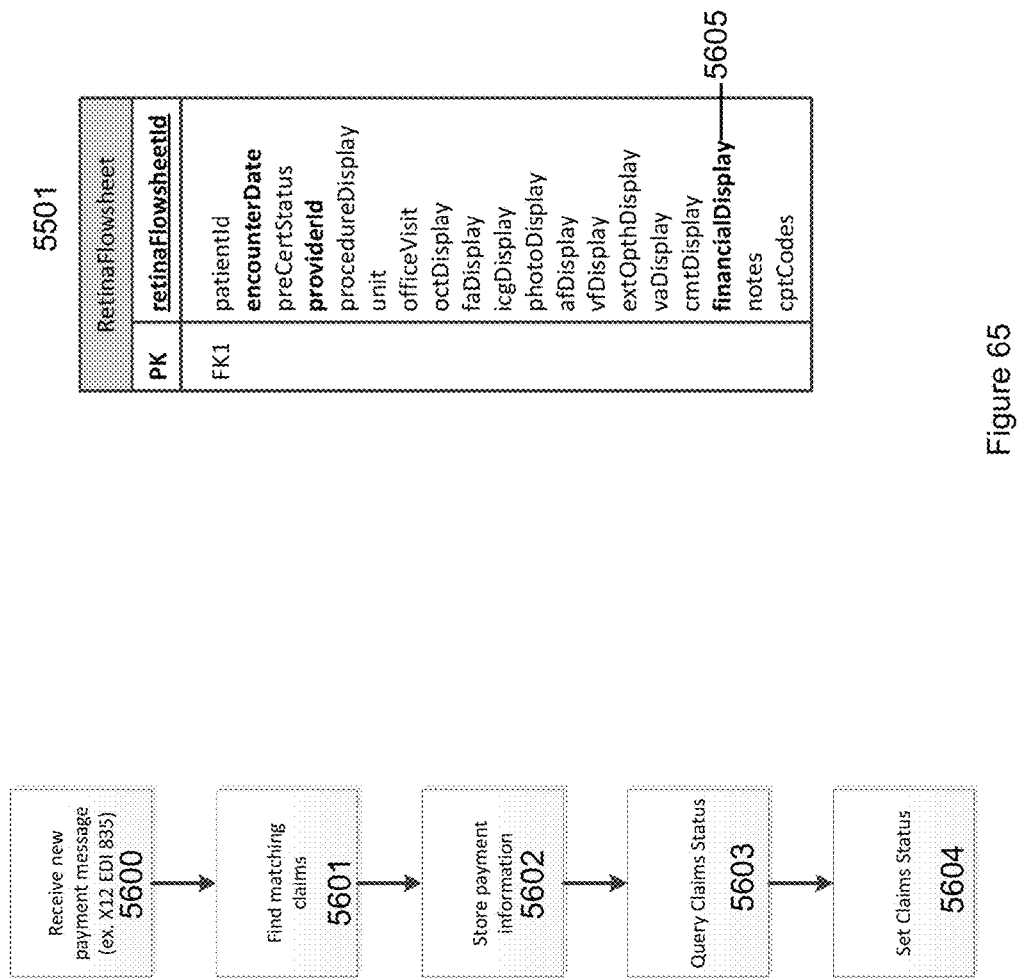
FIG. 65 illustrates a Financial Analysis Algorithm for processing financial payment information in accordance with the invention.

FIG. 65 illustrates a Financial Analysis Algorithm for processing financial payment information. As illustrated, when financial information is received (5600), the matching claim is located (5601) and the payment information is stored (5602). In an exemplary embodiment, a third-party a claims clearinghouse or insurance company is used to provide an electronic claims status message (5603) that is sent to determine the status of the claim. This status is then stored (5604) in the RetinaFlowsheet table 5501 in the financialDisplay column 5605.

Preauthorization and Referral Processing

Figure 66A:
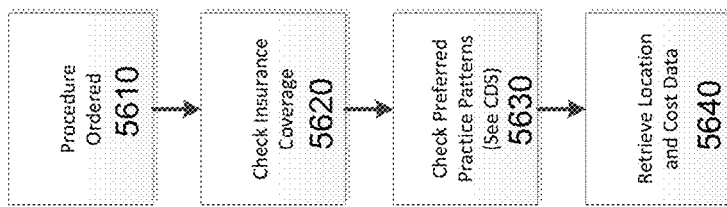
FIG. 66A illustrates generally the process for ordering a procedure in accordance with the invention.

FIG. 66A generally illustrates the process the system follows when the user orders a procedure. When a procedure is ordered at 5610, the Command Center 5000 evaluates the insurance coverage at 5620. This process is described in detail in FIGS. 66B, 67 and 68 below. Next, the Command Center 5000 evaluates the Preferred Practice Patterns and other clinical decision support rules at 5630. This process is described in FIG. 72. The last step in the process is to retrieve location, if applicable, and cost data 5640. This information is then displayed in the Smart Evaluation Control panel in FIGS. 44-55.

Figure 66B:
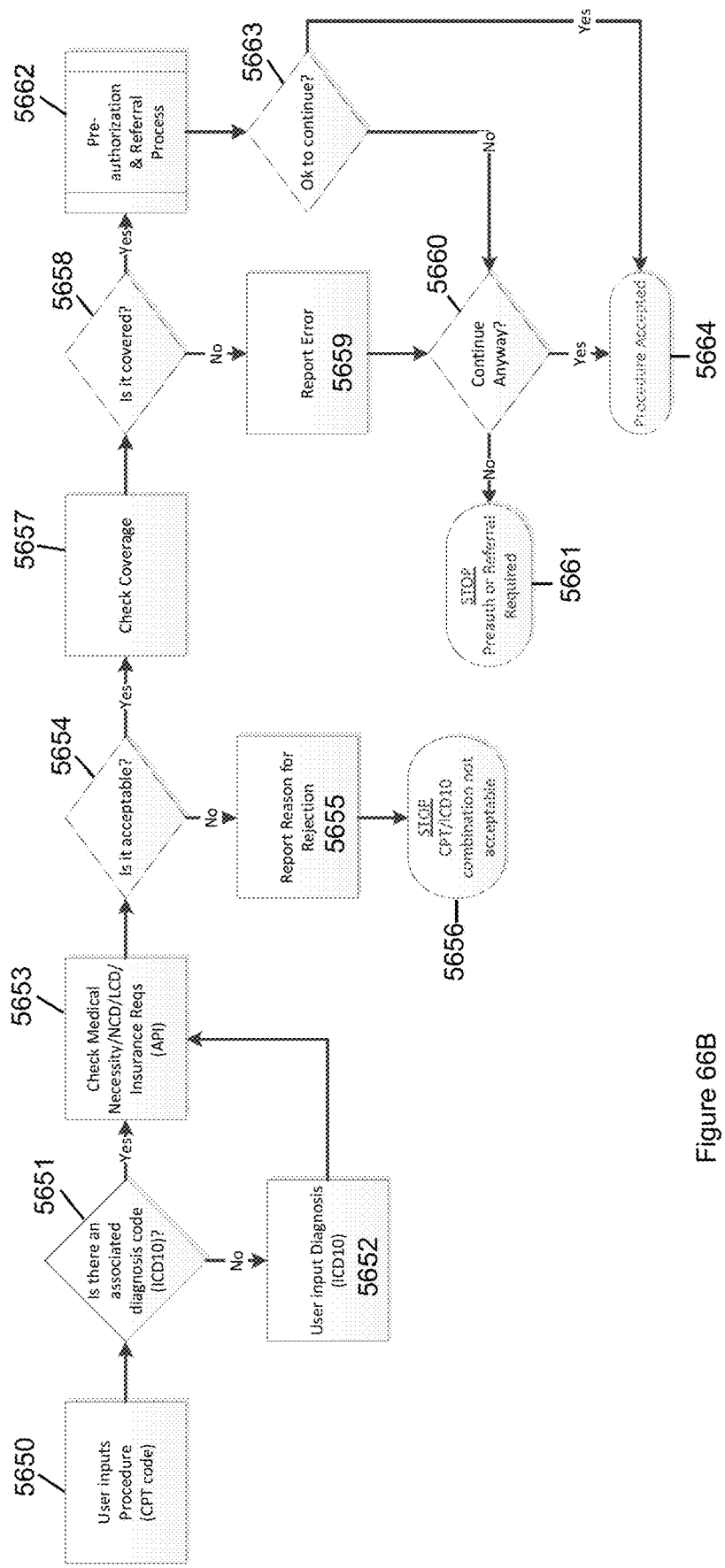
FIG. 66B illustrates the logic used to check for pre-authorization and/or a referral in accordance with the invention.

FIG. 66B illustrates the logic used to check for preauthorization and/or a referral. As illustrated, when a new procedure is ordered (5650), the Command Center 5000 reviews the input data (5651) for an associated ICD10 Diagnosis code. If no ICD10 Diagnosis code is found, the user is prompted to provide one (5652). Once the ICD10 Diagnosis code has been associated with the CPT procedure code, the Command Center 5000 evaluates the data against the applicable guidelines (5653) using a third party API and determines if the combination of CPT and ICD10 codes is acceptable (5654). If the input is not acceptable (5654), the user is notified of the disposition and provided with a rejection reason (5655). A rejection will terminate the process (5656). On the other hand, if the input is acceptable (5654), the system may review the patient's coverage (5657) for the procedure using a third party API. If the procedure is not covered by the patient's insurance (5658), the system may provide the user with an error code (5659). The patient may then have the option (5660) to continue with the procedure (5664) (knowing it will be paid for out of pocket) or to decline the procedure (5661), which terminates the process. If the procedure is covered (5658), the preauthorization and referral process is invoked (5662). If the preauthorization and referral process (5662) does not approve the procedure (5663), the patient may again have the option (5660) to accept the procedure (5664) (knowing it will be paid for out of pocket) or to decline the procedure (5661), which will terminate the process. If the preauthorization and referral process (5662) approves the procedure (5663), the patient can move forward with the procedure knowing it is covered (5664).

Figure 67:
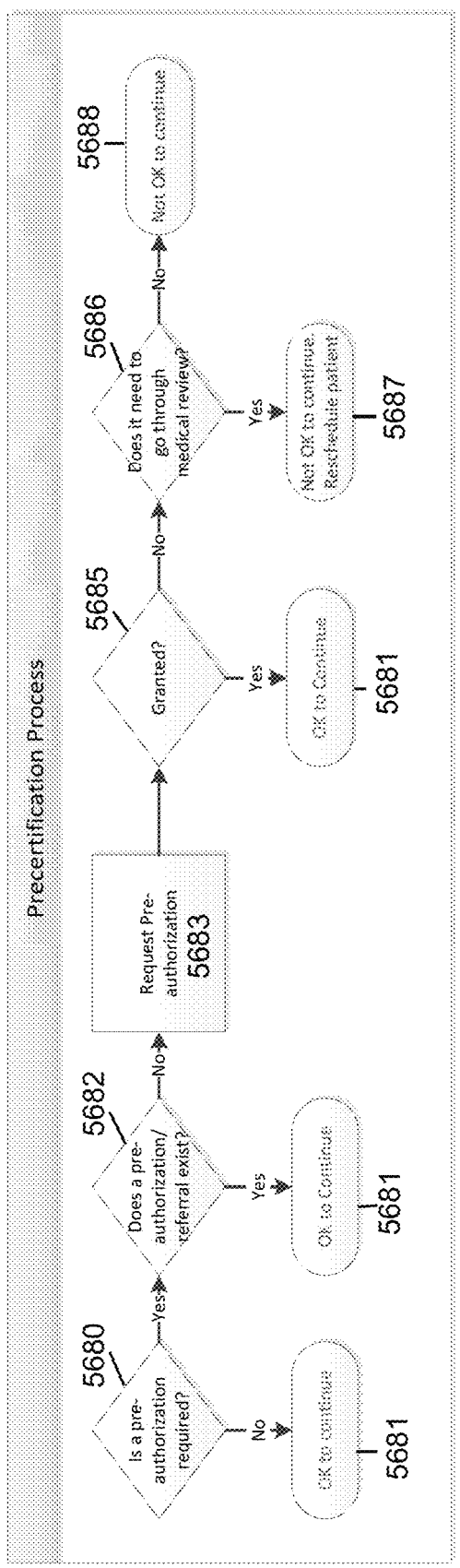
FIG. 67 illustrates the precertification process that is invoked by presentation of a CPT Procedure code and an ICD10 Diagnosis code in accordance with the invention.
Figure 68:
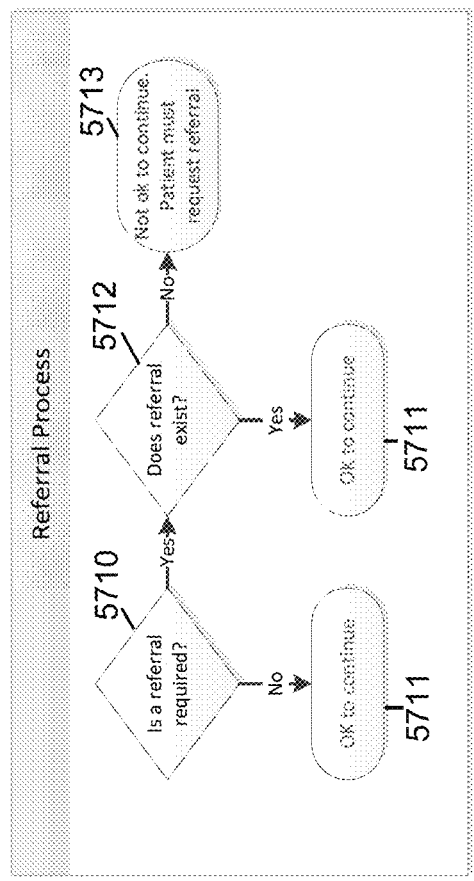
FIG. 68 illustrates the referral process that is invoked by presentation of a CPT Procedure code and an ICD10 Diagnosis code in accordance with the invention.

The preauthorization and referral process (5662) described above with respect to FIG. 66B has two parallel processes, one which evaluates if the procedure requires preauthorization (FIG. 67) and another which evaluates if the procedure requires a referral (FIG. 68). The Precertification process described FIG. 67 is invoked by presentation of a CPT Procedure code and an ICD10 Diagnosis code. It is then determined using a 3rd party API whether or not a preauthorization is required (5680). If preauthorization (5680) is not required, then it is ok to proceed with the process (5681) and the process returns an approval message (5663 from FIG. 66B). If preauthorization 5680 is required, the system may then check for a pre-existing preauthorization (5682) using a third party API. If a preauthorization exists, the authorization code is stored and the procedure can continue (5681) and the process again returns an approval message (5663 from FIG. 66B). If a preauthorization does not exist, the system may request a preauthorization (5683), again using the third party API. If the request for preauthorization (5683) is granted (5685), then it is ok to proceed with the process (5681) and the process returns an approval message (5663 from FIG. 66B). If the request for preauthorization (5683) is not granted (5685), then the system may evaluate if the request for preauthorization (5683) needs to go through medical review (5686). If the request for preauthorization (5683) needs to go through medical review (5686), then it is not ok to proceed with the process (5687) and the process escapes to the negative path of 5663 in FIG. 66B to determine whether to continue anyway. If the request for preauthorization (5683) does not need to go through medical review (5686), then it is not ok to proceed with the process (5688) and the process escapes to the negative path of 5663 in FIG. 66B to determine whether to continue anyway.

The referral process illustrated in FIG. 68 is invoked by presentation of a CPT Procedure code and an ICD10 Diagnosis code. It is then determined using a third party API whether or not a referral is required (5710). If a referral (5710) is not required, then it is ok to proceed with the process (5711) and the process returns an approval message (5663 from FIG. 66B). If a referral (5710) is required, the system may determine if a referral exists. If a referral exists (5712), then it is ok to proceed with the process (5711) and the process returns an approval message (5663 from FIG. 66B). If a referral does not exist, then it is not ok to proceed with the process (5713) and the process escapes to the negative path of 5663 in FIG. 66B to determine whether to continue anyway.

Data Model Overview

The Command Center data model is grouped into core tables, supporting tables and interoperability tables. The core tables 5014 (FIG. 37) drive the Command Center (e.g. FIGS. 1 and 15) and store the patient demographics and insurance information, images and the patient's clinical and financial data. The supporting tables 5015 (FIG. 37) are largely used behind the scenes to drive functionality and are not directly related to a specific patient. The System Messaging tables in interoperability database 5020 (FIG. 37) support health information technology interoperability.

The Command Center data model is based on a relational database model. Each table uses a surrogate primary key. A surrogate primary key is a unique value within the table used to identify the row that is not directly tied to the data in that row. This allows any of the columns to be changed without impacting the primary key. The data is stored in two types of tables—transactional for capturing clinical and billing data as discrete data, and reporting where data is aggregated for a particular physician, practice, health system or other entity. Reporting may extract and report on any data elements captured within the Command Center 5000. These data extracts or reports can be used for clinical practice, population health management or clinical research or other purposes to improve patient health and well-being and/or the financial outcomes of a practice. Reports can be generated in real-time or batch mode executed on a pre-determine schedule and automatically delivered to interested parties.

Figure 69:
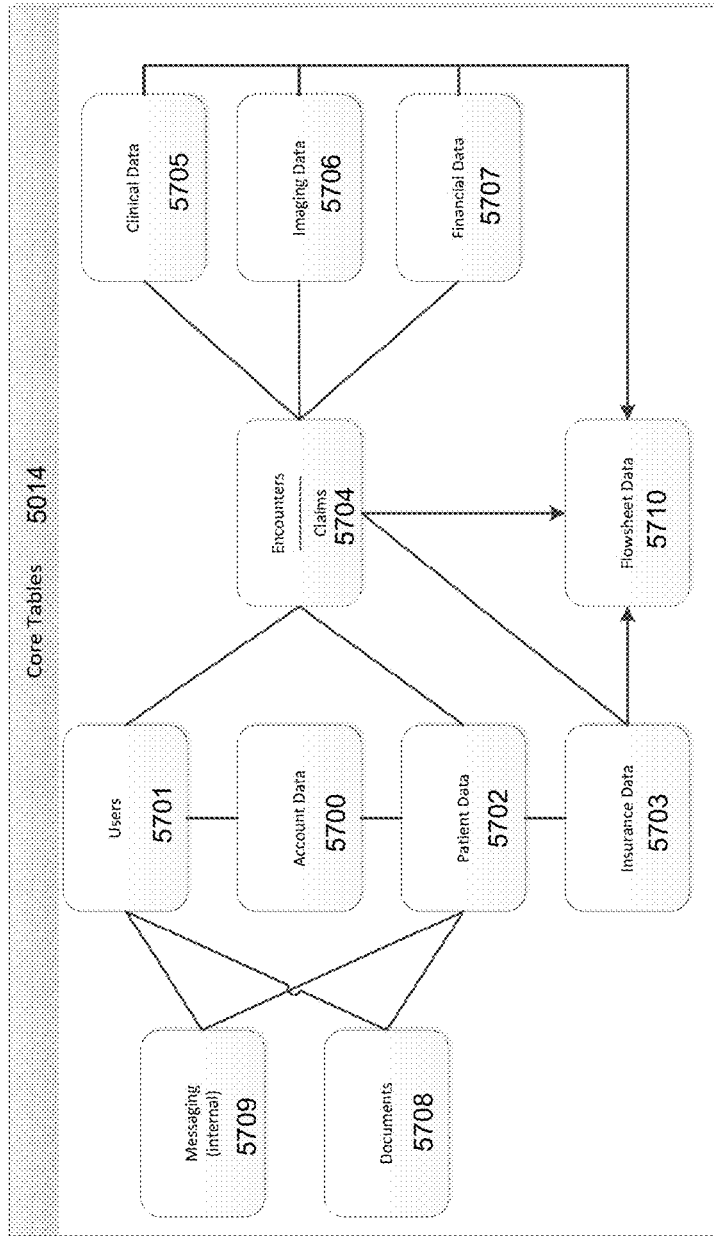
FIG. 69 illustrates the classes of data that are stored as part of the core tables in accordance with the invention.

Core Tables (FIG. 69)

The core tables 5014 largely follow industry standard design patterns for storing patient, clinical and financial data in a relational format. One example embodiment of the data model is the Observational Health Data Sciences and Informatics (OHDSI) standard—(http://www.ohdsi.org/). Another has been established by OpenEHR group 13 http://www.openehr.org/. The classes of data illustrated in FIG. 69 are stored as part of the core tables 5014. The Account Data tables 5700 store information about customer accounts and physical locations as well as group Users and Patients so they can share information and communicate among each other. The Users tables 5701 store user accounts, credentials, personal configuration information, and data related to an individual user's profile including password and password history. Users are medical professionals such as clinicians, physicians, nurses, and billers, not patients. Patient tables 5702 store demographics and basic contact information. Insurance tables 5703 contain references to the patient's insurance information including benefits and amount paid and/or remaining deductible for the calendar year. Insurance data also includes referrals and pre-authorization information as required by the insurance company. Access to this data is compartmentalized to ensure compliance with global privacy and security regulations. The Encounter/Claim tables 5704 store encounter based data including but not limited to chief complaint, the review of systems, and the patient plan of care. Associated with encounters is claims data, which is also stored in these tables 5704. The Encounter/Claim tables 5704 are also the key set of tables that tie patient information together with the clinical and financial data. Clinical tables 5705 store data sets for vitals, procedures, diagnoses, problem lists, medications, allergies, admission/discharge information, and surgeries. Imaging tables 5706 store references to the different patient images. Example image types include fundus photography, optical coherence tomography, fluorescein angiography, indocyanine green angiography, magnetic resonance, X-ray, and ultrasound. The actual images are stored on a PACS or similar service and are not typically directly stored in the Command Center core database 5014. Financial tables 5707 include the payments by the insurance companies as well as information about claim adjustments and write-offs. The Financial tables 5707 also include a general ledger. The Document tables 5708 store key information about documents either sent or received from other providers as well as other documents pertinent to the patient care. Messaging tables 5709 hold the actual notes and messages created within the Command Center 5000 and track external notifications. Finally, the Flowsheet tables 5710 contain the processed/aggregated data used in presentation of the Flowsheets within the application.

Figure 70:
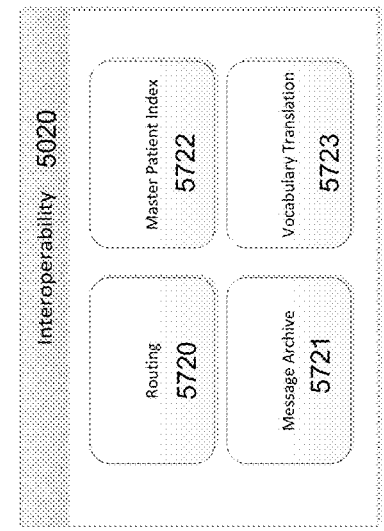
FIG. 70 illustrates the interoperability tables that are used to handle receiving and sending of data between systems in accordance with the invention.

Interoperability Tables (FIG. 70)

The interoperability tables 5020 illustrated in FIG. 70 are used to handle receiving and sending of data between systems. The Routing tables 5720 store information about the connections between different systems. The Routing tables 5720 are designed to ensure data that is received are stored with the correct customer account and data that is transmitted is routed to the proper system. For auditing and debugging purposes, all inbound and outbound messages are stored in the Message Archive tables 5721. The Master Patient Index (MPI) tables 5722 are used to identify a patient record so data is properly attributed. For instance, a patient named Robert could be identified as Robert, Bob, Robbie or even Bert. The MPI tables 5722 are used to handle this patient attribution. Different systems use different vocabularies to encode data. The Vocabulary Translation tables 5723 are used to translate one system such as CPT to another like SNOMED-CT. This allows the data in the Command Center 5000 to be stored in a common format, so it is more easily processed.

Figure 71:
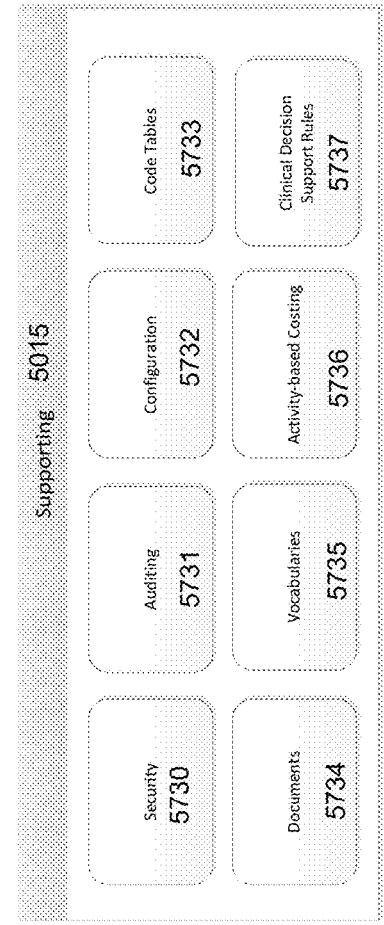
FIG. 71 illustrates the supporting tables that include tables for handling behind the scenes processing in accordance with the invention.

Supporting Tables (FIG. 71)

The supporting tables 5015 in FIG. 71 include tables for handling behind the scenes processing. For example, Security tables 5730 handle authorization and authentication of user accounts and system requests. This is to ensure compliance with global privacy and security regulations. Auditing tables 5731 store data related to which user accessed which patient account and how long it was accessed, but also data about who entered or changed information within the system. The audit trail would include the date/time of the change, the user performing the action, the old data and the new data. The audit trail may be sent with any medical record requests from insurance companies, peer groups, or legal requests. The Configuration tables 5732 are used to store Application and Account-specific configuration changes. Code tables 5733 provide storage and access to common drop downs and filters used throughout the system to standardize the data and make it easier to update. The Document tables 5734 store references to the insurance benefits and guidelines, CMS NCD and LCD documents, Preferred Practice Patterns, and Clinical Practice Guidelines as well as the information unique to the Command Center 5000 such as the summary, similarities and differences between documents covering common conditions. The Vocabulary tables 5735 store the core reference tables used throughout the Command Center 5000 related to clinical data. The Vocabulary tables 5735 include but are not limited to ICD-10, CPT, RxNorm, and LOINC codes. Other examples could be SNOMED-CT or ICD-10 PCS codes. The Activity-based costing tables 5736 provide cost information related to performing procedures including but not limited to human capital expenses, material expenses, ancillary services and overhead. Finally, the Clinical Decision Support tables 5737 contain the rules and algorithm supporting data that drive the Command Center clinical decision support capabilities.

Clinical Decision Support (CDS)

The Command Center clinical decision support logic is implemented in a variety of methods. Pre-authorization, referral management, claims scrubbing, medical necessity checking for compliance with governmental and insurance regulations, and similar rules are embodied in the system through the use of third party systems. Internally, the Lab and Diagnosis Data Evaluation (FIG. 63) is an implementation of the if-then style of clinical decision support.

Figure 72A:
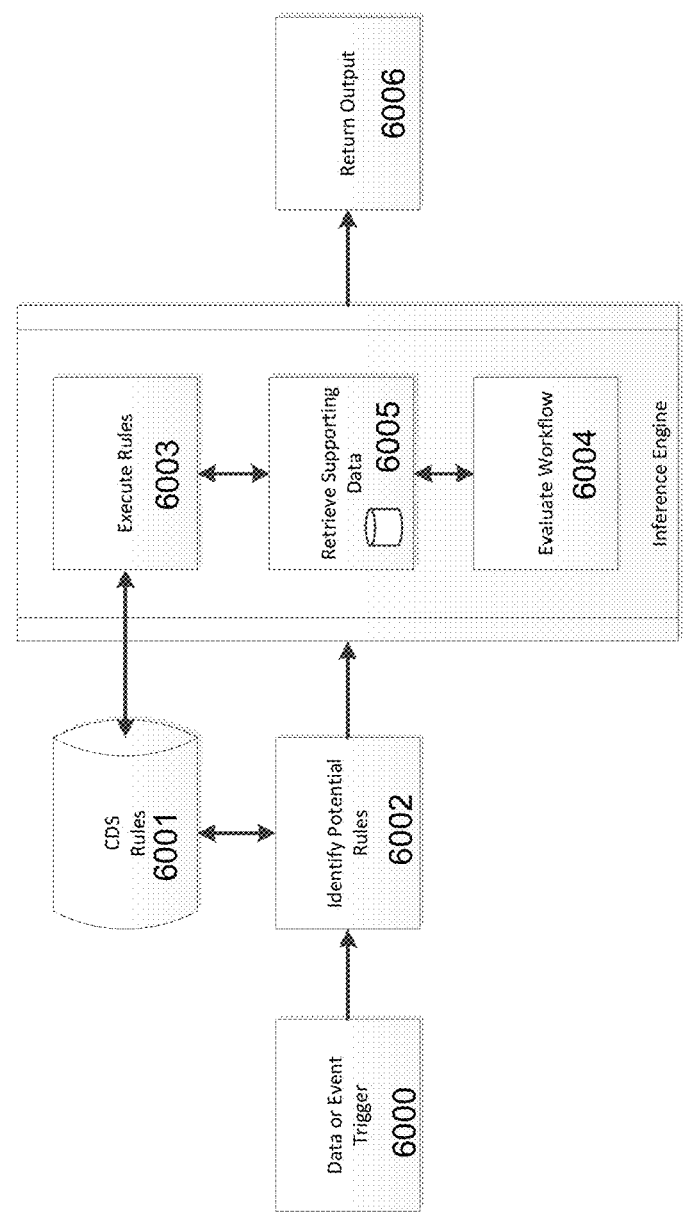
FIG. 72A illustrates an exemplary clinical decision support system in accordance with the invention.
Figure 72B:
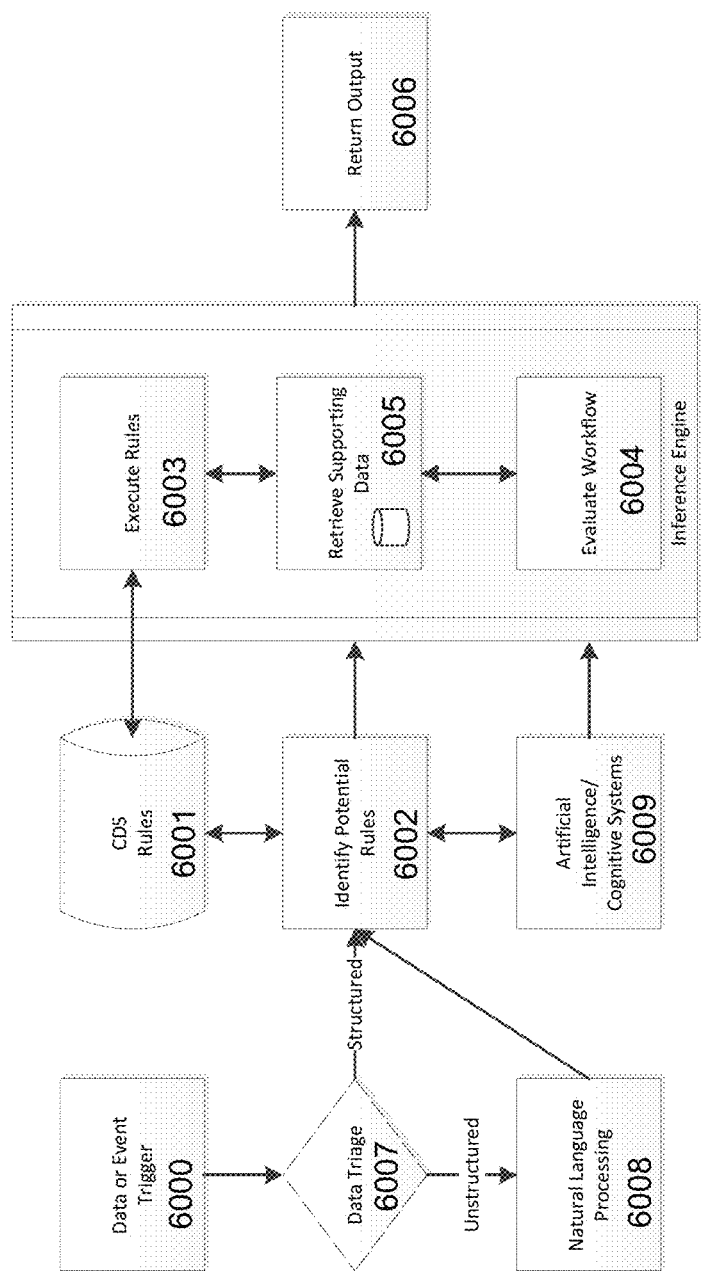
FIG. 72B illustrates an exemplary cognitive system enhanced clinical decision support system for providing cognitive enhanced guidance.

More complex clinical decision support is illustrated in FIG. 72A. In FIG. 72A, the support is handled through the use of a RETE style (pattern matching, rules-based) algorithm. A RETE rules engine or inference engine embodies a set of rules built around a data model whereby when an event is triggered 6000 (data input or a new day starts) potential rules 6001 are identified (6002) that relate to the data/event. If rules are identified, they are executed (6003) along with the evaluation of workflow rules 6004 using supporting data retrieved (6005) as needed from the patient, insurance, clinical, financial and imaging data repositories. Once complete, the outcome is returned (6006) to the requesting system for processing. Typically, the output is displayed on the screen for the user to consume or for storage in the designated database in the Command Center 5000. In exemplary embodiments, the Command Center CDS illustrated in FIG. 72A is based on the Health Level (HL7) and Object Management Group (OMG) Decision Support Standards making it flexible and compatible with other similar systems. Those skilled in the art will appreciate that the inference engine may implement conventional artificial intelligence techniques such as those provided commercially by Watson Health and Truven Health Analytics, Inc. to process received data in connection with data repositories to provide diagnostic feedback and the like.

Certain Command Center interpretations may be the product of cognitive system enhanced clinical decision support ("CDS"). As illustrated in FIG. 72B, certain guidance requests triggered at 6000 are triaged at 6007 and structured data may be simultaneously routed to the core Command Center CDS 6002 while unstructured data is routed through 3rd party commercially available Natural Language Processing services 6008. The systems 6002 and 6008 compare the incoming request against their curated knowledge base to contextually interpret the guidance as well as to provide suggestions beyond the scope of the guidelines based decision support. For example, an artificial intelligence cognitive system 6009 may continuously learn about billing and reimbursement processes, medications, insurance formularies, and patient outcomes. In such a system, an incoming medication recommendation request would then not only receive both the adopted clinical best practice recommendation but also inform the clinician of recently approved alternatives that may be both more clinically and financially effective. The cognitive system enhanced CDS of FIG. 72B may be adapted to provide guidance on: Value Management; Medication Management; Medication Pricing/Formulary Optimization; Co-Management; chart completeness; patient to treatment center matching; billing and billing code optimization; and insurance submission/audit procedures. Those skilled in the art will further appreciate that cognitive system enhanced CDS may be applied to medical records to compare medical data and to notice patterns, errors and anomalies in different entries or EMR notes. For example, when one internist is calling something a disease or has a finding yet another physician is finding something else different, or there is a disease or a billing anomaly between two different physicians, and the like. Cognitive system enhanced CDS may also be used to find discrepancies in payments, to alert physicians about inconsistent medical documentation or improper orders, to speed up the process of complying with regulations, or to alert the physician that a plan or order is inconsistent with a preferred practice plan for a patient.

Figure 72C:
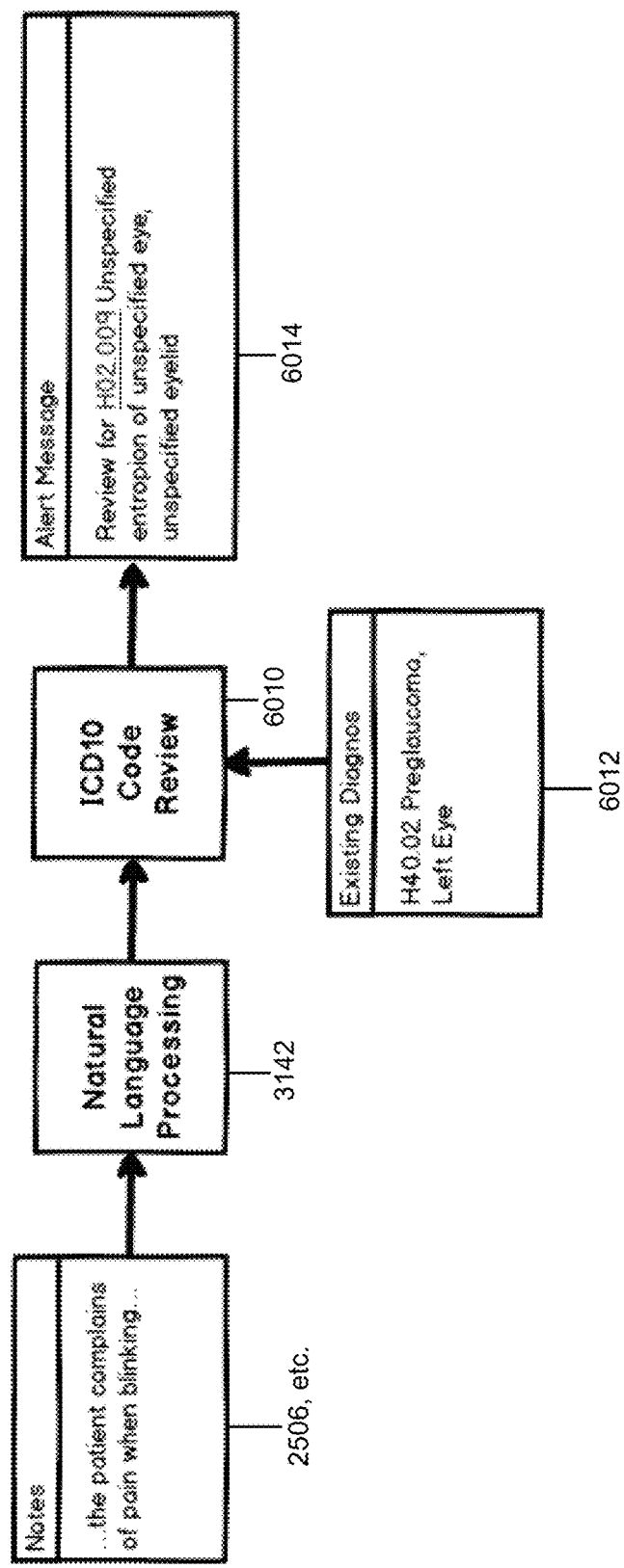
FIG. 72C illustrates an exemplary cognitive system enhanced clinical decision support system for alternative diagnosis identification.

Other embodiments of the cognitive system enhanced CDS provide direction and review of process details via Natural Language Interpretation using natural language processing (NLP) 3142 of system notes (e.g., notes 2506/2668/ 2701/3066/3078/et al.) described above. In FIG. 72C, visit notes 2506, etc. are parsed by NLP 3142 for alternative diagnosis identification. The unstructured data content in notes 2506, etc. is evaluated for potential ICD10 codes via Natural Language Interpretation 3142. If the potential rules process 6002 identifies IDC10 codes at 6010 not covered by existing diagnostic codes 6012, the user is alerted to the potentially viable alternative diagnosis at 6014. This code may then be selected for introduction into the Clinical Evaluation Algorithm shown in FIG. 63 for further review. The mechanics of this process may be replicated for other structured evaluation processes identifiable through Natural Language Interpretation of unstructured data.

CDS is used proactively and reactively within the Command Center 5000. Proactively, users are warned that billing certain procedures might not be covered. An example embodiment is demonstrated in FIG. 32B item 2938 where according to insurance guidelines the OCT imaging test can only be performed after 30 days have passed since the last test. In this case, the user can override the warning and proceed with the test because they deemed it medically necessary. Another example of a proactive warning is demonstrated in FIG. 32B items 2934 and 2936 where a patient is allergic to the chemical agent used to perform the ICG test so it should not be performed. Decision support is also provided in real time as users use the Command Center 5000. These rules are both clinically and financially focused to ensure lab, procedures, and imaging tests that are ordered will be covered by the insurance companies as well as to provide alternatives that may be more financially affordable for the hospital and patient but provide equivalent clinical care. Examples of these rules are demonstrated in several places including prescribing medications (FIGS. 44 and 45), ordering labs (FIGS. 46 and 47), ordering images (FIGS. 48-50), and ordering procedures (FIGS. 51-54).

Database Schema
Note Tables

Figure 73:
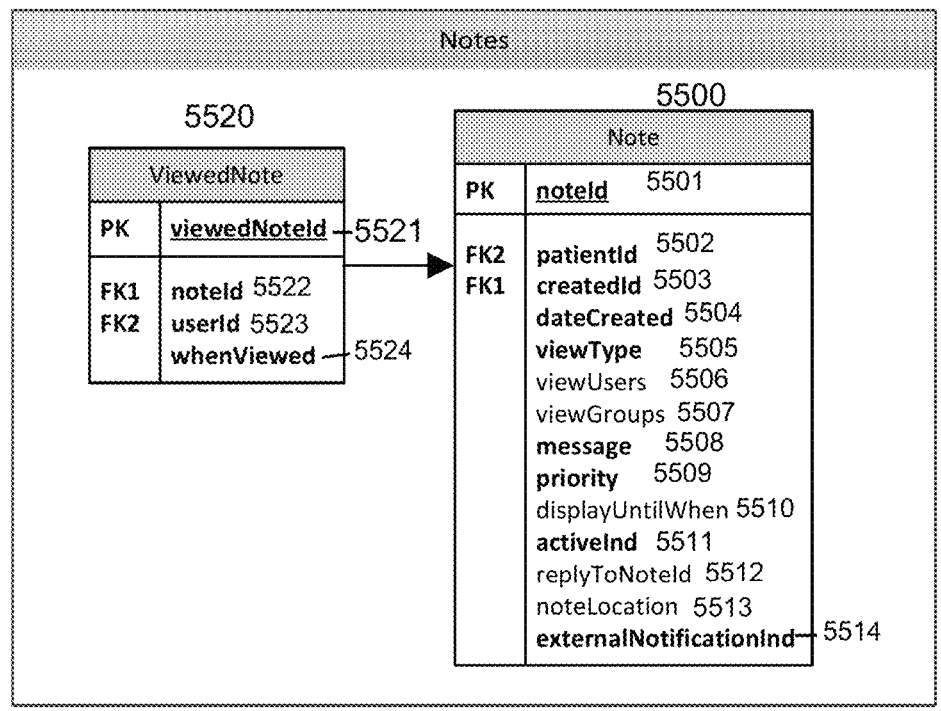
FIG. 73 illustrates a diagram of the tables used to display data on the Note tab (FIG. 39) in accordance with the invention.

FIG. 73 is a diagram of the tables used to display data on the Note tab (FIG. 39). The Note table 5500 has a surrogate primary key, noteId 5501. Notes are uniquely associated to a single patient and the reference or foreign key to the patient is stored in the patientId 5502 column. createdId 5503 is a foreign key to the User that created the note. dateCreated 5504 is the date/time when the note was created. viewType 5505 determines who can see the note. If it is 0, everyone who has access to the Patient can see the note. If the value of ViewType is 1, only specific people can see the note, and if it is 2 only specific groups can see the note. The specific users are stored in the viewUsers 5506 column as a comma-separated list. viewGroups 5507 stores a comma-separated list of the groups that can see the note. The actual message is stored in the message column 5508. The priority is stored in the Priority column 5509 using the convention 0 if low, 1 if normal, 2 if high priority. The displayUntilWhen column 5510 determines how long the note is viewable. If it is null it is viewable until deleted; otherwise it is viewable until the date/time is passed. The activeInd 5511 is set to 1 if the Note can be seen and 0 if deleted or can no longer be seen based on the displayUntilWhen date/time. The activeInd 5511 column is used for convenience in that it allows faster retrieval of Notes because a date comparison is a more computationally expensive process than comparing a bit value. When the user replies to a note, the reference to the original note is stored in replyToNoteId 5512. This is a foreign key to the Note table. If there is a value in noteLocation 5513, it signifies this is a sticky note that is associated with a specific location within the Command Center 5000 (see FIGS. 18-19). The location is specific to a display panel. If it is a static display panel, i.e. the data does not change over time like an order panel, the x/y coordinates relative to the placement of the panel are stored. However, if the panel displays changing data such as rows associated to dates that change over time, the location is stored as a column and row referenced by the primary key id of the row. The externalNotificationInd 5514 stores whether or not the message should be transmitted back to the user's EMR. This process keeps the sticky note associated with the correct content, even when the content includes dynamic data such as new encounters or dates in the flowsheet.

The ViewedNote table 5520 illustrated in FIG. 73 tracks which users viewed the notes and when. The surrogate primary key is viewNoteId 5521 and the note id is stored in noteId 5522. The user who viewed the note is recorded in the userId column 5523. The date/time it is viewed is stored in whenViewed column 5524. A note can be viewed many times by the same user, but only the first time the note is viewed is it recorded in the ViewedNote table 5520.

Alert Tables

Figure 74:
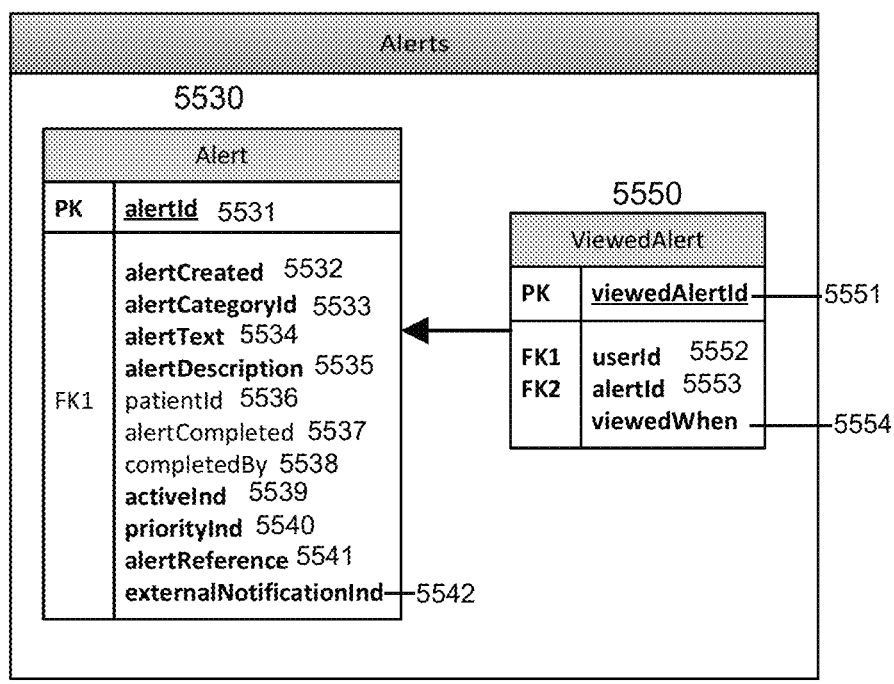
FIG. 74 illustrates a diagram of the tables used to display Alerts that are generated for a patient in accordance with the invention.

FIG. 74 is a diagram of the tables used to display Alerts 5530 that are generated for a patient. The surrogate primary key id is alertId 5531. The alertCreated column 5532 holds the date/time of when the alert is created. The alertCategoryId column 5533 is a method of categorizing the alert, so they can be displayed in proximity or used in the appropriate places in the application. The column in the table is a foreign key to a code table (not depicted), but example categories are Insurance, General Wellness, Diabetes, and Billing. alertText 5534 is a short title used for the purpose of display, while alertDescription 5535 is a longer description of the alert. If the alert is associated with a patient, the patientId 5536 is stored. When the alert is completed, the date/time is stored in alertCompleted 5537 and the completedBy column 5538 stores the user who completed (deletes) the alert. If an alert is active (not deleted) the alertInd 5539=1; otherwise it is 0. Use of this column increases the speed of data retrieval. The alert priority (low, normal or high) is stored in priorityInd 5540. The values are 0 if low, 1 if normal, 2 if high priority. alertReference 5541 is used to store information about the rule/conditions that applied at the time the alert was created to better understand how the system is working. It is not intended for viewing, only troubleshooting and research. Finally, the last column externalNotificationInd 5542 is 0 if it is not transmitted back to the EMR 5021 and 1 if it was transmitted.

The ViewedAlert table 5550 illustrated in FIG. 74 stores data about which users have viewed the alerts and when they viewed it. The surrogate primary key is viewedAlertId 5551. The Alert Id is stored in alertId 5552 and the user is stored in userId 5553. The date/time the alert was viewed is stored in the whenViewed column 5554. An alert can be viewed many times by the same user, but only the first time the alert is viewed is it recorded in the ViewedNote 5550 table.

View/Panel Tables

The Command Center 5000 supports multiple configurations of the data based on the user's interests, patient's condition and task being performed. The ViewLayout table 5570 illustrated in FIG. 75 stores the panels and tabs that make up the view and how they are positioned. The Panel table 5580 illustrated in FIG. 76 stores references to the data displayed within a panel. FIGS. 75 and 76 contain the table diagrams, while FIGS. 77 and 78 are examples of the XML used to store the layout and panel information. The ViewLayout table 5570 and the Panel table 5580 thus store the configuration information generated when the view screens are configured, as described above by way of example with respect to FIGS. 41A, 41B and FIGS. 55-56.

As illustrated in FIG. 75, the ViewLayout table 5570 has a surrogate primary key called viewLayoutInd 5571. The name of the layout used for display purposes is stored in the name column 5572. The actual XML that contains the layout is stored in the gridXML column 5573. If the userid column 5574 is null, the view is a default system view that every user can use the first time they login. The userid 5574 relates custom Views to the User who created them. The defaultInd column 5575 denotes the initial layout for each view so the user can reset the View to the default.

As illustrated in FIG. 76, the Panel table 5580 has a surrogate primary key called panelId 5581. The name of the layout used for display purposes is stored in the name column 5582. The columnXML 5583 store the actual XML that defines how the panel is laid out. Like the ViewLayout table 5570, the Panel table 5580 has Panels specific to users as stored in the userId column 5584 and a defaultInd column 5585 allowing the user to reset a panel presentation.

View XML

The view XML illustrated in FIG. 77 provides means for moving and storing the different display panel and flowsheet views in exemplary embodiments. As illustrated, the view XML contains a collection of panels 5590 and tabs 5591. Within each panel 5590 is the panelId 5593 that links to the Panel tab 5591, its position 5594 and whether or not it is stacked 5595 with the preceding panel, which allows for the positioning of tabs. Whether or not each panel is fixed 5596 in position or moveable is also saved. For tabs, the position 5597 on screen for the tabs to be displayed is stored. Then each tab with reference to a panelId 5598 and its order of display is stored 5599.

PanelXML

The panel XML illustrated in FIG. 78 provides means for setting up the display panels and flowsheets in exemplary embodiments. As illustrated, the panel XML contains a collection of columns 5601. For each column, the name of the column 5602 is specified along with the source 5603—where it comes from (e.g. Table=Labs Column=LabDate) the width 5604 of the column and the order the columns 5605 are also tracked.

Guidelines

Figure 79:
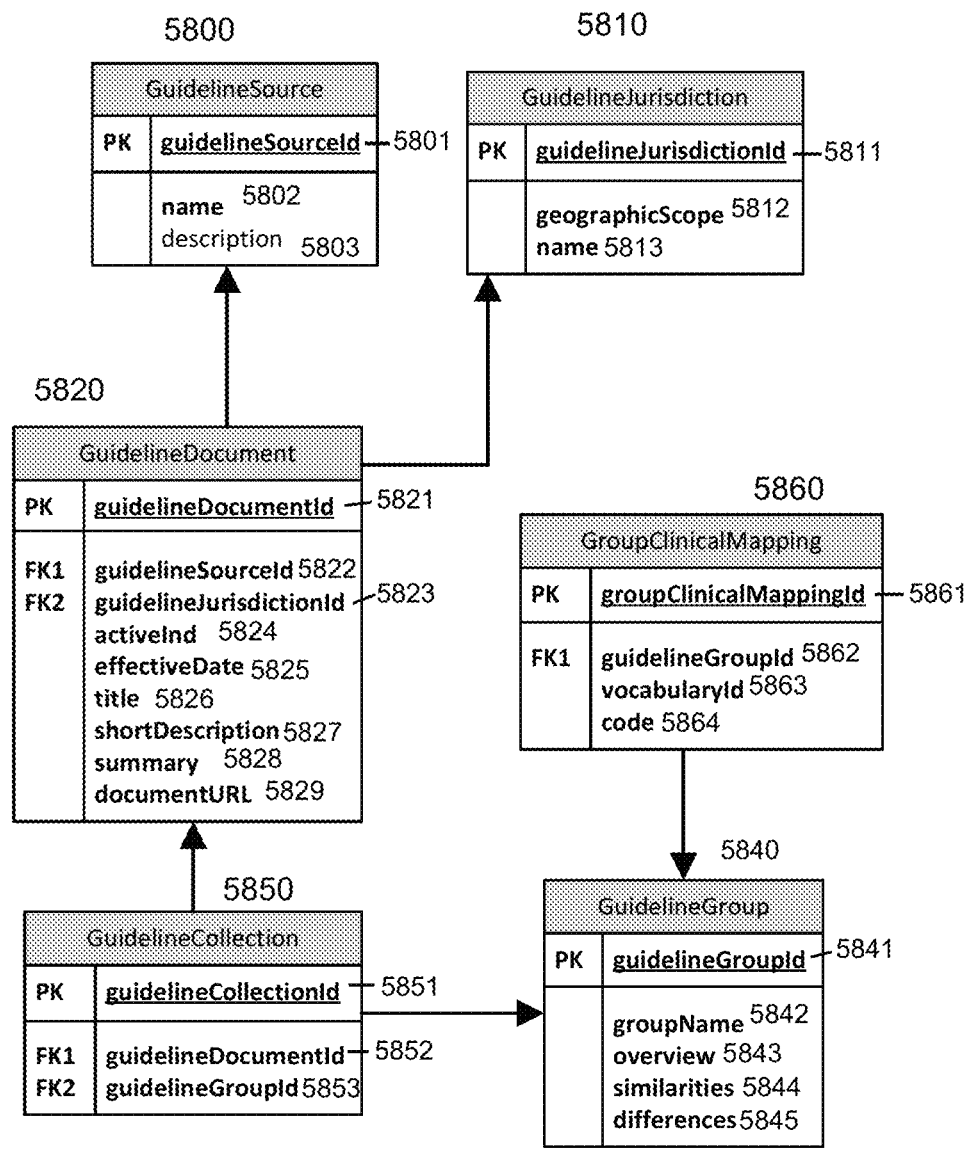
FIG. 79 illustrates the guideline tables that are used to store individual guidelines, groups of guidelines in order to store common information about the group, and associations of those groups with clinical codes (such as ICD10, CPT, RxNorm) in accordance with the invention.

The Guideline tables illustrated in FIG. 79 are used to store individual guidelines, groups of guidelines in order to store common information about the group, and associations of those groups with clinical codes (such as ICD10, CPT, RxNorm) to enable physicians to assimilate the information quickly. GuidelineSource 5800 is a reference table that contains the source of the Guideline. For example, insurance company, a professional society in the case of Preferred Practice Patterns, or the government. The surrogate primary key is guidelineSourceId 5801. The name 5802 is for display purposes and the description 5803 provides more detail. GuidelineJurisdiction 5810 is a reference table that contains geographic locale references. These are applied to the Guidelines to understand where they apply. For instance, insurance guidelines are usually state specific. The surrogate primary key is guidelineJurisdictionId 5811. The geographicScope 5812 is country, state, or region and the name 5813 specifies the specific jurisdiction, so in the case of New Jersey, the geographicScope would be state and the name would be New Jersey. The core table is GuidelineDocument 5820. The GuidelineDocument table 5820 stores information about individual Guidelines. The guidelineDocumentId 5821 is a surrogate primary key. The guidelineSourceId 5822 is a foreign key to the GuidelineSource table 5800 so that it is known where the guideline originates. The guidelineJurisdictionId 5823 is a foreign key to the GuidelineJurisdiction table 5810 so that it is known where the guideline is used. The activeInd 5824 is 1 if it is active and 0 if it is not. This column is used to make retrieval easier. The effectiveDate 5825 is the date when the Guideline is effective, so guidelines can be added before they are actually used. Title 5826 is used for display purposes, while shortDescription 5827 and summary 5828 provide more detailed information about the Guideline. The documentURL 5829 is a link to the actual guideline document for retrieval and display. The Guideline document, usually a PDF, would be stored in the static File Cache 5017 in FIG. 57.

Individual guidelines are then grouped into a collection so an overview can be provided of the guidelines and information about how they are similar and different. This allows the physician to easily assimilate complex information when minute differences may be buried in hundreds of pages of documentation. The GuidelineGroup 5840 table has a surrogate primary key guidelineGroupId 5841, a groupName 5842 for display purposes and then several text fields to capture the overview 5843, similarities 5844 and differences 5845 about the group. The Guidelines are then grouped into a collection using the GuidelineCollection 5850 table. The surrogate primary key is guidelineCollectionId 5851 and the other columns are foreign keys—guidelineDocumentId 5852 and guidelineGroupId 5853. It will be appreciated that these entries enable the user to aggregate all of the guidelines together and to write and store a common overview that outlines the similarities and differences in the guidelines.

The last table related to Guidelines is the GroupClinicalMapping 5860 table. Table 5860 maps clinical codes to GuidelineGroups 5840. Table 5860 has a surrogate primary key groupClinicalMappingId 5861, a foreign key guidelineGroupId 5862 to the GuidelineGroup 5840 table, a vocabularyId 5863 identifying the vocabulary being used and the code 5864 that can be searched. The GroupClinicalMapping table 5860 allows users to easily search for collections of guidelines that apply to a specific clinical code (ICD10, RxNorm, CPT, or other codes) or see at a glance a set of guidelines based on patient specific data (see FIG. 42).

Those skilled in the art will appreciate that the operations described herein are implemented in software implemented as instructions stored in instruction memory and processed in processors of one or more of the servers of the Command Center 5000 illustrated in FIG. 57 and/or the processors 32 of FIG. 14. The design of the data tables and XML structures have been laid out to enable all of the data generated for presentation to the Command Center interface of FIGS. 1 and 15, for example, to be processed in advance and stored in the presentation tables where possible in order to minimize delays in table generation. Also, the display tables are all tied to the Command Center interface so that the user need not navigate away from the Command Center interface to access any of the data described herein. The software operations may be implemented in a special purpose system of the type illustrated in FIG. 57, for example, or the software may be implemented in a general purpose computer that can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data is obtained over a network the data can be processed by other computers on the network, e.g. a cloud of computing resources.

Those skilled in the art will appreciate that the software instructions for implementing the algorithms and XML functionality described herein may be stored in conventional computer-readable storage media. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way.

Those skilled in the art will appreciate that while XML is used to encode data in the illustrated embodiments, other data formats can be used, for example JSON or simple comma delimited text files. Also, those skilled in the art will appreciate that the Command Center embodiments described herein may be modified to include automated mobile messages to patients for usage of medication with feedback to the patient's Command Center along with appointment reminders, bill reminders, etc. A summary of this information may be provided in a display panel of the Command Center in succinct form for the physician. This information enables the physician to determine at a glance whether the patient is reliable or unreliable regarding taking medications, following medical directions, and the like.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. For example, while detailed embodiments describe the use of systems for presenting medical and financial data related to treatment of patients by an ophthalmologist, those skilled in the art will appreciate that the medical data may relate to other medical practices such as dentistry, orthopedics, oncology, and the like. In addition, the techniques described herein may be applied to the presentation of data in other contexts, such as the presentation of stock market and other types of dynamic data. These and other features and advantages of the invention are set forth in the following claims.

The invention claimed is:

1. A data command center visual display system that displays data on a display screen, comprising:
    a patient database that stores patient identification information and patient medical information;
    a computer readable storage medium having instructions stored thereon; and
    a processor that executes said instructions, said instructions when executed causing said processor to perform operations including:
        creating adjustable display panels configured to display predetermined combinations of said patient identification information and patient medical information;
        creating a patient flowsheet including a table that presents the patient's medical information by at least one of medical service, medical procedure, diagnostic test, medication, and diagnosis that is prescribed, ordered, performed, or selected during an encounter with at least one medical provider;
        in response to selection by a user of the visual display system, presenting means for at least one of ordering and scheduling at least one of the medical service, medical procedure, diagnostic test, medication, and diagnosis; and
        presenting the adjustable display panels, patient flowsheet, and means for at least one of ordering and scheduling to the display screen,
        wherein the patient flowsheet is adapted to provide at least portions of the patient medical information into respective data entry fields of the table,
        wherein respective data entries in the table are arranged by time in one direction and by a combination of one or more of medical service, medical procedure, diagnostic test, medication, and diagnosis in another direction, whereby data entries for the combination of one or more of medical service, medical procedure, diagnostic test, medication, and diagnosis relating to the patient's medical condition are shown in a corresponding row or column of the table for tracking changes in the one or more of medical service, medical procedure, diagnostic test, medication, and diagnosis, and
        wherein the means for at least one of ordering and scheduling at least one of the medical service, medical procedure, diagnostic test, medication, and diagnosis is accessible from the display screen while portions of the patient's medical information remain in view in the table.

2. A method of displaying data on a display screen, comprising:
    storing patient identification information and patient medical information;
    creating adjustable display panels configured to display predetermined combinations of said patient identification information and patient medical information;
    creating a patient flowsheet including a table that presents the patient's medical information by at least one of medical service, medical procedure, diagnostic test, medication, and diagnosis that is prescribed, ordered, performed, or selected during an encounter with at least one medical provider;
    in response to selection by a user of the visual display system, presenting means for at least one of ordering and scheduling at least one of the medical service, medical procedure, diagnostic test, medication, and diagnosis; and
    presenting the adjustable display panels, patient flowsheet, and means for at least one of ordering and scheduling to the display screen,
    wherein the patient flowsheet is adapted to provide at least portions of the patient medical information into respective data entry fields of the table,
    wherein respective data entries in the table are arranged by time in one direction and by a combination of one or more of medical service, medical procedure, diagnostic test, medication, and diagnosis in another direction, whereby data entries for the combination of one or more of medical service, medical procedure, diagnostic test, medication, and diagnosis relating to the patient's medical condition are shown in a corresponding row or column of the table for tracking changes in the one or more of medical service, medical procedure, diagnostic test, medication, and diagnosis, and wherein the means for at least one of ordering and scheduling at least one of the medical service, medical procedure, diagnostic test, medication, and diagnosis is accessible from the display screen while portions of the patient's medical information remain in view in the table.

3. The method of claim 2, wherein presenting the means for at least one of ordering and scheduling comprises presenting a prescription panel for ordering medication or a medical procedure ordering panel for ordering a medical procedure.

4. The method of claim 3, wherein presenting the medical procedure ordering panel comprises presenting a link to a quality reporting panel that displays quality reporting metrics and/or peer data related to the medical procedure that is being ordered.

5. The method of claim 2, wherein presenting the means for at least one of ordering and scheduling comprises presenting an imaging order panel for ordering a medical image of the patient or a lab order panel for ordering a lab test of the patient.

6. The method of claim 2, further comprising creating an image icon in an adjustable display panel and/or the patient flowsheet that, when selected by the user of the visual data system, opens a display window for viewing of one or more images without leaving the display screen.

7. A data command center visual display system that displays data on a display screen, comprising:
- a patient database that stores patient identification information and patient medical information;
- a computer readable storage medium having instructions stored thereon; and
- a processor that executes said instructions, said instructions when executed causing said processor to perform operations including:
- creating adjustable display panels configured to display predetermined combinations of said patient identification information and patient medical information;
- creating a patient flowsheet including a table that presents the patient's medical information by at least one of medical service, medical procedure, diagnostic test, medication, and diagnosis that is prescribed, ordered, performed, or selected during an encounter with at least one medical provider;
- in response to selection by a user of the visual display system, moving the adjustable display panels and patient flowsheet into a task-based or specialty-specific display configuration such that said patient identification information and patient medical information may be accessed without leaving the display screen; and
- presenting the task-based or specialty-specific display configuration to the display screen,
- wherein the patient flowsheet is adapted to provide at least portions of the patient medical information into respective data entry fields of the table,
- wherein respective data entries in the table are arranged by time in one direction and by a combination of one or more of medical service, medical procedure, diagnostic test, medication, and diagnosis in another direction, whereby data entries for the combination of one or more of medical service, medical procedure, diagnostic test, medication, and diagnosis relating to the patient's medical condition are shown in a corresponding row or column of the table for tracking changes in the one or more of medical service, medical procedure, diagnostic test, medication, and diagnosis, and wherein presenting the display configuration to the display screen further comprises presenting means for at least one of ordering and scheduling at least one of the medical service, medical procedure, diagnostic test, medication, and diagnosis, the means for at least one of ordering and scheduling being accessible from the display screen while portions of the patient's medical information remain in view in the table.

8. The visual display system of claim 7, further comprising instructions that when executed open display windows to associated patient medical information and/or financial data that overlay a portion of the display screen whereby the associated patient medical information and/or financial data may be viewed by the user of the visual display system while the adjustable display panels and said patient flowsheet are displayed in a background on the display screen.

9. The visual display system of claim 7, further comprising instructions that when executed create links in said patient flowsheet or display panels to compliance information about compliance with insurance guidelines and/or good clinical practice guidelines for a procedure or action.

10. The visual display system of claim 9, wherein the compliance information comprises aggregated medical treatment guidelines and an overview outlining similarities and differences amongst different medical treatment guidelines making up the aggregated medical treatment guidelines.

11. The visual display system of claim 10, wherein the aggregated medical treatment guidelines include information related to recommended follow-up with the patient, information related to procedures permitted or prevented by the patient's insurance or contra-indications, and information relating to proper billing for the procedure or action selected from said patient flowsheet or display panels.

12. The visual display system of claim 10, further comprising instructions that when executed access a clinical decision support system that uses a rules engine and/or natural language processing to aggregate the medical treatment guidelines and to generate the overview outlining similarities and differences amongst different medical treatment guidelines making up the aggregated medical treatment guidelines.

13. The visual display system of claim 7, further comprising instructions that when executed access a clinical decision support system that uses a rules engine and/or natural language processing to compare medical data to notice patterns, errors and anomalies in different entries or notes, to find discrepancies in payments, to alert the user of the visual display system about inconsistent medical documentation or improper orders, to speed up the process of complying with regulations, to alert the user of the visual display system that a plan or order is inconsistent with a preferred practice plan for a patient, or to warn the user of the visual display system that billing certain procedures might not be covered.

14. The visual display system of claim 7, further comprising instructions that when executed access a natural language processing system to parse notes in the patient flowsheet or display panels for potential ICD 10 codes or alternative diagnosis.

15. The visual display system of claim 7, further comprising instructions that when executed create an alert icon in an adjustable display panel and/or the patient flowsheet that, when selected by the user of the visual data system, opens an alert message without leaving the display screen.

16. The visual display system of claim 7, wherein one of said display panels is configured to accept today's visit notes from the user of the visual display system in connection with a patient visit for storage for access with other data of said one display panel.

17. The visual display system of claim 7, further comprising instructions that when executed create a moveable note icon for association with context information in a corresponding one of said adjustable display panels and/or said patient flowsheet, said note icon moving with said context information as said context information is moved on said display screen, and wherein said note icon, when selected, enables the user of the visual display system to enter a note relating to said context information.

18. The visual display system of claim 7, further comprising instructions that when executed accept input data from the user of the visual display system and trigger auto-population of information in the adjustable display panels and patient flowsheet and auto-population of the patient's medical record in an electronic medical record system in response to said input data, said auto-population occurring without leaving the display screen.

19. The visual display system of claim 7, further comprising instructions that when executed provide new clinical information for the patient to a diagnosis evaluation algorithm for comparison of the new clinical information with previous corresponding clinical information for the patient to determine whether the new clinical information is indicative of an improvement or worsening of the patient's medical condition, generate diagnosis indicators providing a visual representation of an improvement of a medical problem, disease, or symptom, or a worsening of a medical problem, disease, or symptom as a result of taking a particular medication or undergoing a particular medical procedure, and display said diagnosis indicators in said adjustable display panels and/or said patient flowsheet.

20. The visual display system of claim 7, wherein the patient database comprises a remote database and a local database, said local database storing a subset of patient identification information, patient insurance information, patient medical information, and patient payment information, said subset including the patient identification information, patient insurance information, patient medical information, and patient payment information for patients having an appointment within a predetermined time window.

21. The visual display system of claim 7, further comprising an interface to external health information system including at least one of an electronic medical records system, a practice management system, a health information exchange, a picture archive and communications system, a clearing house/billing system, and a laboratory system.

22. The visual display system of claim 7, further comprising an interface to third party service systems including at least one of an ePrescribing system, an insurance verification/referral/pre-authorization system, a system for establishing medical necessity by verifying that a procedure or medication is associated with a correct ICD 10 code supporting its use, a clinical services pricing and location system, a claim status checking system, services in support of the National Correct Coding Initiative, services to proactively ensure claims are coded correctly to prevent issues in billing, claims compliance services that evaluate claims against National Coverage Determination (NCD) and Local Coverage Determination (LCD) guidelines as well as local insurance regulations to establish and document medical necessity, a natural language processing system, and artificial intelligence/cognitive systems that provide clinical decision support.

23. The visual display system of claim 7, wherein the patient identification information and patient medical information is stored in the patient database in transactional tables that capture clinical data and reporting tables where data is aggregated for a particular physician, practice, health system or other entity, each table using a surrogate primary key that is a unique value within the table used to identify a row that is not directly tied to data in that row.

24. The visual display system of claim 7, wherein the instructions for moving the adjustable display panels and patient flowsheet into a task-based or specialty-specific display configuration in response to selection by the user of the visual display system comprises XML code that moves and stores different display panel and flowsheet views, the XML code identifying a collection of panels and tabs, wherein within each panel is a panel ID that links the panel to a tab, the panel's position, and whether or not the panel is stacked with another panel.

25. The visual display system of claim 7, wherein the instructions for moving the adjustable display panels and patient flowsheet into a task-based or specialty-specific display configuration in response to selection by the user of the visual display system comprises XML code that sets up the display panels and patient flowsheet on said display screen, the XML code identifying a collection of columns and, for each column, a name of the column along with a data source.

26. The visual display system of claim 7, wherein the instructions for moving the adjustable display panels and patient flowsheet into a task-based or specialty-specific display configuration in response to selection by the user of the visual display system comprises instructions for presenting display panels to the display screen for selection and for manipulating display panel frames on said display screen for receiving selected display panels.

27. The visual display system of claim 7, wherein the patient flowsheet is organized around patient medical information corresponding to a particular disease state and procedures or actions for treating the particular disease state.

28. The visual display system of claim 7, wherein the patient database includes patient medical information from a plurality of medical providers and the instructions further comprise instructions for creating the patient flowsheet with medical information from more than one medical provider providing shared treatment of the patient.

29. The visual display system of claim 7, further comprising instructions that when executed create a summary table illustrating everything the user of the visual display system has done for each patient in a particular time frame or for each patient having a particular disease state or a particular insurance in a particular time frame.

30. The visual display system of claim 7, wherein said plurality of adjustable display panels are further configured to display patient payment information as part of said combination of one or more of medical service, medical procedure, diagnostic test, medication, and diagnosis, and wherein creating the patient flowsheet further comprises providing the patient medical information and patient payment information into in the table, the table further including entries indicating whether a corresponding medical service, medical procedure, diagnostic test, medication, or diagnosis in the table has been paid for in part or in full, said entries further providing links to patient payment information.

31. The visual display system of claim 7, wherein entries in the table are represented by icons representing at least one of findings by a medical service provider, diagnostic test results, clinical information, and medical procedures, each icon providing a link to associated patient medical information in the patient database.

* * * * *